US008232288B2

(12) United States Patent
Schunk et al.

(10) Patent No.: US 8,232,288 B2
(45) Date of Patent: Jul. 31, 2012

(54) SUBSTITUTED BENZIMIDAZOLES, BENZOTHIAZOLES AND BENZOXAZOLES

(75) Inventors: Stefan Schunk, Aachen (DE); Melanie Reich, Aachen (DE); Michael Engels, Turnhout (BE); Tieno Germann, Aachen (DE); Jean De Vry, Stolberg (DE); Ruth Jostock, Stolberg (DE); Sabine Hees, Aachen (DE)

(73) Assignee: Gruenenthal GmbH, Aachen (DE)

( * ) Notice: Subject to any disclaimer, the term of this patent is extended or adjusted under 35 U.S.C. 154(b) by 72 days.

(21) Appl. No.: 12/795,314

(22) Filed: Jun. 7, 2010

(65) Prior Publication Data

US 2011/0009382 A1 Jan. 13, 2011

Related U.S. Application Data

(60) Provisional application No. 61/185,045, filed on Jun. 8, 2009.

(30) Foreign Application Priority Data

Jun. 8, 2009 (EP) .................................... 09007517

(51) Int. Cl.
*A61K 31/435* (2006.01)
*C07D 221/20* (2006.01)

(52) U.S. Cl. ......................................... 514/278; 546/16

(58) Field of Classification Search .................. 514/278; 546/16
See application file for complete search history.

(56) References Cited

FOREIGN PATENT DOCUMENTS

| | | | |
|---|---|---|---|
| EP | 2 055 705 | A1 | 5/2009 |
| WO | WO 2007/101007 | A2 | 9/2007 |
| WO | WO 2007/140383 | A2 | 12/2007 |
| WO | WO 2008/019363 | A2 | 2/2008 |
| WO | WO 2008/004092 | A1 | 4/2008 |
| WO | WO 2008/046573 | A1 | 4/2008 |

OTHER PUBLICATIONS

J. Fred Hess, et al, "Generation and Characterization of a Humanized bradykinin B1 Receptor Mouse", Biol. Chem., Feb. 2006, pp. 195-201, vol. 387.
R. Hayashi, et al., "Bradykinin Stimulates IL-6 and IL-8 Production by Human Lung Fibroblasts through ERK- and p38 MAPK-dependent Mechanisms", European Respiratory Journal, 2000, pp. 452-458, vol. 16.
Bichoy H. Gabra, et al, "The Kinin System Mediates Hyperalgesia through the Inducible Bradykinin B1 Receptor Subtype: Evidence in Various Experimental Animal Models of Type 1 and Type 2 Diabetic Neuropathy", Biol. Chem., Feb. 2006, pp. 127-143, vol. 387.
Joao B. Calixto, et al., "Kinin $B_1$ Receptors: Key G-Protein-Coupled Receptors and Their Role in Inflammatory and Painful Processes", British Journal of Pharmacology, 2004, pp. 803-818, vol. 143.
Sara H. Bengtson, et al., "Kinin Receptor Expression During *Staphylococcus aureus* Infection", Blood, 2006, pp. 2055-2063, vol. 108.
Antoni Stadnicki, et al., "Immunolocalization and Expression of Kinin $B_1R$ and $B_2R$ Receptors in Human Inflammatory Bowel Disease", AJP Gastrointest Liver Physiol, Aug. 2005, pp. G361-G366, vol. 289.
A. Prat, et al., "Bradykinin $B_1$ Receptor Expression and Function on T Lymphocytes in Active Multiple Sclerosis", Dec. 10, 1999, pp. 2087-2092, vol. 53, No. 9, American Academy of Neurology.
Joao B. Pesquero, et al., Genetically Altered Animal Models in the Kallikrein-Kinin System, Biol. Chem., Feb. 2006, pp. 119-126, vol. 387.
Joao B. Pesquero, et al., "Hypoalgesia and Altered Inflammatory Responses in Mice Lacking Kinin B1 Receptors", PNAS, Jul. 5, 2000, pp. 8140-8145, vol. 97, No. 14.
Giselle F. Passos, et al., "Kinin $B_1$ Receptor Up-Regulation after Lipopolysaccharide Administration: Role of Proinflammatory Cytokines and Neutrophil Influx[1]", The Journal of Immunology, 2004, pp. 1839-1847, vol. 172.
L. M. Fredrik Leeb-Lundberg, et al., "International Union of Pharmacology. XLV. Classification of the Klnin Receptor Family: from Molecular Mechanisms to Pathophysiological Consequences", Pharmacological Reviews, 2005, pp. 27-77, vol. 57, No. 1.
European Search Report including partial translation dated Dec. 23, 2009 (Eight (8) pages).

*Primary Examiner* — Rebecca Anderson
*Assistant Examiner* — Samantha Shterengarts
(74) *Attorney, Agent, or Firm* — Crowell & Moring LLP

(57) ABSTRACT

Substituted benzimidazoles, benzothiazoles and benzoxazoles, processes for their preparation, pharmaceutical compostions containing these compounds and the use of these compounds for treating or inhibiting disorders or disease states mediated at least in part by bradykinin receptor 1 (BR1).

22 Claims, No Drawings

SUBSTITUTED BENZIMIDAZOLES, BENZOTHIAZOLES AND BENZOXAZOLES

CROSS REFERENCE TO RELATED APPLICATIONS

This application claims priority from U.S. provisional patent application No. 61/185,045, filed Jun. 8, 2009, the entire disclosure of which is incorporated herein by reference. Priority is also claimed based on European patent application no. 09007517.7, filed Jun. 8, 2009.

BACKGROUND OF THE INVENTION

The present invention relates to substituted benzimidazoles, benzothiazoles and benzoxazoles, processes for the preparation thereof, medicaments containing these compounds and the use of these compounds for the preparation of medicaments.

In contrast to the constitutive expression of the bradykinin 2 receptor (B2R), in most tissues the bradykinin 1 receptor (B1R) is not expressed or is expressed only weakly. Nevertheless, expression of B1R can be induced on various cells. For example, in the course of inflammation reactions a rapid and pronounced induction of B1R takes place on neuronal cells, but also various peripheral cells, such as fibroblasts, endothelial cells, granulocytes, macrophages and lymphocytes. In the course of inflammation reactions, a switch from a B2R to a B1R dominance thus occurs on the cells involved. The cytokines interleukin-1 (IL-1) and tumour necrosis factor alpha (TNFα) are involved to a considerable degree in this upwards regulation of B1R (Passos et al. J. Immunol. 2004, 172, 1839-1847). After activation with specific ligands, B1R-expressing cells then themselves can secrete inflammation-promoting cytokines such as IL-6 and IL-8 (Hayashi et al., Eur. Respir. J. 2000, 16, 452-458). This leads to inwards migration of further inflammation cells, e.g. neutrophilic granulocytes (Pesquero et al., PNAS 2000, 97, 8140-8145). The bradykinin B1R system can contribute towards chronification of diseases via these mechanisms. This is demonstrated by a large number of animal studies (overviews in Leeb-Lundberg et al., Pharmacol Rev. 2005, 57, 27-77 and Pesquero et al., Biol. Chem. 2006, 387, 119-126). On humans too, an enhanced expression of B1R, e.g. on enterocytes and macrophages in the affected tissue of patients with inflammatory intestinal diseases (Stadnicki et al., Am. J. Physiol. Gastrointest. Liver Physiol. 2005, 289, G361-366) or on T lymphocytes of patients with multiple sclerosis (Prat et al., Neurology. 1999; 53, 2087-2092) or an activation of the bradykinin B2R-B1R system in the course of infections with *Staphylococcus aureus* (Bengtson et al., Blood 2006, 108, 2055-2063) is found. Infections with *Staphylococcus aureus* are responsible for syndromes such as superficial infections of the skin up to septic shock.

Based on the pathophysiological relationships described, there is a great therapeutic potential for the use of B1R antagonists on acute and, in particular, chronically inflammatory diseases. These include diseases of the respiratory tract (bronchial asthma, allergies, COPD/chronic obstructive pulmonary disease, cystic fibrosis etc.), inflammatory intestinal diseases (ulcerative colitis, CD/Crohn's disease etc.), neurological diseases (multiple sclerosis, neurodegeneration etc.), inflammations of the skin (atopic dermatitis, psoriasis, bacterial infections etc.) and mucous membranes (Behcet's disease, pelvitis, prostatitis etc.), rheumatic diseases (rheumatoid arthritis, osteoarthritis etc.), septic shock and reperfusion syndrome (following cardiac infarction, stroke).

The bradykinin (receptor) system is moreover also involved in regulation of angiogenesis (potential as an angiogenesis inhibitor in cancer cases and macular degeneration on the eye), and B1R knockout mice are protected from induction of obesity by a particularly fat-rich diet (Pesquero et al., Biol. Chem. 2006, 387, 119-126). B1R antagonists are therefore also suitable for treatment of obesity.

B1R antagonists are suitable in particular for treatment of pain, in particular inflammation pain and neuropathic pain (Calixto et al., Br. J. Pharmacol 2004, 1-16), and here in particular diabetic neuropathy (Gabra et al., Biol. Chem. 2006, 387, 127-143). They are furthermore suitable for treatment of migraine.

In the development of B1R modulators, however, there is the problem that the human and the rat B1 receptor differ so widely that many compounds which are good B1R modulators on the human receptor have only a poor or no affinity for the rat receptor. This makes pharmacological studies on animals considerably difficult, since many studies are usually conducted on the rat. However, if no activity exists on the rat receptor, neither the action nor side effects can be investigated on the rat. This has already led to transgenic animals with human B1 receptors being produced for pharmacological studies on animals (Hess et al., Biol. Chem. 2006; 387(2): 195-201). Working with transgenic animals, however, is more expensive than working with the unmodified animals.

PCT patent applications WO 2008/040492 and WO 2008/046573 describe compounds which, in in vitro assays, show an antagonistic action both on the human B1 receptor and on the B1 receptor of the rat.

PCT patent applications WO 2007/140383 and WO 2007/101007 describe compounds which have an antagonistic action on the macaque B1 receptor in in vitro assays. Experimental data on the activity on the human B1 receptor or the B1 receptor of the rat are not disclosed.

There continues to be a need for novel B1R modulators, B1R modulators which bind both to the rat receptor and to the human receptor offering particular advantages.

SUMMARY OF THE INVENTION

One object of the present invention was therefore to provide novel compounds which are suitable in particular as pharmacological active compounds in medicaments, preferably in medicaments for treatment of disorders or diseases which are at least partly mediated by B1R receptors.

This object is achieved by the substituted benzimidazoles, benzothiazoles and benzoxazoles according to the invention.

The present invention therefore provides substituted benzimidazoles, benzothiazoles and benzoxazoles of formula (I)

(I)

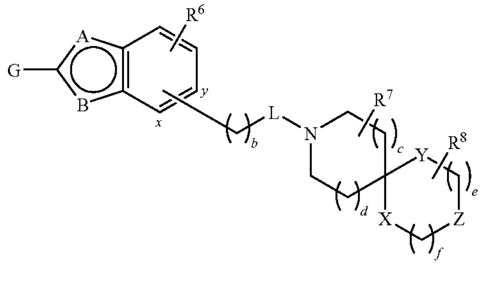

wherein

L represents C(═O) or $CH_2$;

A and B independently of each other are in each case selected from the group consisting of N, $NR^{100}$, O and S, wherein $R^{100}$ represents H, $C_{1-6}$-alkyl, $C_{3-8}$-cycloalkyl, aryl, heteroaryl or a $C_{3-8}$-cycloalkyl, aryl or heteroaryl bonded via a $C_{1-6}$-alkylene group;

b represents 0, 1 or 2;

c, d, e and f each independently represent 0, 1 or 2;

G represents one of the following groups G1 or G2

G1

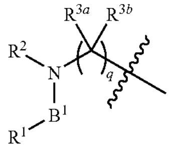

G2

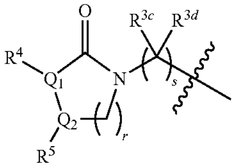

q represents 0, 1, 2 or 3;

s represents 0, 1, 2 or 3;

r represents 1, 2 or 3;

$B^1$ represents C(═O), S(═O)$_2$ or the group —C(═O)—N($R^9$), wherein the nitrogen atom thereof is bonded to $R^1$;

$Q_1$ and $Q_2$ each independently represent C, CH or N;

$R^1$ represents $C_{1-6}$-alkyl, aryl, heteroaryl, —CH(aryl)$_2$, $C_{3-8}$-cycloalkyl or an aryl, heteroaryl or $C_{3-8}$-cycloalkyl bonded via a $C_{1-6}$-alkylene group, $C_{2-6}$-alkenylene group or $C_{2-6}$-alkynylene group;

$R^2$ represents H, $C_{1-6}$-alkyl, $C_{3-8}$-cycloalkyl, aryl, heteroaryl or a $C_{3-8}$-cycloalkyl, aryl or heteroaryl bonded via a $C_{1-6}$-alkylene group;

$R^{3a}$ and $R^{3b}$ each independently denote H, F, $CF_3$, $C_{1-6}$-alkyl, $C_{3-8}$-cycloalkyl, aryl or heteroaryl, or represent a $C_{3-8}$-cycloalkyl, aryl or heteroaryl bonded via a $C_{1-6}$-alkylene group;

$R^{3a}$ and $R^{3b}$ together with the C atom joining them form a saturated ring, which is unsubstituted or substituted on one or more, for example 1, 2, 3 or 4, of its carbon ring members by one or more, for example 1, 2, 3 or 4, substituents independently selected from the group consisting of F, $CF_3$, $C_{1-6}$-alkyl, O—$C_{1-6}$-alkyl, OH, $OCF_3$, aryl and heteroaryl, wherein the ring is 3-, 4-, 5- or 6-membered, and can optionally contain one or more, for example 1 or 2, oxygen atoms; or one of $R^{3a}$ or $R^{3b}$ and $R^2$ together with the N and C atoms joining them form a saturated ring, which is unsubstituted or substituted on one or more, for example 1, 2, 3 or 4, of its carbon ring members by one or more substituents, for example 1, 2, 3 or 4, independently selected from the group consisting of F, $CF_3$, $C_{1-6}$-alkyl, O—$C_{1-6}$-alkyl, OH, $OCF_3$, aryl and heteroaryl; wherein the ring is 4-, 5-, 6- or 7-membered, and can optionally contain one or more, for example 1, 2 or 3, hetero atoms or hetero atom groups independently selected from the group consisting of N, $NR^{100a}$, O, S, S(═O) and S(═O)$_2$; wherein $R^{100a}$ represents H, $C_{1-6}$-alkyl, $C_{3-8}$-cycloalkyl, aryl, heteroaryl or a $C_{3-8}$-cycloalkyl, aryl or heteroaryl bonded via a $C_{1-6}$-alkylene group;

$R^{3c}$ and $R^{3d}$ each independently denote H, F, $CF_3$, $C_{1-6}$-alkyl, $C_{3-8}$-cycloalkyl, aryl or heteroaryl, or represent a $C_{3-8}$-cycloalkyl, aryl or heteroaryl bonded via a $C_{1-6}$-alkylene group, or $R^{3c}$ and $R^{3d}$ together with the C atom joining them form a saturated ring, which is unsubstituted or substituted on one or more, for example 1, 2, 3 or 4, of its carbon ring members by one or more, for example 1, 2, 3 or 4, substituents independently selected from the group consisting of F, $CF_3$, $C_{1-6}$-alkyl, O—$C_{1-6}$-alkyl, OH, $OCF_3$, aryl and heteroaryl, wherein the ring is 3-, 4-, 5- or 6-membered, and can optionally contain one or more, for example 1 or 2, oxygen atoms;

$R^4$ and $R^5$ together with the group -$Q_1$-$Q_2$- joining them form a ring, which is unsubstituted or substituted on one or more, for example 1, 2, 3 or 4, of its carbon ring members by one or more, for example 1, 2, 3 or 4, substituents independently selected from the group consisting of F, Cl, Br, I, $CF_3$, $C_{1-6}$-alkyl, O—$C_{1-6}$-alkyl, OH, $OCF_3$, SH, $SCF_3$, aryl and heteroaryl and/or can be fused with at least one aryl or heteroaryl, wherein the ring is saturated, unsaturated one or more times or aromatic, is 4-, 5-, 6- or 7-membered, and can optionally contain one or more, for example 1, 2 or 3, hetero atoms or hetero atom groups independently selected from the group consisting of N, $NR^{50}$, O, S, S(═O) and S(═O)$_2$; wherein $R^{50}$ denotes H, $C_{1-6}$-alkyl, —C(═O)—$R^{51}$, $C_{3-8}$-cycloalkyl, aryl, heteroaryl or a $C_{3-8}$-cycloalkyl, aryl or heteroaryl bonded via a $C_{1-3}$-alkylene group, and $R^{51}$ denotes $C_{1-6}$-alkyl, $C_{3-8}$-cycloalkyl, aryl, heteroaryl or a $C_{3-8}$-cycloalkyl, aryl or heteroaryl bonded via a $C_{1-3}$-alkylene group;

$R^6$ represents 0, 1, 2 or 3 substituents, which independently of each other are selected from the group consisting of F, Cl, $CF_3$, CN, $OCF_3$, OH, $C_{1-6}$-alkyl, $C_{3-8}$-cycloalkyl and O—$C_{1-6}$-alkyl;

$R^7$ and $R^8$ each independently represent 0, 1, 2, 3 or 4 substituents, which in each case independently of each other are selected from the group consisting of F, Cl, OH, ═O, $C_{1-6}$-alkyl, O—$C_{1-6}$-alkyl, $C_{3-8}$-cycloalkyl, aryl, heteroaryl and $C_{3-8}$-cycloalkyl, aryl or heteroaryl bonded via a $C_{1-6}$-alkylene group and/or two adjacent substituents $R^7$ or $R^8$ form a fused-on aryl or heteroaryl;

$R^9$ represents H, $C_{1-6}$-alkyl, $C_{3-8}$-cycloalkyl, aryl, heteroaryl or a $C_{3-8}$-cycloalkyl, aryl or heteroaryl bonded via a $C_{1-3}$-alkylene group;

X represents $CR^{10a}R^{10b}$, $NR^{11}$ or O;

Y represents $CR^{12a}R^{12b}$, $NR^{13}$ or O;

Y represents $CR^{12a}R^{12b}$, $NR^{13}$ or O;

with the proviso that X does not denote $NR^{11}$ if Y denotes $NR^{13}$; and with the proviso that X and Y do not simultaneously denote ═O;

wherein $R^{10a}$; $R^{10b}$; $R^{12a}$ and $R^{12b}$ each independently denote H, F, Cl, OH, $C_{1-6}$-alkyl, alkyl, $C_{3-8}$-cycloalkyl, aryl or heteroaryl, or represent a $C_{3-8}$-cycloalkyl, aryl or heteroaryl bonded via a $C_{1-6}$-alkylene group, and/or in each case $R^{10a}$ and $R^{10b}$ together can represent ═O and/or in each case $R^{12a}$ and $R^{12b}$ together can represent ═O;

$R^{11}$ and $R^{13}$ each independently represent H, $C_{1-6}$-alkyl, $C_{3-8}$-cycloalkyl, aryl or heteroaryl, or denote a $C_{3-8}$-cycloalkyl, aryl or heteroaryl bonded via a $C_{1-6}$-alkylene group;

Z represents $CR^{14a}R^{14b}$, $NR^{15}$ or O;

$R^{14a}$ represents H, $NR^{16}R^{17}$, $C_{1-6}$-alkylene-$NR^{16}R^{17}$, O—$C_{1-6}$-alkylene-$NR^{16}R^{17}$, C(═O)—$NR^{16}R^{17}$, $OR^{18}$, $C_{1-6}$-alkylene-$OR^{18}$, $C_{1-6}$-alkylene-O—$C_{1-6}$-alkylene- $OR^{18}$, $C_{1-6}$-alkyl, $C_{3-8}$-cycloalkyl, heterocyclyl, aryl or heteroaryl, or denotes a $C_{3-8}$-cycloalkyl, heterocyclyl, aryl or heteroaryl bonded via a $C_{1-6}$-alkylene group, $R^{14b}$ represents H, $NR^{16}R^{17}$, $C_{1-6}$-alkylene-$NR^{16}R^{17}$, O—$C_{1-6}$-alkylene-$NR^{16}R^{17}$, C(═O)—$NR^{16}R^{17}$, $OR^{18}$, $C_{1-6}$-alkylene-$OR^{18}$, $C_{1-6}$-alkylene-O—$C_{1-6}$-alkylene-$OR^{18}$, $C_{1-8}$-alkyl, $C_{3-8}$-cycloalkyl, heterocyclyl, aryl or heteroaryl, or denotes a $C_{3-8}$-cycloalkyl, heterocyclyl, aryl or heteroaryl bonded via a $C_{1-6}$-alkylene group, $R^{15}$ represents H, —C(═O)—$R^{19}$, —S(═O)$_2$—$R^{19}$, —C(═O)—N($R^{20}$)—$R^{19}$, $CHR^{25}R^{26}$, $C_{1-10}$-alkyl, $C_{3-8}$-cycloalkyl, heterocyclyl, aryl or heteroaryl or denotes a $CHR^{25}R^{26}$, $C_{3-8}$-cycloalkyl, heterocyclyl, aryl or heteroaryl bonded via a $C_{1-6}$-alkylene group;

$R^{16}$ and $R^{17}$ each independently represent H, $C_{1-6}$-alkyl or $C_{3-8}$-cycloalkyl, or $R^{16}$ and $R^{17}$ together with the nitrogen atom joining them form a heterocycle, which is unsubstituted or substituted on one or more of its carbon ring members by one or more substituents independently selected from the group consisting of F, Cl, Br, I, $CF_3$, $C_{1-6}$-alkyl, O—$C_{1-6}$-alkyl, OH, $OCF_3$, SH, $SCF_3$, $NR^AR^B$, aryl and heteroaryl and/or can be fused with at least one aryl or heteroaryl, wherein the heterocycle is saturated or unsaturated one or more times, is 4-, 5-, 6- or 7-membered, and can optionally contain one or more hetero atoms or hetero atom groups independently selected from the group consisting of N, $NR^{50a}$, O, S, S(═O) and S(═O)$_2$; wherein $R^{50a}$ denotes H, $C_{1-6}$-alkyl, —C(═O)—$R^{51a}$, $C_{3-8}$-cycloalkyl, aryl, heteroaryl or a $C_{3-8}$-cycloalkyl, aryl or heteroaryl bonded via a $C_{1-3}$-alkylene group, and $R^{51a}$ denotes $C_{1-6}$-alkyl, $C_{3-8}$-cycloalkyl, aryl, heteroaryl or a $C_{3-8}$-cycloalkyl, aryl or heteroaryl bonded via a $C_{1-3}$-alkylene group;

$R^{18}$ represents H, $C_{1-6}$-alkyl, $C_{3-8}$-cycloalkyl, heterocyclyl, aryl, heteroaryl or $C_{2-6}$-alkylene-$NR^{16}R^{17}$ or denotes a heterocyclyl, $C_{3-8}$-cycloalkyl, aryl or heteroaryl bonded via a $C_{1-6}$-alkylene group;

$R^{19}$ represents $C_{1-6}$-alkyl, aryl, heteroaryl, —CH(aryl)$_2$, $C_{3-8}$-cycloalkyl, heterocyclyl or an aryl, heteroaryl, $C_{3-8}$-cycloalkyl or heterocyclyl bonded via a $C_{1-6}$-alkylene group, $C_{2-6}$-alkenylene group or $C_{2-6}$-alkynylene group;

$R^{20}$ represents H, $C_{1-6}$-alkyl, $C_{3-8}$-cycloalkyl, aryl, heteroaryl or a $C_{3-8}$-cycloalkyl, aryl or heteroaryl bonded via a $C_{1-3}$-alkylene group; or if X represents O and f represents 0, then Z denotes —C($R^{21}$)—C($R^{22}$))—, wherein $R^{21}$ and $R^{22}$ together with the carbon atoms joining them form a fused-on aryl or heteroaryl; or if X represents O and f represents 0, then Z denotes ═(N($CR^{23}$))—, wherein the N atom is bonded to the O atom via a single bond, and $R^{23}$ represents H, $C_{1-6}$-alkyl, $C_{3-8}$-cycloalkyl, aryl or heteroaryl or denotes a $C_{3-8}$-cycloalkyl, aryl or heteroaryl bonded via a $C_{1-6}$-alkylene group;

$R^{25}$ and $R^{26}$ each independently represent H, $C_{1-4}$-alkyl, $C_{3-8}$-cycloalkyl, aryl or heteroaryl, or $R^{25}$ and $R^{26}$ together with the CH grouping joining them form a ring, which is unsubstituted or substituted on one or more of its carbon ring members by one or more substituents independently selected from the group consisting of F, Cl, Br, I, $CF_3$, $C_{1-6}$-alkyl, O—$C_{1-6}$-alkyl, OH, $OCF_3$, SH, $SCF_3$, $NR^AR^B$, aryl and heteroaryl, wherein the ring is saturated or unsaturated one or more times, but is not aromatic, is 4-, 5-, 6- or 7-membered, and can optionally contain one or more hetero atoms or hetero atom groups independently selected from the group consisting of N, $NR^{50b}$, O, S, S(═O) and S(═O)$_2$; wherein $R^{50b}$ denotes H, $C_{1-6}$-alkyl, —C(═O)—$R^{51b}$, $C_{3-8}$-cycloalkyl, aryl, heteroaryl or a $C_{3-8}$-cycloalkyl, aryl or heteroaryl bonded via a $C_{1-3}$-alkylene group, and $R^{51b}$ denotes $C_{1-6}$-alkyl, $C_{3-8}$-cycloalkyl, aryl, heteroaryl or a $C_{3-8}$-cycloalkyl, aryl or heteroaryl bonded via a $C_{1-3}$-alkylene group;

$R^A$ and $R^B$ each independently represent H, $C_{1-6}$-alkyl or $C_{3-8}$-cycloalkyl, or $R^A$ and $R^B$ together with the nitrogen atom joining them form a heterocycle, which is unsubstituted or substituted on one or more of its carbon ring members by one or more substituents independently selected from the group consisting of F, Cl, Br, I, $CF_3$, $C_{1-6}$-alkyl, O—$C_{1-6}$-alkyl, OH, $OCF_3$, SH, $SCF_3$, aryl and heteroaryl, wherein the heterocycle is saturated or unsaturated one or more times, but is not aromatic, is 4-, 5-, 6- or 7-membered, and can optionally contain one or more hetero atoms or hetero atom groups independently selected from the group consisting of N, $NR^C$, O, S, S(═O) and S(═O)$_2$; wherein $R^C$ denotes H, $C_{1-6}$-alkyl, —C(═O)—$R^D$, $C_{3-8}$-cycloalkyl, aryl, heteroaryl or a $C_{3-8}$-cycloalkyl, aryl or heteroaryl bonded via a $C_{1-3}$-alkylene group, and $R^D$ denotes $C_{1-6}$-alkyl, $C_{3-8}$-cycloalkyl, aryl, heteroaryl or a $C_{3-8}$-cycloalkyl, aryl or heteroaryl bonded via a $C_{1-3}$-alkylene group;

wherein the structural part

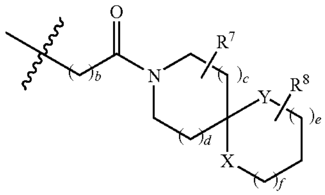

in the compounds of formula I is bonded to the base structure in position x or y, and wherein the abovementioned $C_{1-4}$-alkyl, $C_{1-3}$-alkylene, $C_{1-6}$-alkylene, $C_{2-6}$-alkylene, $C_{2-6}$-alkenylene, $C_{2-6}$-alkynylene, $C_{3-8}$-cycloalkyl, $C_{4-8}$-cycloalkyl, heterocyclyl, aryl and heteroaryl groups may in each case be unsubstituted or substituted one or more times by identical or different substituents and the abovementioned radicals $C_{1-4}$-alkyl, $C_{1-6}$-alkyl, $C_{1-3}$-alkylene, $C_{1-6}$-alkylene, $C_{2-6}$-alkylene, $C_{2-6}$-alkenylene and $C_{2-6}$-alkynylene can in each case be branched or unbranched; in the form of the free compounds; of the tautomers; of the N-oxides; of the racemate; of the enantiomers, diastereomers, mixtures of the enantiomers or diastereomers or of an individual enantiomer or diastereomer; or in the form of the salts of physiologically acceptable acids or bases.

In the context of the present invention, the term "halogen" preferably represents the radicals F, Cl, Br and I, in particular the radicals F and Cl.

In the context of this invention, the expression "$C_{1-10}$-alkyl", "$C_{1-6}$-alkyl" or "$C_{1-4}$-alkyl" includes acyclic saturated hydrocarbon radicals having 1-10 atoms, 1, 2, 3, 4, 5 or 6 C atoms or, respectively, 1, 2, 3 or 4 atoms, which can be branched- or straight-chain (unbranched) and unsubstituted or substituted one or more times, for example 2, 3, 4 or 5 times, by identical or different substituents. The alkyl radicals can preferably be selected from the group consisting of methyl, ethyl, n-propyl, iso-propyl, n-butyl, iso-butyl, sec-butyl, tert-butyl, n-pentyl, iso-pentyl, neo-pentyl and hexyl. Particularly preferred alkyl radicals can be selected from the group consisting of methyl, ethyl, n-propyl, iso-propyl, n-butyl, sec-butyl, iso-butyl and tert-butyl.

In the context of this invention, the expression "$C_{3-8}$-cycloalkyl", "$C_{4-8}$-cycloalkyl" or "$C_{3-6}$-cycloalkyl" denotes cyclic saturated hydrocarbons having 3, 4, 5, 6, 7 or 8, having 4, 5, 6, 7 or 8 or, respectively, having 3, 4, 5 or 6 carbon atoms, which can be unsubstituted or substituted one or more times, for example by 2, 3, 4 or 5 identical or different radicals, on one or more ring members. $C_{3-8}$-Cycloalkyl can preferably be selected from the group consisting of cyclopropyl, cyclobutyl, cyclopentyl, cyclohexyl, cycloheptyl and cyclooctyl.

The term "heterocyclyl" includes saturated or unsaturated (but not aromatic) cycloalkyls having three to seven ring members, in which one, two or three carbon atoms are replaced by a hetero atom in each case independently of each other chosen from the group S, N or O, wherein the ring members can be unsubstituted or substituted one or more times. The bonding of the heterocyclyl to the main structure can be via any desired and possible ring member of the heterocyclyl radical. The heterocyclyl radicals can also be condensed with further saturated, (partially) unsaturated or aromatic or heteroaromatic ring systems, which in turn can be unsubstituted or substituted one or more times. Heterocyclyl radicals from the group azetidinyl, aziridinyl, azepanyl, dioxanyl, dioxolanyl, morpholinyl, pyranyl, pyrrolidinyl, piperazinyl, piperidinyl, pyrazolidinyl, pyrazolinonyl or thiomorpholinyl are preferred.

In the context of this invention, the expression "aryl" denotes aromatic hydrocarbons, in particular phenyls and naphthyls. The aryl radicals can also be condensed with further saturated, (partially) unsaturated or aromatic ring systems. Each aryl radical can be unsubstituted or substituted one or more times, for example 2, 3, 4 or 5 times, wherein the substituents on the aryl can be identical or different and can be in any desired and possible position of the aryl. Aryl can advantageously be selected from the group consisting of phenyl, 1-naphthyl and 2-naphthyl, which in each case can be unsubstituted or substituted one or more times, for example by 2, 3, 4 or 5 radicals.

In the context of the present invention, the expression "heteroaryl" represents a 5-, 6- or 7-membered cyclic aromatic radical which contains at least 1, optionally also 2, 3, 4 or 5 hetero atoms, wherein the hetero atoms can be identical or different and the heteroaryl can be unsubstituted or substituted one or more times, for example 2, 3, 4 or 5 times, by identical or different substituents. The substituents can be bonded in any desired and possible position of the heteroaryl. The heterocycle can also be part of a bi- or polycyclic, in particular a mono-, bi- or tricyclic system, which can then be more than 7-membered in total, preferably up to 14-membered. Preferred hetero atoms independently of each other are selected from the group consisting of N, O and S. The heteroaryl radical can preferably be selected from the group consisting of pyrrolyl, indolyl, furyl (furanyl), benzofuranyl, thienyl (thiophenyl), benzimidazolyl, benzothienyl, benzothiadiazolyl, benzothiazolyl, benzotriazolyl, benzodioxolanyl, benzodioxanyl, benzooxazolyl, benzooxadiazolyl, imidazothiazolyl, dibenzofuranyl, dibenzothienyl, phtalazinyl, pyrazolyl, imidazolyl, thiazolyl, oxazolyl, oxadiazolyl, triazinyl, triazole, tetrazole, isoxazolyl, thiadiazolyl, pyridinyl (pyridyl), pyridazinyl, pyrimidinyl, pyrazinyl, pyranyl, indazolyl, purinyl, indolizinyl, quinolinyl, isoquinolinyl, quinazolinyl, quinoxalinyl, carbazolyl, phenazinyl, phenothiazinyl and oxadiazolyl, in particular from the group consisting of thienyl (thiophenyl), pyridinyl (pyridyl), pyrimidinyl, thiazolyl, triazolyl, imidazolyl, oxazolyl, oxadiazolyl, quinazolinyl, quinolinyl and isoquinolinyl, wherein bonding to the general structure (I) can be via any desired and possible ring member of the heteroaryl group. The heteroaryl group can particularly preferably be selected from the group consisting of thienyl, imidazoyl, thiazolyl, triazolyl, pyridinyl and pyrimidinyl.

In the context of the present invention, the expression "$C_{1-3}$-alkylene group", "$C_{1-6}$-alkylene group" or "$C_{2-6}$-alkylene group" includes acyclic saturated hydrocarbon radicals having 1, 2 or 3 C atoms, 1, 2, 3, 4, 5 or 6 C atoms or, respectively, 2, 3, 4, 5 or 6 C atoms, which can be branched- or straight-chain (unbranched) and unsubstituted or substituted one or more times, for example 2, 3, 4 or 5 times, by identical or different substituents and which link a corresponding radical to the main structure. The alkylene groups can preferably be selected from the group consisting of $—CH_2—$, $—CH_2—CH_2—$, $—CH(CH_3)—$, $—CH_2—CH_2—CH_2—$, $—CH(CH_3)—CH_2—$, $—CH(CH_2CH_3)—$, $—CH_2—(CH_2)_2—CH_2—$, $—CH(CH_3)—CH_2—CH_2—$, $—CH_2—CH(CH_3)—CH_2—$, $—CH(CH_3)—CH(CH_3)—$, $—CH(CH_2CH_3)—CH_2—$, $—C(CH_3)_2—CH_2—$, $—CH(CH_2CH_2CH_3)—$, $—C(CH_3)(CH_2CH_3)—$, $—CH_2—(CH_2)_3—CH_2—$, $—CH(CH_3)—CH_2—CH_2—CH_2—$, $—CH_2—CH(CH_3)—CH_2—CH_2—$, $—CH(CH_3)—CH_2—CH(CH_3)—$, $—CH(CH_3)—CH(CH_3)—CH_2—$, $—C(CH_3)_2—CH_2—CH_2—$, $—CH_2—C(CH_3)_2—CH_2—$, $—CH(CH_2CH_3)—CH_2—CH_2—$, $—CH_2—CH(CH_2CH_3)—CH_2—$, $—C(CH_3)_2—CH(CH_3)—$, $—CH(CH_2CH_3)—CH(CH_3)—$, $—C(CH_3)(CH_2CH_3)—CH_2—$, $—CH(CH_2CH_2CH_3)—CH_2—$, $—C(CH_2CH_2CH_3)—CH_2—$, $—CH(CH_2CH_2CH_2CH_3)—$, $—C(CH_3)(CH_2CH_2CH_3)—$, $—C(CH_2CH_3)_2—$ and $—CH_2—(CH_2)_4—CH_2—$. The alkylene groups can particularly preferably be selected from the group consisting of $—CH_2—$, $—CH_2—CH_2—$ and $—CH_2—CH_2—CH_2—$.

In the context of the present invention, the expression "$C_{2-6}$-alkenylene group" includes acyclic hydrocarbon radicals having 2, 3, 4, 5 or 6 C atoms, which are unsaturated one or more times, for example 2, 3 or 4 times, and can be branched- or straight-chain (unbranched) and unsubstituted or substituted one or more times, for example 2, 3, 4 or 5 times, by identical or different substituents and which link a corresponding radical to the main structure. In this context, the alkenylene groups contain at least one C═C double bond. The alkenylene groups can preferably be selected from the group consisting of $—CH{=}CH—$, $—CH{=}CH—CH_2—$, $—C(CH_3){=}CH_2—$, $—CH{=}CH—CH_2—CH_2—$, $—CH_2—CH{=}CH—CH_2—$, $—CH{=}CH—CH{=}CH—$, $—C(CH_3){=}CH—CH_2—$, $—CH{=}C(CH_3)—CH_2—$, $—C(CH_3){=}C(CH_3)—$, $—C(CH_2CH_3){=}CH—$, $—CH{=}CH—CH_2—CH_2—CH_2—$, $—CH_2—CH{=}CH_2—CH_2—CH_2—$, $—CH{=}CH{=}CH—CH_2—CH_2—$ and $—CH{=}CH_2—CH—CH{=}CH_2—$.

In the context of the invention, the expression "$C_{2-6}$-alkynylene group" includes acyclic hydrocarbon radicals having 2, 3, 4, 5 or 6 C atoms which are unsaturated one or more times, for example 2, 3 or 4 times, and can be branched- or straight-chain (unbranched) and unsubstituted or substituted one or more times, for example 2, 3, 4 or 5 times, by identical or different substituents and which link a corresponding radical to the main structure. In this context, the alkynylene groups contain at least one C≡C triple bond. The alkynylene groups can preferably be selected from the group consisting of $—C{\equiv}C—$, $—C{\equiv}C—CH_2—$, $—C{\equiv}C—CH_2—CH_2—$, $—C{\equiv}C—CH(CH_3)—$, $—CH_2—C{\equiv}C—CH_2—$, $—C{\equiv}C—C{\equiv}C—$, $—C{\equiv}C—C(CH_3)_2—$, $—C{\equiv}C—CH_2—CH_2—CH_2—$, $—CH_2—C{\equiv}C—CH_2—CH_2—$, $—C{\equiv}C—C{\equiv}C—CH_2—$ and $—C{\equiv}C—CH_2—C{\equiv}C—$.

In the context of the present invention, the expression "aryl or heteroaryl bonded via a $C_{1-3}$-alkylene group, a $C_{1-6}$-alkylene group, "$C_{2-6}$-alkylene group", $C_{2-6}$-alkenylene group or $C_{2-6}$-alkynylene group" means that the $C_{1-3}$-alkylene groups, $C_{1-6}$-alkylene groups, $C_{2-6}$-alkylene groups, $C_{2-6}$-alkenylene groups, $C_{2-6}$-alkynylene groups and aryl or heteroaryl have the meanings defined above and the aryl or heteroaryl is bonded to the main structure via a $C_{1-3}$-alkylene group, $C_{1-6}$-alkylene group, $C_{2-6}$-alkylene group, $C_{2-6}$-alkenylene group or $C_{2-6}$-alkynylene group. There may be mentioned by way of example benzyl, phenethyl and phenylpropyl.

In the context of the present invention, the expression "$C_{3-8}$-cycloalkyl and heterocyclyl bonded via a $C_{1-3}$-alkylene group, $C_{1-6}$-alkylene group, $C_{2-6}$-alkylene group, $C_{2-6}$-alkenylene group or $C_{2-6}$-alkynylene group" means that the $C_{1-3}$-alkylene group, $C_{1-6}$-alkylene group, $C_{2-6}$-alkylene group, $C_{2-6}$-alkenylene group, $C_{2-6}$-alkynylene group, $C_{3-8}$-cycloalkyl and heterocyclyl have the meanings defined above and $C_{3-8}$-cycloalkyl and heterocyclyl is bonded to the main structure via a $C_{1-3}$-alkylene group, $C_{1-6}$-alkylene group, $C_{2-6}$-alkylene group, $C_{2-6}$-alkenylene group or $C_{2-6}$-alkynylene group.

In connection with "alkyl", "alkylene", alkenylene", "alkynylene", "cycloalkyl" and "heterocyclyl", in the context of this invention the term "substituted" is understood as meaning replacement of a hydrogen radical by F, Cl, Br, I, $CF_3$, $OCF_3$, CN, $NH_2$, NH—$C_{1-6}$-alkyl, NH—$C_{1-6}$-alkylene-OH, $C_{1-6}$-alkyl, N($C_{1-6}$-alkyl)$_2$, N($C_{1-6}$-alkylene-OH)$_2$, $NO_2$, SH, $C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, $CO_2H$, $CO_2$—$C_{1-6}$-alkyl, phenyl, phenoxy, benzyl, naphthyl, furyl, thienyl and pyridinyl, wherein radicals substituted several times are to be understood as meaning those radicals which are substituted several times, for example two or three times, either on different or on the same atoms, for example three times on the same C atom, as in the case of $CF_3$ or $CH_2CF_3$, or at different places, as in the case of CH(Cl)—CH=CH—$CHCl_2$. Substitution several times can be by identical or different substituents, such as, for example, in the case of CH(OH)—CH=CH—$CHCl_2$. In particular, this is to be understood as meaning replacement of one or more hydrogen radicals by F, Cl, $NH_2$, OH, phenyl, O—$CF_3$ or O—$C_{1-6}$-alkyl, in particular methoxy.

With respect to "aryl" and "heteroaryl", in the context of this invention "substituted" is understood as meaning replacement one or more times, for example 2, 3, 4 or 5 times, of one or more hydrogen atoms of the corresponding ring system by F, Cl, Br, I, CN, $NH_2$, $NR^AR^B$, C(=O)—$NR^AR^B$, NH—$C_{1-6}$-alkyl, NH—$C_{1-6}$-alkylene-OH, N($C_{1-6}$-alkyl)$_2$, N($C_{1-6}$-alkylene-OH)$_2$, NH-aryl$^1$, N(aryl$^1$)$_2$, N($C_{1-6}$-alkyl) aryl$^1$, pyrrolinyl, piperazinyl, morpholinyl, azetidinyl, piperidinyl, thiazolinyl, azepanyl, diazepanyl, ($C_{1-3}$-alkylene)-azetidinyl, ($C_{1-3}$-alkylene)-pyrrolinyl, ($C_{1-3}$-alkylene)-piperidinyl, ($C_{1-3}$-alkylene)-morpholinyl, ($C_{1-3}$-alkylene)-piperazinyl, ($C_{1-3}$-alkylene)-thiazolinyl, ($C_{1-3}$-alkylene)-azepanyl, ($C_{1-3}$-alkylene)-diazepanyl, $NO_2$, SH, S—$C_{1-6}$-alkyl, OH, O—$C_{1-6}$-alkyl, O—$C_{1-6}$-alkyl-OH, C(=O)$C_{1-6}$-alkyl, $NHSO_2C_{1-6}$-alkyl, $NHCOC_{1-6}$-alkyl, $CO_2H$, $CH_2SO_2$-phenyl, $CO_2$—$C_{1-6}$-alkyl, $OCF_3$, $CF_3$, —O—$CH_2$—O—, —O—$CH_2$—$CH_2$—O—, —O—C($CH_3$)$_2$—$CH_2$—, unsubstituted $C_{3-6}$-cycloalkyl, O—$C_{3-6}$-cycloalkyl, pyrrolidinyl, imidazolyl, benzyloxy, phenoxy, phenyl, naphthyl, pyridinyl, pyrimidinyl, —$C_{1-3}$-alkylene-aryl$^1$, benzyl, thienyl, furyl or $OCF_3$, OH, O—$C_{1-6}$-alkyl, SH, S—$C_{1-6}$-alkyl, $C_{3-6}$-cycloalkyl, O—$C_{3-6}$-cycloalkyl, $NR^AR^B$, C(=O)—$NR^AR^B$, phenyl, pyridyl or pyrimidyl bonded via a $C_{1-6}$-alkylene group, wherein aryl$^1$ represents phenyl, thiazolyl, thienyl or pyridinyl, on one or various atoms, wherein the abovementioned substituents—unless stated otherwise—can optionally be substituted in their turn by the substituents mentioned. Substitution of aryl and heteroaryl several times can be by identical or different substituents. Preferred substituents for aryl and heteroaryl can be selected from the group consisting of —O—$C_{1-3}$-alkyl, unsubstituted $C_{1-6}$-alkyl, F, Cl, Br, I, CN, $CF_3$, $OCF_3$, OH, SH, —$CH_2$-azetidinyl, —$CH_2$-pyrrolidinyl, —$CH_2$-piperidinyl, —$CH_2$-piperazinyl, —$CH_2$-morpholinyl, phenyl, naphthyl, thiazolyl, thienyl and pyridinyl, in particular from the group consisting of F, Cl, CN, $CF_3$, $CH_3$; $OCH_3$, $OCF_3$, and —$CH_2$-azetidinyl.

In the chemical structural formulae used here to describe the compounds according to the invention, the symbol

is also used to describe one or more substitution patterns, this group not being bonded to a particular atom within the chemical structural formula, in contrast to the representation of a bond to a particular atom (by way of example $R^a$ here represents a substituent R having a numbering represented by the variable "a"). For example—if the symbol is used in connection with a ring, the particular substituent can be bonded to any possible ring atom.

In the context of the present invention, the symbol

used in formulae designates a linking of a corresponding radical to the particular main structure.

Persons skilled in the art understand that identical radicals which are used for definition of different substituents are in each case independent of each other, such as, for example, in the groupings $NR^{16}R^{17}$, $C_{1-6}$-alkylene-$NR^{16}R^{17}$, O—$C_{1-6}$-alkylene-$NR^{16}R^{17}$ and C(=O)—$NR^{16}R^{17}$.

Persons skilled in the art furthermore understand that if $R^{3a}$, $R^{3b}$, $R^{3c}$ and $R^{3d}$ occur several times, i.e. in the case where q and/or s represent 2 or 3, the radicals at each occurrence may be independently selected from the list of stated meanings.

In the context of this invention, the term "physiologically acceptable salt" is understood as meaning preferably salts of the compounds according to the invention with inorganic or organic acids, which are physiologically acceptable—in particular when used on humans and/or mammals. Examples of suitable acids are hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, 1,1-dioxo-1,2-dihydro-1$\lambda^6$-benzo[d]isothiazol-3-one (saccharic acid), monomethylsebacic acid, 5-oxo-proline, hexane-1-sulfonic acid, nicotinic acid, 2-, 3- or 4-aminobenzoic acid, 2,4,6-trimethyl-benzoic acid, $\alpha$-liponic acid, acetylglycine, hippuric acid, phosphoric acid and/or aspartic acid. The salts of hydrochloric acid (hydrochlorides) and of citric acid (citrates) are particularly preferred. This term is furthermore also understood as meaning those compounds which are obtained by quaternization of a nitrogen atom present in the structure (e.g. pyridyl, N-methylpiperidinyl). Such compounds can be obtained, for example, by alkylation with generation of the corresponding cation, with counter-ions such as, for example, $Cl^-$ and $F^-$.

In the context of the present invention the term "isolated" when used with reference to a stereoisomer, means substantially separated from the opposite stereoisomer, but not necessarily from other substances.

In a preferred embodiment of the present invention L represents C(=O) to yield formula (I) as given below (I)

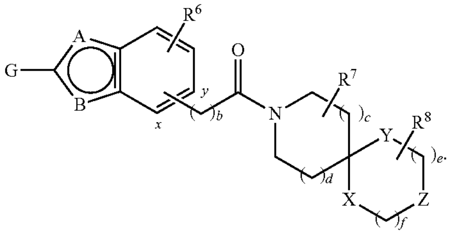

In preferred embodiments of the compounds according to the invention, b represents 0.

In embodiments of the compounds according to the invention which are furthermore preferred, the structural part (Ac)

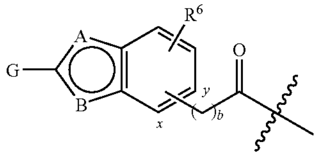

can represent a structural part which is selected from the group consisting of (Ac 1)

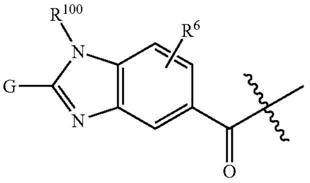

(Ac 2)

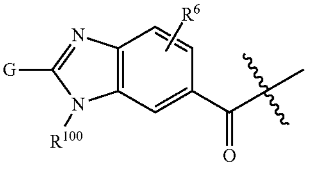

(Ac 3)

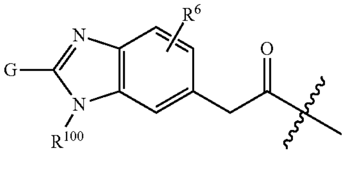

-continued (Ac 4)

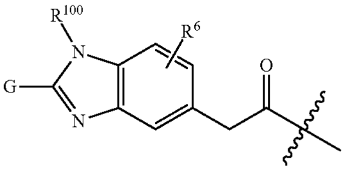

(Ac 5)

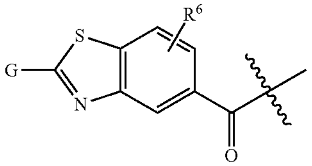

(Ac 6)

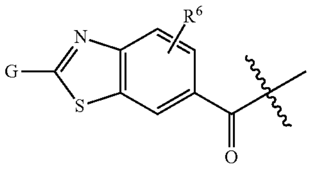

(Ac 7)

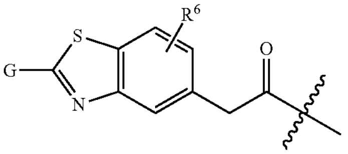

(Ac 8)

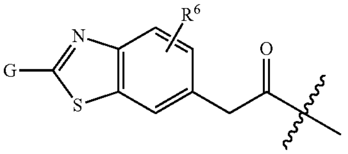

(Ac 9)

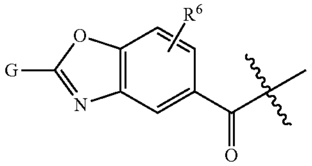

(Ac 10)

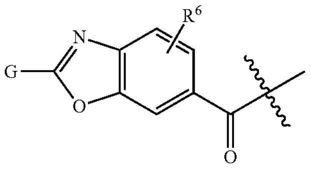

(Ac 11)

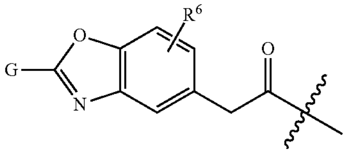

(Ac 12)

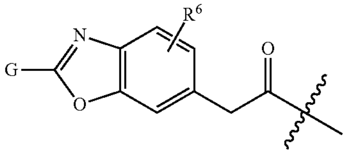

-continued
(Ac 13)
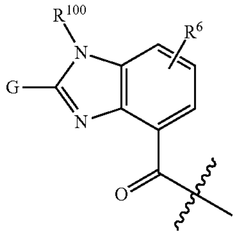
(Ac 14)
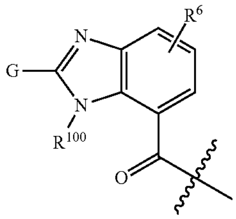
(Ac 15)
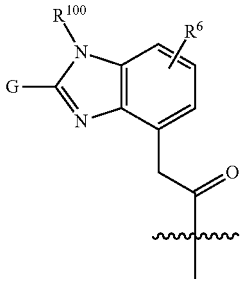
(Ac 16)
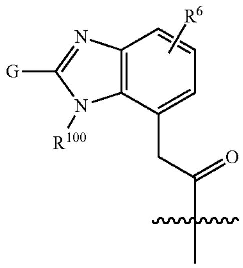
(Ac 17)
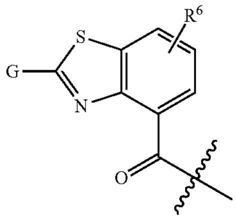
(Ac 18)
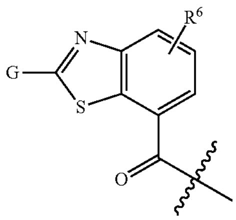
-continued
(Ac 19)
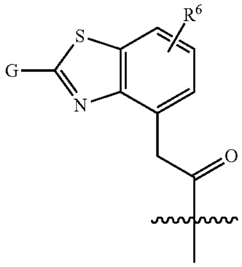
(Ac 20)
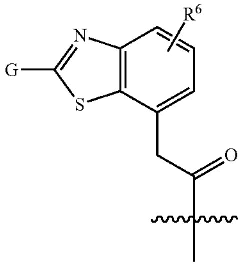
(Ac 21)
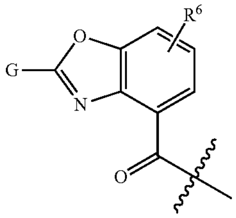
(Ac 22)
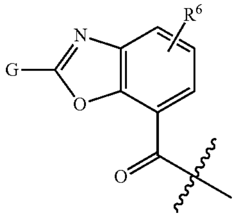
(Ac 23)
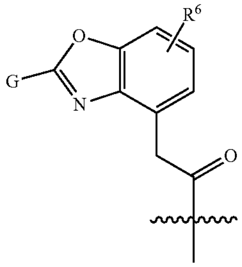
(Ac 24)
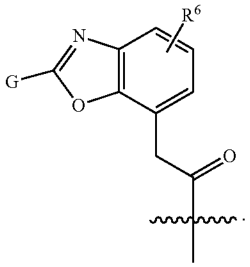

In other embodiments of the compounds according to the invention which are furthermore preferred, the structural part (Acc)
(Acc)
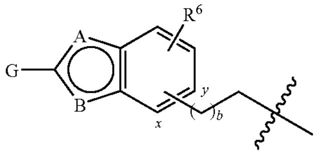
can represent a structural part which is selected from the group consisting of
(Acc 1)
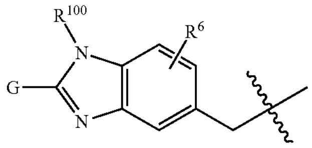
(Acc 2)
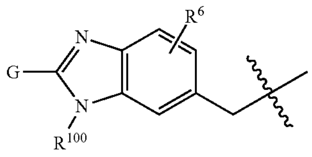
(Acc 3)
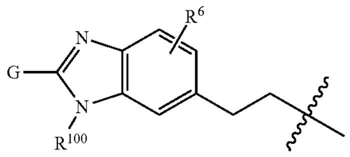
(Acc 4)
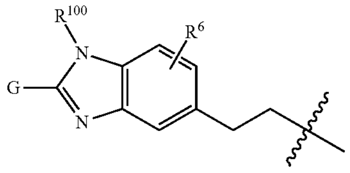
(Acc 5)
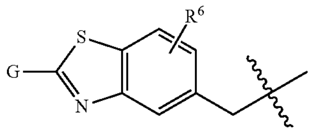
(Acc 6)
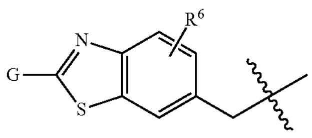
(Acc 7)
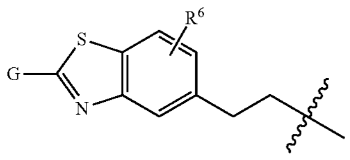
-continued
(Acc 8)
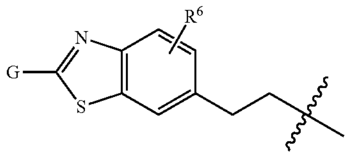
(Acc 9)
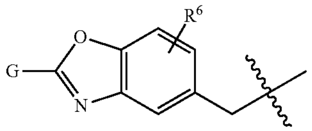
(Acc 10)
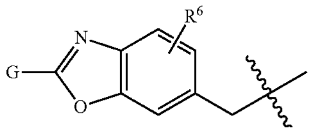
(Acc 11)
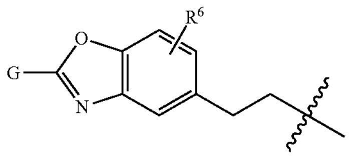
(Acc 12)
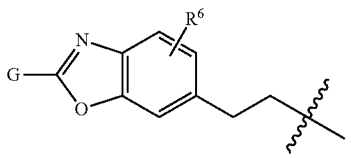
(Acc 13)
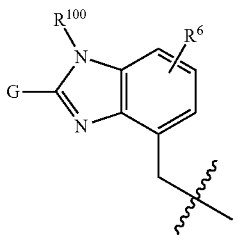
(Acc 14)
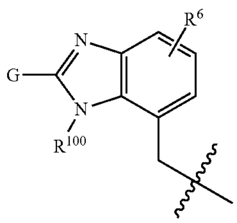
(Acc 15)
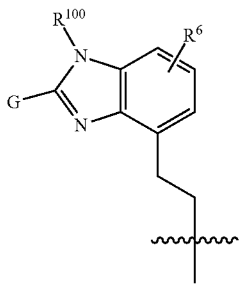

-continued
(Acc 16)
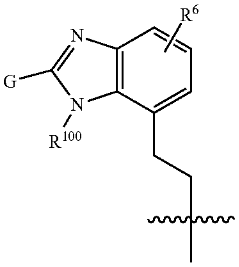
(Acc 17)
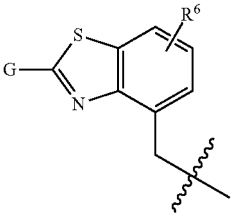
(Acc 18)
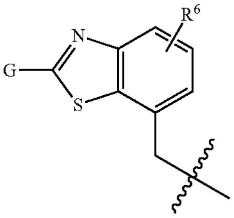
(Acc 19)
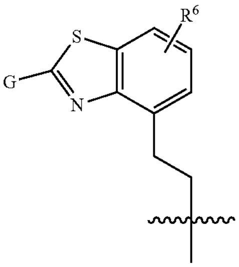
(Acc 20)
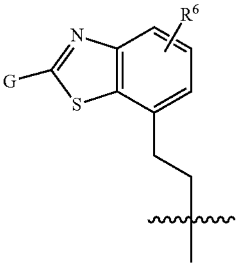
(Acc 21)
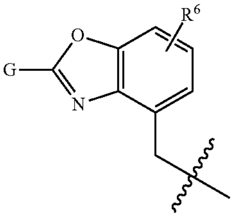
-continued
(Acc 22)
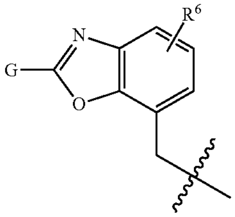
(Acc 23)
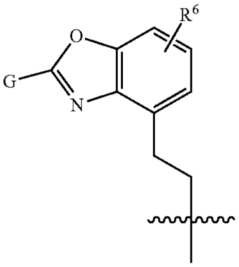
(Acc 24)
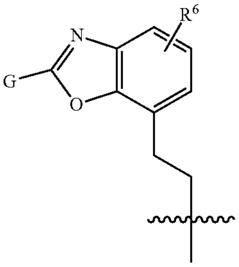
In embodiments of the compounds according to the invention which are furthermore preferred, the structural part G1 is selected from the group consisting of
G1-1
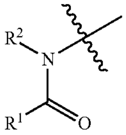
G1-2
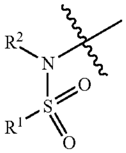
G1-3
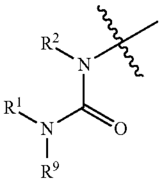
G1-4
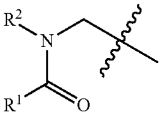

-continued
G1-5
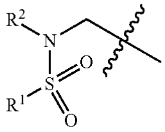
G1-6
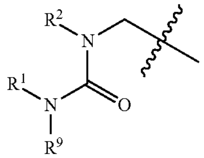
G1-7
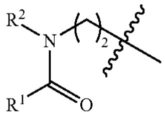
G1-8
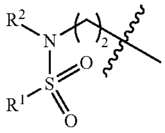
G1-9
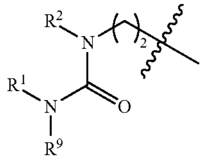
G1-10
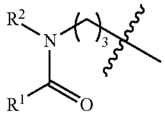
G1-11
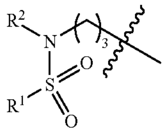
G1-12
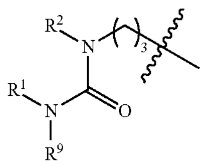
G1-13
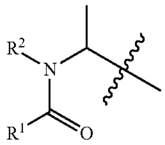
G1-14
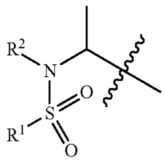
-continued
G1-15
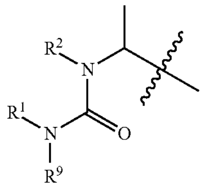
G1-16
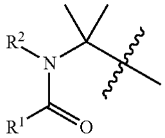
G1-17
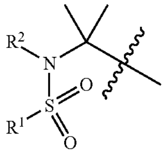
G1-18
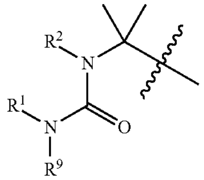
G1-19
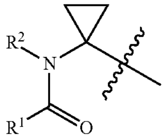
G1-20
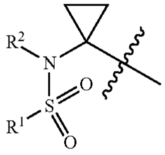
G1-21
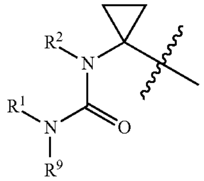
G1-22
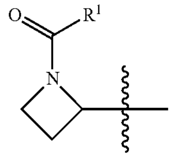
G1-23
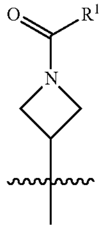

-continued
G1-24
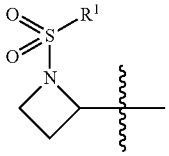
G1-25
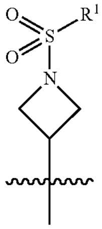
G1-26
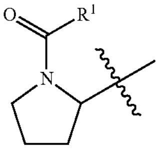
G1-27
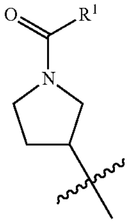
G1-28
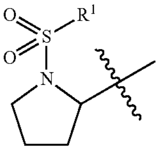
G1-29
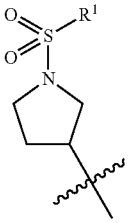
G1-30
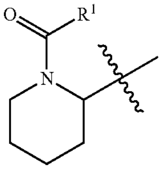
G1-31
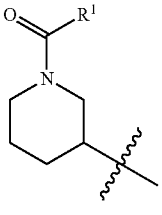
-continued
G1-32
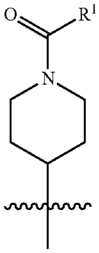
G1-33
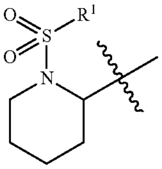
G1-34
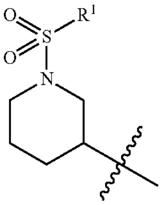
G1-35
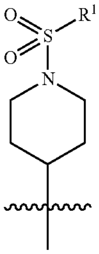
G1-36
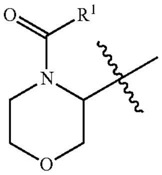
G1-37
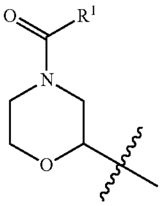
G1-38
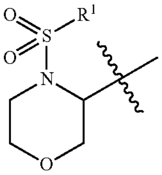

-continued

G1-39

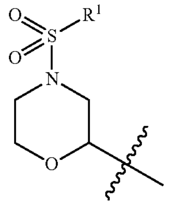

G1-40

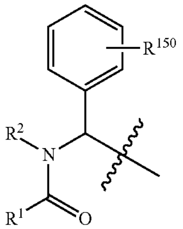

G1-41

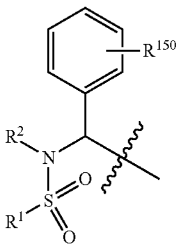

G1-42

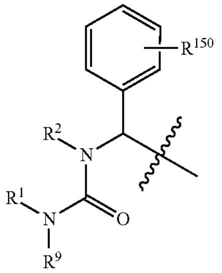

wherein $R^{150}$ represents 0, 1, 2, 3, 4 or 5 substituents, which independently of each other are selected from the group consisting of F, Cl, Br, I, $CF_3$, O—$CF_3$, $C_{1-4}$-alkyl and O—$C_{1-4}$-alkyl.

In embodiments of the compounds according to the invention which are furthermore preferred, $R^{100}$ represents H or $C_{1-6}$-alkyl, in particular H or methyl.

In embodiments which are likewise preferred, the structural part

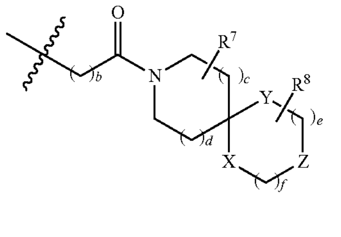

in the compounds of formula I is bonded to the base structure in position x.

$R^1$ in the compounds according to the invention preferably represents $C_{1-6}$-alkyl, —CH(phenyl)$_2$, $C_{3-8}$-cycloalkyl, phenyl, naphthyl, chromanyl, indolyl, benzofuranyl, benzothiophenyl (benzothienyl), benzooxazolyl, benzooxadiazolyl, pyrrolyl, furanyl, thienyl, pyridinyl, pyridazinyl, pyrimidinyl, pyrazinyl, imidazothiazolyl, carbazolyl, dibenzofuranyl, dibenzothiophenyl (dibenzothienyl) or a phenyl or naphthyl bonded via a $C_{1-3}$-alkylene group, a $C_{2-3}$-alkenylene group or a $C_{2-3}$-alkynylene group, particularly preferably $C_{1-4}$-alkyl, —CH(phenyl)$_2$, $C_{3-6}$-cycloalkyl, phenyl, naphthyl, chromanyl, benzothiophenyl (benzothienyl), benzooxadiazolyl, thienyl, pyridinyl, imidazothiazolyl, dibenzofuranyl or a phenyl bonded via a $C_{1-3}$-alkylene group or a $C_{2-3}$-alkenylene group, very particularly preferably $C_{1-4}$-alkyl, —CH(phenyl)$_2$, $C_{3-6}$-cycloalkyl, phenyl, naphthyl, chromanyl, benzothiophenyl (benzothienyl), pyridinyl, thienyl or a phenyl bonded via a $C_{1\ or\ 2}$-alkylene group or —CH═CH— group, wherein the abovementioned aryl or heteroaryl radicals are in each case unsubstituted or substituted one or more times by identical or different substituents, wherein the substituents independently of each other in particular are selected from the group consisting of —O—$C_{1-3}$-alkyl, F, Cl, Br, I, $CF_3$, $OCF_3$, OH, SH, phenyl, phenoxy, naphthyl, furyl, thienyl and pyridinyl and wherein the abovementioned alkyl, alkylene, alkenylene and alkynylene groups are in each case unsubstituted or substituted one or more times by identical or different substituents, wherein the substituents independently of each other in particular are selected from the group consisting of —O—$C_{1-3}$-alkyl, F, Cl, Br, I, $CF_3$, $OCF_3$, OH, SH, phenyl, phenoxy, naphthyl, furyl, thienyl and pyridinyl.

$R^1$ can represent in particular —CH(phenyl)$_2$, phenyl, naphthyl, pyridinyl or thienyl or a phenyl bonded via a $C_{1\ or\ 2}$-alkylene group or —CH═CH— group, wherein the phenyl, naphthyl, pyridinyl and thienyl is in each case unsubstituted or substituted one or more times, for example 2, 3, 4 or 5 times, by identical or different substituents selected from the group of methyl, methoxy, $CF_3$, $OCF_3$, F and Cl.

In embodiments of the compounds according to the invention which are likewise preferred, $R^1$ can be selected from the group consisting of pyridin-2-yl, pyridin-3-yl, pyridin-4-yl, 3-chloro-thien-2-yl, 5-chloro-thien-2-yl, 4-methoxy-2,3,6-trimethylphenyl, 4-methoxy-2,6-dimethylphenyl, 4-methoxy-2,3,5-trimethylphenyl, 2,4,6-trimethylphenyl, 2-chloro-6-methylphenyl, 2,4,6-trichlorophenyl, 1,3-dichloro-5-trifluoromethylphenyl, 2-chloro-6-(trifluoromethyl)phenyl, 2,6-dichloro-4-methoxyphenyl, 2,6-dichloro-4-trifluoromethyl, 2-methylnaphthyl, 2-chloronaphthyl, 2-fluoronaphthyl, 2-chloro-4-(trifluoromethoxy)phenyl, 4-chloro-2,5-dimethylphenyl, 2-chloro-6-methylphenyl, 2,3-dichlorophenyl, 3,4-dichlorophenyl, 2,4-dichlorophenyl, 2,4,5-trichlorophenyl, 2,4,6-trichlorophenyl, 2-(trifluoromethyl)phenyl, 3-(trifluoromethyl)phenyl, 4-(trifluoromethyl)phenyl, 1-naphthyl and 2-naphthyl. In particular, $R^1$ can represent 4-methoxy-2,6-dimethylphenyl or 2-chlorophenyl.

$R^2$ in the compounds according to the invention represents H, methyl, ethyl, n-propyl, iso-propyl, n-butyl, iso-butyl, sec-butyl, tert-butyl, cyclopropyl, cyclobutyl, cyclopentyl or cyclohexyl, preferably H, methyl, ethyl or cyclopropyl. $R^2$ particularly preferably represents methyl.

In preferred embodiments of the compounds according to the invention, $R^6$ can represent 0 substituents, i.e. can be absent.

$R^9$ in the compounds according to the invention preferably represents H, methyl, ethyl, n-propyl, iso-propyl, n-butyl, iso-butyl, sec-butyl, tert-butyl, cyclopropyl, cyclobutyl, cyclopentyl, cyclohexyl, preferably H, methyl, ethyl or cyclopropyl. $R^9$ particularly preferably represents H.

Embodiments of the compounds according to the invention which are likewise preferred are those in which the structural part G2 is selected from the group consisting of
G2-1
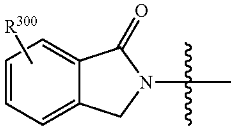
G2-2
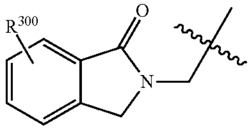
G2-3
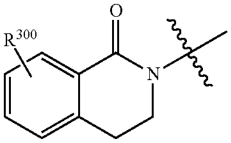
G2-4
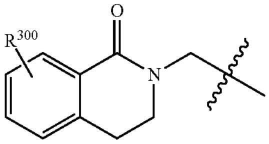
G2-5
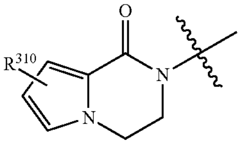
G2-6
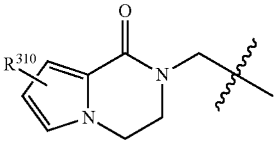
G2-7
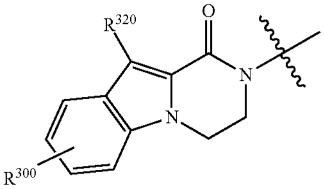
G2-8
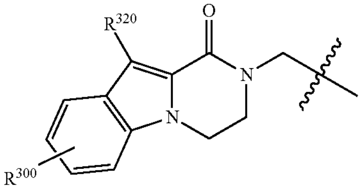
G2-9
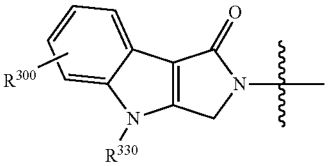
-continued
G2-10
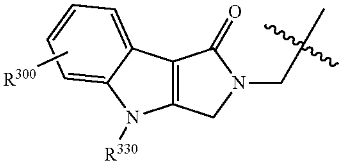
G2-11
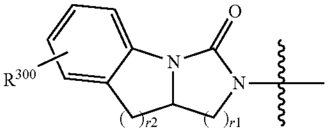
G2-12
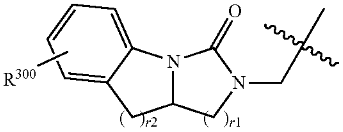
G2-13
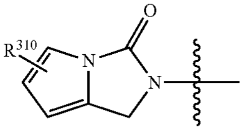
G2-14
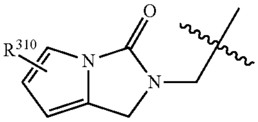
G2-15
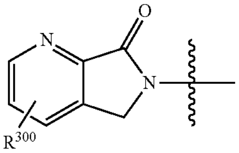
G2-16
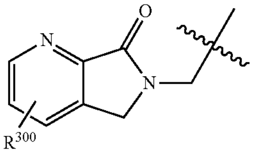
G2-17
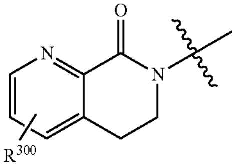
G2-18
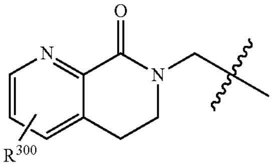
G2-19
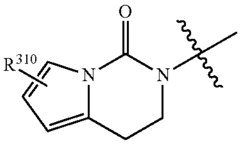

-continued

G2-20

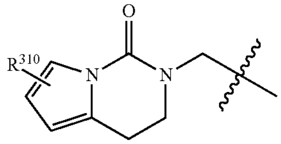

wherein $R^{300}$ represents 0, 1, 2, 3 or 4 substituents, which independently of each other are selected from the group consisting of F, Cl, Br, I, $CF_3$, O—$CF_3$, $C_{1-4}$-alkyl and O—$C_{1-4}$-alkyl;

$R^{310}$ represents 0, 1, 2 or 3 substituents, which independently of each other are selected from the group consisting of F, Cl, Br, I, $CF_3$, O—$CF_3$, $C_{1-4}$-alkyl and O—$C_{1-4}$-alkyl;

$R^{320}$ represents a substituent selected from the group consisting of H, F, Cl, Br, I, $CF_3$, O—$CF_3$ and $C_{1-4}$-alkyl;

$R^{330}$ represents a substituent selected from the group consisting of H, $C_{1-4}$-alkyl, aryl, $CH_2$-aryl and heteroaryl;

r1 represents 1 or 2 and r2 represents 1 or 2.

In embodiments of the compounds according to the invention which are likewise preferred, G2 represents a radical selected from the group consisting of G2-1a

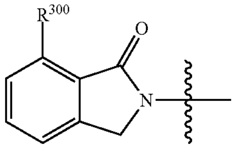

G2-5a

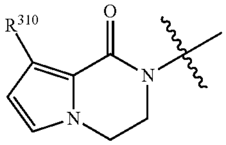

G2-7a

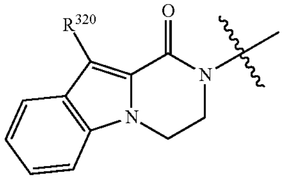

G2-9a

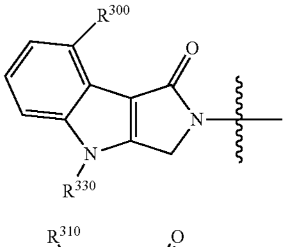

and

G2-13a

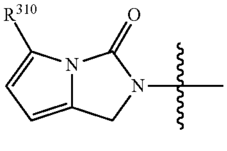

, wherein $R^{300}$ represents a substituent which is selected from the group consisting of H, F, Cl, Br, I, —$CF_3$, —O—$CF_3$, $C_{1-4}$-alkyl and O—$C_{1-4}$-alkyl;

$R^{310}$ represents a substituent which is selected from the group consisting of H, F, Cl, Br, I, —$CF_3$, —O—$CF_3$, $C_{1-4}$-alkyl and O—$C_{1-4}$-alkyl;

$R^{320}$ represents a substituent which is selected from the group consisting of H, F, Cl, Br, I, —$CF_3$, —O—$CF_3$ and $C_{3-8}$-alkyl and $R^{330}$ represents a substituent which is selected from the group consisting of H, $C_{1-4}$-alkyl, aryl, —$CH_2$-aryl and heteroaryl.

In embodiments of the compounds according to the invention which are furthermore preferred, G2 represents a radical selected from the group consisting of

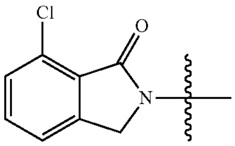

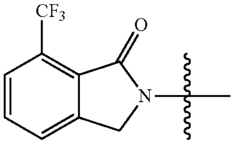

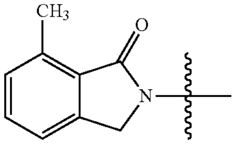

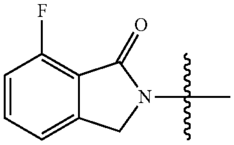

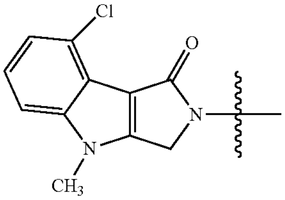

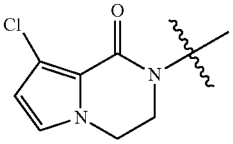

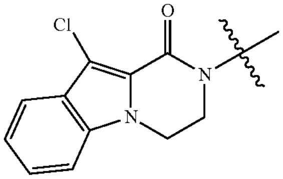

and

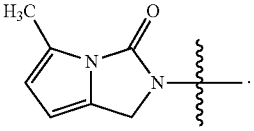

.

Embodiments of the substituted compounds according to the invention which are likewise preferred are those in which $R^{14a}$ represents H, aryl, heteroaryl, $C_{1-3}$-alkylene-aryl or $C_{1-3}$-alkylene-heteroaryl;

$R^{14b}$ represents aryl, heteroaryl, $C_{1-3}$-alkylene-aryl, $C_{1-3}$-alkylene-heteroaryl, $NR^{16}R^{17}$, $C_{1-3}$-alkylene-$NR^{16}R^{17}$, C(=O)—$NR^{16}R^{17}$, $OR^{35}$ or $C_{1-3}$-alkylene-$OR^{35}$;

$R^{16}$ and $R^{17}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or $R^{16}$ and $R^{17}$ together with the nitrogen atom joining them form a structure selected from the group consisting of

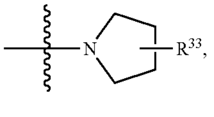

,

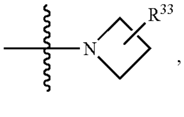

,

-continued

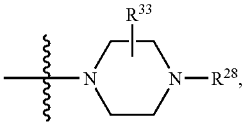

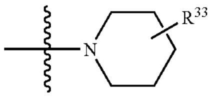

and

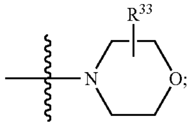

$R^{28}$ represents a substituent which is selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl;

$R^{33}$ represents 0, 1 or 2 substituents, each independently selected from the group consisting of F, Cl, $CF_3$, $OCF_3$, $C_{1-6}$-alkyl, O—$C_{1-3}$-alkyl and $NR^{34a}R^{34b}$;

$R^{34a}$ and $R^{34b}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or $R^{34a}$ and $R^{34b}$ together with the nitrogen atom joining them form a structure selected from the group consisting of:

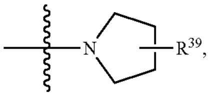

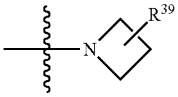

,

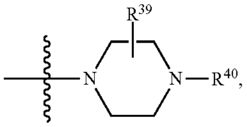

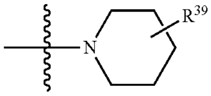

and

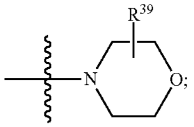

$R^{39}$ represents 0, 1 or 2 substituents, each independently selected from the group consisting of F, Cl, $CF_3$, $OCF_3$, $C_{1-6}$-alkyl and O—$C_{1-3}$-alkyl;

$R^{40}$ represents a substituent which is selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl;

$R^{35}$ represents H, $C_{1-6}$-alkyl, $C_{3-6}$-cycloalkyl, aryl, heteroaryl, $C_{1-3}$-alkylene-$C_{3-6}$-cycloalkyl, $C_{1-3}$-alkylene-aryl, $C_{1-3}$-alkylene-heteroaryl or the group

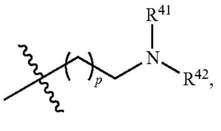

wherein p represents 1, 2 or 3, wherein $R^{41}$ and $R^{42}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or $R^{41}$ and $R^{42}$ together with the nitrogen atom joining them form a structure selected from the group consisting of

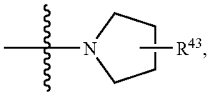

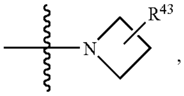

,

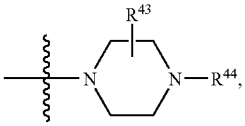

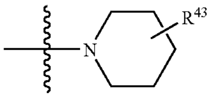

and

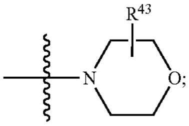

$R^{43}$ represents 0, 1 or 2 substituents, each independently selected from the group consisting of F, Cl, $CF_3$, $OCF_3$, $C_{1-6}$-alkyl, O—$C_{1-3}$-alkyl and $NR^{45a}R^{45b}$;

$R^{44}$ represents a substituent which is selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl;

$R^{45a}$ and $R^{45b}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or $R^{45a}$ and $R^{45b}$ together with the nitrogen atom joining them form a structure selected from the group consisting of:

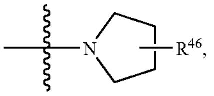

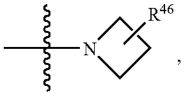

,

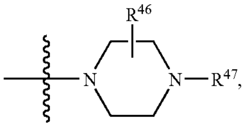

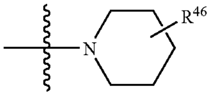

and

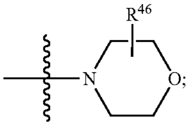

$R^{46}$ represents 0, 1 or 2 substituents, each independently selected from the group consisting of F, Cl, $CF_3$, $OCF_3$, $C_{1-6}$-alkyl and O—$C_{1-3}$-alkyl; and $R^{47}$ represents a substituent which is selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl.

Embodiments which are furthermore preferred are substituted compounds according to the invention wherein $R^{15}$ represents H, $C_{1-6}$-alkyl, —$CHR^{25}R^{26}$, $C_{1-3}$-alkylene-$CHR^{25}R^{26}$, aryl, heteroaryl, $C_{1-3}$-alkylene-aryl, $C_{1-3}$-alkylene-heteroaryl, —C(═O)—$R^{19}$, —S(═O)$_2$—$R^{19}$ or the group —C(═O)—N($R^{20}$)—$R^{19}$;

$R^{25}$ and $R^{26}$ each independently represent H, $C_{1-4}$-alkyl, $C_{3-6}$-cycloalkyl, aryl or heteroaryl, or $R^{25}$ and $R^{26}$ together with the CH grouping joining them form a structure selected from the group consisting of

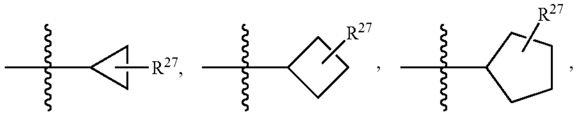

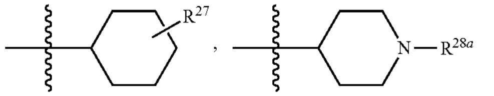

and

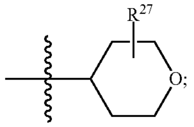

$R^{27}$ represents 0, 1 or 2 substituents, each independently selected from the group consisting of F, Cl, $CF_3$, $OCF_3$, $C_{1-6}$-alkyl, O—$C_{1-3}$-alkyl and $NR^{48a}R^{48b}$;

$R^{28a}$ represents a substituent which is selected from the group consisting of H, methyl, ethyl, n-propyl, iso-propyl, n-butyl, iso-butyl, sec-butyl, tert-butyl, aryl and heteroaryl;

$R^{48a}$ and $R^{48b}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or $R^{48a}$ and $R^{48b}$ together with the nitrogen atom joining them form a structure selected from the group consisting of:

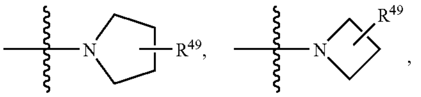

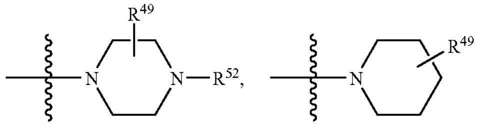

and

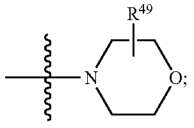

$R^{49}$ represents 0, 1 or 2 substituents, each independently selected from the group consisting of F, Cl, $CF_3$, $OCF_3$, $C_{1-6}$-alkyl and O—$C_{1-3}$-alkyl;

$R^{52}$ represents a substituent which is selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl;

$R^{19}$ represents $C_{1-6}$-alkyl, aryl, heteroaryl, —CH(aryl)$_2$, $C_{3-8}$-cycloalkyl, heterocyclyl or an aryl, heteroaryl, $C_{3-8}$-cycloalkyl or heterocyclyl bonded via a $C_{1-6}$-alkylene group, $C_{2-6}$-alkenylene group or $C_{2-6}$-alkynylene group; and $R^{20}$ represents H, methyl, ethyl, n-propyl, iso-propyl, n-butyl, iso-butyl, sec-butyl, tert-butyl, cyclopropyl, cyclobutyl, cyclopentyl or cyclohexyl.

Further preferred embodiments of the compounds according to the invention are those compounds in which the following structural part SP (SP)

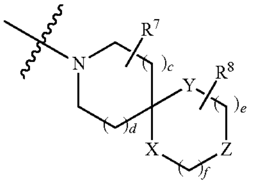

is selected from the group consisting of

SP 1

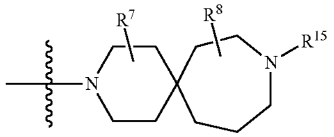

SP 2

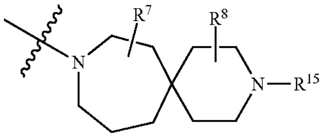

SP 3

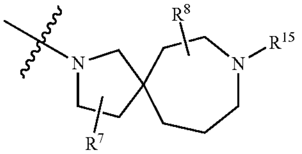

SP 4

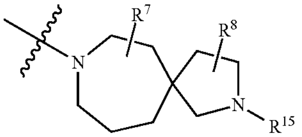

SP 5

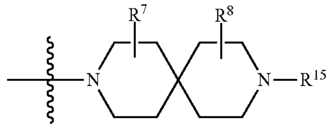

SP 6

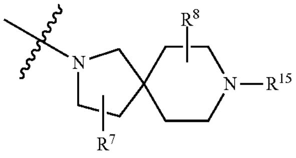

SP 7

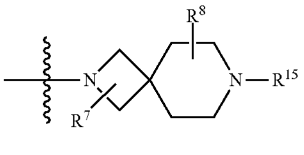

SP 8

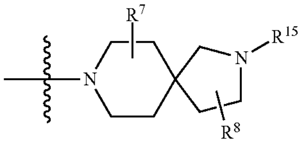

-continued
SP 9
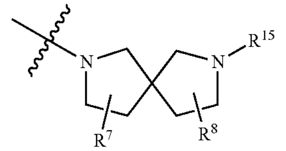
SP 10
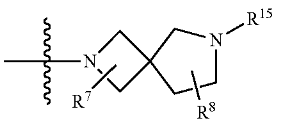
SP 11
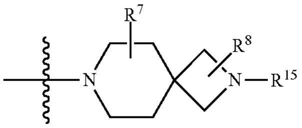
SP 12
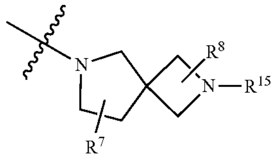
SP 13
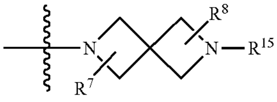
SP 14
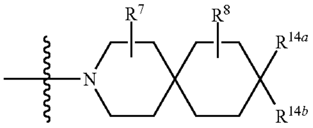
SP 15
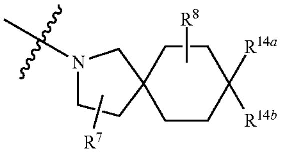
SP 16
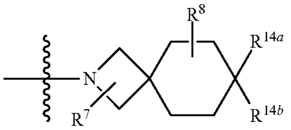
SP 17
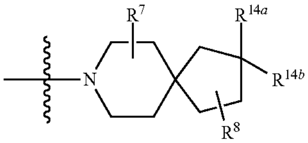
SP 18
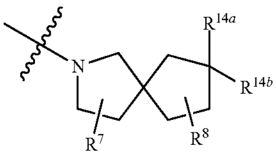
-continued
SP 19
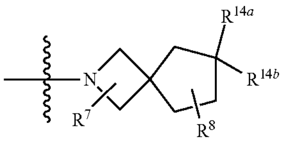
SP 20
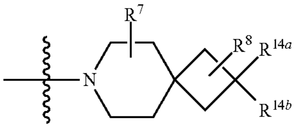
SP 21
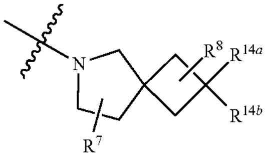
SP 22
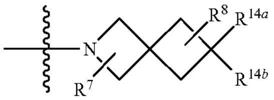
SP 23
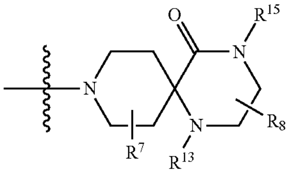
SP 24
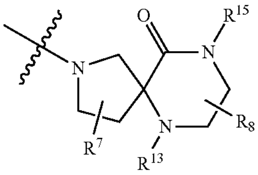
SP 25
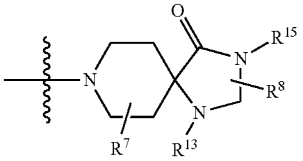
SP 26
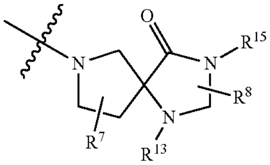
SP 27
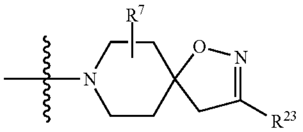
SP 28
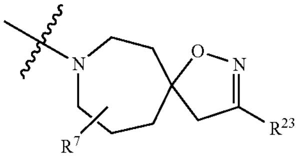

-continued

SP 29

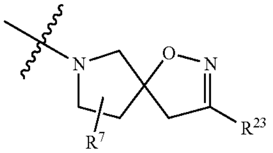

SP 30

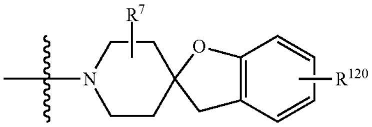

SP 31

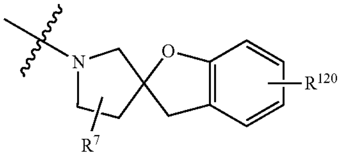

SP 32

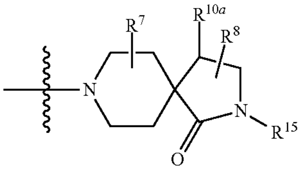

SP 33

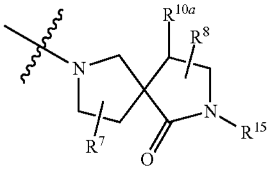

SP 34

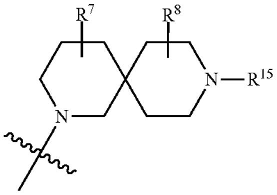

SP 35

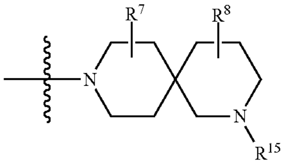

SP 36

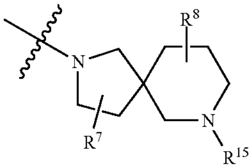

SP 37

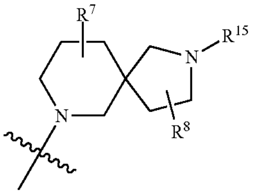

-continued

SP 38

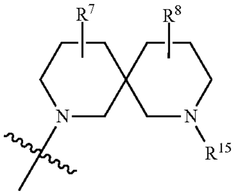

wherein $R^8$, $R^{10a}$, $R^{13}$, $R^{14a}$, $R^{14b}$, $R^{15}$ and $R^{23}$ have the abovementioned meanings and $R^{120}$ represents 0, 1, 2, 3 or 4 substituents each independently selected from the group consisting of F, Cl, $OCF_3$, $CF_3$, CN, methyl and methoxy.

Further preferred embodiments of the compounds according to the invention are those compounds in which the abovementioned structural part SP is selected from the group consisting of

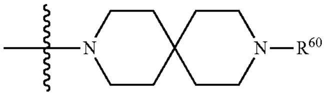

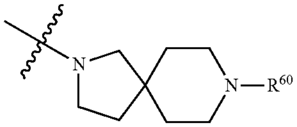

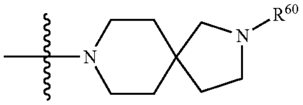

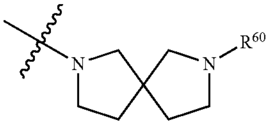

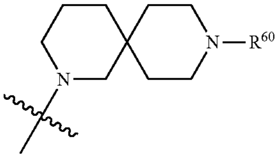

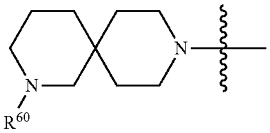

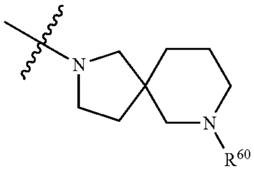

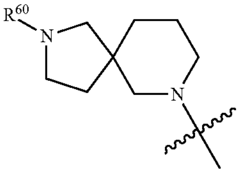

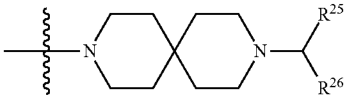

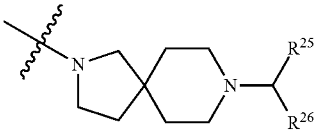

-continued
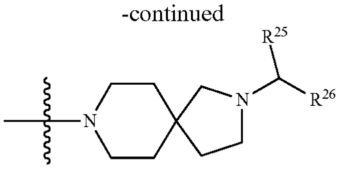
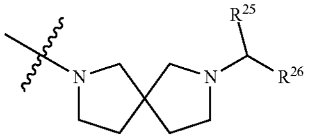
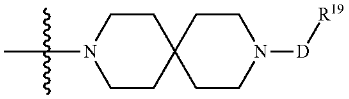
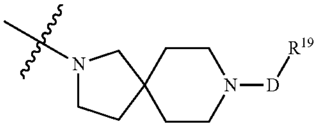
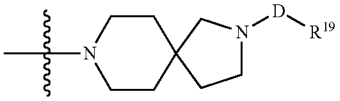
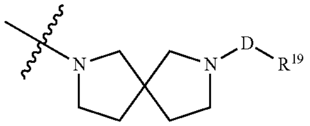
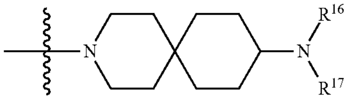
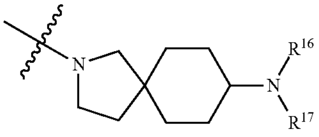
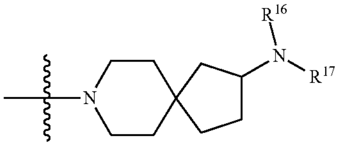
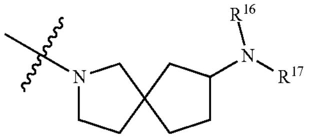
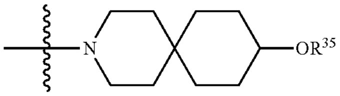
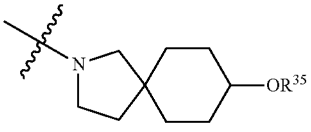
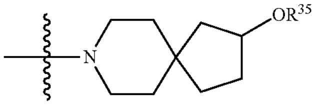
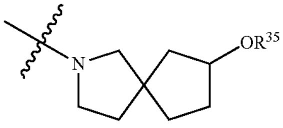
-continued
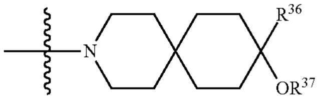
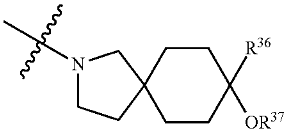
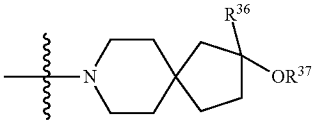
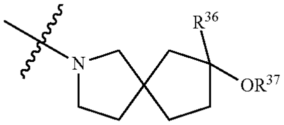
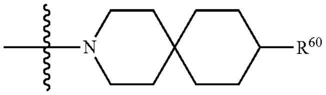
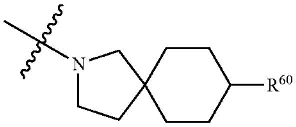
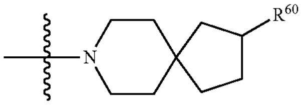
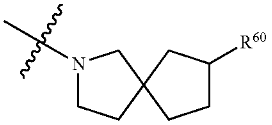
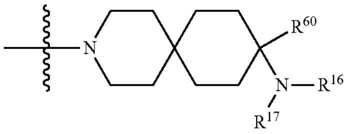
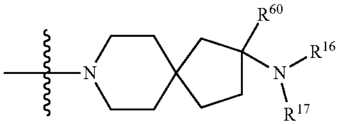
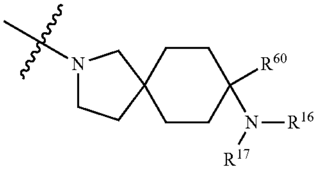
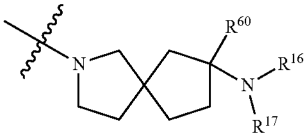
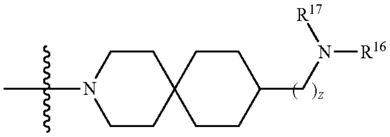

-continued
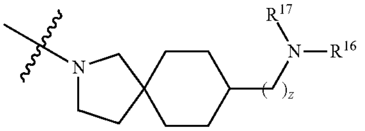
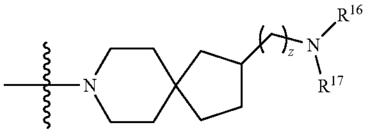
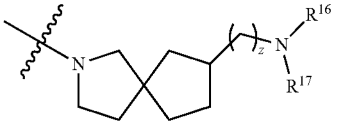
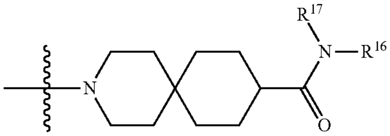
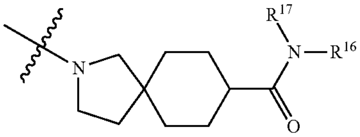
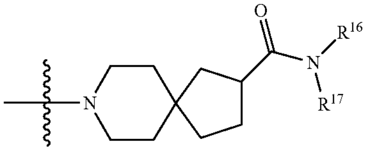
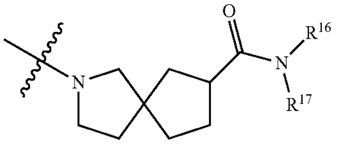
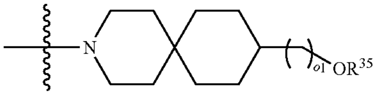
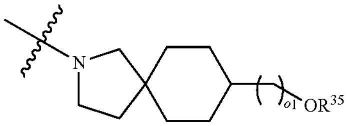
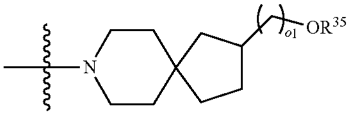
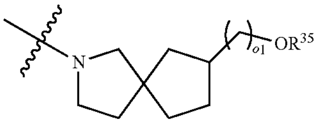
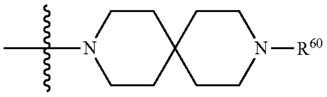
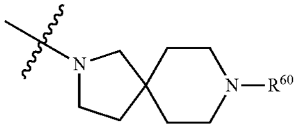
-continued
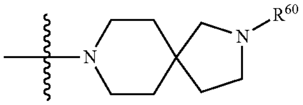
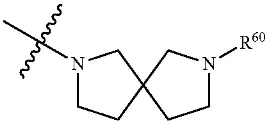
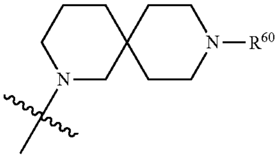
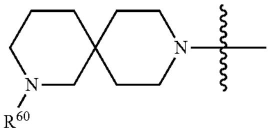
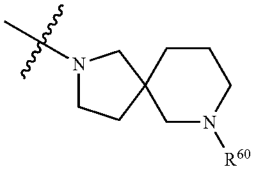
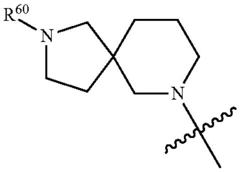
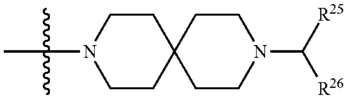
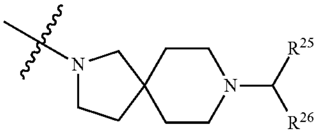
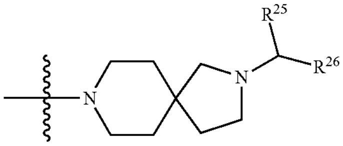
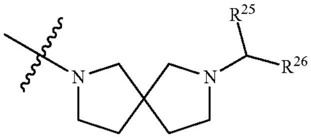
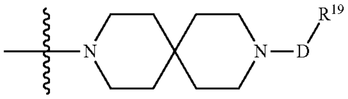
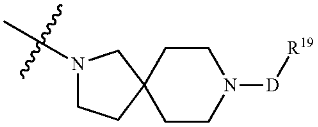
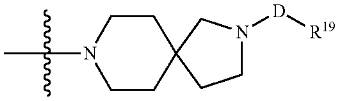
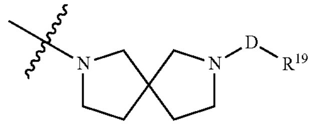
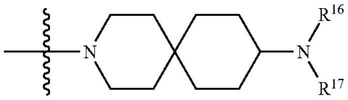

-continued
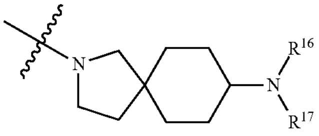
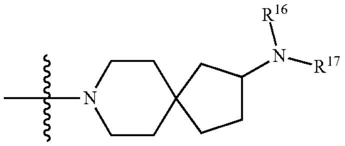
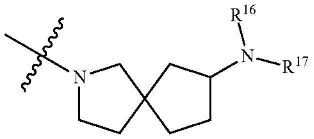
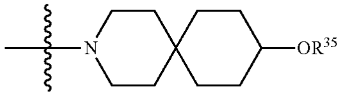
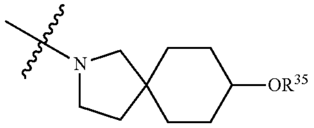
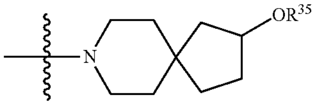
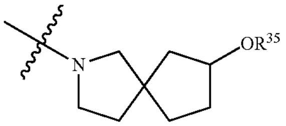
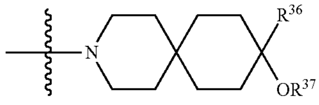
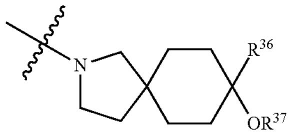
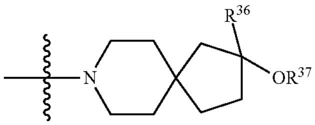
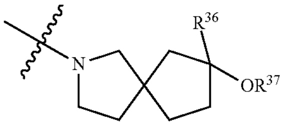
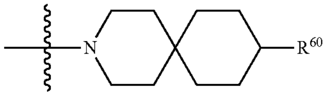
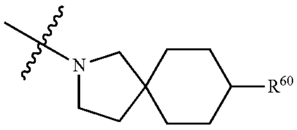
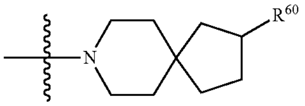
-continued
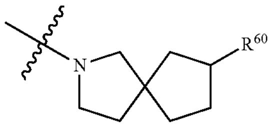
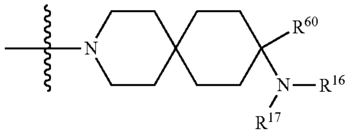
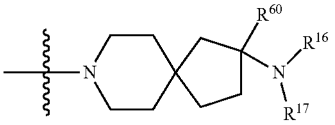
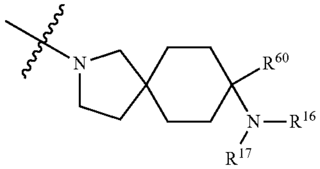
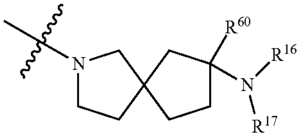
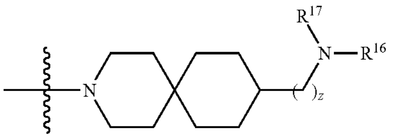
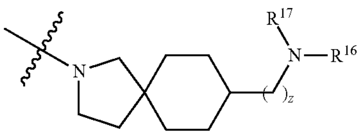
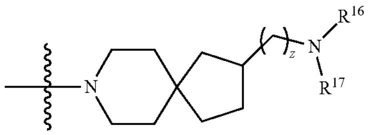
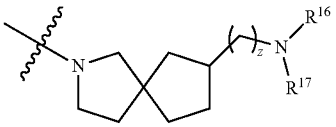
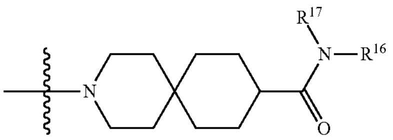
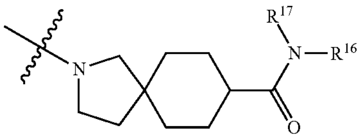
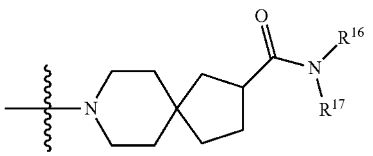

-continued

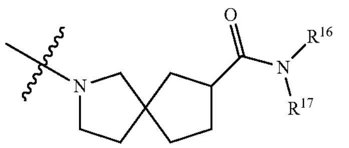

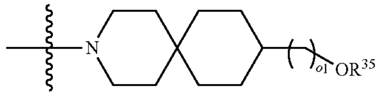

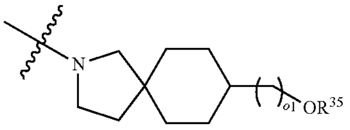

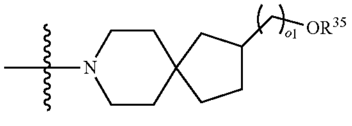

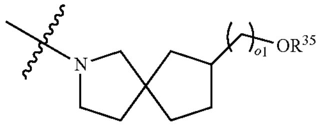

wherein z represents 1, 2 or 3;

o1 represents 1;

$R^{60}$ in each case represents (het)aryl or $C_{1-3}$-alkylene-(het)aryl;

$R^{25}$ and $R^{26}$ each independently represent H, $C_{1-6}$-alkyl, $C_{3-6}$-cycloalkyl or (het)aryl, or $R^{25}$ and $R^{26}$ together with the CH grouping joining them form a structure selected from the group consisting of

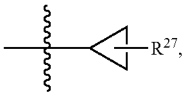 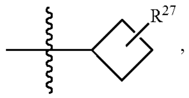 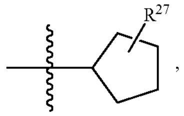

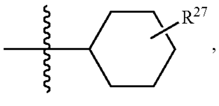 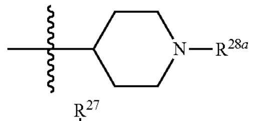 and

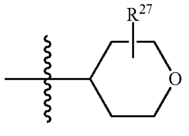

$R^{27}$ represents 0, 1 or 2 substituents, each independently selected from the group consisting of F, Cl, $CF_3$, $OCF_3$, $C_{1-6}$-alkyl, O—$C_{1-3}$-alkyl and $NR^{48a}R^{48b}$;

$R^{28a}$ represents a substituent which is selected from the group consisting of H, methyl, ethyl, n-propyl, iso-propyl, n-butyl, iso-butyl, sec-butyl, tert-butyl and het(aryl);

$R^{48a}$ and $R^{48b}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or $R^{48a}$ and $R^{48b}$ together with the nitrogen atom joining them form a structure selected from the group consisting of:

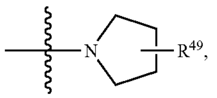 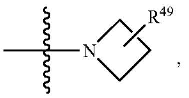

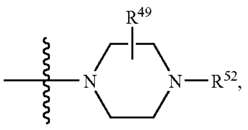 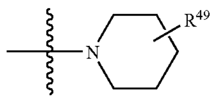 and

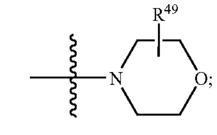

$R^{49}$ represents 0, 1 or 2 substituents each independently selected from the group consisting of F, Cl, $CF_3$, $OCF_3$, $C_{1-6}$-alkyl and O—$C_{1-3}$-alkyl;

$R^{52}$ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl and (het)aryl;

D represents C(═O), S(═O)$_2$ or the group —C(═O)—N($R^{20}$), wherein the nitrogen atom thereof is bonded to $R^{19}$, $R^{19}$ represents $C_{1-6}$-alkyl, (het)aryl, —CH(aryl)$_2$, $C_{3-8}$-cycloalkyl, heterocyclyl or a (het)aryl, $C_{3-8}$-cycloalkyl or heterocyclyl bonded via a $C_{1-6}$-alkylene group, $C_{2-6}$-alkenylene group or $C_{2-6}$-alkynylene group;

$R^{20}$ represents H, methyl, ethyl, n-propyl, iso-propyl, n-butyl, iso-butyl, sec-butyl, tert-butyl, cyclopropyl, cyclobutyl, cyclopentyl or cyclohexyl;

$R^{16}$ and $R^{17}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or $R^{16}$ and $R^{17}$ together with the nitrogen atom joining them form a structure selected from the group consisting of

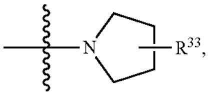 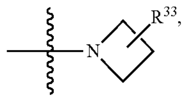

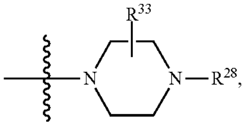 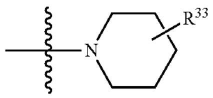 and

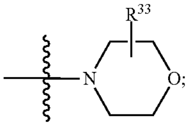

$R^{28}$ represents a substituent which is selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl and (het)aryl;

$R^{33}$ represents 0, 1 or 2 substituents each independently selected from the group consisting of F, Cl, $CF_3$, $OCF_3$, $C_{1-6}$-alkyl, O—$C_{1-3}$-alkyl and $NR^{34a}R^{34b}$;

$R^{34a}$ and $R^{34b}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or $R^{34a}$ and $R^{34b}$ together with the nitrogen atom joining them form a structure selected from the group consisting of:

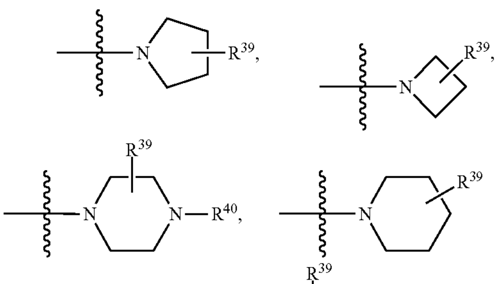

and

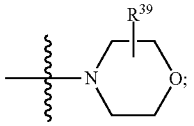

$R^{39}$ represents 0, 1 or 2 substituents, each independently selected from the group consisting of F, Cl, $CF_3$, $OCF_3$, $C_{1-6}$-alkyl and O—$C_{1-3}$-alkyl;

$R^{40}$ represents a substituent which is selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl;

$R^{35}$ represents H, $C_{1-6}$-alkyl, $C_{3-6}$-cycloalkyl, (het)aryl or a $C_{3-6}$-cycloalkyl or (het)aryl bonded via a $C_{1-3}$-alkylene group;

$R^{36}$ represents (het)aryl or $C_{1-3}$-alkylene-(het)aryl;

$R^{37}$ represents H, $C_{1-6}$-alkyl or for the group

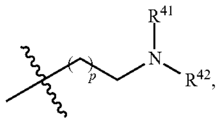

wherein p represents 1, 2 or 3, wherein $R^{41}$ and $R^{42}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or $R^{41}$ and $R^{42}$ together with the nitrogen atom joining them form a structure selected from the group consisting of

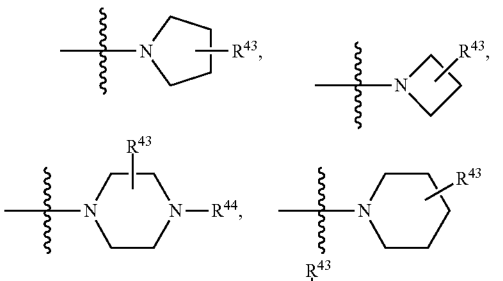

and

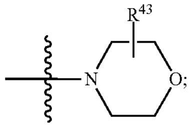

$R^{43}$ represents 0, 1 or 2 substituents, each independently selected from the group consisting of F, Cl, $CF_3$, $OCF_3$, $C_{1-6}$-alkyl, O—$C_{1-3}$-alkyl and $NR^{45a}R^{45b}$;

$R^{44}$ represents a substituent which is selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl;

$R^{45a}$ and $R^{45b}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or $R^{45a}$ and $R^{45b}$ together with the nitrogen atom joining them form a structure selected from the group consisting of:

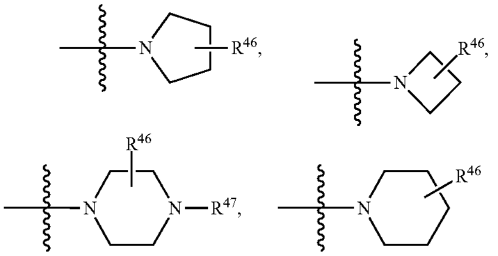

and

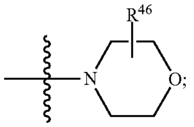

$R^{46}$ represents 0, 1 or 2 substituents, each independently selected from the group consisting of F, Cl, $CF_3$, $OCF_3$, $C_{1-6}$-alkyl and O—$C_{1-3}$-alkyl;

$R^{47}$ represents a substituent which is selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl, and het(aryl) in each case represents a structure selected from the group consisting of (1)

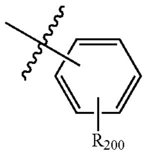

(2)

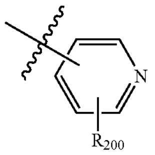

(3)

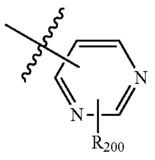

(4)

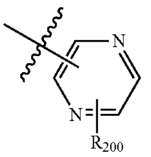

-continued
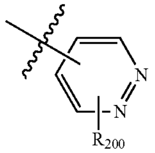
(5)
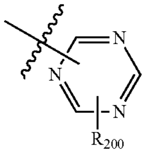
(6)
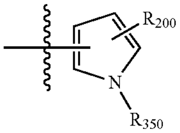
(7)
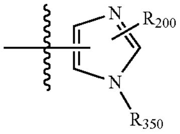
(8)
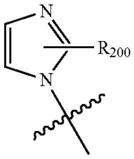
(9)
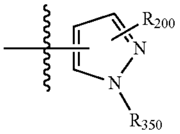
(10)
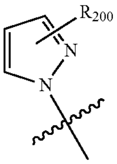
(11)
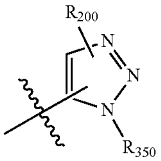
(12)
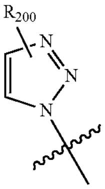
(13)
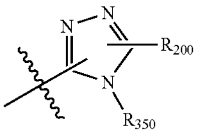
(14)
-continued
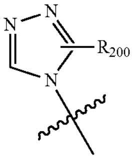
(15)
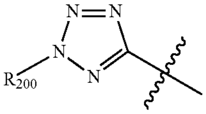
(16)
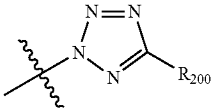
(17)
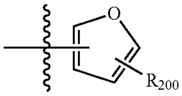
(18)
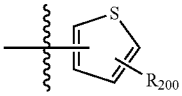
(19)
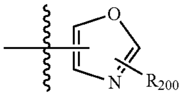
(20)
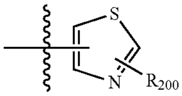
(21)
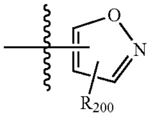
(22)
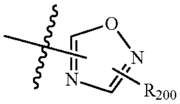
(23)
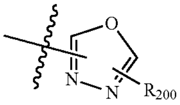
(24)
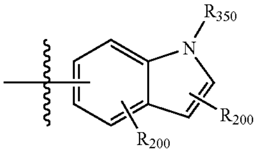
(25)
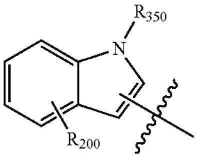
(26)

-continued (27)

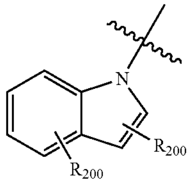

(28)

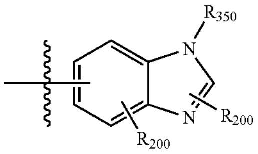

(29)

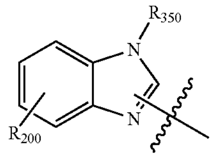

(30)

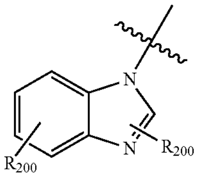

(31)

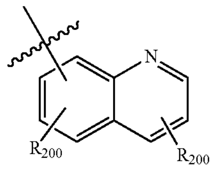

(32)

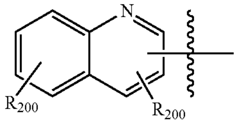

(33)

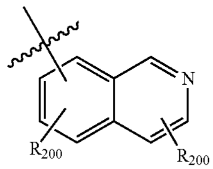

(34)

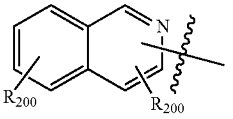

(35)

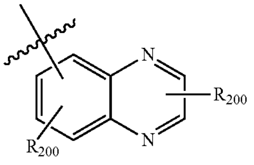

-continued (36)

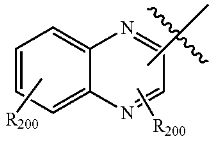

(37)

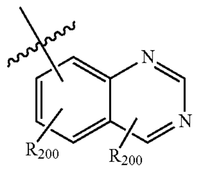

(38)

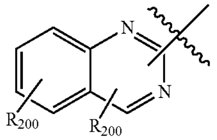

wherein $R^{200}$ represents 0, 1, 2 or 3 substituents each independently selected from the group consisting of F, Cl, $CF_3$, $OCF_3$, OH, O—$C_{1-6}$-alkyl, SH, S—$C_{1-6}$-alkyl, $C_{1-6}$-alkyl, $C_{3-6}$-cycloalkyl, O—$C_{3-6}$-cycloalkyl, $NR^{61}R^{62}$, C(═O)—$NR^{61}R^{62}$, phenyl, pyridyl, pyrimidyl or $OCF_3$, OH, SH, $C_{3-6}$-cycloalkyl, O—$C_{3-6}$-cycloalkyl, $NR^{61}R^{62}$, C(═O)—$NR^{61}R^{62}$, phenyl, pyridyl or pyrimidyl bonded via a $C_{1-6}$-alkylene group;

$R^{61}$ and $R^{62}$ each independently represent H, $C_{1-6}$-alkyl or $C_{3-6}$-cycloalkyl, or $R^{61}$ and $R^{62}$ together with the nitrogen atom joining them form a structure selected from the group consisting of:

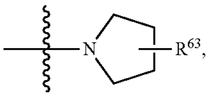 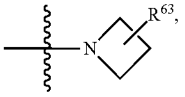

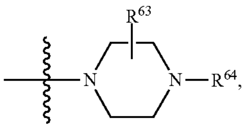 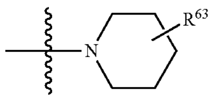 and

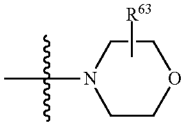

$R^{63}$ represents 0, 1 or 2 substituents, each independently selected from the group consisting of F, Cl, $CF_3$, $OCF_3$, $C_{1-6}$-alkyl and O—$C_{1-3}$-alkyl;

$R^{64}$ represents a substituent which is selected from the group consisting of H, methyl, ethyl, n-propyl, iso-propyl, n-butyl, iso-butyl, sec-butyl, tert-butyl, cyclopropyl, cyclobutyl, cyclopentyl and cyclohexyl; and $R^{350}$ represents H, $CF_3$, phenyl, pyridyl, pyrimidyl or a phenyl, pyridyl or pyrimidyl bonded via a $C_{1-6}$-alkylene group.

In embodiments of the compounds according to the invention which are furthermore preferred, the abovementioned structure (SP) is selected from the group consisting of
(1)
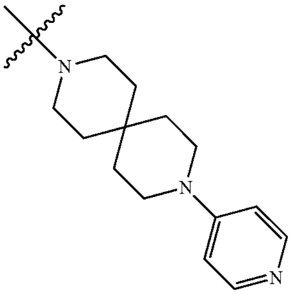
(2)
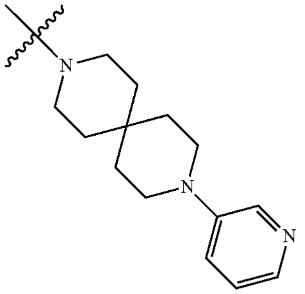
(3)
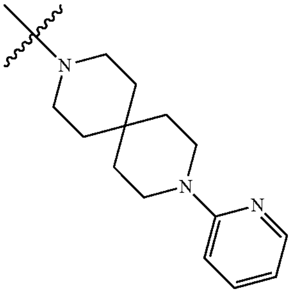
(4)
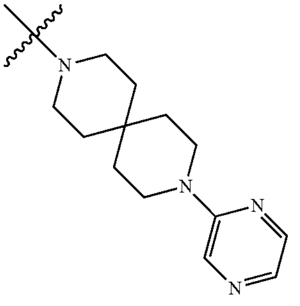
(5)
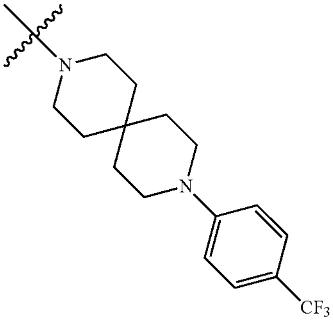
-continued
(6)
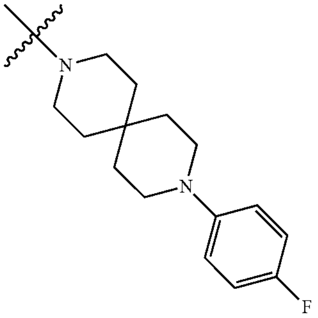
(7)
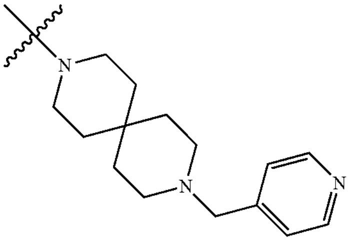
(8)
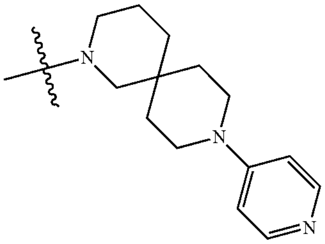
(9)
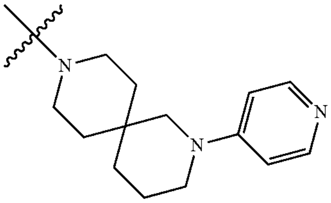
(10)
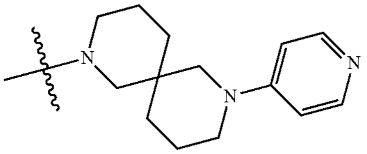
(11)
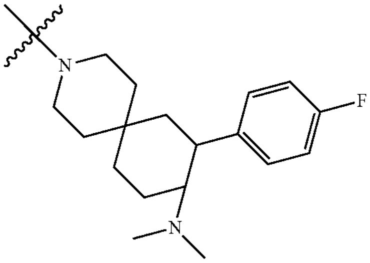

-continued
(12)
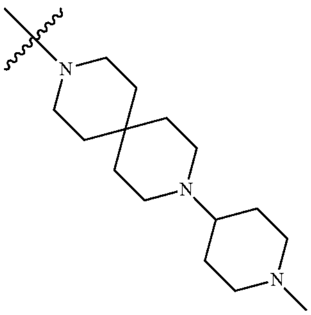
(13)
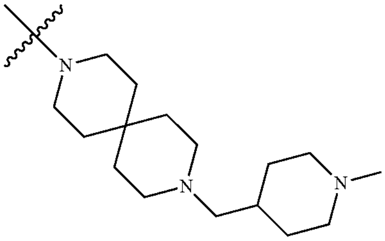
(14)
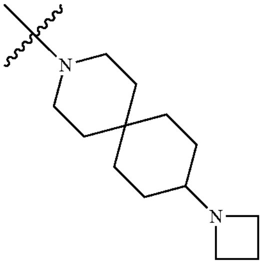
(15)
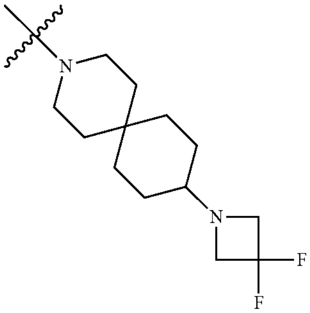
(16)
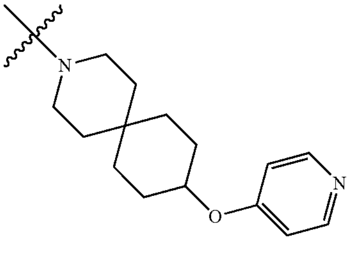
-continued
(17)
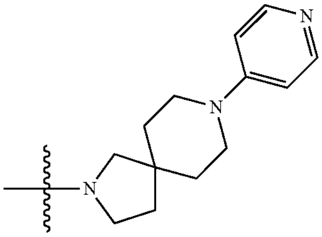
(18)
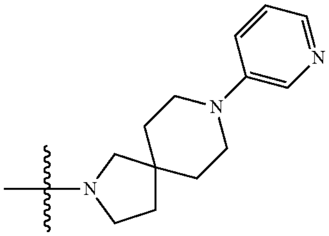
(19)
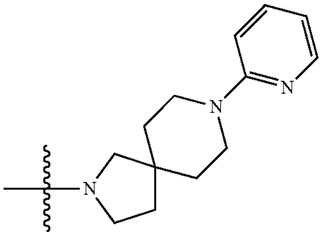
(20)
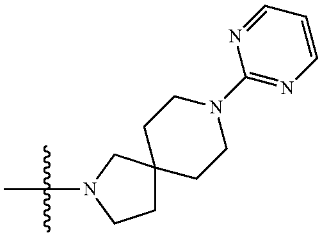
(21)
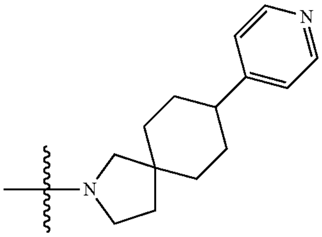
(22)
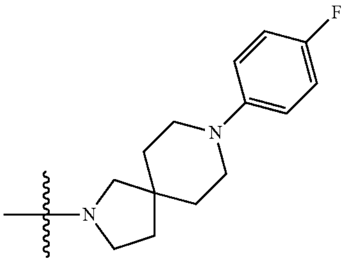

-continued
(23)
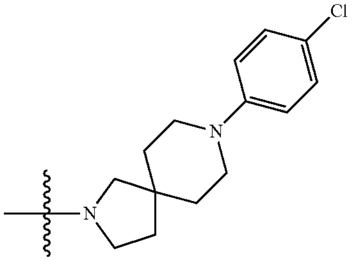
(24)
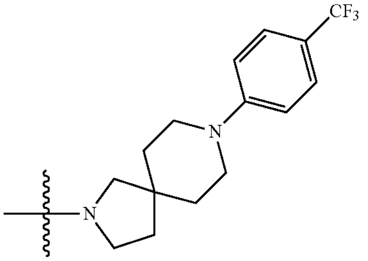
(25)
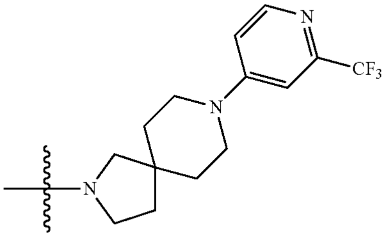
(26)
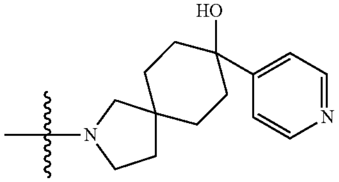
(27)
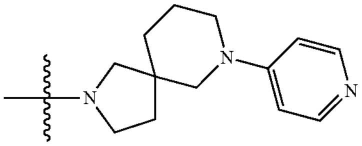
(28)
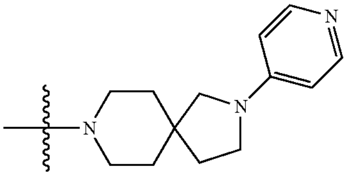
(29)
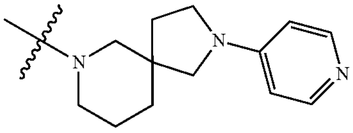
-continued
(30)
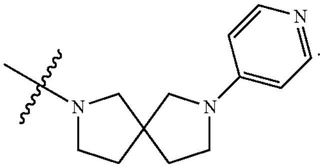
Further embodiments of the compounds according to the invention are those which are represented by the general formulae $C_1$-$C_{21}$ shown in the following:
C1
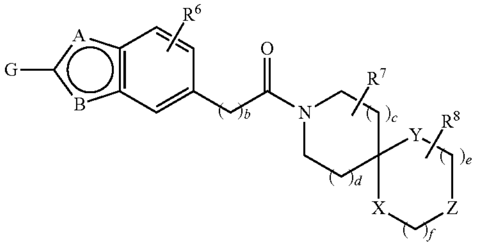
C2
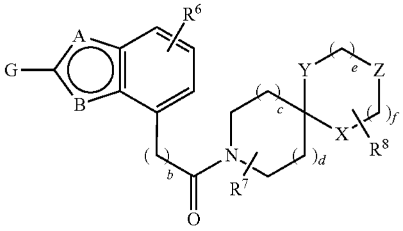
C3
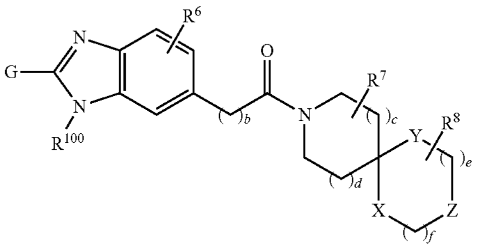
C4
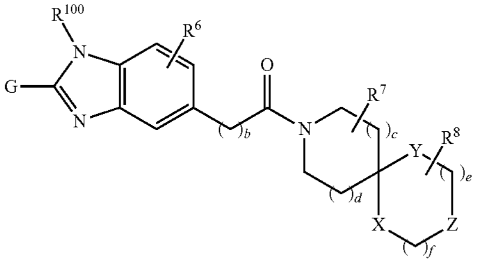
C5
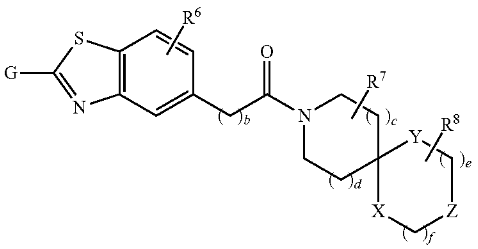

-continued
C6
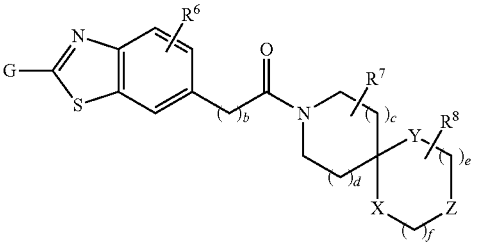
C7
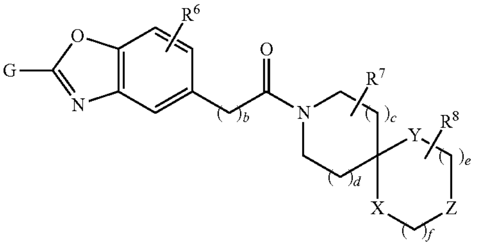
C8
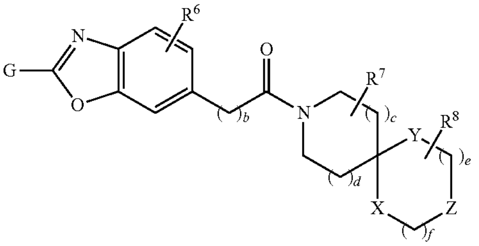
C9
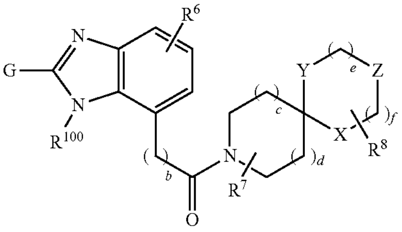
C10
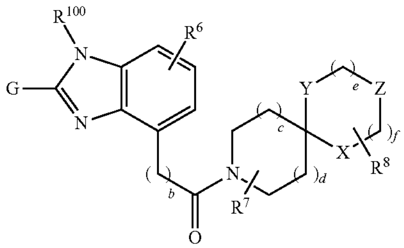
C11
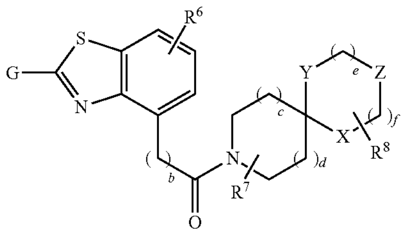
-continued
C12
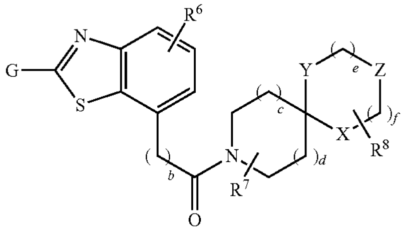
C13
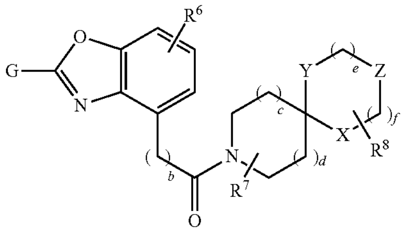
C14
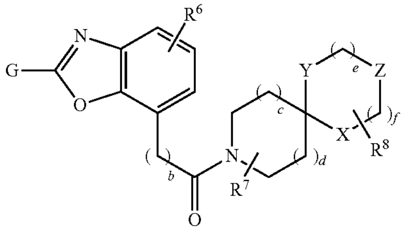
C15
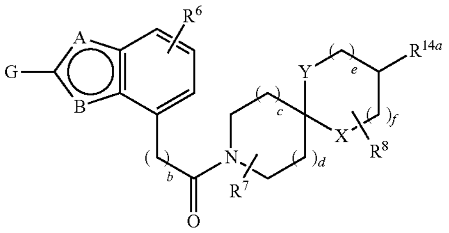
C16
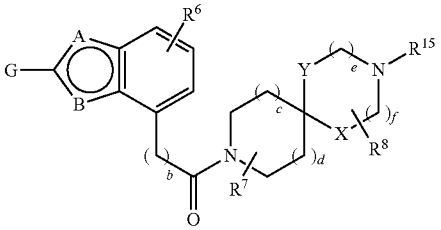
C17
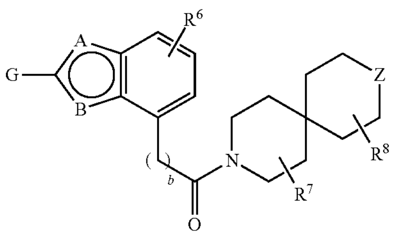

-continued

C18

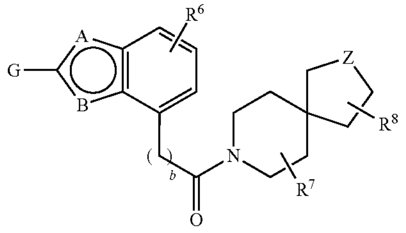

C19

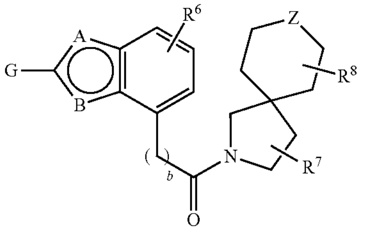

C20

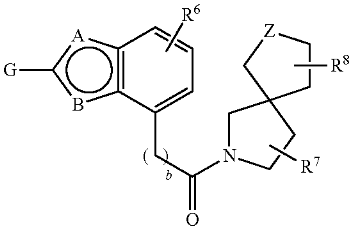

C21

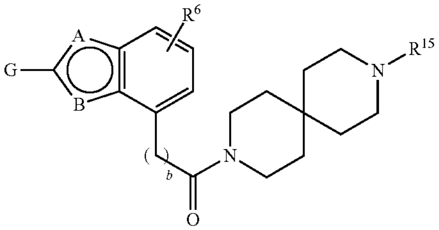

wherein the particular substituent groups, variables and indices have the meanings described herein in connection with the compounds according to the invention and preferred embodiments thereof.

In a further preferred embodiment of the present invention, the substituted compounds according to the invention can be selected from the group consisting of

[I-01] 4-methoxy-N,2,6-trimethyl-N-[[7-(9-pyridin-4-yl-3,9-diazaspiro[5.5]undecane-3-carbonyl)-1H-benzoimidazol-2-yl]-methyl]-benzenesulfonic acid amide,

[I-02] 4-methoxy-N,2,6-trimethyl-N-[2-[4-(9-pyridin-4-yl-3,9-diazaspiro[5.5]undecane-3-carbonyl)-1H-benzoimidazol-2-yl]-ethyl]-benzenesulfonic acid amide,

[I-03] 4-methoxy-N,2,6-trimethyl-N-[[7-(9-pyridin-4-yloxy-3-azaspiro[5.5]undecane-3-carbonyl)-1H-benzoimidazol-2-yl]-methyl]-benzenesulfonic acid amide,

[I-04] N-[[7-[9-(azetidin-1-yl)-3-azaspiro[5.5]undecane-3-carbonyl]-1H-benzoimidazol-2-yl]-methyl]-4-methoxy-N,2,6-trimethyl-benzenesulfonic acid amide,

[I-05] N-[[7-[9-(3,3-difluoro-azetidin-1-yl)-3-azaspiro[5.5]undecane-3-carbonyl]-1H-benzoimidazol-2-yl]-methyl]-4-methoxy-N,2,6-trimethyl-benzenesulfonic acid amide,

[I-06] 4-methoxy-N,2,6-trimethyl-N-[1-[7-(9-pyridin-4-yl-3,9-diazaspiro[5.5]undecane-3-carbonyl)-1H-benzoimidazol-2-yl]-ethyl]-benzenesulfonic acid amide,

[I-07] N-methyl-N-[[7-(9-pyridin-4-yl-3,9-diazaspiro[5.5]undecane-3-carbonyl)-1H-benzoimidazol-2-yl]-methyl]-naphthalene-1-sulfonic acid amide,

[I-08] N-methyl-N-[[7-(9-pyridin-4-yl-3,9-diazaspiro[5.5]undecane-3-carbonyl)-1H-benzoimidazol-2-yl]-methyl]-2-(trifluoromethyl)-benzenesulfonic acid amide,

[I-09] 4-methoxy-N,2,6-trimethyl-N-[[7-(8-pyridin-4-yl-3,8-diazaspiro[4.5]decane-3-carbonyl)-1H-benzoimidazol-2-yl]-methyl]-benzenesulfonic acid amide,

[I-10] 4-methoxy-N,2,6-trimethyl-N-[[7-(8-pyridin-4-yl-3,8-diazaspiro[4.4]nonane-3-carbonyl)-1H-benzoimidazol-2-yl]-methyl]-benzenesulfonic acid amide,

[I-11] 2-chloro-N-methyl-N-[[7-(9-pyridin-4-yl-3,9-diazaspiro[5.5]undecane-3-carbonyl)-1H-benzoimidazol-2-yl]-methyl]-4-(trifluoromethyloxy)-benzenesulfonic acid amide,

[I-12] 4-methoxy-N,2,6-trimethyl-N-[1-[7-(9-pyridin-4-yl-3,9-diazaspiro[5.5]undecane-3-carbonyl)-1H-benzoimidazol-2-yl]-cyclopropyl]-benzenesulfonic acid amide,

[I-13] N-[[6-fluoro-7-(9-pyridin-4-yl-3,9-diazaspiro[5.5]undecane-3-carbonyl)-1H-benzoimidazol-2-yl]-methyl]-4-methoxy-N,2,6-trimethyl-benzenesulfonic acid amide,

[I-14] N-cyclopropyl-4-methoxy-2,6-dimethyl-N-[[7-(9-pyridin-4-yl-3,9-diazaspiro[5.5]undecane-3-carbonyl)-1H-benzoimidazol-2-yl]-methyl]-benzenesulfonic acid amide,

[I-15] 4-methoxy-N,2,6-trimethyl-N-[[7-[(9-pyridin-4-yl-3,9-diazaspiro[5.5]undecan-3-yl)-methyl]-1H-benzoimidazol-2-yl]-methyl]-benzenesulfonic acid amide,

[I-16] 5-chloro-N-methyl-N-[[7-(9-pyridin-4-yl-3,9-diazaspiro[5.5]undecane-3-carbonyl)-1H-benzoimidazol-2-yl]-methyl]-thiophene-2-carboxylic acid amide,

[I-17] 2,6-dichloro-N,3-dimethyl-N-[[7-(9-pyridin-4-yl-3,9-diazaspiro[5.5]undecane-3-carbonyl)-1H-benzoimidazol-2-yl]-methyl]-benzenesulfonic acid amide,

[I-18] [2-[1-[(4-methoxy-2,6-dimethyl-phenyl)sulfonyl]-piperidin-2-yl]-3H-benzoimidazol-4-yl]-(9-pyridin-4-yl-3,9-diazaspiro[5.5]undecan-3-yl)-methanone,

[I-19] [2-[1-[(4-methoxy-2,6-dimethyl-phenyl)sulfonyl]-pyrrolidin-2-yl]-3H-benzoimidazol-4-yl]-(9-pyridin-4-yl-3,9-diazaspiro[5.5]undecan-3-yl)-methanone,

[I-20] 4-methoxy-N,2,6-trimethyl-N-[[1-methyl-4-(9-pyridin-4-yl-3,9-diazaspiro[5.5]undecane-3-carbonyl)-1H-benzoimidazol-2-yl]-methyl]-benzenesulfonic acid amide,

[I-21] 4-methoxy-N,2,6-trimethyl-N-[[7-[2-oxo-2-(9-pyridin-4-yl-3,9-diazaspiro[5.5]undecan-3-yl)-ethyl]-1H-benzoimidazol-2-yl]-methyl]-benzenesulfonic acid amide,

[I-22] 4-methoxy-N,2,6-trimethyl-N-[[6-(9-pyridin-4-yl-3,9-diazaspiro[5.5]undecane-3-carbonyl)-1H-benzoimidazol-2-yl]-methyl]-benzenesulfonic acid amide,

[I-23] 2-chloro-N,6-dimethyl-N-[[6-(9-pyridin-4-yl-3,9-diazaspiro[5.5]undecane-3-carbonyl)-1H-benzoimidazol-2-yl]-methyl]-benzenesulfonic acid amide,

[I-24] N-methyl-N-[[6-(9-pyridin-4-yl-3,9-diazaspiro[5.5]undecane-3-carbonyl)-1H-benzoimidazol-2-yl]-methyl]-2-(trifluoromethyl)-benzenesulfonic acid amide,

[I-25] N-methyl-N-[[6-(9-pyridin-4-yl-3,9-diazaspiro[5.5]undecane-3-carbonyl)-1H-benzoimidazol-2-yl]-methyl]naphthalene-1-sulfonic acid amide,

[I-26] 4-methoxy-N,2,6-trimethyl-N-[2-[6-(9-pyridin-4-yl-3,9-diazaspiro[5.5]undecane-3-carbonyl)-1H-benzoimidazol-2-yl]-ethyl]-benzenesulfonic acid amide,

[I-27] 4-methoxy-N,2,6-trimethyl-N-[[7-(3-pyridin-4-yl-1-oxa-2,8-diazaspiro[4.5]dec-2-ene-8-carbonyl)-1H-benzoimidazol-2-yl]-methyl]-benzenesulfonic acid amide,

[I_CC-01] 4-chloro-N,2,5-trimethyl-N-[[7-(3-pyridin-4-yl-3,9-diazaspiro[5.5]undecane-9-carbonyl)-1H-benzoimidazol-2-yl]-methyl]-benzenesulfonic acid amide,

[I_CC-02] 2-chloro-N-methyl-N-[[7-(4-oxo-1-pyridin-4-yl-3,8-diazaspiro[4.5]decane-8-carbonyl)-1H-benzoimidazol-2-yl]-methyl]-benzamide,

[I_CC-03] 4-methoxy-N,2,6-trimethyl-N-[[7-(3-pyridin-4-yl-3,9-diazaspiro[5.5]undecane-9-carbonyl)-1H-benzoimidazol-2-yl]-methyl]-benzenesulfonic acid amide,

[I_CC-04] 2-chloro-N-methyl-N-[[7-(3-pyridin-4-yl-3,9-diazaspiro[5.5]undecane-9-carbonyl)-1H-benzoimidazol-2-yl]-methyl]-benzamide,

[I_CC-05] 3-chloro-N-methyl-N-[[7-(3-pyridin-4-yl-3,9-diazaspiro[5.5]undecane-9-carbonyl)-1H-benzoimidazol-2-yl]-methyl]-thiophene-2-carboxylic acid amide,

[I_CC-06] 4-methoxy-N,2,6-trimethyl-N-[[7-(3-pyridin-4-yl-3,8-diazaspiro[4.5]decane-8-carbonyl)-1H-benzoimidazol-2-yl]-methyl]-benzenesulfonic acid amide,

[I_CC-07] 2-chloro-N,6-dimethyl-N-[[7-(3-pyridin-4-yl-3,8-diazaspiro[4.5]decane-8-carbonyl)-1H-benzoimidazol-2-yl]-methyl]-benzenesulfonic acid amide,

[I_CC-08] 2-chloro-N-methyl-N-[[7-(3-pyridin-4-yl-3,8-diazaspiro[4.5]decane-8-carbonyl)-1H-benzoimidazol-2-yl]-methyl]-benzamide,

[I_CC-09] 3-chloro-N-methyl-N-[[7-(3-pyridin-4-yl-3,8-diazaspiro[4.5]decane-8-carbonyl)-1H-benzoimidazol-2-yl]-methyl]-thiophene-2-carboxylic acid amide,

[I_CC-10] 4-chloro-N,2,5-trimethyl-N-[[7-(3-pyridin-4-yl-3,8-diazaspiro[4.5]decane-8-carbonyl)-1H-benzoimidazol-2-yl]-methyl]-benzenesulfonic acid amide,

[I_CC-11] 2-chloro-N,6-dimethyl-N-[[7-(3-pyridin-4-yl-3,9-diazaspiro[5.5]undecane-9-carbonyl)-1H-benzoimidazol-2-yl]-methyl]-benzenesulfonic acid amide,

[I_CC-12] 7-chloro-2-[[7-(3-pyridin-4-yl-3,9-diazaspiro[5.5]undecane-9-carbonyl)-1H-benzoimidazol-2-yl]-methyl]-2,3-dihydro-isoindol-1-one,

[I_CC-13] 7-chloro-2-[[7-(3-pyridin-4-yl-3,8-diazaspiro[4.5]decane-8-carbonyl)-1H-benzoimidazol-2-yl]-methyl]-2,3-dihydro-isoindol-1-one,

[I_CC-14] 4-methoxy-N,2,6-trimethyl-N-[1-methyl-7-(3-pyridin-4-yl-3,9-diazaspiro[5.5]undecane-9-carbonyl)-1H-benzoimidazol-2-yl]-benzenesulfonic acid amide,

[I_CC-15] 4-methoxy-N,2,6-trimethyl-N-[1-methyl-7-(3-pyridin-4-yl-3,8-diazaspiro[4.5]decane-8-carbonyl)-1H-benzoimidazol-2-yl]-benzenesulfonic acid amide,

[I_CC-16] 4-methoxy-N,2,6-trimethyl-N-[1-methyl-7-(4-oxo-1-pyridin-4-yl-3,8-diazaspiro[4.5]decane-8-carbonyl)-1H-benzoimidazol-2-yl]-benzenesulfonic acid amide,

[I_CC-17] 4-methoxy-N,2,6-trimethyl-N-[1-methyl-6-(3-pyridin-4-yl-3,9-diazaspiro[5.5]undecane-9-carbonyl)-1H-benzoimidazol-2-yl]-benzenesulfonic acid amide,

[I_CC-18] 4-methoxy-N,2,6-trimethyl-N-[1-methyl-6-(3-pyridin-4-yl-3,8-diazaspiro[4.5]decane-8-carbonyl)-1H-benzoimidazol-2-yl]-benzenesulfonic acid amide,

[I_CC-19] 4-methoxy-N,2,6-trimethyl-N-[4-(3-pyridin-4-yl-3,9-diazaspiro[5.5]undecane-9-carbonyl)-benzothiazol-2-yl]-benzenesulfonic acid amide,

[I_CC-20] 4-methoxy-N,2,6-trimethyl-N-[[4-(3-pyridin-4-yl-3,8-diazaspiro[4.5]decane-8-carbonyl)-benzothiazol-2-yl]-methyl]-benzenesulfonic acid amide,

[I_CC-21] 4-methoxy-N,2,6-trimethyl-N-[[4-(3-pyridin-4-yl-3,8-diazaspiro[4.5]decane-8-carbonyl)-benzothiazol-2-yl]-benzenesulfonic acid amide,

[I_CC-22] 4-methoxy-N,2,6-trimethyl-N-[[4-(3-pyridin-4-yl-3,9-diazaspiro[5.5]undecane-9-carbonyl)-benzothiazol-2-yl]-methyl]-benzenesulfonic acid amide,

[I_CC-23] 4-methoxy-N,2,6-trimethyl-N-[[7-(3-pyridin-4-yl-3,9-diazaspiro[5.5]undecane-9-carbonyl)-1H-benzoimidazol-2-yl]-methyl]-benzamide,

[I_CC-24] 4-methoxy-N,2,6-trimethyl-N-[[7-(3-pyridin-4-yl-3,8-diazaspiro[4.5]decane-8-carbonyl)-1H-benzoimidazol-2-yl]-methyl]-benzamide,

[I_CC-25] N-[1-[7-[9-(1H-Imidazol-4-yl-methyl)-3,9-diazaspiro[5.5]undecane-3-carbonyl]-1H-benzoimidazol-2-yl]-ethyl]-4-methoxy-N,2,6-trimethyl-benzenesulfonic acid amide,

[I_CC-26] 4-Methoxy-N,2,6-trimethyl-N-[1-[7-[9-(pyridin-2-yl-methyl)-3,9-diazaspiro[5.5]undecane-3-carbonyl]-1H-benzoimidazol-2-yl]-ethyl]-benzenesulfonic acid amide,

[I_CC-27] 4-Methoxy-N,2,6-trimethyl-N-[1-[7-[9-(pyridin-4-yl-methyl)-3,9-diazaspiro[5.5]undecane-3-carbonyl]-1H-benzoimidazol-2-yl]-ethyl]-benzenesulfonic acid amide,

[I_CC-28] 4-Methoxy-N,2,6-trimethyl-N-[1-[7-[9-(pyridin-3-yl-methyl)-3,9-diazaspiro[5.5]undecane-3-carbonyl]-1H-benzoimidazol-2-yl]-ethyl]-benzenesulfonic acid amide,

[I_CC-29] N-[1-[7-[9-[(2,6-Difluoro-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide,

[I_CC-30] N-[1-[7-[9-[(3,4-Difluoro-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide,

[I_CC-31] N-[1-[7-[9-[(2,5-Difluoro-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide,

[I_CC-32] N-[1-[7-[9-[(2,4-Difluoro-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide,

[I_CC-33] N-[1-[7-[9-[(3-Fluoro-4-methoxy-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide,

[I_CC-34] N-[1-[7-[9-[(2-Fluoro-6-methoxy-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide,

[I_CC-35] 4-Methoxy-N,2,6-trimethyl-N-[1-[7-[9-[(5-methyl-3H-imidazol-4-yl)-methyl]-3,9-diazaspiro[5.5]undecane-3-carbonyl]-1H-benzoimidazol-2-yl]-ethyl]-benzenesulfonic acid amide,

[I_CC-36] 4-Methoxy-N,2,6-trimethyl-N-[1-[7-[9-[(3-methyl-3H-imidazol-4-yl)-methyl]-3,9-diazaspiro[5.5]undecane-3-carbonyl]-1H-benzoimidazol-2-yl]-ethyl]-benzenesulfonic acid amide,

[I_CC-37] 4-Methoxy-N,2,6-trimethyl-N-[1-[7-[9-[(2-methyl-1H-imidazol-4-yl)-methyl]-3,9-diazaspiro[5.5]undecane-3-carbonyl]-1H-benzoimidazol-2-yl]-ethyl]-benzenesulfonic acid amide,

[I_CC-38] 4-Methoxy-N,2,6-trimethyl-N-[1-[7-[9-([1,2,3]thiadiazol-4-yl-methyl)-3,9-diazaspiro[5.5]undecane-3-carbonyl]-1H-benzoimidazol-2-yl]-ethyl]-benzenesulfonic acid amide,

[I_CC-39] N-[1-[7-[9-[(2-Chloro-4-fluoro-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide,

[I_CC-40] N-[1-[7-[9-[(2-Chloro-6-fluoro-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide,

[I_CC-41] N-[1-[7-[9-[(1,5-Dimethyl-1H-pyrazol-4-yl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide,

[I_CC-42] N-[1-[7-[9-[(3,5-Dimethyl-isoxazol-4-yl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide,

[I_CC-43] N-[1-[7-[9-[(4-Cyano-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide,

[I_CC-44] N-[1-[7-[9-[(3-Cyano-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide,

[I_CC-45] N-[1-[7-[9-[(2-Cyano-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide,

[I_CC-46] 4-Methoxy-N,2,6-trimethyl-N-[1-[7-[9-[5-(trifluoromethyl)-pyridine-2-carbonyl]-3,9-diazaspiro[5.5]undecane-3-carbonyl]-1H-benzoimidazol-2-yl]-ethyl]-benzenesulfonic acid amide,

[I_CC-47] 4-Methoxy-N,2,6-trimethyl-N-1-[7-[9-(pyrazine-2-carbonyl)-3,9-diazaspiro[5.5]undecane-3-carbonyl)-1H-benzoimidazol-2-yl]-ethyl]-benzenesulfonic acid amide,

[I_CC-48] 4-Methoxy-N,2,6-trimethyl-N-[1-[7-[9-(2-methylsulfanyl-pyridine-3-carbonyl)-3,9-diazaspiro[5.5]undecane-3-carbonyl]-1H-benzoimidazol-2-yl]-ethyl]-benzenesulfonic acid amide,

[I_CC-49] N-[1-[7-[9-(4-Cyano-benzoyl)-3,9-diazaspiro[5.5]undecane-3-carbonyl]-1H-benzoimidazol-2-yl]-ethyl]-4-methoxy-N,2,6-trimethyl-benzenesulfonic acid amide,

[I_CC-50] N-[1-[7-[9-(Cyclopropanecarbonyl)-3,9-diazaspiro[5.5]undecane-3-carbonyl]-1H-benzoimidazol-2-yl]-ethyl]-4-methoxy-N,2,6-trimethyl-benzenesulfonic acid amide,

[I_CC-51] N-[4-[7-[9-(3,3-Dimethyl-butanoyl)-3,9-diazaspiro[5.5]undecane-3-carbonyl]-1H-benzoimidazol-2-yl]-ethyl]-4-methoxy-N,2,6-trimethyl-benzenesulfonic acid amide,

[I_CC-52] N-[1-[7-[9-(2-Chloro-4-fluoro-benzoyl)-3,9-diazaspiro[5.5]undecane-3-carbonyl]-1H-benzoimidazol-2-yl]-ethyl]-4-methoxy-N,2,6-trimethyl-benzenesulfonic acid amide,

[I_CC-53] N-[1-[7-[9-(2,4-Difluoro-benzoyl)-3,9-diazaspiro[5.5]undecane-3-carbonyl]-1H-benzoimidazol-2-yl]-ethyl]-4-methoxy-N,2,6-trimethyl-benzenesulfonic acid amide,

[I_CC-54] N-[1-[7-[9-(5-tert-Butyl-2-methyl-2H-pyrazole-3-carbonyl)-3,9-diazaspiro[5.5]undecane-3-carbonyl]-1H-benzoimidazol-2-yl]-ethyl]-4-methoxy-N,2,6-trimethyl-benzenesulfonic acid amide,

[I_CC-55] N-[1-[7-[9-(2-tert-Butyl-5-methyl-2H-pyrazole-3-carbonyl)-3,9-diazaspiro[5.5]undecane-3-carbonyl]-1H-benzoimidazol-2-yl]-ethyl]-4-methoxy-N,2,6-trimethyl-benzenesulfonic acid amide,

[I_CC-56] N-[1-[7-[9-[(5-Chloro-thiophen-2-yl)sulfonyl]-3,9-diazaspiro[5.5]undecane-3-carbonyl]-1H-benzoimidazol-2-yl]-ethyl]-4-methoxy-N,2,6-trimethyl-benzenesulfonic acid amide,

[I_CC-57] N-[1-[7-[9-[(2,4-Difluoro-phenyl)sulfonyl]-3,9-diazaspiro[5.5]undecane-3-carbonyl]-1H-benzoimidazol-2-yl]-ethyl]-4-methoxy-N,2,6-trimethyl-benzenesulfonic acid amide,

[I_CC-58] N-[1-[7-[9-[(3-Cyano-4-fluoro-phenyl)sulfonyl]-3,9-diazaspiro[5.5]undecane-3-carbonyl]-1H-benzoimidazol-2-yl]-ethyl]-4-methoxy-N,2,6-trimethyl-benzenesulfonic acid amide,

[I_CC-59] N-[1-[7-[9-[(2-Cyano-phenyl)sulfonyl]-3,9-diazaspiro[5.5]undecane-3-carbonyl]-1H-benzoimidazol-2-yl]-ethyl]-4-methoxy-N,2,6-trimethyl-benzenesulfonic acid amide, and

[I_CC-60] 4-Methoxy-N,2,6-trimethyl-N-[1-[7-[9-[(1-methyl-1H-indol-4-yl)sulfonyl]-3,9-diazaspiro[5.5]undecane-3-carbonyl]-1H-benzoimidazol-2-yl]-ethyl]-benzenesulfonic acid amide, in the form of the free compounds; of the tautomers; of the N-oxides; of the racemate; of the enantiomers, diastereomers, mixtures of the enantiomers or diastereomers or of an individual enantiomer or diastereomer; or in the form of the salts of physiologically acceptable acids or bases.

The numbering of the individual embodiments of the compounds according to the invention used above is retained in the following explanations of the present invention, in particular in the description of the examples.

According to one aspect of the present invention, the compounds according to the invention preferably have an antagonistic action on the human B1R receptor or the B1R receptor of the rat. In a preferred embodiment of the invention, the compounds according to the invention have an antagonistic action both on the human B1R receptor (hB1R) and on the B1R receptor of the rat (rB1R).

In a preferred embodiment of the present invention, the compounds according to the invention show an inhibition of at least 15%, 25%, 50%. 70%, 80% or 90% on the human B1R receptor and/or on the B1R receptor of the rat in the FLIPR assay at a concentration of 10 μM. Compounds which show an inhibition on the human B1R receptor and on the B1R receptor of the rat of at least 70%, in particular of at least 80% and particularly preferably of at least 90% at a concentration of 10 μM are very particularly preferred.

The agonistic or antagonistic action of substances can be quantified on the bradykinin receptor 1 (B1R) of the human and rat species with ectopically expressing cell lines (CHO K1 cells) and with the aid of a $Ca^{2+}$-sensitive dyestuff (Fluo-4) in a fluorescent imaging plate reader (FLIPR). The figure in % activation is based on the $Ca^{2+}$ signal after addition of Lys-Des-$Arg^9$-bradykinin (0.5 nM) or Des-$Arg^9$-bradykinin (100 nM). Antagonists lead to a suppression of the $Ca^{2+}$ inflow after addition of the agonist. % inhibition compared with the maximum achievable inhibition is stated.

The substances according to the invention preferably act, for example, on the B1R relevant in connection with various diseases, so that they are suitable as a pharmaceutical active compound in medicaments.

The invention therefore also provides pharmaceutical compositions containing at least one compound according to the invention and optionally suitable additives and/or auxiliary substances and/or optionally further active compounds. The present invention also provides at least one compound as described herein for use in a medicament. The medicaments according to the invention optionally contain, in addition to at least one compound according to the invention, suitable additives and/or auxiliary substances, that is to say also carrier materials, fillers, solvents, diluents, dyestuffs and/or binders, and can be administered as liquid medicament forms in the form of injection solutions, drops or juices or as semi-solid medicament forms in the form of granules, tablets, pellets, patches, capsules, plasters/spray-on plasters or aerosols. The choice of auxiliary substances etc. and the amounts thereof to be employed depend on whether the medicament is to be administered orally, perorally, parenterally, intravenously, intraperitoneally, intradermally, intramuscularly, nasally, buccally, rectally or topically, for example on the skin, the mucous membranes or into the eyes. Formulations in the form of tablets, coated tablets, capsules, granules, drops, juices and syrups are suitable for oral administration, and solutions, suspensions, easily reconstitutable dry formulations and sprays are suitable for parenteral, topical and inhalatory administration. Substituted compounds according to the invention in a depot, in dissolved form or in a plaster, optionally with the addition of agents which promote penetration through the skin, are suitable formulations for percutaneous administration. Formulation forms which can be used orally or percutaneously can release the substituted compounds according to the invention in a delayed manner. The substituted compounds according to the invention can also be used in parenteral long-term depot forms, such as e.g. implants or implanted pumps. In principle, other further active compounds known to the person skilled in the art can be added to the medicaments according to the invention.

The amount of active compound to be administered to patients varies as a function of the weight of the patient, of the mode of administration, the indication and the severity of the disease. 0.00005 to 50 mg/kg, in particular 0.01 to 5 mg/kg of at least one compound according to the invention are conventionally administered.

In one form of the medicament, a substituted compound according to the invention contained therein is present as an isolated diastereomer and/or enantiomer, as a racemate or as a non-equimolar or equimolar mixture of the diastereomers and/or enantiomers. Suitable methods for separation of stereoisomers are known to the person skilled in the art.

B1R is involved in particular in the pain event. The substituted compounds according to the invention can accordingly be used in particular for the preparation of a medicament for treatment of pain, in particular acute, visceral, neuropathic or chronic pain or inflammation pain.

The invention therefore also relates to the use of at least one substituted compound according to the invention for the preparation of a medicament for treatment of pain, in particular acute, visceral, neuropathic or chronic pain. A particular embodiment of the present invention is the use of at least one of the substituted compounds according to the invention for the preparation of a medicament for treatment of inflammation pain.

Furthermore, the invention also provides for use of at least one substituted compound according to the invention for the treatment of pain, in particular acute, visceral, neuropathic or chronic pain. A particular embodiment of the present invention is the use of at least one of the substituted compounds according to the invention for the treatment of inflammation pain.

The invention also provides the use of at least one substituted compound according to the invention for treatment of pain, in particular acute, visceral, neuropathic or chronic pain or inflammation pain.

The invention also provides for the use of at least one substituted compound according to the invention for the preparation of a medicament for the treatment of pain, in particular acute, visceral, neuropathic or chronic pain or inflammation pain.

The invention also provides for the use of at least one substituted compound according to the invention for the treatment of diabetes, diseases of the respiratory tract, for example bronchial asthma, allergies, COPD/chronic obstructive pulmonary disease or cystic fibrosis; inflammatory intestinal diseases, for example ulcerative colitis or CD/Crohn's disease; neurological diseases, for example multiple sclerosis, neurodegenerative diseases, fibrotic diseases, inflammations of the skin, for example atopic dermatitis, psoriasis or bacterial infections; rheumatic diseases, for example rheumatoid arthritis or osteoarthritis; septic shock; reperfusion syndrome, for example following cardiac infarction or stroke, obesity; and as an angiogenesis inhibitor.

The invention also provide the use of at least one substituted compound according to the invention for the preparation of a medicament for treatment of diabetes, diseases of the respiratory tract, for example bronchial asthma, allergies, COPD/chronic obstructive pulmonary disease or cystic fibrosis; inflammatory intestinal diseases, for example ulcerative colitis or CD/Crohn's disease; neurological diseases, for example multiple sclerosis, neurodegenerative diseases, fibrotic diseases, inflammations of the skin, for example atopic dermatitis, psoriasis or bacterial infections; rheumatic diseases, for example rheumatoid arthritis or osteoarthritis; septic shock; reperfusion syndrome, for example following cardiac infarction or stroke, obesity; and as an angiogenesis inhibitor.

The invention also provides the use of at least one substituted compound according to the invention for treatment of one of the abovementioned indications.

In this context, in one of the above uses it may be preferable for a substituted compound which is used to be present as an isolated diastereomer and/or enantiomer, as a racemate or as a non-equimolar or equimolar mixture of the diastereomers and/or enantiomers.

The invention also provides a method for treatment, in particular in one of the abovementioned indications, of a non-human mammal or a human requiring treatment of the appropriate indication by administration of a therapeutically active dose of a substituted compound according to the invention or of a medicament according to the invention.

The invention also provides a method for treatment of pain, in particular one of the abovementioned forms of pain, in a non-human mammal or a human requiring treatment in particular of pain, in particular of acute, visceral, neuropathic or chronic pain or inflammation pain, by administration of a therapeutically active dose of a substituted compound according to the invention, or of a medicament according to the invention.

The present invention also relates to a process for preparing the compounds according to the invention as described in the description and the examples.

General Process for the Preparation of Substituted Benzimidazoles

Part 1—General Process for the Preparation of the Substituted Benzimidazoles (IX)

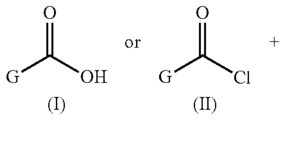
(I) or (II) +

-continued

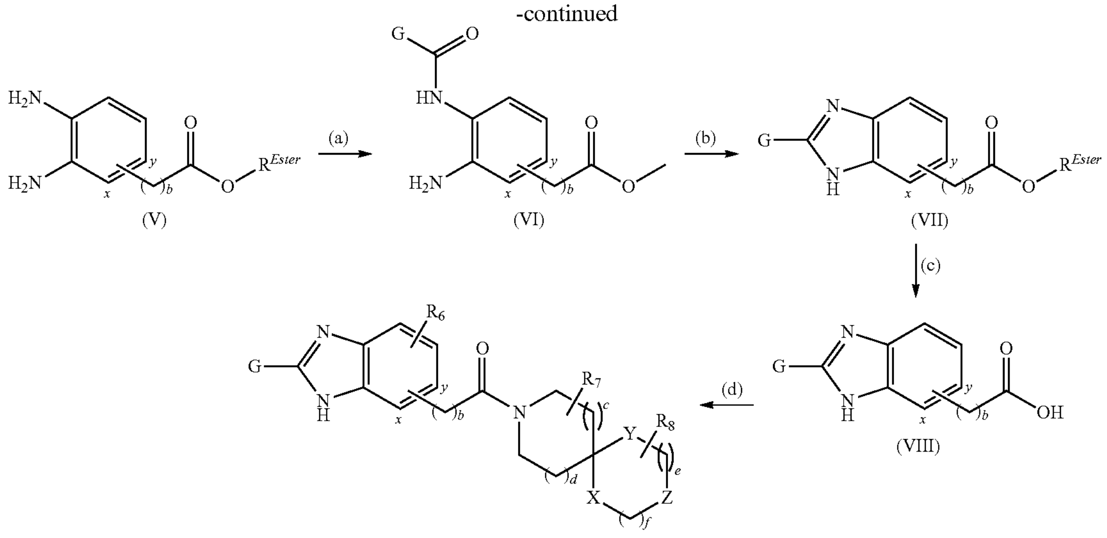

(V) (VI) (VII) (VIII) (IX)

Educts of formula (I), (II), (III), (IV) and (V) either are commercially obtainable or can be synthesized by conventional methods known to person skilled in the art.

Stage (a)—In stage (a), compounds of formula (VI) are prepared analogously to stage (n) (cf. below, Part 2).

Stage (b)—In stage (b), compounds of formula (IV) are reacted in optionally a solvent, preferably selected from the group consisting of methylene chloride, methanol, ethanol, isopropanol, diethyl ether, ethyl acetate, tetrahydrofuran, acetonitrile, dioxane, dimethylformamide and dimethylsulfoxide, with an acid, preferably selected from the group consisting of acetic acid, trifluoroacetic acid, hydrochloric acid and sulfuric acid, or a Lewis acid, preferably selected from the group consisting of trimethylsilyl chloride, boron tribromide, boron trifluoride etherate, trimethylaluminium and aluminium trichloride, at temperatures of from preferably 0° C. to 100° C. to give compounds of formula (VII).

Stage (c)—In stage (c) compounds of formula (VII) are reacted in at least one solvent, preferably selected from the group consisting of water, methanol, ethanol, isopropanol, diethyl ether, tetrahydrofuran, toluene, acetonitrile, dimethylformamide, dioxane and dimethylsulfoxide, with an inorganic base, preferably selected from the group consisting of lithium hydroxide, sodium hydroxide, potassium hydroxide, potassium tert-butanolate, lithium propanethiolate and sodium phenylselenolate, optionally with the addition of HMPA or lithium chloride, or with a Lewis acid, preferably selected from the group consisting of trimethylsilyl chloride, boron tribromide and aluminium trichloride, optionally with the addition of thiolene, sodium iodide or lithium chloride, at temperatures of from preferably 0° C. to 100° C. to give compounds of formula (VIII).

Stage (d)—In stage (d), compounds of formula (IX) are prepared analogously to stage (a).

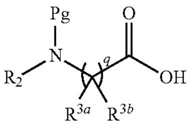

(III)

or

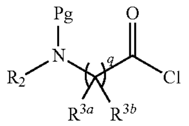

(IV)

+

-continued

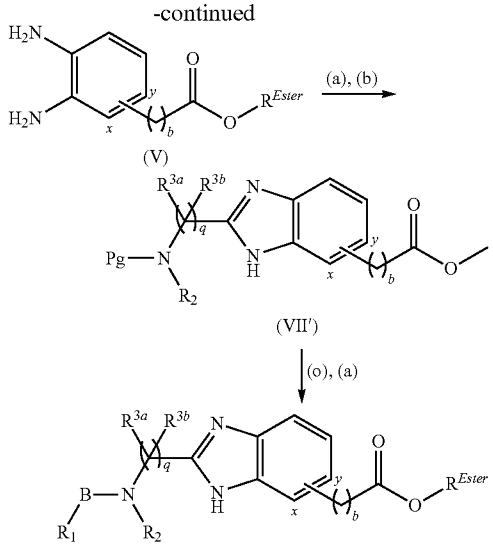

(V) (VII') (VIII')

Compounds of formula (VIII') can also be prepared from (III) or (IV) in accordance with the sequence shown above, and converted further into (IX).

General Process for the Preparation of Spiro-Amines

Educts of formula (XIII), (XX) and (XXXIII) either are commercially obtainable or can be synthesized by conventional methods known to persons skilled in the art. In stage (o), the amine-protecting group (Pg) is split off from the corresponding compounds by a method known from the literature (cf. (a) Protecting Groups, Philip J. Kocienski, Thieme, Stuttgart; 3rd revised edition (14 Feb. 2005) (b) Protective Groups in Organic Synthesis, Theodora W. Greene and Peter G. M. Wuts, Wiley & Sons; 4th edition (30 Oct. 2006)). In particular, for Pg=Boc: In stage (o), the corresponding compounds are reacted in at least one solvent, preferably selected from the group consisting of water, methanol, ethanol, isopropanol, diethyl ether, tetrahydrofuran, acetonitrile, dioxane, dimethylformamide and dimethylsulfoxide, with an acid, preferably selected from the group consisting of trifluoroacetic acid, sulfuric acid and hydrochloric acid, or acetyl chloride/methanol, at temperatures of from preferably 0° C. to 80° C. to give the corresponding deprotected compounds.

Part 2—General Process for the Preparation of the Amines (XV), (XVII) and (XIX)

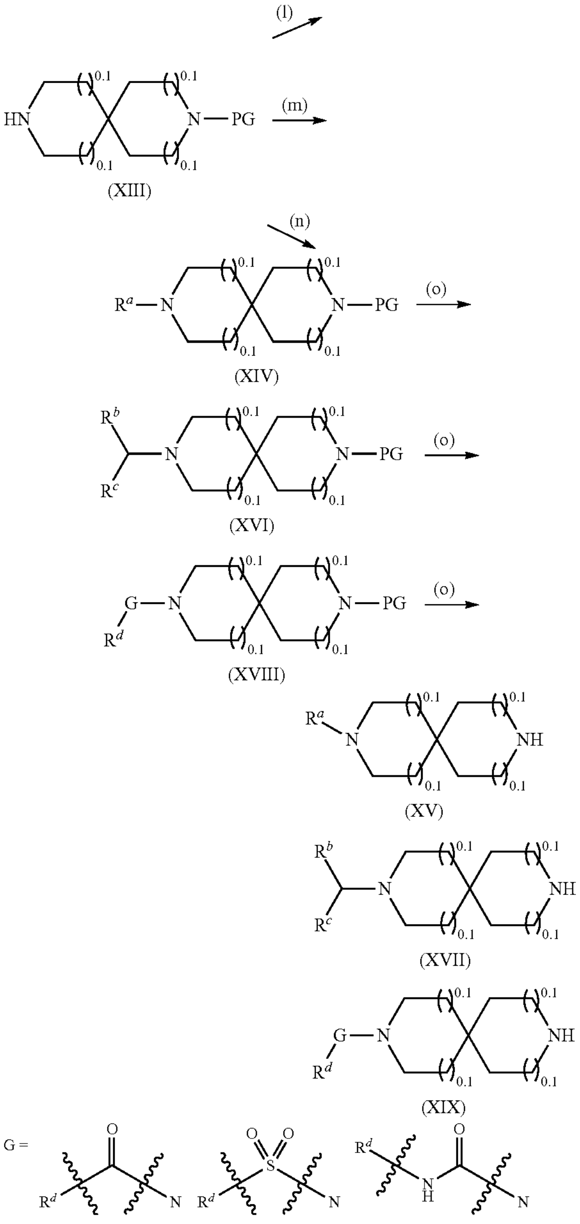

(XIII)
(XIV)
(XVI)
(XVIII)
(XV)
(XVII)
(XIX)
G =

Equation 2: Preparation of the Amines (XV), (XVII) and (XIX)

In stage (l), compounds of formula (XIII) are reacted in at least one solvent, preferably selected from the group consisting of ethanol, methanol, n-butanol, iso-propanol, 2-butanone, DMSO, diethyl ether, water, benzene, toluene, THF, MC, acetonitrile, acetone, DMF and pentane, with boronic acids, iodide, bromide, chloride or mesylate compounds, optionally with the addition of at least one base, preferably selected from the group consisting of potassium hydroxide, sodium hydroxide, optionally in aqueous or alcoholic solution, potassium carbonate, potassium hexamethyldisilazane, sodium hydride, potassium hydride, sodium methanolate, sodium ethanolate, sodium tert-butylate and diisopropylethylamine, optionally with the addition of an auxiliary substance, preferably selected from the group consisting of 18-crown-6, 15-crown-5, tetrabutylammonium bromide or sulfate, benzyltriethylammonium chloride, 1-n-butyl-3-methylimidazolium tetrafluoroborate and DMAP, optionally using a catalyst, preferably selected from the group consisting of Pd(Pcyclohexyl$_3$)$_2$Cl$_2$, Pd$_2$(dba)$_3$, Ni(OAc)$_2$. Cu(OAc)$_2$, optionally using a ligand, preferably selected from the group consisting of P(o-tolyl)$_3$, P(1,1'-bis(diphenylphosphino)ferrocene, 2,2'-bipyridine, P(tri-o-tolylphosphine)$_3$, to give compounds of formula (XIV).

Compounds of formula (XIV) are furthermore obtained by reaction of compounds of formula (XIII) with iodide, bromide, chloride or mesylate compounds under Buchwald-Hartwig conditions.

In stage (m), compounds of formula (XIII) are reacted with aldehydes of formula $R^b$CHO or ketones of formula $R^b$COR$^C$, wherein $R^b$ and $R^c$ have the abovementioned meanings, in at least one solvent, preferably from the group consisting of diethyl ether, tetrahydrofuran, methanol, ethanol, dichloroethane, methylene chloride and toluene, with the addition of at least one reducing agent, preferably from the group consisting borane-pyridine complex, sodium borohydride, sodium triacetoxyborohydride, sodium cyanoborohydride and triethylsilane, optionally in the presence of at least one acid, preferably selected from the group consisting of formic acid, acetic acid, hydrochloric acid and trifluoroacetic acid, at temperatures of from preferably −70 to 100° C. to give compounds of formula (XVI).

In stage (n), amines of formula (XIII) are reacted in at least one solvent, preferably selected from the group consisting of methylene chloride, acetonitrile, dimethylformamide, diethyl ether, dioxane, tetrahydrofuran, methanol, ethanol and isopropanol, with acid chlorides $R^d$COCl, or sulfonyl chlorides $R^d$SO$_2$Cl, or isocyanates $R^d$NCO, wherein $R^d$ has the abovementioned meaning, in the presence of at least one inorganic base, preferably selected from the group consisting of potassium carbonate and cesium carbonate, or an organic base, preferably selected from the group consisting of triethylamine, diisopropylethylamine and pyridine, and optionally with the addition of 4-(dimethylamino)pyridine or 1-hydroxybenzotriazole, at temperatures of from preferably −15° C. to 50° C. to give compounds with the general formula (XVIII).

In stage (n), instead of the carboxylic acid chlorides the corresponding carboxylic acids can optionally also be employed. These acids of formula $R^d$CO$_2$H, wherein $R^d$ has the abovementioned meaning, are reacted in at least one solvent, preferably selected from the group consisting of methylene chloride, acetonitrile, dimethylformamide, diethyl ether, dioxane and tetrahydrofuran, with amines (XIII), with the addition of at least one coupling reagent, preferably selected from the group consisting of carbonyldiimidazole (CDI), 2-chloro-1-methylpyridinium iodide (Mukaiyama reagent), N-(3-dimethylaminopropyl)-N'-ethylcarbodiimide (EDCl), O-(benzotriazol-1-yl)-N,N,N',N'-tetramethyluronium tetrafluoroborate (TBTU), N,N'-dicyclohexylcarbodiimide (DCC) and 1-benzotriazolyloxy-tris-(dimethylamino)-phosphonium hexafluorophosphate (BOP), optionally in the presence of at least one inorganic base, preferably selected from the group consisting of potassium carbonate and cesium carbonate, or an organic base, preferably selected from the group consisting of triethylamine, diisopropylethylamine and pyridine, and optionally with the addition of 4-(dimethylamino)pyridine or 1-hydroxybenzotriazole, to give compounds with the general formula (XVIII).

Stage (o)—See above.

Part 3—General Process for the Preparation of the Amines (XXII), (XXV), (XXVIII), (XXXI) and (XXXII)

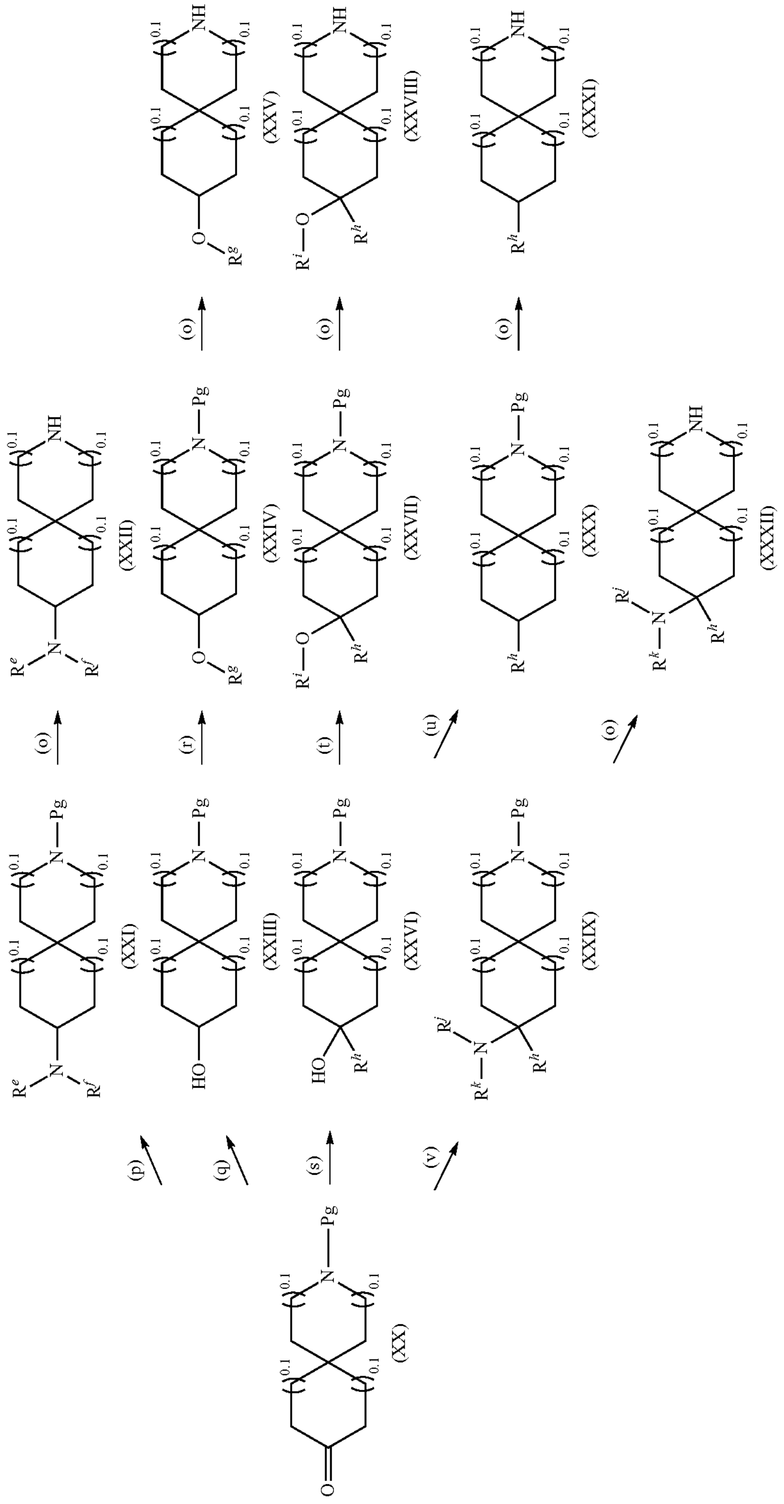
(XX)
(p)
(q)
(s)
(v)
(XXI)
(XXIII)
(XXVI)
(XXIX)
(o)
(r)
(t)
(u)
(o)
(XXII)
(XXIV)
(XXVII)
(XXX)
(XXXII)
(o)
(o)
(o)
(XXV)
(XXVIII)
(XXXI)

Equation 3: Preparation of the Amines (XXII), (XXV), (XXVIII), (XXXI) and (XXXII)

In stage (p), compounds of formula (XX) are reacted with amines of formula $R^eNHR^f$, wherein $R^e$ and $R^f$ have the abovementioned meanings, in at least one organic solvent, preferably from the group consisting of diethyl ether, tetrahydrofuran, methanol, ethanol, dichloroethane, methylene chloride and toluene, with the addition of at least one reducing agent, preferably from the group consisting borane-pyridine complex, sodium borohydride, sodium triacetoxyborohydride, sodium cyanoborohydride and triethylsilane, optionally in the presence of at least one acid, preferably selected from the group consisting of formic acid, acetic acid, hydrochloric acid and trifluoroacetic acid, at temperatures of from preferably −70° C. to 100° C. to give compounds of formula (XXI).

In stage (q), compounds of formula (XX) are reacted in at least one organic solvent, preferably from the group consisting of diethyl ether, tetrahydrofuran, methanol, ethanol, dichloroethane, methylene chloride and toluene, with the addition of at least one reducing agent, preferably from the group consisting of lithium aluminium hydride, RedAl® (sodium bis(2-methoxyethoxy)aluminium hydride), lithium tri-tert-butoxyaluminium hydride, sodium borohydride, sodium triacetoxyborohydride, sodium cyanoborohydride, diborane, Selectride® and triethylsilane, optionally in the presence of at least one acid, preferably selected from the group consisting of formic acid, acetic acid, hydrochloric acid and trifluoroacetic acid, at temperatures of from preferably −25° C. to 100° C. to give compounds of formula (XXIII).

In stage (r), compounds of formula (XXIII) are converted, by introduction of a suitable leaving group, such as, for example, halogen or mesylate, and subsequent reaction with alcohols, into compounds of formula (XXIV). Compounds of formula (XXII) are reacted in at least one solvent, preferably selected from the group consisting of methylene chloride, dioxane, diethyl ether, tetrahydrofuran, acetonitrile and dimethylformamide, with a sulfonyl chloride, preferably selected from the group consisting of methylsulfonyl chloride, trifluoromethylsulfonyl chloride, tolylsulfonyl chloride, and at least one base, preferably selected from the group consisting of cesium carbonate, calcium carbonate, potassium carbonate, triethylamine, diisopropylethylamine and pyridine, at temperatures of from preferably 0° C. to 80° C. into the corresponding mesylates. These are reacted in at least one solvent, preferably selected from the group consisting of methylene chloride, dioxane, diethyl ether, tetrahydrofuran, acetonitrile, toluene and dimethylformamide, with a suitable alcohol in the presence of an excess of a base, preferably selected from the group consisting of cesium carbonate, calcium carbonate, potassium carbonate, potassium bicarbonate, sodium bicarbonate, triethylamine, diisopropylethylamine and pyridine, at temperatures of from preferably 0 to 80° C. to give compounds of formula (XXIV).

Alternatively, in stage (r), compounds of formula (XXIV) can be prepared from compounds of formula (XXIV) in a Mitsunobu reaction.

Stage (r) can moreover be carried out analogously to stage (t).

In stage (s), the carbonyl compounds (XX) are reacted with metal organyls, typically Li or Mg organyls (Grignard), in solvents, such as, for example, toluene, benzene, hexane, pentane, THF or diethyl ether, optionally with the addition of, for example, $CeCl_3$, to give the tertiary alcohols (XXVI).

In stage (t), in a substitution reaction alcohols of formula (XXVI) are dissolved in a suitable solvent, such as, for example, ethanol, methanol, n-butanol, iso-propanol, 2-butanone, DMSO, diethyl ether, water, benzene, toluene, THF, MC, acetonitrile, acetone, DMF or pentane or a mixture of these solvents, and a suitable base is added, such as, for example, potassium hydroxide, sodium hydroxide, optionally in aqueous or alcoholic solution, potassium carbonate, potassium hexamethyldisilazane, sodium hydride, potassium hydride, sodium methanolate, sodium ethanolate, sodium tert-butylate or diisopropylethylamine, optionally with the addition of an auxiliary substance, such as, for example, 18-crown-6,15-crown-5, tetrabutylammonium bromide or sulfate, benzyltriethylammonium chloride, 1-n-butyl-3-methylimidazolium tetrafluoroborate or DMAP, and the reaction is carried out with an iodide, bromide, chloride or mesylate compound.

In stage (u), compounds of formula (XXI) are reacted in at least one solvent, preferably selected from the group consisting of methanol, ethanol, isopropanol, methylene chloride, dioxane, diethyl ether, dimethylsulfoxide, tetrahydrofuran, acetonitrile and dimethylformamide, in the presence of at least one acid, preferably selected from the group consisting of formic acid, acetic acid hydrochloric acid, sulfuric acid and trifluoroacetic acid, at temperatures of from preferably 0 to 100° C.

The unsaturated systems formed by this procedure are reduced to the compounds of formula (XXX) by a method known to the person skilled in the art. In stage (v), compounds of formula (XXIX) are converted by Method A or Method B into compounds of formula (XXXII).

Method A: Compounds of formula (XXIX) are reacted in an aminal formation reaction by reaction with an amine and 1H-benzotriazole to give the benzotriazole aminal, it being known to the person skilled in the art that the benzotriazole aminal can exist in equilibrium both in the 1H and in the 2H form. Suitable solvents are, for example, benzene, toluene, ethanol, diethyl ether or THF. The use of a Dean-Stark water separator, a molecular sieve or other dehydrating means may be necessary. The reaction time can be between 1 and 20 h at a reaction temperature of from +20° C. to +110° C. The benzotriazole aminal obtained as the intermediate product is then reacted with metal organyls, such as magnesium, zinc or lithium organyls, in organic solvents, for example diethyl ether, dioxane or THF, to give compounds of formula (XXXII).

Method B: Compounds of formula (XXIX) are reacted by addition of an amine and a source of cyanide to give nitrile-amines. This reaction can be carried out in one or two stages. In the two-stage variant, a nitrile-alcohol is first formed and isolated. The formation of the nitrile alcohol can be carried out by reaction of compounds of formula (XXIX) with HCN, KCN or NaCN as the source of cyanide, if NaCN and KCN are used the required cyanide being liberated by the addition of, for example, sodium hydrogen sulfite, sulfuric acid, acetic acid or hydrochloric acid. Preferred solvents are water, methanol, ethanol, THF, piperidine, diethyl ether or a mixture of these solvents. Trimethylsilyl cyanide, for example, is likewise suitable as a source of cyanide; the cyanide can be liberated, for example, by boron trifluoride etherate, $InF_3$ or HCl. Preferred solvents are water or toluene. (Cyano-C)diethylaluminium, for example, is suitable as a further source of cyanide. THF, toluene or a mixture of the two solvents can be used as the solvent. The reaction temperature for all the variants is preferably between −78° C. and +25° C. Alcohols, such as methanol or ethanol, are particularly suitable as the solvent for the reaction of the nitrile alcohol with the amine to give nitrile-amines. The reaction temperature can be between 0° C. and +25° C. In the one-stage variant, the nitrile alcohol primarily formed is formed in situ and reacted with the amine to give nitrile-amines. The nitrile-amine obtained as the intermediate product is then reacted with metal organyls, such as magnesium, zinc or lithium organyls, in organic solvents, for example diethyl ether, dioxane or THF, to give compounds of formula (XXXII).

Stage (o)—See above.

Part 4—General Process for the Preparation of the Amines (XXXVI), (XXXVIII), (XLI) and (XLIV)

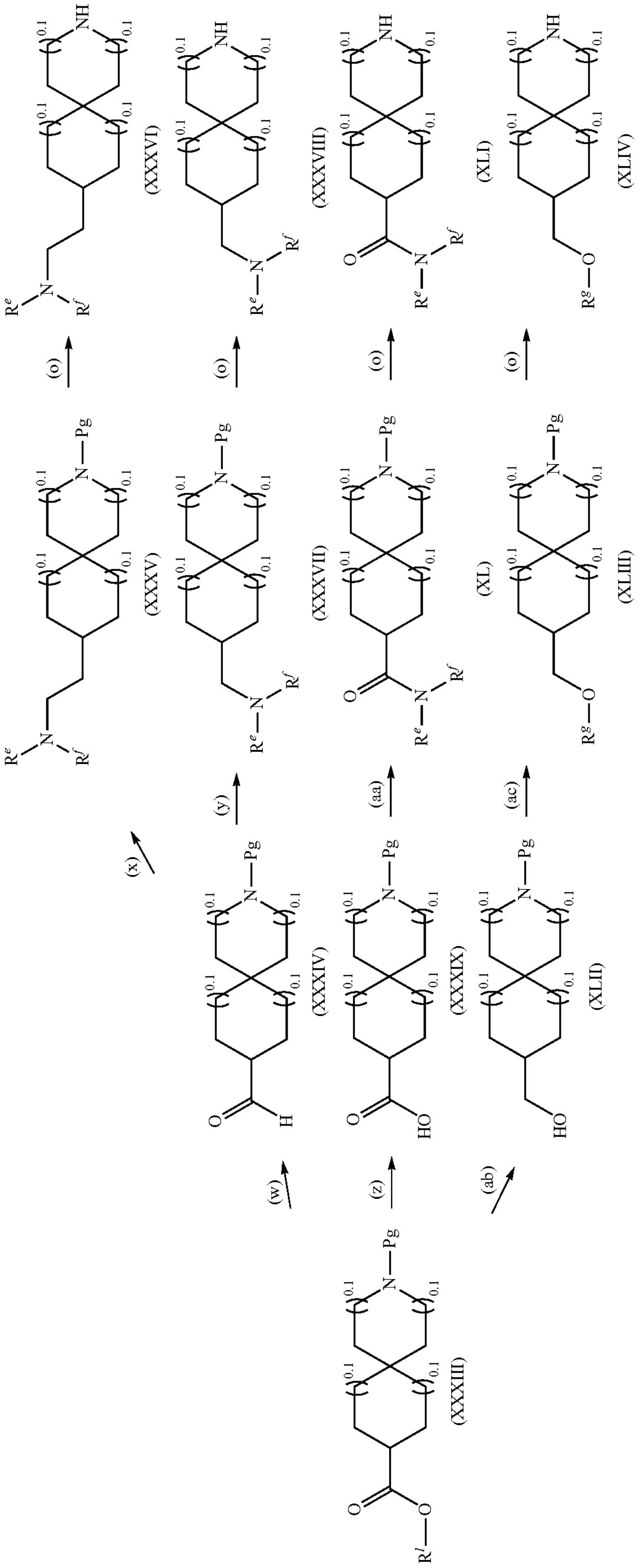
(XXXIII)
(w)
(z)
(ab)
(XXXIV)
(XXXIX)
(XLII)
(x)
(y)
(aa)
(ac)
(XXXV)
(XXXVII)
(XL)
(XLIII)
(o)
(o)
(o)
(o)
(XXXVI)
(XXXVIII)
(XLI)
(XLIV)

Equation 4: Preparation of the Amines (XXXVI), (XLI) and (XLIV)

In stage (w), the ester of formula (XXXIII) is reduced by a method known to the person skilled in the art to give the aldehyde of formula (XXXIV), or the corresponding alcohol is oxidized by a method known to the person skilled in the art to give the aldehyde of formula (XXXIV).

In stage (x), aldehydes of formula (XXXIV) are first reacted by methods known to the person skilled in the art in a Wittig reaction with (methoxymethyl)triphenyl-phosphonium chloride, and a strong base, for example potassium tert-butylate, n-butyllithium, s-butyllithium, phenyllithium, lithium diisopropylamide or lithium hexamethyldisilazide, in organic solvents, for example THF, diethyl ether, cyclohexane, toluene or corresponding mixtures. The aldehydes obtained in this way are then reacted with amines of formula $R^eNHR^f$ analogously to stage (y) to give compounds of formula (XXXV).

In stage (y), compounds of formula (XXXIV) are reacted with amines of formula $R^eNHR^f$, wherein $R^e$ and $R^f$ have the abovementioned meanings, in at least one organic solvent, preferably from the group consisting of diethyl ether, tetrahydrofuran, methanol, ethanol, dichloroethane, methylene chloride and toluene, with the addition of at least one reducing agent, preferably from the group consisting borane-pyridine complex, sodium borohydride, sodium triacetoxyborohydride, sodium cyanoborohydride and triethylsilane, optionally in the presence of at least one acid, preferably selected from the group consisting of formic acid, acetic acid, hydrochloric acid and trifluoroacetic acid, at temperatures of from preferably −70° C. to 100° C. to give compounds of formula (XXXVII).

In stage (z), compounds of formula (XXXIII) are reacted analogously to the methods described for stage (i) to give compounds of formula (XXXIX).

In stage (aa), compounds of formula (XXXIX) are reacted in at least one solvent, preferably selected from the group consisting of methylene chloride, acetonitrile, dimethylformamide, diethyl ether, dioxane and tetrahydrofuran, with amines of formula $R^eNHR^f$, wherein $R^e$ and $R^f$ have the abovementioned meanings, with the addition of at least one coupling reagent, preferably selected from the group consisting of carbonyldiimidazole (CDI), 2-chloro-1-methylpyridinium iodide (Mukaiyama reagent), N-(3-dimethylaminopropyl)-M-ethylcarbodiimide (EDCl), O-(benzotriazol-1-yl)-N,N,N',N'-tetramethyluronium tetrafluoroborate (TBTU), N,N'-dicyclohexylcarbodiimide (DCC) and 1-benzotriazolyloxy-tris-(dimethylamino)-phosphonium hexafluorophosphate (BOP), optionally in the presence of at least one inorganic base, preferably selected from the group consisting of potassium carbonate and cesium carbonate, or an organic base, preferably selected from the group consisting of triethylamine, diisopropylethylamine and pyridine, and optionally with the addition of 4-(dimethylamino)pyridine or 1-hydroxybenzotriazole, to give compounds with the general formula (XL). In stage (aa), compounds of formula (XXXIX) are optionally reacted in at least one solvent, preferably selected from the group consisting of methylene chloride, acetonitrile, dimethylformamide, diethyl ether, dioxane and tetrahydrofuran, using at least one coupling reagent, preferably selected from the group consisting of thienyl chloride, oxalyl chloride and phosphoryl chloride, in the presence of at least one inorganic base, preferably selected from the group consisting of potassium carbonate and cesium carbonate, or an organic base, preferably selected from the group consisting of triethylamine, diisopropylethylamine and pyridine, with amines of formula $R^eNHR^f$, wherein $R^e$ and $R^f$ have the abovementioned meanings, to give compounds with the general formula (XL).

In stage (ab), carboxylic acid esters or carboxylic acids of formula (XXXIII) are reacted using suitable reducing agents, such as, for example, $LiBH_4$, $LiAlH_4$, Dibal-H, $BF_3$ etherate, $BH_3$×DMS or $NaBH_4$, optionally with the addition of auxiliary reagents, such as, for example, boric acid esters, in an organic solvent, such as THF, MC, toluene, methanol, ethanol, DME, hexane, diethyl ether or mixtures of these solvents, at temperatures of from 0° C. to the reflux temperature, in a reduction to the alcohols of formula (XLI).

In stage (ac), compounds of formula (XXXLII) are reacted analogously to the methods described for stages (r) and (t) to give compounds of formula (XXXLIII).

Stage (o)—See above.

Pharmacological Methods

1. Functional Investigation on the Bradykinin Receptor 1 (B1R)

The agonistic or antagonistic action of substances can be determined on the bradykinin receptor 1 (B1R) of the human and rat species with the following assay. In accordance with this assay, the $Ca^{2+}$ inflow through the channel is quantified with the aid of a $Ca^{2+}$-sensitive dyestuff (type Fluo-4, Molecular Probes Europe BV, Leiden Holland) in a fluorescent imaging plate reader (FLIPR, Molecular Devices, Sunnyvale, USA).

2. Method:

Chinese hamster ovary cells (CHO K1 cells) transfected stably with the human B1R gene (hB1R cells) or the B1R gene of the rat (rB1R cells) are used. For functional studies, these cells are plated out on black 96-well plates with a clear base (BD Biosciences, Heidelberg, Germany or Greiner, Frickenhausen, Germany) in a density of 20,000-35,000 cells/well. The cells are left overnight at 37° C. and 5% $CO_2$ in culture medium (hB1R cells: Nutrient Mixture Ham's F12, Gibco Invitrogen GmbH, Karlsruhe, Germany or DMEM, Sigma-Aldrich, Taufkirchen, Germany; rB1R cells: D-MEM/F12, Gibco Invitrogen GmbH, Karlsruhe, Germany) with 10 vol. % FBS (foetal bovine serum, Gibco Invitrogen GmbH, Karlsruhe, Germany or PAN Biotech GmbH, Aidenbach, Germany). On the following day, the cells are loaded for 60 min at 37° C. with 2.13 μM Fluo-4 (Molecular Probes Europe BV, Leiden Holland) in HBSS buffer (Hank's buffered saline solution, Gibco Invitrogen GmbH, Karlsruhe, Germany) with 2.5 mM probenecid (Sigma-Aldrich, Taufkirchen, Germany) and 10 mM HEPES (Sigma-Aldrich, Taufkirchen, Germany). The plates are then washed 2× with HBSS buffer, and HBSS buffer which additionally contains 0.1% BSA (bovine serum albumin; Sigma-Aldrich, Taufkirchen, Germany), 5.6 mM glucose and 0.05% gelatine (Merck KGaA, Darmstadt, Germany) is added. After a further incubation of 20 minutes at room temperature, the plates are inserted into the FLIPR for the $Ca^{2+}$ measurement.

Alternatively, the plates are washed with buffer A (15 mM HEPES, 80 mM NaCl, 5 mM KCl, 1.2 mM $CaCl_2$, 0.7 mM $MgSO_4$, 2 g/l glucose, 2.5 mM probenecid), buffer A is added and the plates are loaded with 2.5 μM Fluo-4 and 0.025% Pluronic F127 (Sigma-Aldrich, Taufkirchen, Germany). Thereafter, the cells are washed 2× with buffer A and incubated for 30 minutes at room temperature with buffer A, which additionally contains 0.05% BSA and 0.05% gelatine, and thereafter inserted into the FLIPR for the $Ca^{2+}$ measurement.

The $Ca^{2+}$-dependent fluorescence is measured here before and after addition of substances ($\lambda_{ex}$=488 nm, $\lambda_{em}$=540 nm).

Quantification is by measurement of the highest fluorescence intensity (FC, fluorescence counts) over time.

3. FLIPR Assay:

The FLIPR protocol consists of 2 additions of substance. Test substances (10 μM) are first pipetted on to the cells and the $Ca^{2+}$ inflow is compared with the control (hB1R: Lys-Des-$Arg^9$-bradykinin>=50 nM; rB1R: Des-$Arg^9$-bradykinin 10 μM). This gives the result in % activation based on the $Ca^{2+}$ signal after addition of Lys-Des-$Arg^9$-bradykinin (>=50 nM) or Des-$Arg^9$-bradykinin (10 μM). After incubation for 10-20 minutes, Lys-Des-$Arg^9$-bradykinin (hB1R) or Des-$Arg^9$-bradykinin (rB1R) in the concentration of the $EC_{80}$ is applied and the inflow of $Ca^{2+}$ is likewise determined. Antagonists lead to a suppression of the $Ca^{2+}$ inflow. % inhibition compared with the maximum achievable inhibition is calculated.

In order to determine the $IC_{50}$ value, the substances are added in various concentrations. Duplicate or triplicate determinations (n=2 or n=3) are carried out, and these are repeated in at least one further independent experiment (N>=2).

The compounds preferably have a B1R-antagonistic action on the human receptor and/or on the rat receptor.

The invention is explained in further detail hereinafter with reference to illustrative examples, without limiting the scope of the general inventive idea.

EXAMPLES

List of abbreviations

DIBAL-H=diisobutylaluminum hydride

BOP=1-benzotriazolyloxy-tris-(dimethylamino)-phosphonium hexafluorophosphate eq. equiv.=equivalents h=hours d=days min=minutes Boc=tert-butoxycarbonyl Cbz=benzyloxycarbonyl DMSO=dimethylsulfoxide THF=tetrahydrofuran MC=methylene chloride MeOH=methanol DMF=dimethylformamide TFA=trifluoroacetic acid wt. %=percent by weight conc.=concentrated sat.=saturated R.t.=retention time RT=room temperature The chemicals and solvents employed were obtained commercially from conventional suppliers (Acros, Aldrich, Fluka, Lancaster, Maybridge, TCI, Fluorochem, Tyger, ABCR, Fulcrum, FrontierScientific, Milestone etc.). The reactions were carried out in some cases under inert gas (nitrogen). The yields of the compounds prepared are not optimized. The mixing ratios of solvents are always stated in volume/volume ratio. The equivalent amounts of reagents employed and the amounts of solvent and reaction temperatures and times can vary slightly between different reactions carried out by the same method. Work-up and purification methods were adapted according to the characteristic properties of the compounds.

Syntheses of Units

A: Synthesis of the Acid Units

1) Universal Units

Synthesis of 2,3-diamino-benzoic acid methyl ester (D-01)

Figure 1: Synthesis of diamine (D-01)

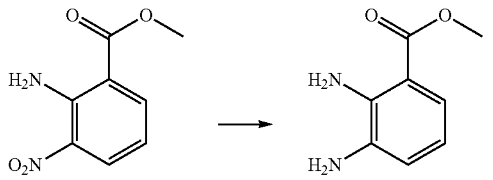

2-Amino-3-nitro-benzoic acid methyl ester (50.7 g, 258.7 mmol) was suspended in methanol (441 ml) and ethyl acetate (441 ml) with palladium-on-active charcoal 10% (1.93 g, 1.81 mmol). The suspension was hydrogenated at room temperature under an $H_2$ pressure of 2.5 bar. When the reaction was complete, the suspension was filtered over Celite and the residue was rinsed with ethyl acetate. The filtrate was concentrated to dryness under reduced pressure, the residue was dissolved in ethyl acetate (50 ml) and hexane (50 ml) was added. After addition of starting crystals, a precipitate precipitated out. Hexane (200 ml) was added to the suspension and the precipitate was filtered off, washed with hexane and dried in vacuo. Methyl 2,3-diaminobenzoate (D-01) was obtained (35.8 g, 83%).

Synthesis of 3.4-diamino-benzoic acid ethyl ester (D-02)

Commercially obtainable e.g. from Acros [37466-90-3]

Synthesis of 2,3-diamino-6-fluoro-benzoic acid ethyl ester (D-03)

Cf. synthesis of benzimidazole ester F-20 stage (I).

2) Synthesis of the Amides or Sulfonamides C

General Method for Synthesis of the Sulfonamides (C)

Figure 2: Synthesis of the sulfonamides (C)

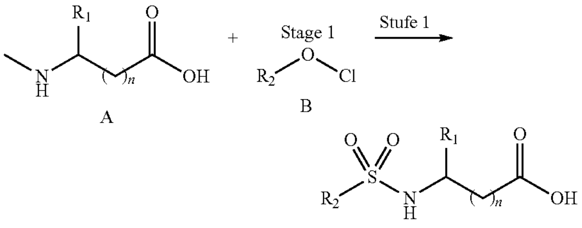

A
B
C

General working instructions 1 (GWI-1): The corresponding amino acid (A) (1.5 eq.) was suspended in ethanol, N-ethyl-diisopropylamine (3 eq.) and the sulfonyl chloride (B) (1 eq.) were added and the mixture was stirred under an $N_2$ atmosphere at room temperature overnight. When the reaction was complete (TLC control), the ethanol was distilled off, the residue was taken up in methylene chloride and the mixture was washed 4× with 2 M aqueous HCl. The organic phase was dried over $Na_2SO_4$ and concentrated to dryness in order to obtain the crude product (C).

TABLE 1

Synthesis of the sulfonamides (C)

| C no. | Structure | Sulfonic acid (C) | Amino acid (A) | Sulfonyl chloride (B) | Synthesis analogous to: | Yield | Comments |
|---|---|---|---|---|---|---|---|
| C-01 | 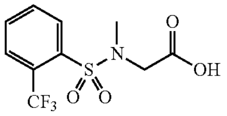 | 2-[methyl-[[2-(trifluoromethyl) phenyl]sulfonyl]-amino]-acetic acid (C-01) | 2-methylamino-acetic acid (A-01) | 2-(trifluoromethyl)-benzenesulfonyl chloride (B-01) | GWI-1 | 59% (36.2 mmol) | — |
| C-02 | 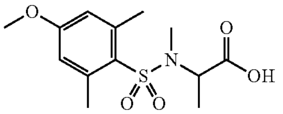 | 2-[[(4-methoxy-2,6-dimethyl-phenyl)sulfonyl]-methyl-amino]-propionic acid (C-02) | 2-methylamino-propionic acid (A-02) | 4-methoxy-2,6-dimethyl-benzenesulfonyl chloride (B-02) | GWI-1 | 64% (19.1 mmol) | 2.5 eq. amino acid-purification by acid/ base extraction |
| C-03 | 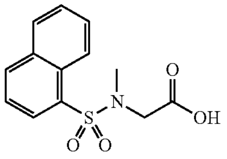 | 2[methyl-(naphthalen-1-ylsulfonyl)-amino]-acetic acid (C-03) | 2-methylamino-acetic acid (A-01) | naphthalene-1-sulfonyl chloride (B-03) | GWI-1 | 97% (64.0 mmol) | — |
| C-04 | 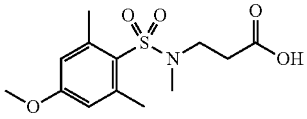 | 3-[[(4-methoxy-2,6-dimethyl-phenyl)sulfonyl]-methyl-amino]-propionic acid (C-04) | 3-methylamino-propionic acid (A-03) | 4-methoxy-2,6-dimethyl-benzenesulfonyl chloride (B-02) | GWI-1 | 80% (823 mmol) | purification by column chromatography (silica; ethyl acetate/hexane) |
| C-05 | 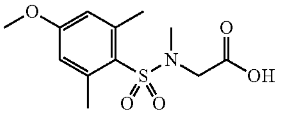 | 2-[[(4-methoxy-2,6-dimethyl-phenyl)sulfonyl]-methyl-amino]-acetic acid (C-05) | 2-methylamino-acetic acid (A-01) | 4-methoxy-2,6-dimethyl-benzenesulfonyl chloride (B-02) | GWI-1 | 77% (22.2 mmol) | — |
| C-06 | 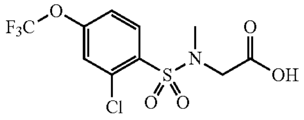 | 2-[[[2-chloro-4-(trifluoromethyloxy)-phenyl]sulfonyl]-methyl-amino]-acetic acid (C-06) | 2-methylamino-acetic acid (A-01) | 2-chloro-4-(trifluoromethyloxy)-benzenesulfonyl chloride (B-04) | GWI-1 | 92% (4.23 mmol) | — |
| C-07 | 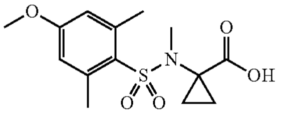 | 1-[[(4-methoxy-2,6-dimethyl-phenyl)sulfonyl]-methyl-amino]-cyclopropane-1-carboxylic acid (C-07) | 1-methylamino-cyclopropane-1-carboxylic acid (A-04) | 4-methoxy-2,6-dimethyl-benzenesulfonyl cloride (B-02) | GWI-1 | 17% (0.447 mmol) | 1 eq. amino acid and 0.9 eq. sulfonyl chloride purification; acid/base extraction |
| C-08 | 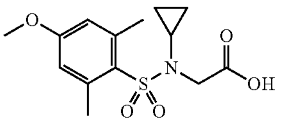 | 2-[cyclopropyl-[(4-methoxy-2,6-dimethyl-phenyl) sulfonyl]-amino]-acetic acid (C-08) | | | | 83% | see below (I-14) |
| C-09 | 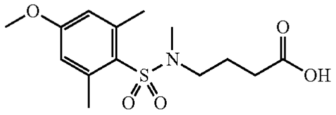 | 2-[[(4-methoxy-2,6-dimethyl-phenyl)sulfonyl]-methyl-amino]-butytic acid (C-09) | 4-methylamino-butyric acid (A-06) | 4-methoxy-2,6-dimethyl-benzenesulfonyl chloride (B-02) | GWI-1 | 39% (19.8 mmol) | 2 eq. amino acid purification by column chromatography (silica; methylene chloride/ methanol) |
| C-17 | 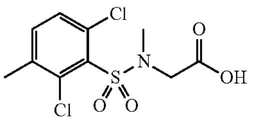 | 2-[[(2,6-dichloro-3-methyl-phenyl)sulfonyl]-methyl-amino]-acetic acid (C-17) | 2-methylamino-acetic acid (A-01) | 2,6-dichloro-3-metyl-benzenesulfonyl chloride (B-07) | GWI-1 | 82% (3.17 mmol) | 30 min reaction time purification: acid/base extraction |

TABLE 1-continued

Synthesis of the sulfonamides (C)

| C no. | Structure | Sulfonic acid (C) | Amino acid (A) | Sulfonyl chloride (B) | Synthesis analogous to: | Yield | Comments |
|---|---|---|---|---|---|---|---|
| C-18 | 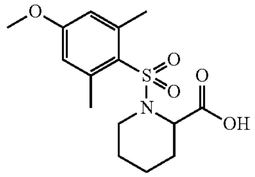 | 1-[(4-methoxy-2,6-dimethyl-phenyl)sulfonyl]-piperidine-2-carboxylic acid (C-18) | piperidine-2-carboxylic acid (A-07) | 4-methoxy-2,6-dimethyl-benzenesulfonyl chloride (B-02) | GWI-1 | 43% (1.68 mmol) | 1 eq. amino acid and 0.9 eq. sulfonyl chloride and 1.2 eq. Hünig's base purification: acid/base extraction |
| C-19 | 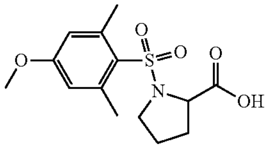 | 1-[(4-methoxy-2,6-dimethyl-phenyl)sulfonyl]-pyridine-2-carboxylic acid (C-19) | pyrrolidine-2-carboxylic acid (A-08) | 4-methoxy-2,6-dimethyl-benzenesulfonyl chloride (B-02) | GWI-1 | 89% (7.75 mmol) | 1 eq. amino acid and 0.9 eq. sulfonyl chloride |

Synthesis of 2-(N-cyclopropyl-4-methoxy-2,6-dimethylphenylsulfonamido)acetic acid (C-08)

Figure 3: Synthesis of 2-(N-cyclopropyl-4-methoxy-2,6-dimethylphenylsulfonamido)acetic acid (C-08)

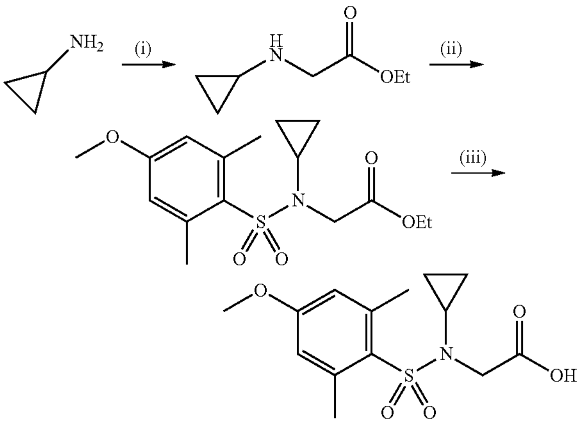

C-08

Stage (i): Ethyl 2-(cyclopropylamino)acetate

Ethyl bromoacetate (1 eq.) was added slowly to an ice-cold mixture of cyclopropylamine (17.5 mmol, 3 eq.) and $K_2CO_3$ (2 eq.) in DMF (25 ml) and the reaction mixture was then stirred at room temperature for 16 h. For working up, the mixture was diluted with water and extracted with 20% ethyl acetate/hexane solution. The organic phase was washed with water and sat. NaCl solution and dried over $Na_2SO_4$. After the solvent had been removed completely, the crude product was employed in the next stage without further purification. Yield: 52%

Stage (ii): Ethyl 2-(N-cyclopropyl-4-methoxy-2,6-dimethylphenylsulfonamido)acetate 4-Methoxy-2,6-dimethylbenzenesulfonyl chloride (1.2 eq. in methylene chloride) was slowly added dropwise to a solution of ethyl 2-(cyclopropylamine)-acetate (8.9 mmol, 1 eq.) and triethylamine (6 eq.) in methylene chloride and the mixture was stirred at room temperature for 16 h. For working up, the reaction mixture was diluted with methylene chloride, washed with water and sat. NaCl and dried over $Na_2SO_4$. After the solvent had been removed completely, the crude product was purified by column chromatography over silica gel. Yield: 30%

Stage (iii): 2-(N-Cyclopropyl-4-methoxy-2,6-dimethylphenylsulfonamido)acetic acid (C-08)

A solution of ethyl 2-(N-cyclopropyl-4-methoxy-2,6-dimethylphenyl-sulfonamido)acetate (2.7 mmol, 1 eq.) and LiOH (5 eq.) in THF/$H_2O$ (1:1) was stirred at room temperature for 12 h. The solvent was removed completely, in vacuo. The crude product was taken up in water and the mixture was washed with ethyl acetate. The aqueous phase was acidified to pH=4 with 1 M HCl and then extracted with ethyl acetate. The organic phase was dried over $Na_2SO_4$. After the solvent had been distilled off completely, the crude product was obtained, and was employed in the next stage without further purification. Yield: 83%

3) Synthesis of the Diaminobenzoates E

General Method for Synthesis of the Diaminobenzoates E

Figure 4: Synthesis of the diaminobenzoates (E)

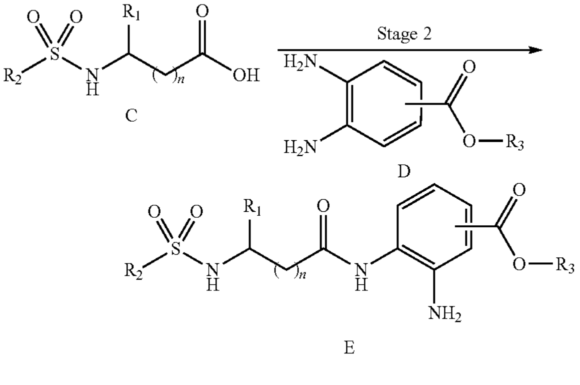

-continued

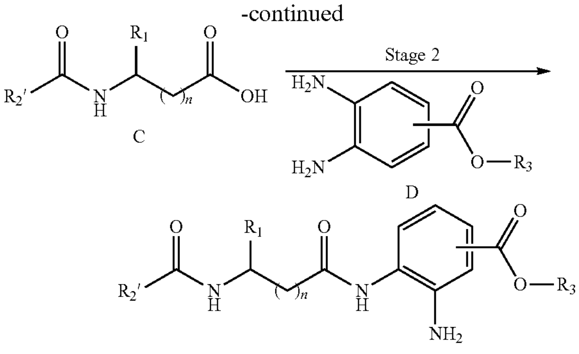

C

D

E

General working instructions 2 (GWI-2): The acid (C) (1 eq.) was dissolved in THF (90 eq.) together with 1-hydroxy-benzotriazole hydrate (1.1 eq.) and N-ethyl-diisopropylamine (2.5 eq.). The mixture was cooled to 0° C. 1-(3-dimethylamino-propyl)-3-ethylcarbodiimide hydrochloride (1.5 eq.) was added at this temperature and the mixture was stirred at 0° C. for 15 min. The corresponding diamine (D) (1.7 eq.) was then added and the mixture was stirred at room temperature overnight. When the reaction was complete (TLC control), sat. $NaHCO_3$ solution and ethyl acetate were added to the reaction mixture and the mixture was stirred for 15 min. The phases were separated and the aqueous phase was extracted 2× with ethyl acetate. The combined organic phases were dried over $Na_2SO_4$, filtered and concentrated to dryness in vacuo. After purification by column chromatography (silica; hexane/ethyl acetate) or recrystallization (hexane/ethyl acetate), the corresponding sulfonamide ester (E) was obtained.

General working instructions 3 (GWI-3): The acid (C) (1 eq.) was dissolved in N,N-dimethylformamide (150 eq.) and 4-methylmorpholine (3 eq.), and benzotriazol-1-yloxytris(dimethylamino)phosphonium hexafluorophosphate (1.3 eq.) was added at room temperature. After stirring for 10 min, the corresponding diamine (D) (1 eq.) was added and stirring was continued at room temperature overnight. For working up, the DMF was evaporated off on a rotary evaporator in vacuo at a water bath temperature of 60° C., the residue was taken up in ethyl acetate and sat. $NaHCO_3$ solution, the phases were separated and the aqueous phase was extracted 2× with ethyl acetate. The combined organic phases were dried over $Na_2SO_4$, filtered and concentrated completely. The crude product was purified by column chromatography (silica; hexane/ethyl acetate) to obtain the desired product (E).

TABLE 2

Synthesis of the diaminobenzoates (E)

| E no. | Structure | Diaminobenzoate (E) | Amide or sulfonamide (C) | Analogous to | Yield | Comments |
|---|---|---|---|---|---|---|
| E-01 | 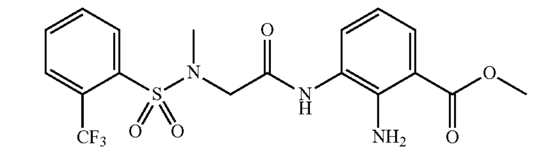 | 2-amino-3-[[2-[methyl-[[2-(trifluoromethyl)-phenyl]sulfonyl]-amino]-acetyl]amino]-benzoic acid methyl ester (E-01) | 2-[methyl-[[2-(trifluoromethyl)phenyl]-sulfonyl]-amino]-acetic acid (C-01) | GWI-2 | 64% (12.3 mmol) | - purification by column chromatography |
| E-02 | 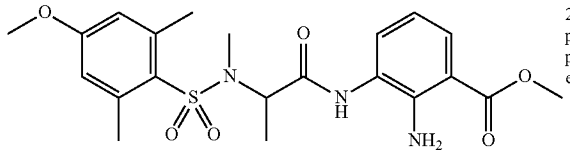 | 2-amino-3-[2-[[(4-methoxy-2,6-dimethyl-phenyl)sulfonyl]-methyl-amino]-propanoylamino]-benzoic acid methyl ester (E-02) | 2-[[(4-methoxy-2,6-dimethyl-phenyl)sulfonyl]-methyl-amino]-propionic acid (C-02) | GWI-2 | 27% (5.14 mmol) | - 1.5 eq. diamine<br>- purification by column chromatography |
| E-03 | 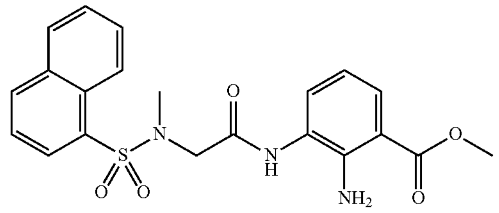 | 2-amino-3-[[2-[methyl-(naphthalen-1-ylsulfonyl)-amino]-acetyl]amino]-benzoic acid methyl ester (E-03) | 2-[methyl-(naphthalen-1-ylsulfonyl)-amino]-acetic acid (C-03) | GWI-2 | 46% (14.6 mmol) | - 1.5 eq. diamine<br>- purification by recrystallization |
| E-04 | 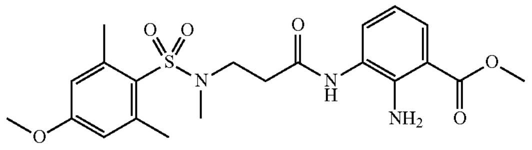 | 2-amino-3-[3-[[(4-methoxy-2,6-dimethyl-phenyl)sulfonyl]-methyl-amino]-propanoylamino]-benzoic acid methyl ester (E-04) | 3-[[(4-methoxy-2,6-dimethyl-phenyl)sulfonyl]-methyl-amino]-propionic acid (C-04) | GWI-2 | 124% (13.1 mmol) | - purification by column chromatography |
| E-05 | 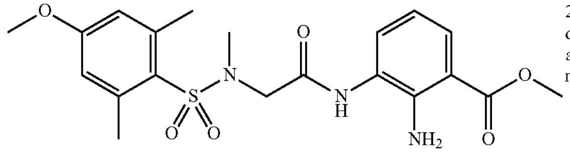 | 2-amino-3-[[2-[[(4-methoxy-2,6-dimethyl-phenyl)sulfonyl]-methyl-amino]-acetyl]amino]-benzoic acid methyl ester (E-05) | 2-[[(4-methoxy-2,6-dimethyl-phenyl)sulfonyl]-methyl-amino]-acetic acid (C-05) | GWI-2 | 77% (15.3 mmol) | - purification by recrystallization |

TABLE 2-continued

Synthesis of the diaminobenzoates (E)

| E no. | Structure | Diaminobenzoate (E) | Amide or sulfonamide (C) | Analogous to | Yield | Comments |
|---|---|---|---|---|---|---|
| E-06 | 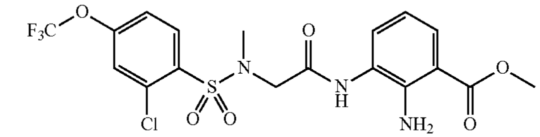 | 2-amino-3-[[2-[[[2-chloro-4-(trifluoromethyloxy)-phenyl]sulfonyl]-methyl-amino]-acetyl]amino]-benzoic acid methyl ester (E-06) | 2-[[[2-chloro-4-(trifluoromethyloxy)-phenyllsulfonyll-methyl-amino]-acetic acid (C-06) | GWI-3 | 63% (0.545 mmol) | - after column chromatography recrystallization from hexane/ethyl acetate was carried out |
| E-07 | 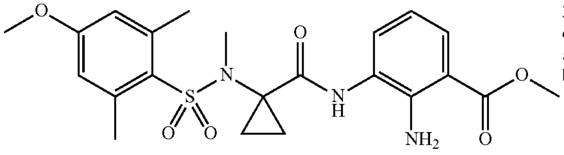 | 2-amino-3-[[1-[[(4-methoxy-2,6-dimethyl-phenyl)sulfonyl]-methyl-amino]-cyclopropanecarbonyl]amino]-benzoic acid methyl ester (E-07) | 1-[[(4-methoxy-2,6-dimethyl-phenyl)sulfonyl]-methyl-amino]-cyclopropane-1-carboxylic acid (C-07) | GWI-3 | 17% (0.390 mmol) | — |
| E-08 | 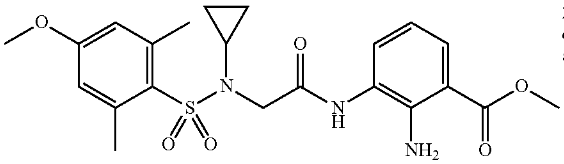 | 2-[cyclopropyl-[(4-methoxy-2,6-dimethyl-phenyl)sulfonyl]-amino]-acetic acid (E-08) | 2-[cyclopropyl-[(4-methoxy-2,6-dimethyl-phenyl)sulfonyl]-amino]-acetic acid (C-08) | | 75% (1.65 mmol) | - employed in the next stage without purificationsee below (I-14) |
| E-09 | 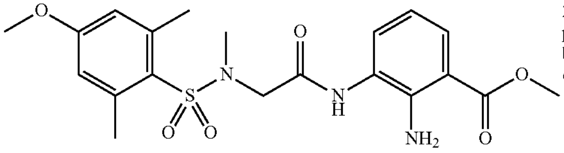 | 2-amino-3-[3-[[(4-methoxy-2,6-dimethyl-phenyl)sulfonyl]-methyl-amino]-butanoylamino]-benzoic acid methyl ester (E-09) | 2-[[(4-methoxy-2,6-dimethyl-phenyl)sulfonyl]-methyl-amino]-butyric acid (C-09) | GWI-2 | 99% (17.6 mmol) | - purification by column chromatography |
| E-17 | 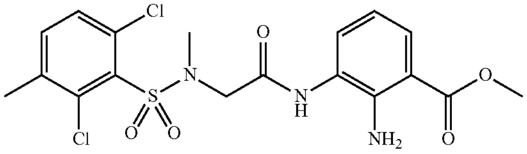 | 2-amino-3-[[2-[[(2,6-dichloro-3-methyl-phenyl)sulfonyl]-methyl-amino]-acetyl)amino]-benzoic acid methyl ester (E-17) | 2-[[(2,6-dichloro-3-methyl-phenyl)sulfonyl]-methyl-amino]-acetic acid (C-17) | GWI-2 | 48% (0.695 mmol) | - purification by column chromatography |

TABLE 2-continued

Synthesis of the diaminobenzoates (E)

| E no. | Structure | Diaminobenzoate (E) | Amide or sulfonamide (C) | Analogous to | Yield | Comments |
| --- | --- | --- | --- | --- | --- | --- |
| E-18 | 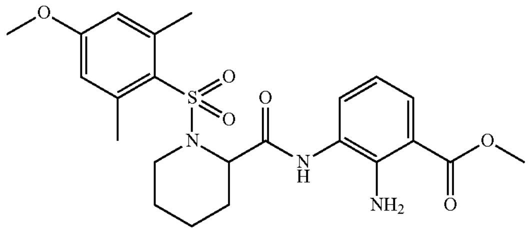 | 2-amino-3-[[1-[(4-methoxy-2,6-dimethyl-phenyl)sulfonyl]-piperidine-2-carbonyl amino]-benzoic acid methyl ester (E-18) | 1-[(4-methoxy-2,6-dimethyl-phenyl)sulfonyl]-piperidine-2-carboxylic acid (C-18) | GWI-3 | 18% (0.294 mmol) | - purification by column chromatography, and subsequent recrystallization from ethyl acetate |
| E-19 | 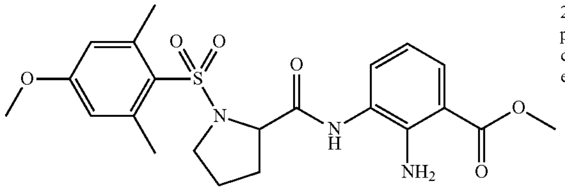 | 2-amino-3-[[1-[(4-methoxy-2,6-dimethyl-phenyl)sulfonyl]-pyrrolidine-2-carbonyl]amino]-benzoic acid methyl ester (E-19) | 1-[(4-methoxy-2,6-dimethyl-phenyl)sulfonyl]-pyrrolidine-2-carboxylic acid (C-19) | GWI-3 | 64% (4.92 mmol) | - 48 h reaction time<br>- purification by column chromatography |
| E-29 | 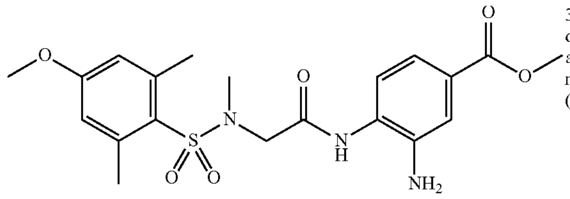 | 3-amino-4-[[2-[[(4-methoxy-2,6-dimethyl-phenyl)sulfonyl]-methyl-amino]-acetyl]amino]-benzoic acid methyl ester (E-29) | 2-[[(4-methoxy-2,6-dimethyl-phenyl)sulfonyl]-methyl-amino]-acetic acid (C-05) | GWI-2 | 82% (18.2 mmol) | - recrystallization from ethyl acetate |
| E-30 | 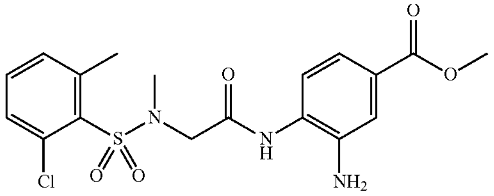 | 3-amino-4-[[2-[[(2-chloro-6-methyl-phenyl)sulfonyl]-methyl-amino]-acetyl]amino]-benzoic acid methyl ester (E-30) | 2-[[(2-chloro-6-methyl-phenyl)sulfonyl]methyl-amino]-acetic acid (C-10) | GWI-2 | 14% (1.89 mmol) | -1.5 eq. diamine<br>- purification by column chromatography (ethyl acetate/hexane)<br>- subsequent recrystallization from ethyl acetate |

TABLE 2-continued

Synthesis of the diaminobenzoates (E)

| E no. | Structure | Diaminobenzoate (E) | Amide or sulfonamide (C) | Analogous to | Yield | Comments |
|---|---|---|---|---|---|---|
| E-31 | 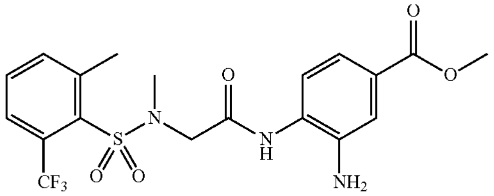 | 3-amino-4-[[2-[methyl-[[2-(trifluoromethyl)-phenyl]sulfonyl]-amino]-acetyl]amino]-benzoic acid methyl ester (E-31) | 2-[methyl-[[2-(trifluoromethyl)phenyl] sulfonyl]-amino]acetic acid (C-01) | GWI-2 | 61% (10.7 mmol) | -1.5 eq. diamine<br>- recrystallization from ethyl acetate<br>- purification by column chromatography ethyl acetate/hexane 6:1→1:2 |
| E-32 | 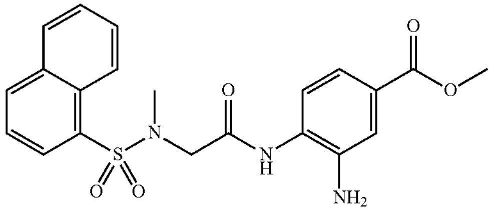 | 3-amino-4-[[2-[methyl-(naphthalen-1-ylsulfonyl)-amino]-acetyl]amino]-benzoic acid methyl ester (E-32) | 2-[methyl-(naphthalene-1-ylsulfonyl)-amino]-acetic acid (C-03) | GWI-2 | 37% (11.7 mmol) | -1.5 eq. diamine<br>- recrystallization from ethyl acetate<br>- purification by column chromatography ethyl acetate/hexane 4:1→1:2<br>- 2nd recrystallization from ethyl acetate |
| E-33 | 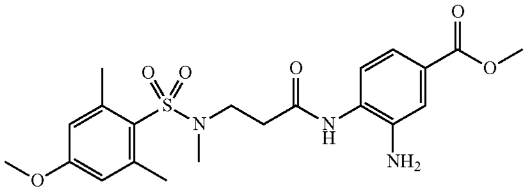 | 3-amino-4-[3-[[(4-methoxy-2,6-dimethyl-phenyl)sulfonyl]-methyl-amino]-propanoylamino]-benzoic acid methyl ester (E-33) | 3-[[(4-methoxy-2,6-dimethyl-phenyl)sulfonyl]-methyl-amino]-propionic acid (C-04) | GWI-2 | 97% (19.4 mmol) | -purification by column chromatography ethyl acetate/hexane 20:80→80:20 |

4) Synthesis of the Benzimidazoles and Benzimidazole Derivatives F

General Method for Synthesis of the Benzimidazoles and Benzimidazole Derivatives F Figure 5: Synthesis of the benzimidazoles and benzimidazole derivatives (F)

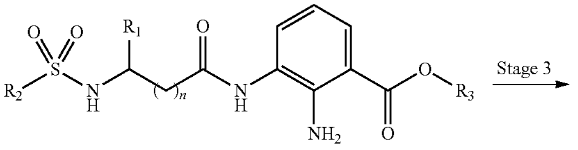

E

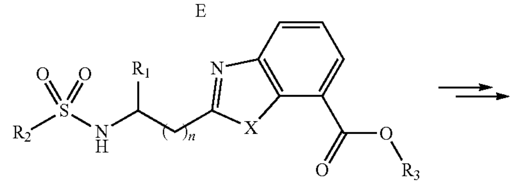

F

-continued

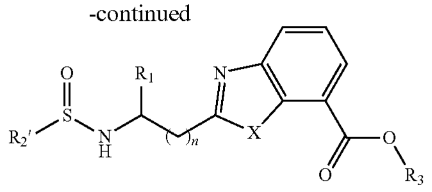

F

X = NH, $NR_4$ or S

General working instructions 4 (GWI-4): The sulfonamide ester (E) (1 eq.) was dissolved in acetic acid and the solution was heated at 100° C. for 3 h. The acetic acid was then distilled off in vacuo, sat. $NaHCO_3$ solution was added to the residue and the mixture was stirred for 15 min. The solution was diluted with ethyl acetate, the phases were separated and the aqueous phase was extracted 2× with ethyl acetate. The combined organic phases were dried over $Na_2SO_4$ and concentrated to dryness. The corresponding benzimidazole ester (F) or the corresponding ester of the benzimidazole derivative was obtained.

TABLE 3

Synthesis of the benzimidazole esters and the esters of benzimidazole derivatives (F)

| F no. | Structure | Benzimidazole ester (F) | Sulfonamide ester (E) | Analogous to | Yield | Comments |
|---|---|---|---|---|---|---|
| F-01 | 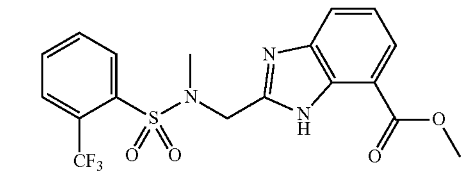 | 2-[[methyl-[[2-(trifluoromethyl)-phenyl]sulfonyl]-amino]-methyl]-3H-benzoimidazole-4-carboxylic acid methyl ester (F-01) | 2-amino-3-[[2-[methyl-[[2-(trifluoromethyl)-phenyl]sulfonyl]-amino]-acetyl]amino]-benzoic acid methyl ester (E-01) | GWI-4 | 82% (10.1 mmol) | — |
| F-02 | 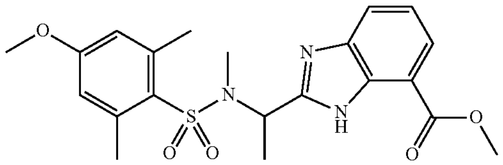 | 2-[1-[[(4-methoxy-2,6-dimethyl-phenyl)sulfonyll-methyl-aminol-ethyl]-3H-benzoinnidazole-4-carboxylic acid methyl ester (F-02) | 2-amino-3-[2-[[(4-methoxy-2,6-dimethyl-phenyl)sulfonyl]-methyl-amino]-propanoylamino]-benzoic acid methyl ester (E-02) | GWI-4 | 91% (4.6 mmol) | — |
| F-03 | 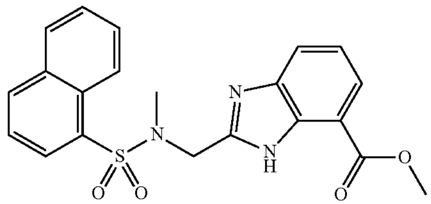 | 2-[[methyl-(naphthalen-1-ylsulfonyl)-amino]-methyl]-3H-benzoimidazole-4-carboxylic acid methyl ester (F-03) | 2-amino-3-[[2-[methyl-(naphthalen-1-ylsulfonyl)-amino]-acetyl]amino]benzoic acid methyl ester (E-03) | GWI-4 | 84% (12.3 mmol) | — |
| F-04 | 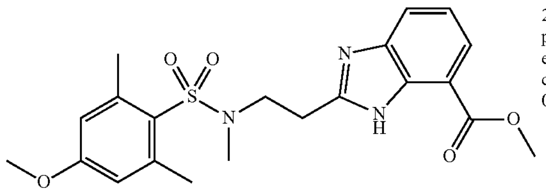 | 2-[2-[[(4-methoxy-2,6-dimethyl-phenyl)sulfonyl]-methyl-amino]-ethyl]-3H-benzoimidazole-4-carboxylic acid methyl ester (F-04) | 2-amino-3-[3-[[(4-methoxy-2,6-dimethyl-phenyl)sulfonyl]-methyl-amino]-propanoylamino]-benzoic acid methyl ester (E-04) | GWI-4 | 94% (12.2 mmol) | - crude product was recrystallized from dietyhl ether/hexane |
| F-05 | 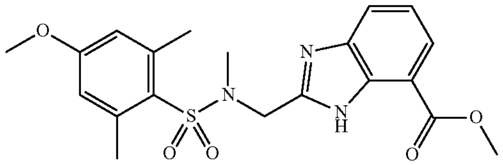 | 2-[[[(4-methoxy-2,6-dimethyl-phenyl)sulfonyl]-methyl-amino]-methyl]-3H-benzoimidazole-4-carboxylic acid methyl ester (F-05) | 2-amino-3-[[2-[[(4-methoxy-2,6-dimethyl-phenyl)sulfonyl]-methyl-amino]-acetyl]amino]-benzoic acid methyl ester (E-05) | GWI-4 | 92% (14.1 mmol) | - crude product boiled thoroughly in diethyl ether |

TABLE 3-continued

Synthesis of the benzimidazole esters and the esters of benzimidazole derivatives (F)

| F no. | Structure | Benzimidazole ester (F) | Sulfonamide ester (E) | Analogous to | Yield | Comments |
|---|---|---|---|---|---|---|
| F-06 | 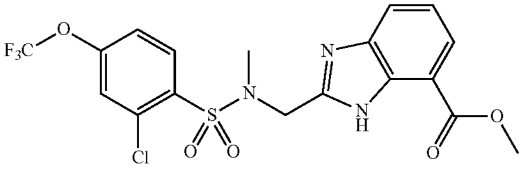 | 2-[[[[2-chloro-4-(trifluoromethyloxy)-phenyl]sulfonyl]-methyl-amino]-methyl]-3H-benzoimidazole-4-carboxylic acid methyl ester (F-06) | 2-amino-3-[[2-[[[2-chloro-4-(trifluoromethyloxy)-phenyl]sulfonyl]-methyl-amino]-acetyl]amino]-benzoic acid methyl ester (E-06) | GWI-4 | 112% (0.58 mmol) | - 2 h at 100° C.<br>- acetic acid was not concentrated, but neutralized directly with sat. $NaHCO_3$ solution |
| F-07 | 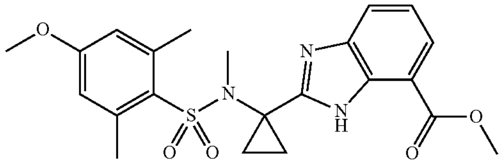 | 2-[1-[[(4-methoxy-2,6-dimethyl-phenyl)sulfonyl]-methyl-amino]-cyclopropyl]-3H-benzoimidazole-4-carboxylic acid methyl ester (F-07) | 2-amino-3-[[1-[[(4-methoxy-2,6-dimethyl-phenyl)sulfonyl]-methyl-amino]-cyclopropanecarbonyl]amino]-benzoic acid methyl ester (E-07) | GWI-4 | 93% (0.36 mmol) | - 4 h at 100° C.<br>- acetic acid was not concentrated, but neutralized directly with sat. $NaHCO_3$ solution |
| F-08 | 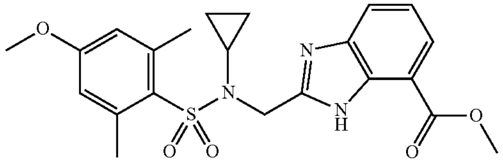 | 2-[[cyclopropyl-[(4-methoxy-2,6-dimethyl-phenyl)sulfonyl]-amino]-methyl]-3H-benzoimidazole-4-carboxylic acid methyl ester (F-08) | 2-[cyclopropyl-[(4-methoxy-2,6-dimethyl-phenyl)sulfonyl]-amino]-acetic acid (E-08) | | 92% | see below I-14 |
| F-09 | 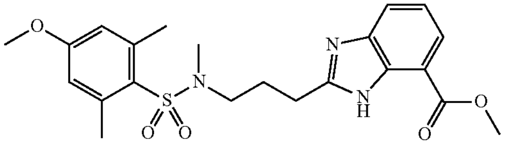 | 2-[3-[[(4-methoxy-2,6-dimethyl-phenyl)sulfonyl]-methyl-amino]-propyl]-3H-benzoimidazole-4-carboxylic acid methyl ester (F-09) | 2-amino-3-[3-[[(4-methoxy-2,6-dimethyl-phenyl)sulfonyl]-methyl-amino]-butanoylamino]-benzoic acid methyl ester (E-09) | GWI-4 | 100% (17.6 mmol) | — |
| F-10 | 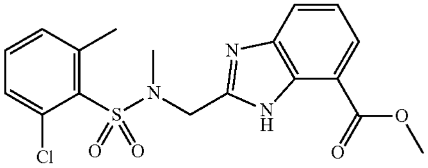 | 2-[[[(2-chloro-6-methyl-phenyl)sulfonyl]-methyl-amino]-methyl]-3H-benzoimidazole-4-carboxylic acid methyl ester (F-10) | | | | see below |

TABLE 3-continued

| F no. | Structure | Benzimidazole ester (F) | Sulfonamide ester (E) | Analogous to | Yield | Comments |
|---|---|---|---|---|---|---|
| Synthesis of the benzimidazole esters and the esters of benzimidazole derivatives (F) | | | | | | |
| F-11 | 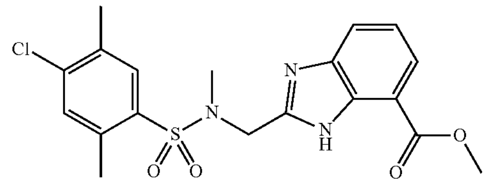 | 2-[[[(4-chloro-2,5-dimethyl-phenyl)sulfonyl]-methyl-amino)-methyl]-3H-benzoimidazole-4-carboxylic acid methyl ester (F-11) | | | | see below |
| F-13 | 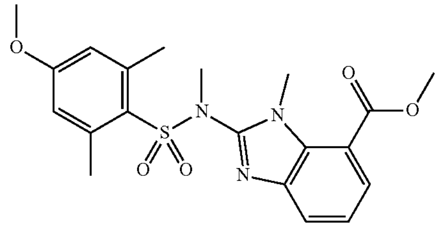 | 2-[[(4-methoxy-2,6-dimethyl-phenyl)sulfonyl]-methyl-amino]-3-methyl-3H-benzoimidazole-4-carboxylic acid methyl ester (F-13) | | | | see below |
| F-14 | 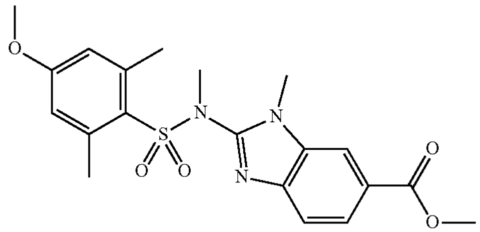 | 2-[[(4-methoxy-2,6-dimethyl-phenyl)sulfonyl]-methyl-amino]-3-methyl-3H-benzoimidazole-5-carboxylic acid methyl ester (F-14) | | | | see below |
| F-16 | 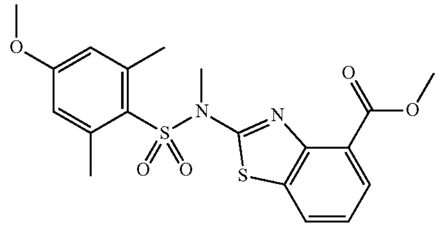 | 2-[[(4-methoxy-2,6-dimethyl-phenyl)sulfonyl]-methyl-amino]-benzothiazole-4-carboxylic acid methyl ester (F-16) | | | | see below |

TABLE 3-continued

Synthesis of the benzimidazole esters and the esters of benzimidazole derivatives (F)

| F no. | Structure | Benzimidazole ester (F) | Sulfonamide ester (E) | Analogous to | Yield | Comments |
|---|---|---|---|---|---|---|
| F-17 | 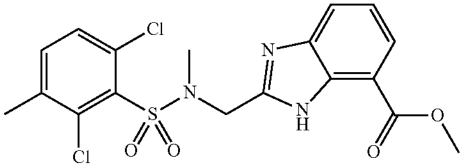 | 2-[[[(2,6-dichloro-3-methyl-phenyl)sulfonyl]-methyl-amino]-methyl]-3H-benzoimidazole-4-carboxylic acid methyl ester (F-17) | 2-amino-3-[[2-[[(2,6-dichloro-3-methyl-phenyl)sulfonyl]-methyl-amino]-acetyl]amino]-benzoic acid methyl ester (E-17) | GWI-4 | 110% (2.22 mmol) | - acetic acid was not distilled off, but diluted with ethyl acetate, and $NaHCO_3$ soln. was then added |
| F-18 | 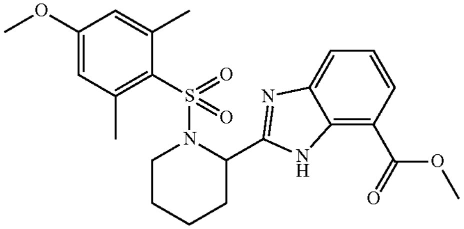 | 2-[1-[(4-methoxy-2,6-dimethyl-phenyl)sulfonyl]-piperidin-2-yl]-3H-benzoimidazole-4-carboxylic acid methyl ester (F-18) | 2-amino-3-[[1-[(4-methoxy-2,6-dimethyl-phenyl)sulfonyl]-piperidine-2-carbonyllamino]-benzoic acid methyl ester (E-18) | GWI-4 | 83% (0.26 mmol) | -2h reaction time<br>- acetic acid was not distilled off, but diluted with ethyl acetate, and $NaHCO_3$ soln. was then added |
| F-19 | 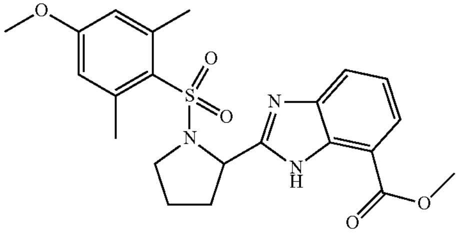 | 2-[1-[(4-methoxy-2,6-dimethyl-phenyl)sulfonyll-pyrrolidin-2-yl] 3H-benzoimidazole-4-carboxylic acid methyl ester (F-19) | 2-amino-3-[[1-[(4-methoxy-2,6-dimethyl-phenyl)sulfonyl]-pyrrolidine-2-carbonyl]amino]-benzoic acid methyl ester (E-19) | GWI-4 | 115% (2.50 mmol) | - acetic acid was not distilled off, but diluted with ethyl acetate, and $NaHCO_3$ soln. was then added |
| F-20 | 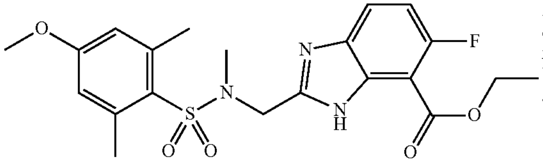 | 5-fluoro-2-[[[(4-methoxy-2,6-dimethyl-phenyl)sulfonyl]-methyl-amino]-methyl]-3H-benzoimidazole-4-carboxylic acid ethyl ester (F-20) | | | | see below |

TABLE 3-continued

Synthesis of the benzimidazole esters and the esters of benzimidazole derivatives (F)

| F no. | Structure | Benzimidazole ester (F) | Sulfonamide ester (E) | Analogous to | Yield | Comments |
|---|---|---|---|---|---|---|
| F-21 | 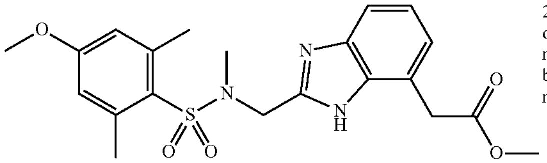 | 2-[2-[[[(4-methoxy-2,6-dimethyl-phenyl)sulfonyl]-methyl-amino]-methyl]-3H-benzoimidazol-4-yl]-acetic acid methyl ester (F-21) | | | | |
| F-23 | 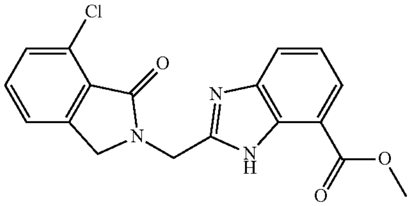 | 2-[(4-chloro-3-oxo-1,2-dihydro-isoindol-2-yl)-methyl]-3H-benzoimidazole-4-carboxylic acid methyl ester (F-23) | | | | see below |
| F-24 | 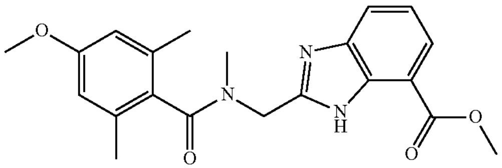 | 2-[[(4-methoxy-2,6-dimethyl-benzoyl)-methyl-amino]-methyl]-3H-benzoimidazole-4-carboxylic acid methyl ester (F-24) | | | | see below |
| F-25 | 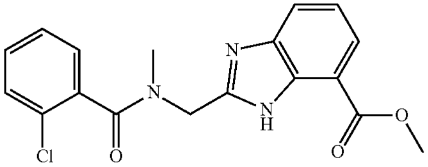 | 2-[[(2-chloro-benzoyl)-methyl-amino]-methyl]-3H-benzoimidazole-4-carboxylic acid methyl ester (F-25) | | | | see below |
| F-26 | 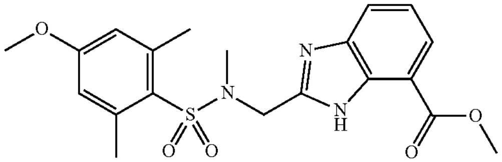 | 2-[[[(4-methoxy-2,6-dimethyl-phenyl)sulfonyl]-methyl-aminol-methyl]-1-methyl-1H-benzoimidazole-4-carboxylic acid methyl ester (F-26) | 2-amino-3-[[2-[[(4-methoxy-2,6-dimethyl-phenyl)sulfonyl]-methyl-amino]-acetyl]amino]-benzoic acid methyl ester (E-05) | | | see below |

TABLE 3-continued

| Synthesis of the benzimidazole esters and the esters of benzimidazole derivatives (F) | | | | | | |
|---|---|---|---|---|---|---|
| F no. | Structure | Benzimidazole ester (F) | Sulfonamide ester (E) | Analogous to | Yield | Comments |
| F-27 | 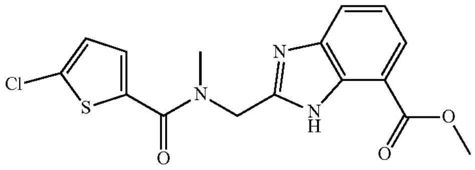 | 2-[[(5-chloro-thiophene-2-carbonyl)-methyl-amino]-methyl]-3H-benzoimidazole-4-carboxylic acid methyl ester (F-27) | | | | see below |
| F-28 | 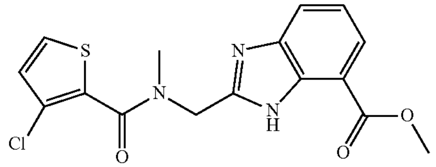 | 2-[[(3-chloro-thiophene-2-carbonyl)-methyl-amino]-methyl]-3H-benzoimidazole-4-carboxylic acid methyl ester (F-28) | | | | see below |
| F-29 | 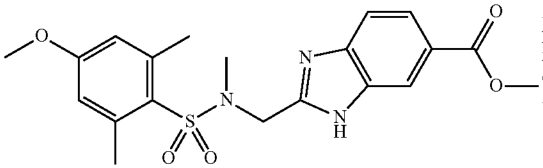 | 2-[[[(4-methoxy-2,6-dimethyl-phenyl)sulfonyl]-methyl-amino]-methyl]-3H-benzoimidazole-5-carboxylic acid methyl ester (F-29) | 3-amino-4-[[2-[[(4-methoxy-2,6-dimethyl-phenyl)sulfonyl]-methyl-amino]acetyl]amino]-benzoic acid methyl ester (E-29) | GWI-4 | 103% (18.7 mmol) | — |
| F-30 | 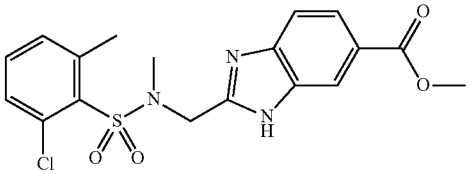 | 2-[[[(2-chloro-6-methyl-phenyl)sulfonyl]-methyl-amino]-methyl]-3H-benzoimidazole-5-carboxylic acid methyl ester (F-30) | 3-amino-4-[[2-[[(2-chloro-6-methyl-phenyl)sulfonyl]-methyl-amino]-benzoic acid methyl ester (E-30) | GWI-4 | 89% (6.00 mmol) | — |
| F-31 | 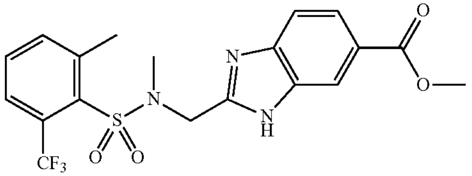 | 2-[[methyl-[[2-(trifluoromethyl)-phenyl]sulfonyl]-amino]-methyl]-3H-benzoimidazole-5-carboxylic acid methyl ester (F-31) | 3-amino-4-[[2-[methyl-[[2-(trifluoromethyl)-phenyl]sulfonyl]-amino]-acetyl]amino]-benzoic acid methyl ester (E-31) | GWI-4 | 91% (9.72 mmol) | — |

TABLE 3-continued

Synthesis of the benzimidazole esters and the esters of benzimidazole derivatives (F)

| F no. | Structure | Benzimidazole ester (F) | Sulfonamide ester (E) | Analogous to | Yield | Comments |
|---|---|---|---|---|---|---|
| F-32 | 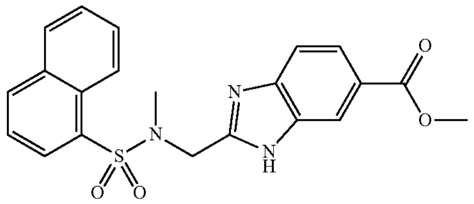 | 2-[[methyl-(naphthalen-1-ylsulfonyl)-amino]-methyl]-3H-benzoimidazole-5-carboxylic acid methyl ester (F-32) | 3-amino-4-[[2-[methyl-(naphthalen-1-ylsulfonyl)-aminoFacetyl]amino]-benzoic acid methyl ester (E-32) | GWI-4 | 94% (12.5 mmol) | — |
| F-33 | 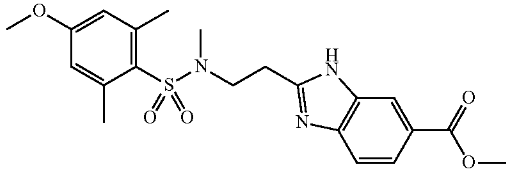 | 2-[2-[[(4-methoxy-2,6-dimethyl-phenyl)sulfonyl]-methyl-amino]-ethyl]-3H-benzoimidazole-5-carboxylic acid methyl ester (F-33) | 3-amino-4-[3-[[(4-methoxy-2,6-dimethyl-phenyl)sulfonyl]-methyl-amino]-propanoylamino]-benzoic acid methyl ester (E-33) | GWI-4 | 97% (18.8 mmol) | — |

Synthesis of benzimidazole ester F-08: 2-[[Cyclopropyl-[(4-methoxy-2,6-dimethyl-phenyl)sulfonyl]-amino]-methyl]-3H-benzoimidazole-4-carboxylic acid methyl ester (F-08)

A solution of 2-[cyclopropyl-[(4-methoxy-2,6-dimethyl-phenyl)sulfonyl]-amino]-acetic acid (E-08) (1.6 mmol, 1 eq.) and acetic acid (5 ml) in xylene (12 ml) was refluxed for 1 h. The reaction mixture was cooled to room temperature and concentrated and the residue was dissolved in methylene chloride. The organic phase was washed with $NaHCO_3$ solution, dried over $Na_2SO_4$ and concentrated to dryness. The crude product (F-08) was employed in the next stage without further purification. Yield: 92%

Synthesis of benzimidazole ester F-10: 2-[[[(2-Chloro-6-methyl-phenyl)sulfonyl]-methyl-amino]-methyl]-3H-benzoimidazol-4-carboxylic acid methyl ester (F-10)

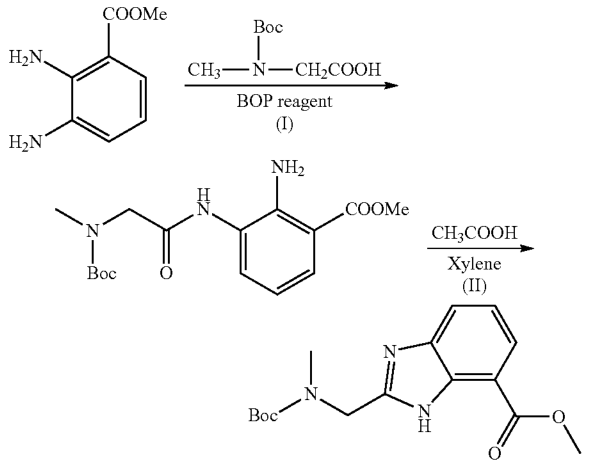

Benzimidazole intermediate A

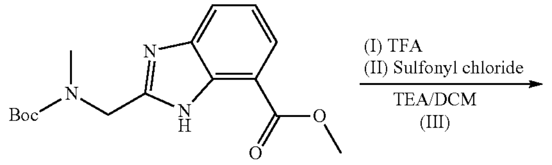

Benzimidazole intermediate A

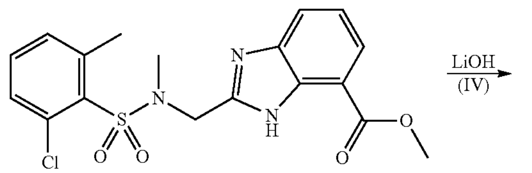

F-10

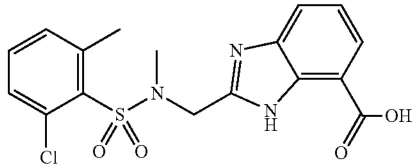

ACI-10

(I) BOP (2 eq.) was added to a solution of N-BOC-N-methyl-glycine (5.6 g, 30 mmol) in DMF (100 ml) and the mixture was stirred for 5 min. 2,3-Diamino-benzoic acid methyl ester (D) (5 g, 30 mmol) and NMM (4 eq.) were then added and the mixture was stirred at room temperature for 18 h. The reaction mixture was diluted with water and extracted with ethyl acetate. The organic phase was washed with water and sat. NaCl solution, dried over $Na_2SO_4$ and concentrated. The crude product was purified by column chromatography (ethyl acetate/hexane) to obtain the desired product. Yield: 64%

(II) Benzimidazole intermediate A: The product just obtained in stage (I) (6.5 g, 19.28 mmol) was refluxed with acetic acid (45 ml) in xylene (130 ml) for 1 h, the mixture was then concentrated and the residue was diluted with ethyl acetate. The organic phase was washed with water and sat. NaCl solution, dried over $Na_2SO_4$ and concentrated to obtain the desired product. Yield: 97.5%

(III) TFA (100 ml) was added to a solution of the benzimidazole intermediate A just obtained in stage (II) (5 g, 22.3 mmol) in methylene chloride (500 ml) and the mixture was stirred at room temperature for 3 h. The reaction mixture was concentrated completely, under reduced pressure, the residue was taken up in methylene chloride (200 ml) and $NEt_3$ (3 eq.) was added. A solution of 2-chloro-6-methyl-benzenesulfonyl chloride was then added at 0° C. and the mixture was stirred at this temperature for 1 h. The reaction mixture was diluted with methylene chloride, washed with water and sat. NaCl solution, dried over $Na_2SO_4$ and concentrated. The crude product (F-10) was purified by column chromatography (ethyl acetate/hexane). Yield: 63%

(IV) The product just obtained in stage (III) (200 mg) was stirred with a mixture of THF-MeOH—$H_2O$ (2:1:1, 10 ml) at room temperature and the mixture was then cooled to 0° C. Lithium hydroxide (3 eq.) was then added and the mixture was stirred at room temperature for 12 h. THF and methanol were distilled off under reduced pressure, the aqueous residue was diluted with water and the mixture was washed with ethyl acetate. The aqueous phase was acidified with 1 N HCl and the solid which had precipitated out (ACI-10) was filtered off and dried to obtain the desired product. Yield: 72%

Synthesis of benzimidazole ester F-11: 2-[[[(4-Chloro-2,5-dimethyl-phenyl)sulfonyl]-methyl-amino]-methyl]-3H-benzoimidazole-4-carboxylic acid methyl ester (F-11)

2-[[[(4-Chloro-2,5-dimethyl-phenyl)sulfonyl]-methyl-amino]-methyl]-3H-benzoimidazole-4-carboxylic acid methyl ester (F-11) was prepared analogously to F-10 stage (III) using benzimidazole intermediate A and 4-chloro-2,5-dimethyl-benzenesulfonyl chloride. Yield 61%

Synthesis of benzimidazole ester F-13: 2-[[(4-Methoxy-2,6-dimethyl-phenyl)sulfonyl]-methyl-amino]-3-methyl-3H-benzoimidazole-4-carboxylic acid methyl ester (F-13)

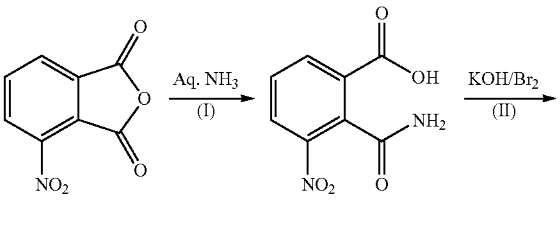

-continued

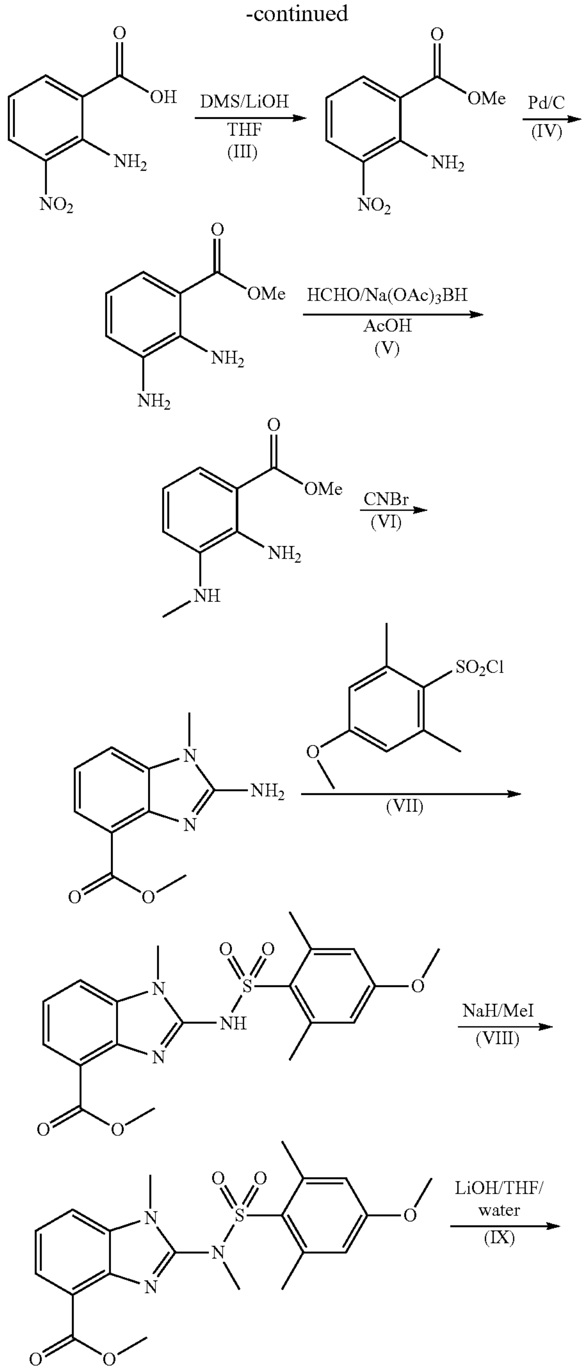

F-13

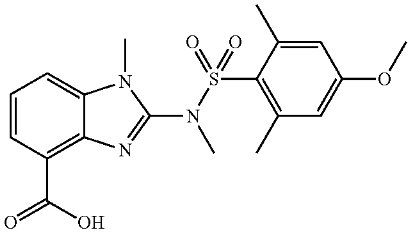

ACI-13

(I) 3-Nitro-phthalic anhydride (20 g) was added to an aqueous ammonia solution (20 ml) and the mixture was heated to 80° C. The mixture became a clear solution. After the reaction mixture had cooled to 0° C., the solid which had precipitated out was filtered off. This was dissolved in water and the solution was acidified with conc. HCl. The solid subsequently obtained was filtered off and dried to obtain the desired product. Yield: 68.9%

(II) Bromine (11.5 ml) was added to a solution of KOH (113 g, 2.02 mol) in water (611 ml) at 0° C. The product obtained in stage (I) (50 g, 0.238 mol) was then added and the reaction mixture was stirred at 60° C. for 3 h and then at room temperature for 16 h. The solid which had precipitated out was filtered off and dissolved in a minimum of water and the solution was acidified with conc. HCl. The pale yellow solid which subsequently precipitated out was filtered off, washed with cold water and dried to obtain the desired product. Yield: 69.2%

(III) LiOH (7.6 g) was added to a solution of the product just obtained in stage (II) (30 g) in THF (450 ml) and the mixture was stirred at room temperature for 1 h. Dimethyl sulfate (17.25 ml) was then added and the mixture was heated under reflux for 24 h. The reaction mixture was cooled to room temperature and filtered and the filtrate was concentrated under reduced pressure. The residue was dissolved in ethyl acetate and the solution was washed with $NH_4OH$ solution, water and sat. NaCl solution. The organic phase was dried over anhydrous $Na_2SO_4$ and concentrated to obtain the desired product. Yield: 83.8%

(IV) The product just obtained in stage (III) (30 g), in methanol (1.5 l), was hydrogenated for 3 h using 10% Pd/C (3 g). The reaction mixture was filtered and concentrated to obtain the desired product. Yield: 90%

(V) Formaldehyde (40% aqueous, 26.5 mmol) and acetic acid (2.06 ml, 36.15 mmol) were added to a solution of the product just obtained in stage (IV) (2 g, 12.5 mmol) in methylene chloride (35 ml). The reaction mixture was stirred at room temperature for 30 min and then cooled to 10° C. and sodium triacetoxyborohydride (7.6 g, 36.1 mmol) was added. The mixture was stirred at room temperature for a further 45 min and then quenched with sat. $NaHCO_3$ solution and diluted with methylene chloride. The organic phase was washed with water and sat. NaCl solution, dried over $Na_2SO_4$ and concentrated. The crude product was purified by column chromatography (ethyl acetate/hexane) to obtain the desired product. Yield: 17%

(VI) A solution of cyanogen bromide (636 mg, 6 mmol) in THF (4.2 ml) and water (30 ml) was added to a solution of the product just obtained in stage (V) (900 mg, 5 mmol) in water (10 ml) at room temperature. The reaction mixture was stirred at 50° C. for 4 h and then diluted with ethyl acetate. The organic phase was washed with water and sat. NaCl solution, dried over $Na_2SO_4$ and concentrated to obtain the crude product. The crude product was recrystallized from methanol/diethyl ether to obtain the desired product. Yield: 97%

(VII) DMAP (0.74 g, 6 mmol) and a solution of 2,6-dimethyl-4-methoxyphenyl-sulfonyl chloride (3 eq.) in pyridine (15 ml) was added to a solution of the product just obtained in stage (VI) (1.25 g, 6.09 mmol) in pyridine (15 ml). The reaction mixture was stirred at 100° C. for 14 h and then diluted with methylene chloride and washed with sat. $CuSO_4$ solution. The organic phase was washed with water and sat. NaCl solution, dried over $Na_2SO_4$ and concentrated to obtain the crude product, which was recrystallized from methanol/diethyl ether. Yield: 10%

(VIII) A solution of the product just obtained in stage (VII) (360 mg, 0.893 mmol) in DMF (5 ml) was added to a suspension of NaH (107 mg, 2.23 mmol) in DMF (10 ml) while cooling with an ice bath and the mixture was stirred at room temperature for 1 h. Methyl iodide (3 eq.) was then added and the mixture was stirred at room temperature for a further 16 h. The reaction mixture was diluted with ethyl acetate and the organic phase was washed with water and sat. NaCl solution, dried over $Na_2SO_4$ and concentrated. The crude product (F-13) was purified by column chromatography (ethyl acetate/hexane). Yield: 47%

(IX) The product just obtained in stage (VIII) (200 mg) was stirred in a mixture of THF-MeOH—$H_2O$ (2:1:1, 10 ml) at room temperature and the mixture was then cooled to 0° C. Lithium hydroxide (3 eq.) was added and the mixture was stirred at room temperature for 12 h. THF and methanol were distilled off, the aqueous residue was diluted with water and the mixture was washed with ethyl acetate. The aqueous phase was acidified with 1 N HCl and the solid was filtered off and dried to obtain the desired acid (ACI-13), which was purified via HPLC. Yield: 30%

Synthesis of benzimidazole ester F-14: 2-[[(4-Methoxy-2,6-dimethyl-phenyl)sulfonyl]-methyl-amino]-3-methyl-3H-benzoimidazole-5-carboxylic acid methyl ester (F-14)

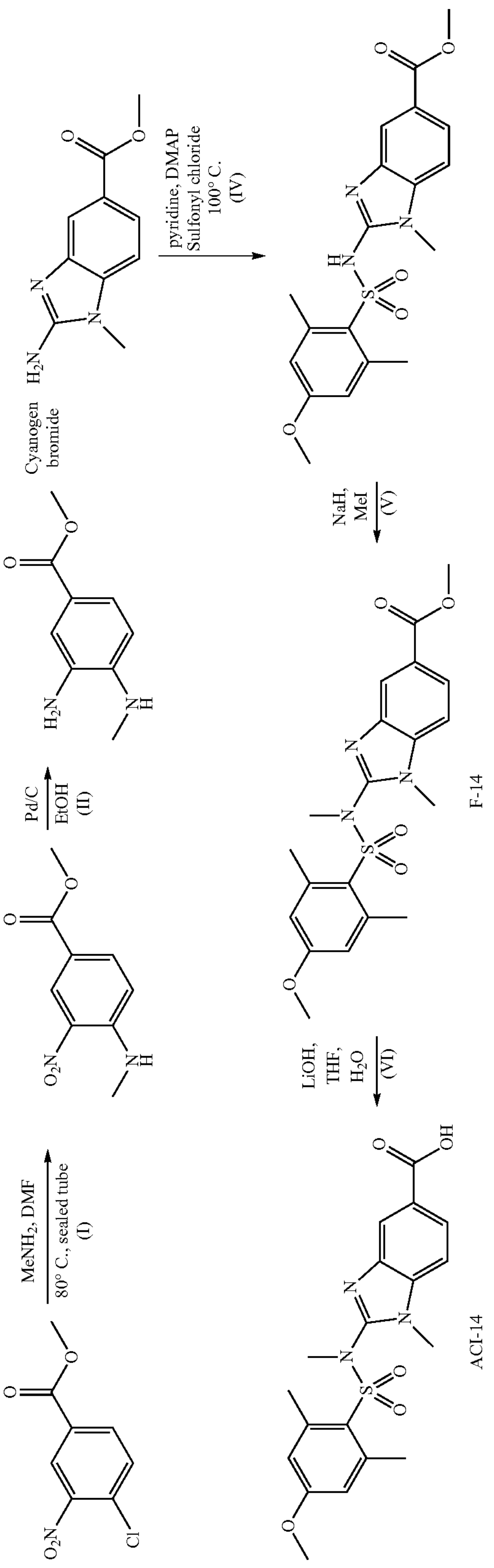
F-14
ACI-14

(I) Methylamine (9.26 mmol, 2 eq.) was added to a solution of methyl 4-chloro-3-nitro benzoate (4.6 mmol) in DMF (1.5 ml) and the mixture was heated at 80° C. in a sealed tube for 16 h, subsequently cooled to room temperature and diluted with water. The yellow precipitate formed was filtered off and washed with water, and 3× toluene was added and the mixture evaporated on a rotary evaporator. Yield: 82%

(II) A solution of the product just obtained in stage (I) (4.7 mmol) in ethanol (120 ml) was hydrogenated with $H_2$ and 10% Pd—C (110 mg) in the course of for 12 h. The catalyst was filtered off over Celite and rinsed with ethanol and the filtrate was concentrated under reduced pressure. The crude product was employed in the next stage without further purification. Yield: 94.5%

(II) A solution of the product just obtained in stage (II) (4.4 mmol) in water (10 ml) was added cyanogen bromide (5.28 mmol) in THF (4 ml) and water (30 ml) at room temperature and the reaction mixture was stirred at 50° C. for 4 h. The reaction mixture was diluted with ethyl acetate and the organic phase was washed with water and sat. NaCl solution, dried over $Na_2SO_4$ and concentrated. The crude product was recrystallized from methanol/diethyl ether. Yield: 96%

(IV) DMAP (0.74 g, 6 mmol) and a solution of 4-methoxy-2,6-dimethyl-benzenesulfonyl chloride (3 eq.) in pyridine (15 ml) was added to a solution of the product just obtained in stage (III) (5.95 mmol) in pyridine (15 ml). The reaction mixture was heated at 100° C. for 14 h. It was then diluted with methylene chloride and washed with sat. $CuSO_4$ solution. The organic phase was washed with water and sat. NaCl solution, dried over $Na_2SO_4$ and concentrated. The crude product was recrystallized from methanol/diethyl ether. Yield: 25%

(V) While cooling with an ice bath, the compound (360 mg, 0.893 mmol) in DMF (5 ml) was added to a suspension of NaH (107 mg, 2.23 mmol) in DMF (10 ml) and the mixture was stirred at room temperature for 1 h. Methyl iodide (3 eq.) was then added and the mixture was stirred at room temperature for a further 16 h. The reaction mixture was diluted with ethyl acetate and the organic phase was washed with water and sat. NaCl solution, dried over $Na_2SO_4$ and concentrated. The crude product (F-14) was purified by column chromatography (ethyl acetate/hexane). Yield: 40.6%

(VI) The product just obtained in stage (V) (200 mg) was stirred with a mixture of THF-MeOH—$H_2O$ (2:1:1, 10 ml) at room temperature and the mixture was then cooled to 0° C. Lithium hydroxide (3 eq.) was added to the reaction mixture and the mixture was stirred at room temperature for 12 h. THF and methanol were removed under reduced pressure, the residue was diluted with water and the mixture was washed with ethyl acetate. The aqueous phase was acidified with 1 N HCl and the solid (ACI-14) was filtered off and dried. Yield: 55.6%

Synthesis of benzimidazole ester F-16: 2-[[(4-Methoxy-2,6-dimethyl-phenyl)sulfonyl]-methyl-amino]-benzothiazole-4-carboxylic acid methyl ester (F-16)

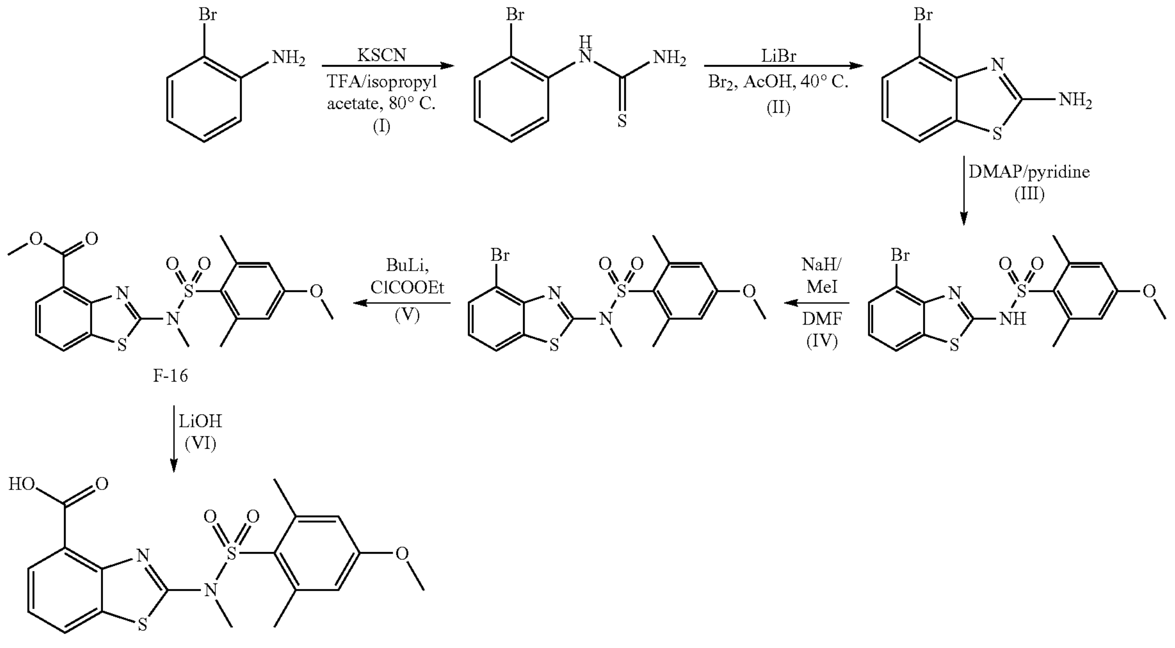

F-16

ACI-16

(I) KSCN was added to a solution of 2-bromoaniline (10 g, 58 mmol) in isopropyl acetate (120 ml) at room temperature, TFA (2.5 eq.) was then added dropwise at 0° C. and the mixture was stirred at 70° C. for 16 h. The reaction mixture was quenched with sat. $NaHCO_3$ solution and diluted with ethyl acetate and the organic phase was washed with water and sat. NaCl solution, dried over $Na_2SO_4$ and concentrated under reduced pressure. The crude product was purified by column chromatography (ethyl acetate/hexane) to obtain the desired product. Yield: 37.2%

(II) LiBr (1.5 eq.) was added to a solution of the product just obtained in stage (I) (5 g, 21.64 mmol) in acetic acid (50 ml) at room temperature. The reaction mixture was cooled to 0° C., bromine (1 eq.) was added and the mixture was then heated at 85° C. for 16 h. The reaction mixture was quenched with sodium thiosulfate solution and diluted with ethyl acetate. The organic phase was washed with water and sat. NaCl solution, dried over $Na_2SO_4$ and concentrated. The crude product was purified by column chromatography (ethyl acetate/hexane) to obtain the desired product. Yield: 68.3%

(III) DMAP (1 eq.) and a solution of 4-methoxy-2,6-dimethyl-benzenesulfonyl chloride (3 eq.) in pyridine (15 ml) was added to a solution of the product just obtained in stage (II) (2.4 g, 10.5 mmol) in pyridine (40 ml). The reaction mixture was heated at 100° C. for 14 h and then diluted with methylene chloride and washed with sat. $CUSO_4$ solution. The organic phase was washed with water and sat. NaCl solution, dried over $Na_2SO_4$ and concentrated to obtain the crude product. The crude product was recrystallized from methanol/diethyl ether. Yield: 66%

(IV) A solution of the product just obtained in stage (III) (3.8 g, 8.89 mmol) in DMF (15 ml) was added to a suspension of NaH (1.06 g, 60%, 22.2 mmol) in DMF (20 ml) while cooling with an ice bath and the mixture was stirred at room temperature for 1 h. Methyl iodide (3 eq.) was then added and the mixture was stirred at room temperature for 16 h. The reaction mixture was diluted with ethyl acetate and the organic phase was washed with water and sat. NaCl solution, dried over $Na_2SO_4$ and concentrated. The crude product was purified by column chromatography (ethyl acetate/hexane). Yield: 46% perature in the course of 2 h. The reaction mixture was quenched with sat. $NH_4Cl$ solution and diluted with ethyl acetate. The organic phase was washed with water and sat. NaCl solution, dried over $Na_2SO_4$ and concentrated. The crude product (F-16) was purified by column chromatography (ethyl acetate/hexane). Yield: 17%

(VI) The product just obtained in stage (V) (300 mg) was stirred in a mixture of THF-MeOH—$H_2O$ (2:1:1, 10 ml) at room temperature and the mixture was then cooled to 0° C. Lithium hydroxide (3 eq.) were added and the reaction mixture was stirred at room temperature for 12 h. THF and methanol were distilled off in vacuo, the aqueous residue was diluted with water and the mixture was washed with ethyl acetate. The aqueous phase was acidified with 1 N HCl and the solid was filtered off and dried to obtain the desired product (ACI-16). Yield 35%

Synthesis of benzimidazole ester F-20: 5-Fluoro-2-[[[(4-methoxy-2,6-dimethyl-phenyl)sulfonyl]-methyl-amino]-methyl]-3H-benzoimidazole-4-carboxylic acid methyl ester (F-20)

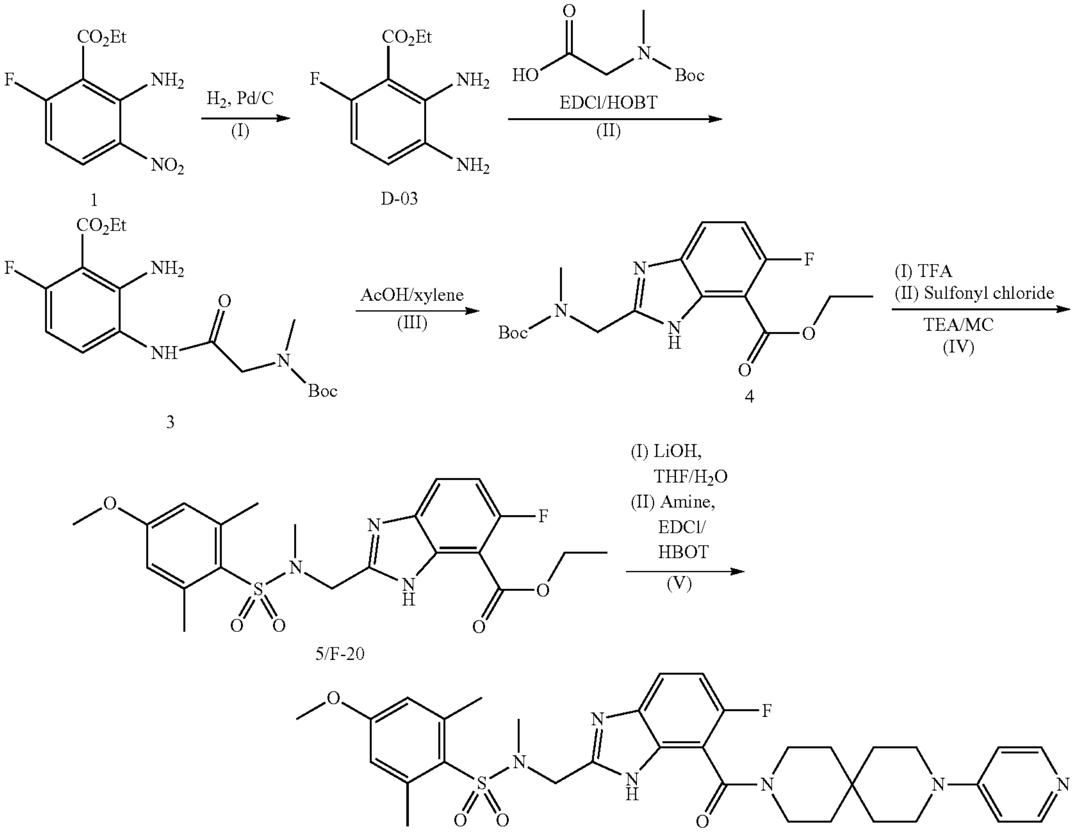

1

D-03

3

4

5/F-20

I-13

(IV) The product just obtained in stage (IV) (200 mg, 0.45 mmol) in THF (0.5 ml) was added to a solution of n-BuLi (1.8 M in hexane, 0.4 ml, 1.5 eq.) in THF (1.5 ml) at −78° C. under an $N_2$ atmosphere and the mixture was stirred at −78° C. for 1 h. Ethyl chloroformate (2 eq.) was then added dropwise at −78° C. and the reaction mixture was warmed to room tem- (I) A solution of ethyl 2-amino-6-fluoro-3-nitrobenzoate (1) (4.4 mmol, 1 eq.) in MeOH was hydrogenated with Pd/C as the catalyst. Yield: 77%

(II) Using standard peptide coupling reagents, 2,3-diamino-6-fluoro-benzoic acid ethyl ester (D-03) (2.8 mmol, 1 eq.) was coupled with N-Boc sarcosine (1 eq.). The crude amide product which was obtained in this way was purified by column chromatography over silica gel. Yield: 90%

(III) A solution of 3 (2.71 mmol, 1 eq.) and AcOH (30 eq.) in xylene was refluxed for 2 h. The reaction mixture was cooled and the solvent was removed completely and replaced by MC. The organic phase was washed in each case with water, aqueous $NaHCO_3$ and sat. NaCl solution and dried over $Na_2SO_4$. After the solvent had been removed completely, the crude product was employed in the next stage without further purification. Yield: 88%

(IV) Molecule 4 (2.8 mmol, 1 eq.) was Boc-deprotected with a solution of TFA/MC. After the Boc-deprotection, the amine was taken up in MC and the mixture was cooled to 0° C. $NEt_3$ (4 eq.) and 4-methoxy-2,6-dimethyl-benzenesulfonyl chloride (1.1 eq.) was then added. The reaction mixture was warmed to room temperature and stirred for 10 h. For working up, the reaction mixture was washed in each case with water and sat. NaCl solution and dried over $Na_2SO_4$. After the solvent had been removed completely, the crude product was purified by column chromatography over silica gel. Yield: 55%

(V) Ester 5 (2.4 mmol, 1 eq.) was hydrolysed with LiOH in THF/$H_2O$ (1:1). After the hydrolysis, the solvent was removed completely from the reaction mixture in vacuo, the residue was taken up in water and the mixture was washed with ethyl acetate. The aqueous phase was adjusted to pH=4 and then extracted with ethyl acetate. The free acid obtained in this way was coupled with the spiro-amine under standard peptide coupling conditions (I-13). Yield: 20%

Synthesis of benzimidazole ester F-23: 2-[(4-Chloro-3-oxo-1,2-dihydro-isoindol-2-yl)-methyl]-3H-benzoimidazole-4-carboxylic acid methyl ester (F-23)

(I) BOP (1.5 eq.) was added to a solution of N-Boc-glycine (2 g, 12 mmol) in DMF (40 ml) and the mixture was stirred for 5 min. Methyl 2,3-diaminobenzoate (1.9 g, 10.8 mmol) and NMM (4 eq.) were added and the reaction mixture was stirred at room temperature for 18 h. The reaction mixture was diluted with water and extracted with ethyl acetate. The organic phase was washed with water and sat. NaCl solution, dried over $Na_2SO_4$ and concentrated to obtain the crude product. The crude product was purified by column chromatography with ethyl acetate/hexane. Yield: 72%

(II) The product just obtained in stage (I) (2.8 g, 8.66 mmol) was refluxed in xylene (50 ml) with AcOH (20 ml) for 1 h. The reaction mixture was concentrated and the residue was taken up in ethyl acetate. The organic phase was washed with water and sat. NaCl solution, dried over $Na_2SO_4$ and concentrated to obtain the desired product. Yield: 67%

(III) TFA (5 ml) was added to a solution of 2-[(tert-butoxy-carbonylamino)-methyl]-3H-benzoimidazole-4-carboxylic acid methyl ester (0.45 mmol) in methylene chloride (25 ml) and the mixture was stirred at room temperature for 3 h. The reaction mixture was concentrated under reduced pressure, the residue was taken up in benzene (50 ml), and TEA (3 eq.), 2-(bromomethyl)-6-chloro-benzoic acid methyl ester (1 eq.) were added and the mixture was then refluxed under an $N_2$ atmosphere for 16 h. The reaction mixture was concentrated, the residue was diluted with methylene chloride and the organic phase was washed successively with water and sat. NaCl solution. It was dried over $Na_2SO_4$ and concentrated under reduced pressure. The crude product (F-11) was purified by column chromatography (neutral aluminium oxide; methanol/methylene chloride). Yield: 46%

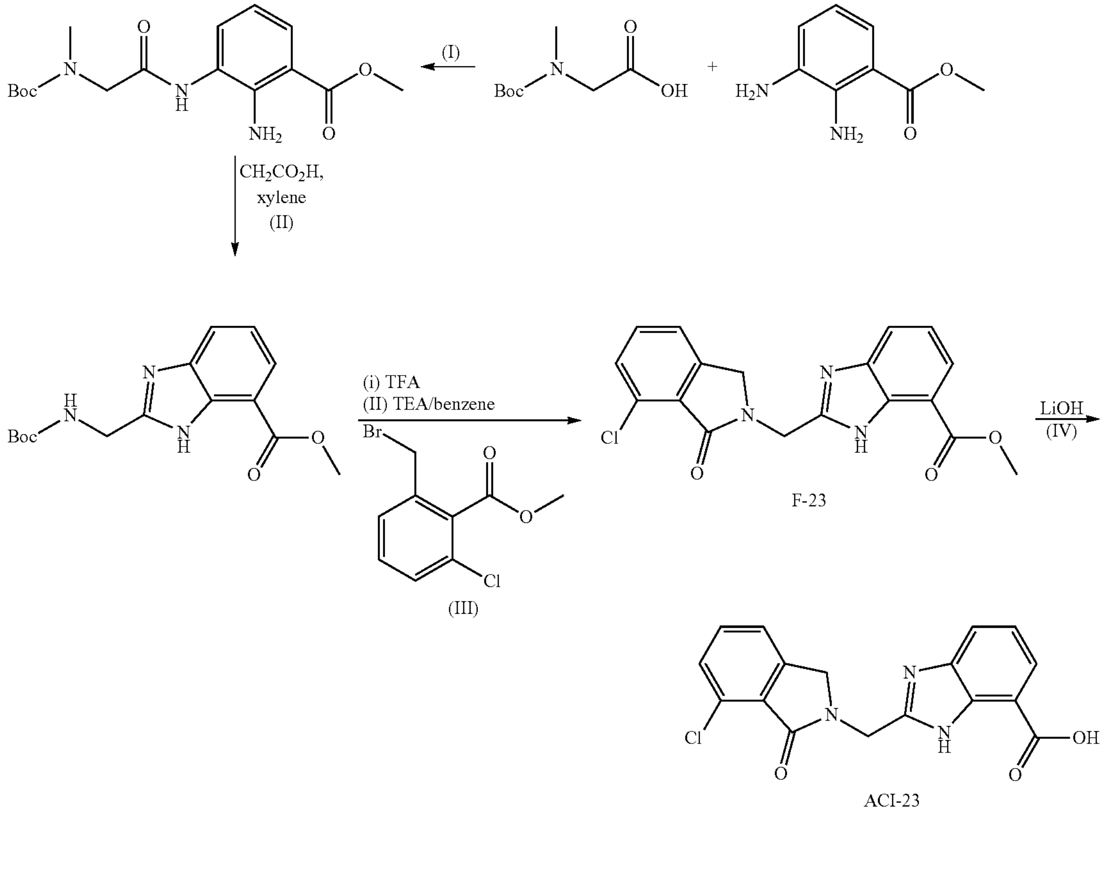

F-23
ACI-23

(IV) 2-[(4-Chloro-3-oxo-1,2-dihydro-isoindol-2-yl)-methyl]-3H-benzoimidazole-4-carboxylic acid methyl ester (ACI-23) was prepared analogously to ACI-10 stage (IV). Yield 70%

Synthesis of benzimidazole ester F-24: 2-[[(4-Methoxy-2,6-dimethyl-benzoyl)-methyl-amino]-methyl]-3H-benzoimidazole-4-carboxylic acid methyl ester (F-24)

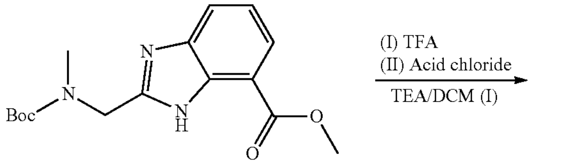

Benzimidazole intermediate A

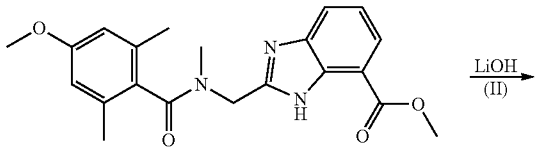

F-24

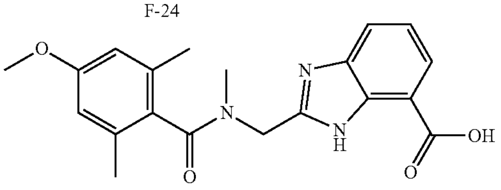

ACI-24

(I) 2-[[(4-Methoxy-2,6-dimethyl-benzoyl)-methyl-amino]-methyl]-3H-benzoimidazole-4-carboxylic acid methyl ester (F-24) was prepared analogously to F-10 stage (III) using benzimidazole intermediate A and 4-methoxy-2,6-dimethyl-benzoic acid chloride. Yield: 41%

(II) 2-[[(4-Methoxy-2,6-dimethyl-benzoyl)-methyl-amino]-methyl]-3H-benzoimidazole-4-carboxylic acid (ACI-24) was prepared analogously to F-10 stage (IV). Yield: 67%

Synthesis of benzimidazole ester F-25: 2-[[(2-Chloro-benzoyl)-methyl-amino]-methyl]-3H-benzoimidazole-4-carboxylic acid methyl ester (F-25)

(I) 2-[[(2-Chloro-benzoyl)-methyl-amino]-methyl]-3H-benzoimidazole-4-carboxylic acid methyl ester (F-25) was prepared analogously to F-10 stage (III) using benzimidazole intermediate A and 2-chloro-benzoic acid chloride. Yield: 68%

(II) 2-[[(2-Chloro-benzoyl)-methyl-amino]-methyl]-3H-benzoimidazole-4-carboxylic acid (ACI-25) was prepared analogously to F-10 stage (IV). Yield: 83%

Synthesis of benzimidazole ester F-26: 2-[[[(4-Methoxy-2,6-dimethyl-phenyl)sulfonyl]-methyl-amino]-methyl]-1-methyl-1H-benzoimidazole-4-carboxylic acid methyl ester (F-26)

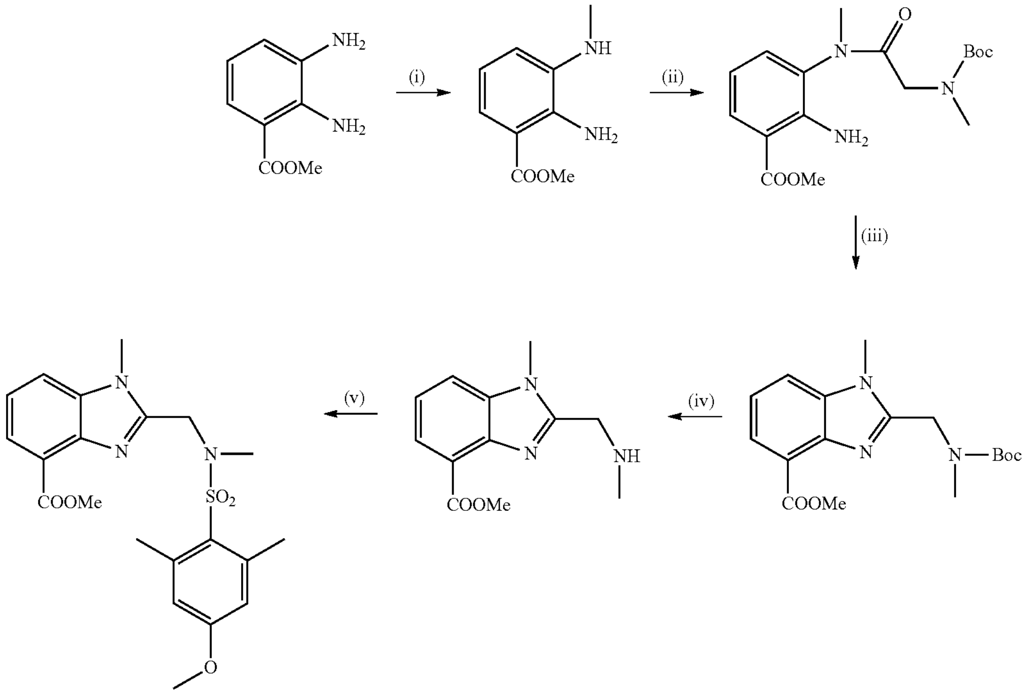

F-26

Step-1: To solution of methyl 2,3-diaminobenzoate (25.3 mmol, 1.0 eq.) in methylene chloride (126 ml) was added formaldehyde (2.2 eq.) and acetic acid (3.0 eq.) at 0° C. and the reaction mixture was stirred for 30 min. Sodium triacetoxyborohydride (3.0 eq.) was added to the reaction mixture at 10° C. and it was stirred for an additional 1 h. the mixture was quenched with ice-water and extracted with methylene chloride. The organic layer was successively washed with sodium bicarbonate, water and brine. It was then dried over sodium sulfate and concentrated under reduced pressure to give the crude product which was purified by silica gel column chromatography. Yield: 25%.

Step-2: To a solution of N-boc sarcosine (5.0 mmol, 1.0 eq.) in THF (40 ml) was added diisopropyl ethylamine (4.0 eq.) at 0° C. followed by HATU (1.5 eq.). The resultant solution was allowed to stir at room temperature for 15 min. It was again cooled to 0° C. and a solution of methyl 2-amino-3-(methylamino)benzoate (5.0 mmol, 1.0 eq.) in THF (5 ml) was added. The reaction mixture was allowed to stir at room temperature for 16 h. The mixture was diluted with ethyl acetate, washed with saturated ammonium chloride solution, saturated sodium bicarbonate solution and finally with brine. The organic layer was dried over sodium sulfate and evaporated to dryness under reduced pressure to give the crude product which was purified by silica gel column chromatography to obtain the desired product. Yield: 35%.

Step-3: To solution of methyl 2-amino-3-(2-(tert-butoxycarbonyl(methyl)amino)-N-methylacetamido)benzoate (1.70 mmol 1.0 eq.) in xylene (9 ml) was added acetic acid (3 ml) and resulting mixture was heated to reflux for 1 h. The solvent was evaporated and the residue was dissolved in ethyl acetate. The organic layer was washed with water and brine, and dried over sodium sulfate. The solvent was evaporated under reduced pressure to give the desired product which was used in the next step without further purification. Yield: 70%.

Step-4: To a cooled (0° C.) solution of methyl 2-((tert-butoxycarbonyl(methyl)amino)methyl)-1-methyl-1H-benzo[d]imidazole-4-carboxylate (1.65 mmol) in methylene chloride (7.5 ml) was added TFA (2.5 mL) and the reaction mixture was allowed to stir at room temperature for 2 h. The solvent was evaporated under reduced pressure, and the residue was azeotroped twice with methylene chloride and used in the next step.

Step-5: To a cooled (0° C.) solution of methyl 1-methyl-2-((methylamino)methyl)-1H-benzo[d]imidazole-4-carboxylate (1.65 mmol, 1.0 eq) and triethylamine (2.5 eq.) in dry methylene chloride (8 ml) was added a solution of 2,6-dimethyl-4-methoxybenzenesulfonyl chloride (1.65 mmol, 1.0 eq.) in methylene chloride (2 ml) and the resulting reaction mixture was stirred at room temperature for 12 h. The mixture was diluted with methylene chloride and successively washed with water and brine. The organic layer was dried over sodium sulfate and the solvent was evaporated under reduced pressure to give the crude product which was purified by silica gel column chromatography to afford F-26. Yield: 70%.

Synthesis of benzimidazole ester F-27: 2-[[(5-Chloro-thiophene-2-carbonyl)-methyl-amino]-methyl]-3H-benzoimidazole-4-carboxylic acid methyl ester (F-27)

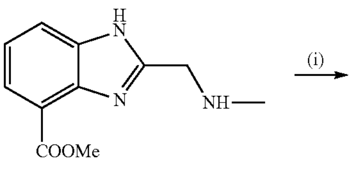

-continued

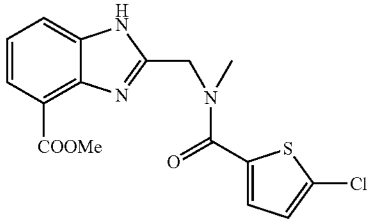

(i) To a solution of 5-chlorothiophene-2-carboxylic acid (1.23 mmol, 1.0 eq.) in THF (8 ml) was added diisopropyl ethylamine (4.0 eq.) at 0° C. followed by the addition of HATU (1.5 eq.). The resultant solution was allowed to stir at room temperature for 15 min. It was again cooled to 0° C. and a solution of methyl 2-((methylamino)methyl)-1H-benzo[d]imidazole-4-carboxylate (stage-3 product of 1-15, see below) (1.48 mmol, 1.2 eq.) in THF (2 ml) was added. The reaction mixture was allowed to stir at room temperature for 16 h. The mixture was then diluted with ethyl acetate, washed with saturated ammonium chloride solution, saturated sodium bicarbonate and finally with brine. The organic layer was dried over sodium sulfate and evaporated to dryness under reduced pressure to give the crude product which was purified by silica gel column chromatography to obtain desired product (F-27). Yield: 85%.

Synthesis of benzimidazole ester F-28: 2-[[(3-Chloro-thiophene-2-carbonyl)-methyl-amino]-methyl]-3H-benzoimidazole-4-carboxylic acid methyl ester (F-28)

(I) 2-[[(3-Chloro-thiophene-2-carbonyl)-methyl-amino]-methyl]-3H-benzoimidazole-4-carboxylic acid methyl ester (F-28) was prepared analogously to F-10 stage (III) using benzimidazole intermediate A and 3-chloro-thiophene-2-carboxylic acid chloride. Yield: 71%

(II) 2-[[(3-Chloro-thiophene-2-carbonyl)-methyl-amino]-methyl]-3H-benzoimidazole-4-carboxylic acid (ACI-28) was prepared analogously to F-10 stage (IV). Yield: 83%

5) Synthesis of the Benzimidazole Acids ACI

General Method for Synthesis of the Benzimidazoles G

Figure 6: Synthesis of the benzimidazoles G

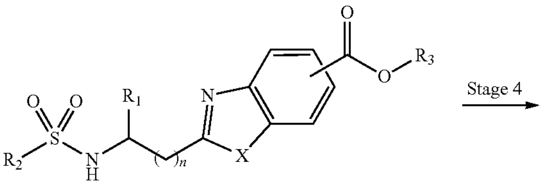

F

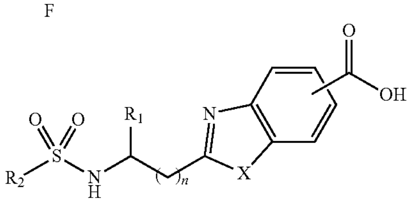

ACI

-continued

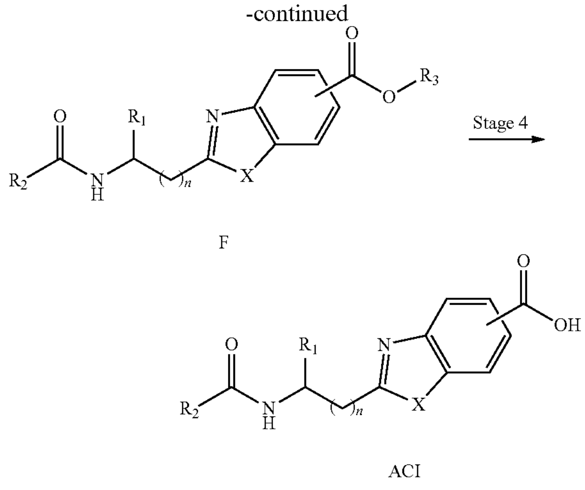

General working instructions 5 (GWI-5): Potassium hydroxide (9 eq.) and water was added to a solution of (F) (1.0 eq.) in methanol. The reaction mixture was heated under reflux for 2 h. The solvent was then distilled off, the residue was taken up in water and the mixture was acidified with 1 M HCl. A solid (ACI) thereby precipitated out and was filtered off and dried in vacuo.

General working instructions 6 (GWI-6): $LiOH.H_2O$ (4.0 eq.) in water was added to a solution of (F) (1 eq.) in THF-MeOH (1:1) at 0° C. The reaction mixture was stirred at room temperature for 16 h. THF and methanol were distilled off under reduced pressure, the residue was diluted with water and the mixture was washed with ethyl acetate. The aqueous phase was acidified with acetic acid and then extracted with methylene chloride. The methylene chloride phase was washed with sat. NaCl solution, dried over $Na_2SO_4$ and concentrated to dryness to obtain the desired product (ACI).

General working instructions 7 (GWI-7): Lithium hydroxide (3 eq.) was added to a solution of (F) (1 eq.) in a mixture of THF-MeOH—$H_2O$ (2:1:1) at 0° C. and the reaction mixture was stirred at room temperature for 12 h. THF and methanol were distilled off under reduced pressure, the residue was diluted with water and the mixture was washed with ethyl acetate. The aqueous phase was acidified with 1 N HCl and the solid which had precipitated out was filtered off and dried to obtain the desired product (ACI) in a pure form.

General working instructions 8 (GWI-8): A solution of (F) (1 eq.) and LiOH (5 eq.) in $THF/H_2O$ (1:1) was stirred at room temperature for 12 h. The solvent was removed completely, under reduced pressure, the residue was taken up in water and the mixture was washed with ethyl acetate. The aqueous phase was adjusted to pH=4 with 1 N HCl and extracted with ethyl acetate. The organic phase was dried over $Na_2SO_4$. After the solvent had been distilled off completely, the crude product (ACI) was obtained, and was employed in the next stage without further purification.

General working instructions 9 (GWI-9): Water and potassium hydroxide (9 eq.) were added to a solution of (F) (1 eq.) in methanol and the mixture was stirred at room temperature for three days. The methanol was distilled off under reduced pressure and the residue was acidified with 1 N HCl. The solid obtained was filtered off and dried to obtain the desired product (ACI) in a pure form.

General working instructions 10 (GWI-10): Water and potassium hydroxide (9 eq.) were added to a solution of (F) (1 eq.) in methanol and the mixture was stirred at room temperature for three days. The methanol was distilled off under reduced pressure and the residue was adjusted to pH=4 with 6 N HCl. The solid obtained was filtered off, washed with water and dried to obtain the desired product (ACI) in a pure form.

TABLE 4

| Synthesis of the benzimidazole acids (ACI) | | | | | | |
|---|---|---|---|---|---|---|
| ACI no. | Structure | Benzimidazole acid (ACI) | Benzimidazole ester (F) | Synthesis according to | Yield | Comments |
| ACI-01 | 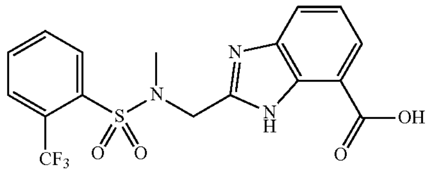 | 2-[[methyl-[[2-(trifluoromethyl)-phenyl]sulfonyl]-amino]-methyl]-3H-benzoimidazole-4-carboxylic acid (ACI-01) | 2-[[methyl-[[2-(trifluoromethyl)-phenyl]sulfonyl]amino]-methyl]-3H-benzoimidazole-4-carboxylic acid methyl ester (F-01) | GWI-5 | 49% (4.93 mmol) | — |
| ACI-02 | 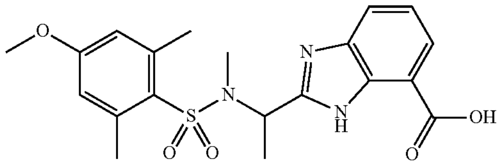 | 2-[1-[[(4-methoxy-2,6-dimethyl-phenyl)sulfonyl]-methyl-amino]-ethyl]-3H-benzoimidazole-4-carboxylic acid (ACI-02) | 2-[1-[[(4-methoxy-2,6-dimethyl-phenyl)sulfonyl]-methyl-amino]-ethyl]-3H-benzoimidazole-4-carboxylic acid methyl ester (F-02) | GWI-5 | 91% (4.22 mmol) | — |
| ACI-03 | 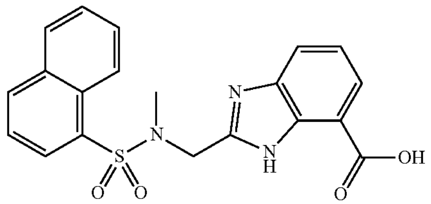 | 2-[[methyl-(naphthalen-1-ylsulfonyl)-amino]-methyl]-3H-benzoimidazole-4-carboxylic acid (ACI-03) | 2-[[methyl-(naphthalen-1-ylsulfonyl)-amino]-methyl]-3H-benzoimidazole-4-carboxylic acid methyl ester (F-03) | GWI-5 | 103% (12.6 mmol) | — |
| ACI-04 | 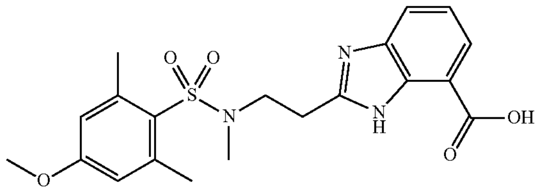 | 2-[2-[[(4-methoxy-2,6-dimethyl-phenyl)sulfonyl]-methyl-aminol-ethyl]-3H-benzoimidazole-4-carboxylic acid (ACI-04) | 2-[2-[[(4-methoxy-2,6-dimethyl-phenyl)sulfonyl]-methyl-amino]-ethyl]-3H-benzoimidazole-4-carboxylic acid methyl ester (F-04) | GWI-5 | 97% (11.9 mmol) | - in the basic state extracted 3 x more with diethyl etehr, then aqueous phase acidified |

TABLE 4-continued

Synthesis of the benzimidazole acids (ACI)

| ACI no. | Structure | Benzimidazole acid (ACI) | Benzimidazole ester (F) | Synthesis according to | Yield | Comments |
|---|---|---|---|---|---|---|
| ACI-05 | 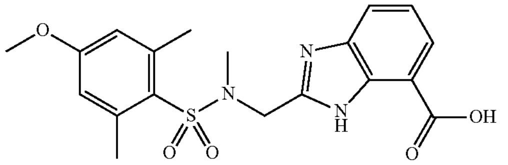 | 2-[[[(4-methoxy-2,6-dimethyl-phenyl)sulfonyl]-methyl-amino]-methyl]-3H-benzoimidazole-4-carboxylic acid (ACI-05) | 2-[[[(4-methoxy-2,6-dimethyl-phenyl)sulfonyl]-methyl-amino]-methyl]-3H-benzoimidazole-4-carboxylic acid methyl ester (F-05) | GWI-5 | 88% (5.19 mmol) | - in the basic state extracted 3 x more with diethyl etehr, then aqueous phase acidified |
| ACI-06 | 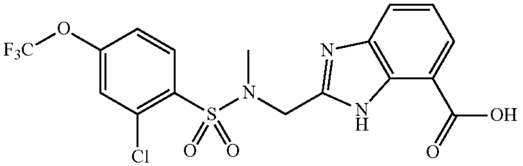 | 2-[[[[2-chloro-4-(trifluoromethyloxy)-phenyl]sulfonyl]-methyl-amino]-methyl]-3H-benzoimidazole-4-carboxylic acid (ACI-06) | 2-[[[[2-chloro-4-(trifluoromethyloxy)-phenyl]sulfonyl]-methyl-amino]-methyl]-3H-benzoimidazole-4-carboxylic acid methyl ester (F-06) | GWI-9 | 63% | |
| ACI-07 | 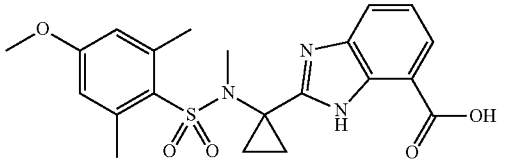 | 2-[1-[[(4-methoxy-2,6-dimethyl-phenyl)sulfonyl]-methyl-amino]-cyclopropyl]-3H-benzoimidazole-4-carboxylic acid (ACI-07) | 2-[1-[[(4-methoxy-2,6-dimethyl-phenyl)sulfonyl]-methyl-amino]-cyclopropyl]-3H-benzoimidazole-4-carboxylic acid methyl ester (F-07) | GWI-9 | 71% | - for 3h at 35° C., then overnight at RT - acid aqueous phase extracted with methylene |
| ACI-08 | 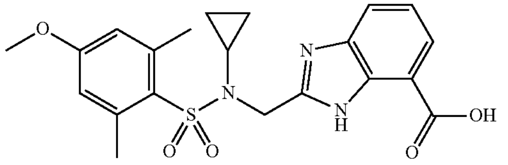 | 2-[[cyclopropyl-[(4-methoxy-2,6-dimethyl-phenyl)sulfonyl]-amino]-methyl]-3H-benzoimidazole-4-carboxylic acid (ACI-08) | 2-[[cyclopropyl-[(4-methoxy-2,6-dimethyl-phenyl)sulfonyl]-amino]-methyl]-3H-benzoimidazole-4-carboxylic acid methyl ester (F-08) | | | -see below (I-14) |
| ACI-09 | 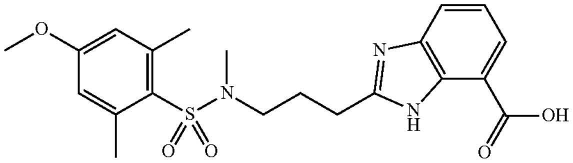 | 2-[3-[[(4-methoxy-2,6-dimethyl-phenyl)sulfonyl]-methyl-aminol-propyl]-3H-benzoimidazole-4-carboxylic acid (ACI-09) | 2-[3-[[(4-methoxy-2,6-dimethyl-phenyl)sulfonyl]-methyl-amino]-propyl]-3H-benzoimidazole-4-carboxylic acid methyl ester (F-09) | GWI-5 | 107% (25.8 mmol) | solvent: methanol/THF; base: 4 M NaOH |

TABLE 4-continued

Synthesis of the benzimidazole acids (ACI)

| ACI no. | Structure | Benzimidazole acid (ACI) | Benzimidazole ester (F) | Synthesis according to | Yield | Comments |
|---|---|---|---|---|---|---|
| ACI-10 | 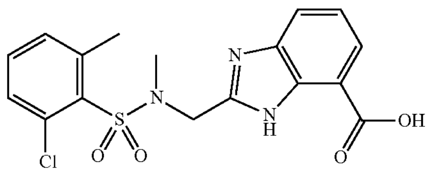 | 2-[[[(2-chloro-6-methyl-phenyl)sulfonyl]-methyl-amino]-methyl]-3H-benzoimidazole-4-carboxylic acid (ACI-10) | 2-[[[(2-chloro-6-methyl-phenyl)sulfonyl]-methyl-amino]-methyl]-3H-benzoimidazole-4-carboxylic acid methyl ester (F-10) | GWI-7 | 72.7% | — |
| ACI-11 | 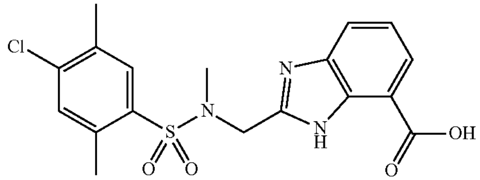 | 2-[[[(4-chloro-2,5-dimethyl-phenyl)sulfonyl]-methyl-amino]-methyl]-3H-benzoimidazole-4-carboxylic acid (ACI-11) | 2-[[[(4-chloro-2,5-dimethyl-phenyl)sulfonyl]-methyl-amino]-methyl]-3H-benzoimidazole-4-carboxylic acid methyl ester (F-11) | GWI-7 | 86.6% | — |
| ACI-13 | 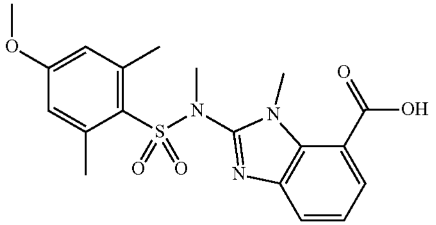 | 2-[[(4-methoxy-2,6-dimethyl-phenyl)sulfonyl]-methyl-amino]-3-methyl-3H-benzoimidazole-4-carboxylic acid (ACI-13) | 2-[[(4-methoxy-2,6-dimethyl-phenyl)sulfonyl]-methyl-aminol-3-methyl-3H-benzoimidazole-4-carboxylic acid methyl ester (F-13) | GWI-7 | 30% (0.14 mmol) | - purification via prep. HPLC |
| ACI-14 | 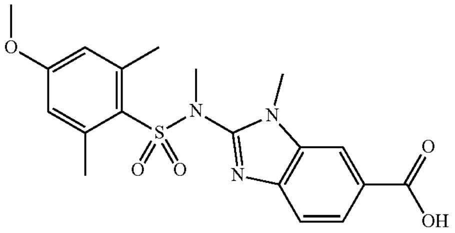 | 2-[[(4-methoxy-2,6-dimethyl-phenyl)sulfonyl]-methyl-amino]-3-methyl-3H-benzoimidazole-5-carboxylic acid (ACI-14) | | | | see F-14 |

TABLE 4-continued

Synthesis of the benzimidazole acids (ACI)

| ACI no. | Structure | Benzimidazole acid (ACI) | Benzimidazole ester (F) | Synthesis according to | Yield | Comments |
|---|---|---|---|---|---|---|
| ACI-16 | 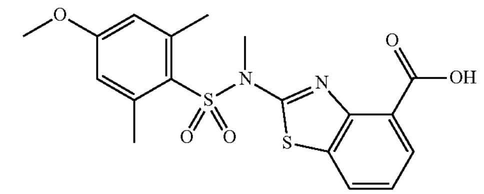 | 2-[[(4-methoxy-2,6-dimethyl-phenyl)sulfonyl]-methyl-amino]-benzothiazole-4-carboxylic acid (ACI-16) | 2-[[(4-methoxy-2,6-dimethyl-phenyl)sulfonyl]-methyl-amino]-benzothiazole-4-carboxylic acid methyl ester (F-16) | GWI-7 | 35% (0.24 mmol) | — |
| ACI-17 | 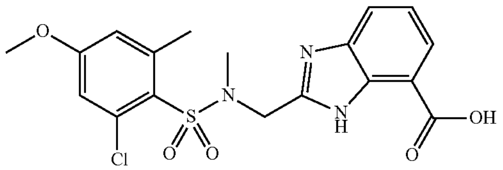 | 2-[[[(2,6-dichloro-3-methyl-phenyl)sulfonyl]-methyl-amino]-methyl]-3H-benzoimidazole-4-carboxylic acid (ACI-17) | 2-[[[(2,6-dichloro-3-methyl-phenyl)sulfonyl]-methyl-amino]-methyl]-3H-benzoimidazole-4-carboxylic acid methyl ester (F-17) | GWI-9 | 50% (1.10 mmol) | -150 eq. methanol - 3 h reaction time - base (diethyl ether)/acid (ethyl acetate) |
| ACI-18 | 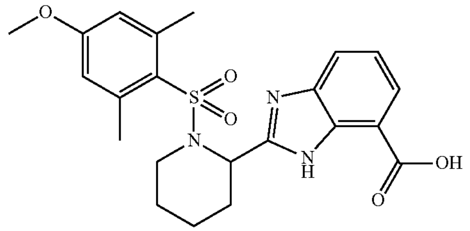 | 2-[1-[(4-methoxy-2,6-dimethyl-phenyl)sulfonyl]-piperidin-2-yl]-3H-benzoimidazole-4-carboxylic acid (ACI-18) | 2-[1-[(4-methoxy-2,6-dimethyl-phenyl)sulfonyl]-piperidin-2-yl]-3H-benzoimidazole-4-carboxylic acid methyl ester (F-18) | GWI-9 | 95% (0.25 mmol) | -150 eq. methanol - 4 h at 50° C., overnight at room temperature - base/acid, with ethyl acetate, extraction |
| ACI-19 | 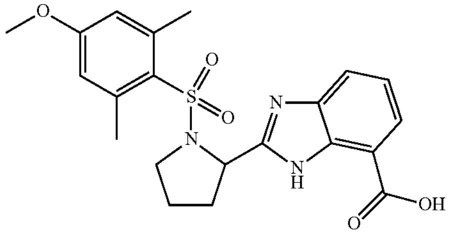 | 2-[1-[(4-methoxy-2,6-dimethyl-phenyl)sulfonyl]-pyrrolidin-2-yl]-3H-benzoimidazole-4-carboxylic acid (ACI-19) | 2-[1-[(4-methoxy-2,6-dimethyl-phenypsulfonyl]-pyrrolidin-2-yl]-3H-benzoimidazole-4-carboxylic acid methyl ester (F-19) | GWI-9 | 77% (1.93 mmol) | -1 h at RT and 1 h under reflux - base extraction with diethyl ether, then acidified in aqueous form, solid filtered off |

TABLE 4-continued

| Synthesis of the benzimidazole acids (ACI) | | | | | | |
|---|---|---|---|---|---|---|
| ACI no. | Structure | Benzimidazole acid (ACI) | Benzimidazole ester (F) | Synthesis according to | Yield | Comments |
| ACI-20 | 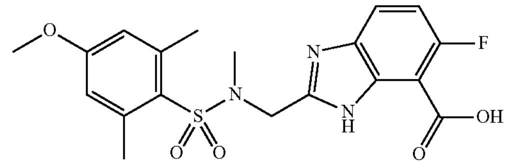 | 5-fluoro-2-[[[(4-methoxy-2,6-dimethyl-phenyl)sulfonyl]-methyl-amino]-methyl]-3H-benzoimidazole-4-carboxylic acid (ACI-20) | 5-fluoro-2-[[[(4-methoxy-2,6-dimethyl-phenyl)sulfonyl]-methl-amino]-methyl]-3H-benzoimidazole-4-carboxylic acid ethyl ester (F-20) | | | cf. Ex. no. I-13 |
| ACI-21 | 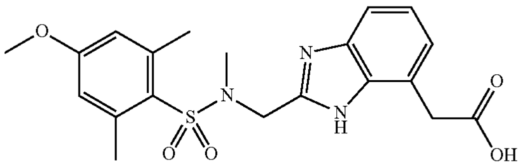 | 2-[2-[[[(4-methoxy-2,6-dimethyl-phenyl)sulfonyl]-methyl-amino]-methyl]-3H-benzoimidazol-4-yl1-acetic acid (ACI-21) | 2-[2-[[[(4-methoxy-2,6-dimethyl-phenyl)sulfonyl]-methyl-amino]-methyl]-3H-benzoimidazol-4-yl]-acetic acid methyl ester (F-21) | | | see below |
| ACI-22 | 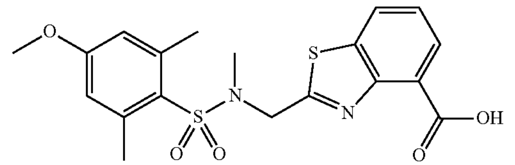 | 2-[[[(4-methoxy-2,6-dimethyl-phenyl)sulfonyl]-methyl-amino]-methyl]-benzothiazole-4-carboxylic acid (ACI-22) | 2-[[[(4-methoxy-2,6-dimethyl-phenyl)sulfonyl]-methyl-amino]-methyl]-benzothiazole-4-carboxylic acid methyl ester (F-22) | | | see below |
| ACI-23 | 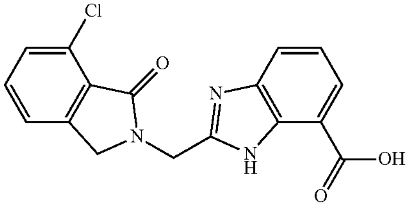 | 2-[(4-chloro-3-oxo-1,2-dihydro-isoindol-2-yl)-methyl]-3H-benzoimidazole-4-carboxylic acid (ACI-23) | 2-[(4-chloro-3-oxo-1,2-dihydro-isoindol-2-yl)methyl]-3H-benzoimidazole-4-carboxylic acid methyl ester (F-23) | GWI-7 | 70% | — |
| ACI-24 | 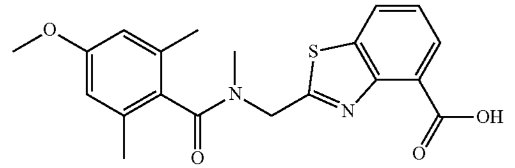 | 2-[[(4-methoxy-2,6-dimethyl-benzoyl)-methyl-amino]-methyl]-3H-benzoimidazole-4-carboxylic acid (ACI-24) | 2-[[(4-methoxy-2,6-dimethyl-benzoyl)-methyl-amino]-methyl]-3H-benzoimidazole-4-carboxylic acid methyl ester (F-24) | GWI-7 | 67% | — |

TABLE 4-continued

Synthesis of the benzimidazole acids (ACI)

| ACI no. | Structure | Benzimidazole acid (ACI) | Benzimidazole ester (F) | Synthesis according to | Yield | Comments |
|---|---|---|---|---|---|---|
| ACI-25 | 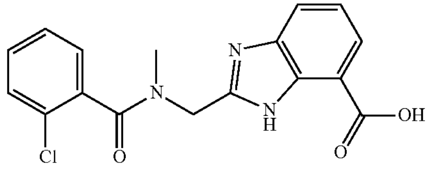 | 2-[[(2-chloro-benzoyl)-methyl-amino]-methyl]-3H-benzoimidazole-4-carboxylic acid (ACI-25) | 2-[[(2-chloro-benzoylymethyl-amino]-methyl]-3H-oimidazole-4-carboxylic acid methyl ester (F-25) | GWI-7 | 83% | — |
| ACI-26 | 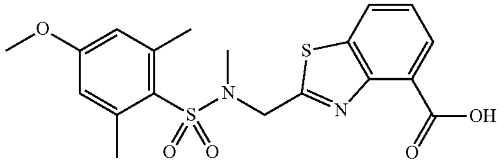 | 2-[[[(4-methoxy-2,6-dimethyl-phenyl)sulfonyl]-methyl-amino]-methyl]-1-methyl-1H-benzoimidazole-4-carboxylic acid (ACI-26) | 2-[[[(4-methoxy-2,6-dimethyl-phenyl)sulfonyl]-methyl-amino]-methyl]-1-methyl-1H-benzoimidazole-4-carboxylic acid methyl ester (F-26) | GWI-8 | 90% | $LiOH.H_2O$ (4 eq.) $MeOH:H_2O$=, 4:1 reaction time: 5 h |
| ACI-27 | 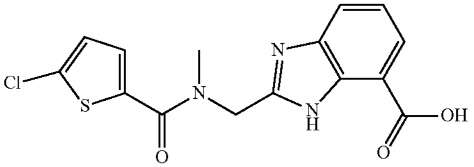 | 2-[[(5-chloro-thiophene-2-carbonyl)-methyl-amino]-methyl]-3H-benzoimidazole-4-carboxylic acid (ACI-27) | 2-[[(5-chloro-thiophene-2-carbonyl)-methyl-amino]-methyl]-3H-benzoimidazole-4-carboxylic acid methyl ester (F-27) | GWI-6 | 30% (0.33 mmol) | — |
| ACI-28 | 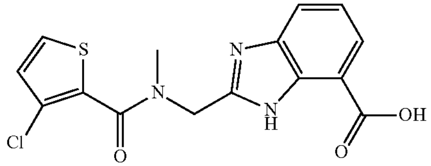 | 2-[[(3-chloro-thiophene-2-carbonyl)-methyl-amino]-methyl]-3H-benzoimidazole-4-carboxylic acid (ACI-28) | 2-[[(3-chloro-thiophene-2-carbonyl)-methyl-amino]-methyl]-3H-benzoimidazole-4-carboxylic acid methyl ester (F-28) | GWI-7 | 83% | — |
| ACI-29 | 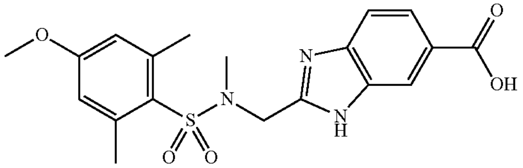 | 2-[[[(4-methoxy-2,6-dimethyl-phenyl)sulfonyl]-methyl-amino]-methyl]-3H-benzoimidazole-5-carboxylic acid (ACI-29) | 2-[[[(4-methoxy-2,6-dimethyl-phenyl)sulfonyl]-methyl-amino]-methyl]-3H-benzoimidazole-5-carboxylic acid methyl ester (F-29) | GWI-10 | 97% (17.6 mmol) | — |

TABLE 4-continued

| Synthesis of the benzimidazole acids (ACI) | | | | | | |
|---|---|---|---|---|---|---|
| ACI no. | Structure | Benzimidazole acid (ACI) | Benzimidazole ester (F) | Synthesis according to | Yield | Comments |
| ACI-30 | 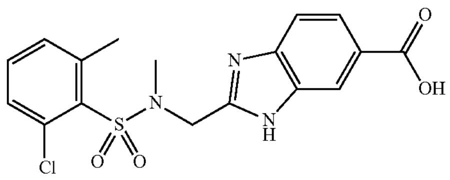 | 2-[[[(2-chloro-6-methyl-phenyl)sulfonyl]-methyl-amino]-methyl]-3H-benzoimidazole-5-carboxylic acid (ACI-30) | 2-[[[(2-chloro-6-methyl-phenyl)sulfonyl]-methyl-amino]-methyl]-3H-benzoimidazole-5-carboxylic acid methyl ester (F-30) | GWI-9 | 82% (4.91 mmol) | - 2 h refluxed |
| ACI-31 | 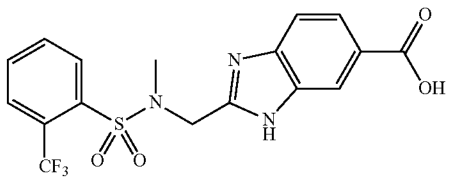 | 2-[[methyl-[[2-(trifluoromethyl)-phenyl]sulfonyl]-aminol-methyl]-3H-benzoimidazole-5-carboxylic acid (ACI-31) | 2-[[methyl-[[2-(trifluoromethyl)-phenyl]sulfonyl]-amino]-methyl]-3H-benzoimidazole-5-carboxylic acid methyl ester (F-31) | GWI-9 | 92% (8.93 mmol) | - 2 h refluxed |
| ACI-32 | 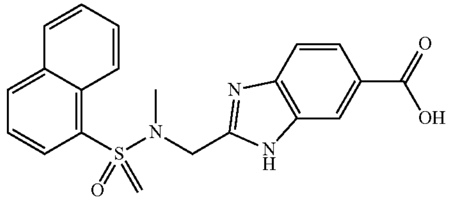 | 2-[[methyl-(naphthalen-1-ylsulfonyl)-amino]-methyl]-3H-benzoimidazole-5-carboxylic acid (ACI-32) | 2-[[methyl-(naphthalen-1-ylsulfonyl)-amino]-methyl]-3H-benzoimidazole-5-carboxylic acid methyl ester (F-32) | GWI-9 | 95% (11.9 mmol) | - 2 h refluxed |
| ACI-33 | 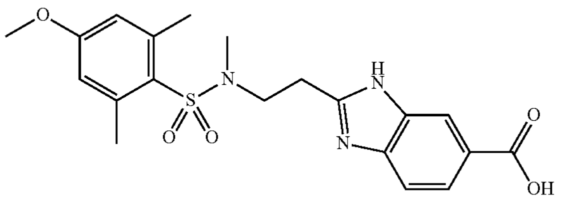 | 2-[2-[[(4-methoxy-2,6-dimethyl-phenyl)sulfonyll-methyl-amino]-ethyl]-3H-benzoimidazole-5-carboxylic acid (ACI-33) | 2-[2-[[(4-methoxy-2,6-dimethyl-phenypsulfonyl]-methyl-amino]-ethyl]-3H-benzoimidazole-5-carboxylic acid methyl ester (F-33) | GWI-10 | 99% (18.0 mmol) | — |

Synthesis of benzimidazole acid ACI-21: 2-[2-[[[(4-Methoxy-2,6-dimethyl-phenyl)sulfonyl]-methyl-amino]-methyl]-3H-benzoimidazol-4-yl]-acetic acid (ACI-21)

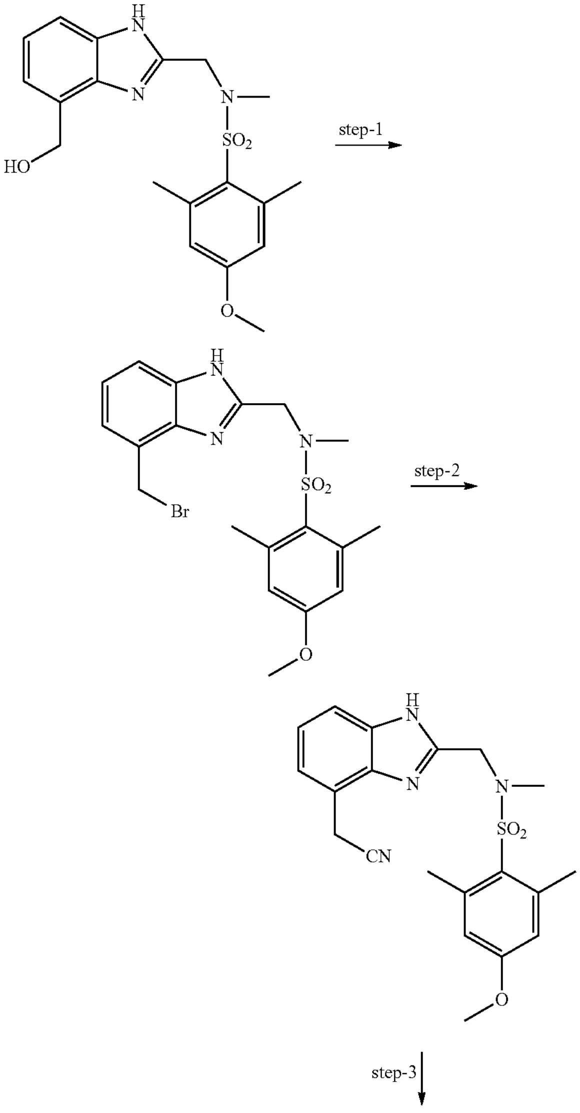

-continued

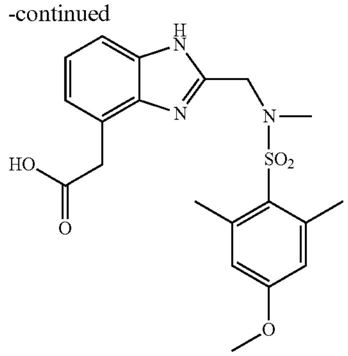

Step-1: To a cooled (0° C.) solution of N-((7-(Hydroxymethyl)-1H-benzo[d]imidazol-2-yl)methyl)-4-methoxy-N,2,6-trimethylbenzenesulfonamide (see stage-5 in the preparation of 1-15) (2.06 mmol, 1.0 eq.) in DMF (8 ml) was added $PBr_3$ (1.5 eq.) and it was stirred at room temperature for 1 h. After completion of the reaction (monitored by TLC), water was added and it was extracted with methylene chloride. The organic layer was washed with brine and water, and dried over sodium sulfate. The solvent was evaporated under reduced pressure to give the crude product which was immediately used in the next step without purification because the bromo compound was unstable.

Step-2: To a solution of N-((4-(bromomethyl)-1H-benzo[d]imidazol-2-yl)methyl)-4-methoxy-N,2,6-trimethylbenzenesulfonamide from step-1 in DMF (10 ml) was added KCN (1.2 eq.) and reaction mixture was heated at 100° C. for 14 h. The reaction mixture was diluted with ethyl acetate and washed with water, brine, saturated $FeSO_4$ solution and finally again with brine. The organic layer was dried over sodium sulfate and the solvent was evaporated under reduced pressure to give the crude product which was purified by silica gel column chromatography. Yield: 22%.

Step-3: A suspension of N-((4-(cyanomethyl)-1H-benzo[d]imidazol-2-yl)methyl)-4-methoxy-N,2,6-trimethylbenzenesulfonamide (0.50 mmol) in 25% KOH solution (15 ml) was heated to reflux for 1 h. The reaction mixture was diluted with water and washed with methylene chloride. The aqueous layer was acidified with acetic acid under cooled conditions and extracted with methylene chloride. The organic layer was dried over sodium sulfate and concentrated to yield ACI-21. Yield: 80%.

Synthesis of benzimidazole acid ACI-22: 2-[[[(4-Methoxy-2,6-dimethyl-phenyl)sulfonyl]-methyl-amino]-methyl]-benzothiazole-4-carboxylic acid (ACI-22)

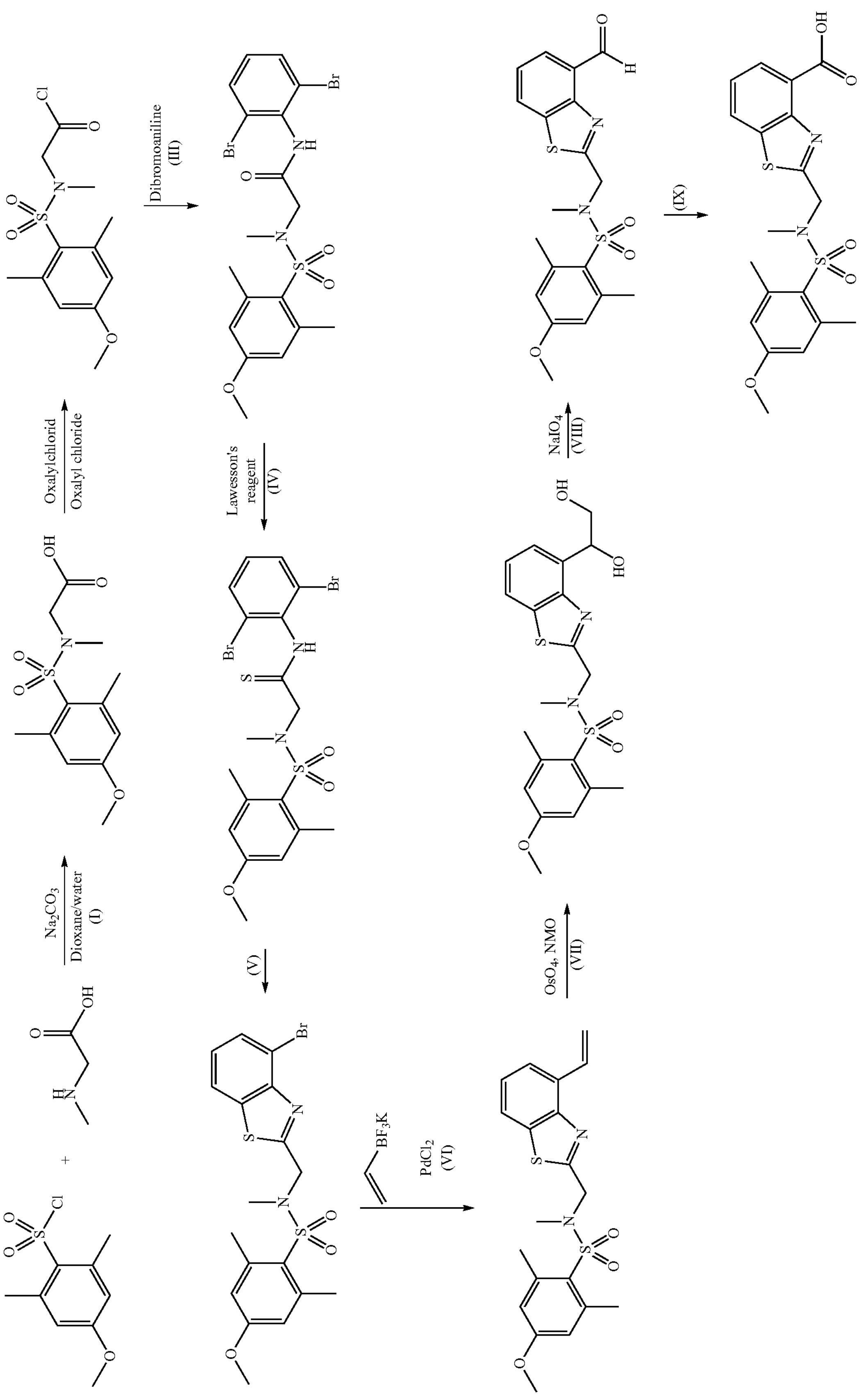
Na$_2$CO$_3$
Dioxane/water
(I)
Oxalylchlorid
Oxalyl chloride
Dibromoaniline
(III)
Lawesson's
reagent
(IV)
(V)
BF$_3$K
PdCl$_2$
(VI)
OsO$_4$, NMO
(VII)
NaIO$_4$
(VIII)
(IX)

(I) $Na_2CO_3$ was added to a mixture of 2-methylaminoacetic acid and 4-methoxy-2,6-dimethyl-benzenesulfonyl chloride in 1:1 dioxane/water (240 ml) and the mixture was stirred at room temperature for 3 h. The reaction mixture was neutralized with dilute HCl and diluted with ethyl acetate. The organic phase was washed with water and sat. NaCl solution, dried over $Na_2SO_4$ and concentrated. The crude product was employed in the next stage without further purification. Yield: 87.5%

(II) Oxalyl chloride (3 eq.) and DMF (2 drops) were added to a solution of the product just obtained in stage (I) (1.5 g, 5.2 mmol) in methylene chloride (15 ml). The reaction mixture was stirred at room temperature for 2 h and then concentrated in order to obtain the crude product that was employed in the next stage without further purification.

(III) 2,6-Dibromoaniline (1 eq.) was added to a solution of the product just obtained in stage (II) (0.53 g, 1.7 mmol) in methylene chloride (10 ml) and the mixture was stirred at room temperature for 2 h. The reaction mixture was diluted with methylene chloride and washed with $NaHSO_3$ solution. The organic phase was washed with water and sat. NaCl solution, dried over $Na_2SO_4$ and concentrated. The crude product was purified by column chromatography (ethyl acetate/hexane). Yield: 40%

(IV) Lawesson's reagent was added to a solution of the product just obtained in stage (III) (0.3 g, 0.57 mmol) in toluene (2.5 ml) and the mixture was refluxed for 2 h. The reaction mixture was cooled to room temperature and diluted with ethyl acetate. The organic phase was washed with water and sat. NaCl solution, dried over $Na_2SO_4$ and concentrated. The crude product was purified by column chromatography (ethyl acetate/hexane). Yield: 30%

(V) $Cs_2CO_3$, $Pd_2$ $dba_3$ and xantphos were added in succession to a solution of the product just obtained in stage (IV) (1 g, 1.86 mmol) in 1,4-dioxane (10 ml) and the mixture was degassed. The reaction mixture was heated at 80° C. under an $N_2$ atmosphere for 4 h and then cooled to room temperature and diluted with ethyl acetate. The organic phase was washed with water and sat. NaCl solution, dried over $Na_2SO_4$ and concentrated. The crude product was purified by column chromatography (ethyl acetate/hexane). Yield: 40%

(VI) Potassium vinyl-trifluoroborate (1.4 eq.), triphenylphosphine (0.09 eq.), $Cs_2CO_3$ (3 eq.) and $PdCl_2$ (0.03 eq.) were added to a solution of the product just obtained in stage (V) (250 mg, 0.56 mmol) in 9:1 THF/water (3 ml) and the reaction mixture was heated at 90° C. in a sealed tube for 24 h. The reaction mixture was then cooled to room temperature and concentrated in vacuo. The residue was taken up in ethyl acetate and the mixture was washed with water and sat. NaCl solution, dried over $Na_2SO_4$ and concentrated. The crude product was purified by column chromatography (ethyl acetate/hexane). Yield: 30%

(VII) NMO (1.1 eq.) and $OsO_4$ (4% wt./volume, 0.03 eq.) was added to a solution of the product just obtained in stage (VI) (150 mg, 0.373 mmol) in 8:1 acetone/water (2 ml) at 0° C. and the mixture was stirred at room temperature for 4 h and finally quenched with sodium sulfite and stirred at room temperature for 30 min. The reaction mixture was diluted with ethyl acetate and the organic phase was washed with water and sat. NaCl solution, dried over $Na_2SO_4$ and concentrated. The crude product was purified by column chromatography (ethyl acetate/hexane). Yield: 87%

(VIII) Sodium periodide (1.1 eq.) was added to a solution of the product just obtained in stage (VII) (80 mg, 0.183 mmol) in 4:1 THF/water (1.5 ml) at 0° C. and the mixture was stirred at room temperature for 3 h. The reaction mixture was quenched with water and diluted with ethyl acetate. The organic phase was washed with water and sat. NaCl solution, dried over $Na_2SO_4$ and concentrated. The crude product was purified by column chromatography (ethyl acetate/hexane). Yield: 95%

(IX) 2-Methyl-2-butene (3.6 eq.) and $NaH_2PO_4.2H_2O$ (4 eq.) was added to a solution of the product just obtained in stage (VIII) (490 mg, 1.212 mmol) in 3:3:1 THF/tert-butanol/water (14 ml) at room temperature. The reaction mixture was then cooled to 0° C., $NaClO_2$ (4.4 eq.) was added in portions and the mixture was stirred at room temperature for 16 h. The reaction mixture was concentrated and the residue was diluted with ethyl acetate. The organic phase was washed with water and sat. NaCl solution, dried over $Na_2SO_4$ and concentrated. The crude product was purified by column chromatography (ethyl acetate/hexane). Yield: 8%

B.) Synthesis of the Amine Units

TABLE 5

Amine units overview (AMN and Boc-AMN)

| AMN unit no. | Structure | AMN name |
|---|---|---|
| AMN-01 | 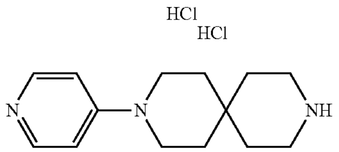 | 9-pyridin-4-yl-3,9-diazaspiro[5.5]undecane dihydrochloride (AMN-01) |
| Boc-AMN-02 | 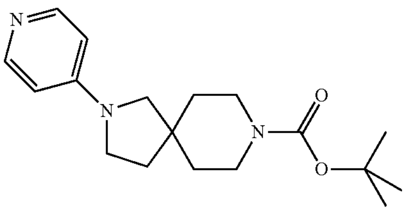 | 3-pyridin-4-yl-3,8-diazaspiro[4.5]decane-8-carboxylic acid tert-butyl ester (Boc-AMN-02) |

TABLE 5-continued

| Amine units overview (AMN and Boc-AMN) | | |
|---|---|---|
| AMN unit no. | Structure | AMN name |
| Boc-AMN-03 | 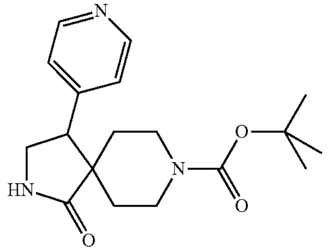 | 4-oxo-1-pyridin-4-yl-3,8-diazaspiro[4.5]decane-8-carboxylic acid tert-butyl ester (Boc-AMN-03) |
| AMN-04 | 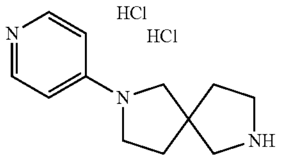 | 8-pyridin-4-yl-3,8-diazaspiro[4.4]nonane dihydrochloride (AMN-04) |
| AMN-05 | 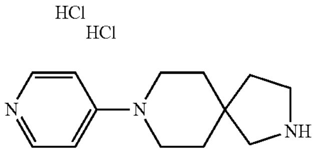 | 8-pyridin-4-yl-3,8-diazaspiro[4.5]decane dihydrochloride (AMN-05) |
| AMN-06 | 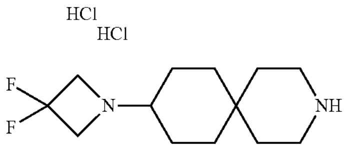 | 9-(3,3-difluoro-azetidin-1-yl)-3-azaspiro[5.5]undecane dihydrochloride (AMN-06) |
| AMN-07 | 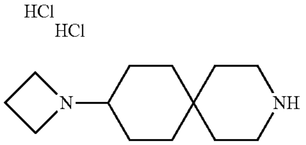 | 9-(azetidin-1-yl)-3-azaspiro[5.5]undecane dihydrochloride (AMN-07) |
| AMN-08 | 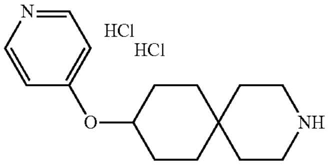 | 9-pyridin-4-yloxy)-3-azaspiro[5.5]undecane dihydrochloride (AMN-08) |
| AMN-09 | 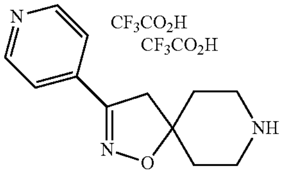 | 3-pyridin-4-yl-1-oxa-2,8-diazaspiro[4.5]dec-2-ene bistrifluoroacetate (AMN-09) |

Amine Unit Syntheses

Synthesis of the amine unit AMN-01: 9-pyridin-4-yl-3,9-diazaspiro[5.5]undecane dihydrochloride (AMN-01)

(i): tert-Butyl 3,9-diazaspiro[5.5]undecane-3-carboxylate (1 g, 3.931 mmol), 4-chloropyridinium chloride (1.765 g, 11.794 mmol) and triethylamine (2.2 ml, 15.725 mmol) were refluxed in 1-butanol (50 ml) for 15 h. Saturated sodium bicarbonate solution (30 ml) and ethyl acetate (80 ml) were added, the phases were separated and the aqueous phase was extracted with ethyl acetate (2×80 ml). The combined organic phases were dried over magnesium sulfate and concentrated in vacuo. The crude product was purified by column chromatography (silica gel) with ethyl acetate/hexane/methanol/ammonia (25% aq.) 400/40/40/1. Yield: 0.52 g, 39%

(ii): Hydrogen chloride in methanol (1.25 mol/l, 6.3 ml) was added to tert-butyl 9-(pyridin-4-yl)-3,9-diazaspiro[5.5]undecane-3-carboxylate (0.52 g, 1.569 mmol) and the mixture was refluxed for 1 h. The solvent was removed in vacuo, the residue was taken up in ethanol (3 ml) and the mixture was cooled. Acetone (80 ml) was added and the mixture was stirred in an ice bath for 30 min. The precipitate was filtered off with suction, washed with diethyl ether and dried in vacuo. Yield: 0.4 g, 83%

Synthesis of the amine unit AMN-02: 3-Pyridin-4-yl-3,8-diazaspiro[4.5]decane-8-carboxylic acid tert-butyl ester (Boc-AMN-02)

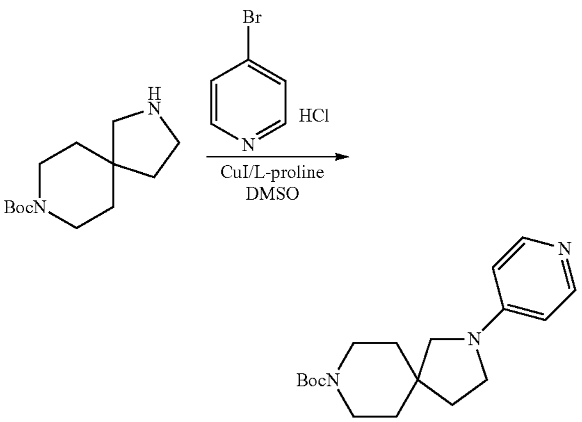

Sodium tertbutanolate (3 eq.) and 4-bromopyridine hydrochlorides (1.2 eq.) were added to a solution of the spiro-amine (1 eq.) in toluene (5 ml/mmol). The reaction mixture was degassed under an argon atmosphere, (+/−) BINAP (0.06 eq.) and $Pd(OAc)_2$ (0.02 eq.) were added and the reaction mixture obtained was refluxed for 2 h. The reaction mixture was cooled to room temperature and diluted with ethyl acetate and the organic phase was washed successively with water and sat. NaCl solution. After drying over $Na_2SO_4$, the organic phase was concentrated under reduced pressure to obtain the crude product, which was purified by column chromatography (5% methanol in methylene chloride). Yield: 40%

Synthesis of the amine unit Boc-AMN-03: 4-oxo-1-pyridin-4-yl-3,8-diazaspiro[4.5]decane-8-carboxylic acid tert-butyl ester (Boc-AMN-03)

Synthesis of 4-(2-nitrovinyl)pyridine

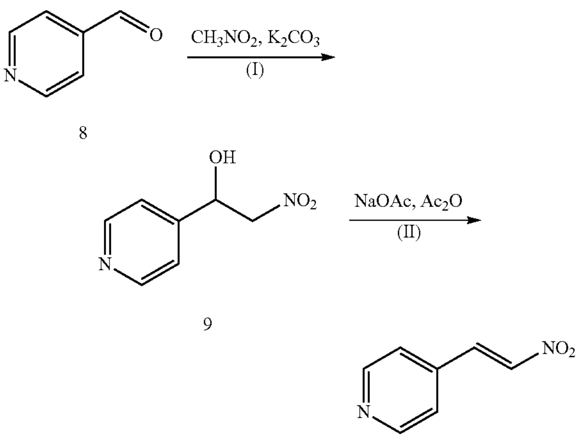

8

9

-continued

Synthesis of Boc_AMN-03

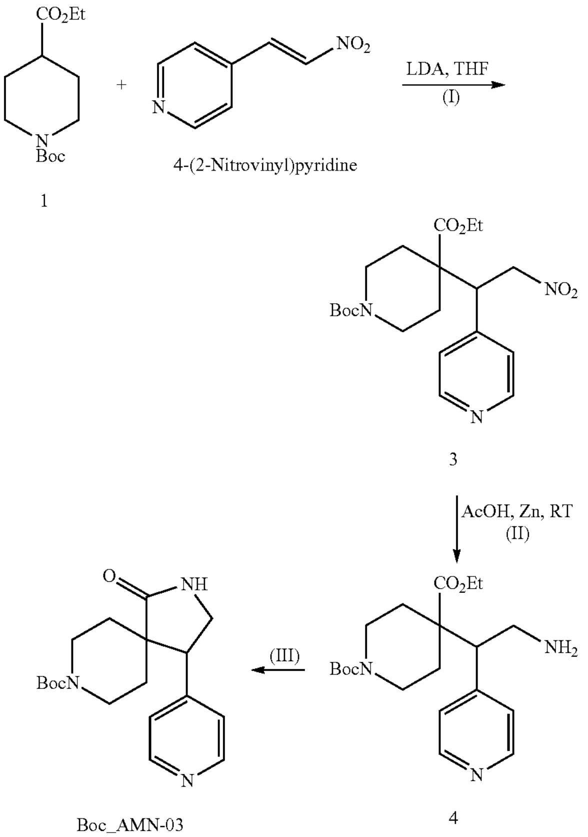

4-(2-Nitrovinyl)pyridine

1

3

4

Boc_AMN-03

Synthesis of 4-(2-nitrovinyl)pyridine (I) $K_2CO_3$ (0.05 g, 3.62 mmol) was added to a solution of 8 (1 g, 9.4 mmol) in nitromethane (3 ml) and the mixture was refluxed for 2 h and then cooled to 25° C. Nitromethane was distilled off under reduced pressure. The residue was taken up in methanol and the mixture was filtered and concentrated in vacuo to obtain the crude product, which was employed in the next stage without further purification. Yield: 72% (crude)

(II) Sodium acetate (0.59 g, 5.3 mmol) was added to a solution of 9 (0.6 g, 3.57 mmol) in acetic anhydride (3 ml) at 0° C. and the mixture was stirred under identical reaction conditions for 3 h. The reaction mixture was extracted with chloroform and the extract was washed with water, dried over $Na_2SO_4$, filtered and concentrated in vacuo to obtain the crude product, which was employed in the next stage without further purification. Yield: 23%

(I) Diisopropylethyl amine (1.26 ml, 8.94 mmol) was reacted with 1.5 M n-butyl lithium (5.7 ml, 8.55 mmol) at −78° C. in abs. THF (15 ml) under an $N_2$ atmosphere and the mixture was warmed to −20° C. in the course of 30 min. The solution was then cooled again to −60° C. and a solution of 1 (2 g, 7.78 mmol) in abs. THF (10 ml) was added at −60° C. The reaction mixture was thawed to −40° C. in the course of 1 h and a solution of 2 (1.16 g, 7.78 mmol) in abs. THF (10 ml) was added dropwise. The reaction mixture was thawed to 25° C. in the course of 1 h, quenched with sat. $NH_4Cl$ solution and extracted with ethyl acetate. The combined organic phases were washed with water and sat. NaCl, dried over $Na_2SO_4$, filtered and concentrated in vacuo. The crude product was purified by column chromatography (100-200 mesh silica gel, 20% ethyl acetate in hexane). Yield: 26.3%

(II) Zinc dust (2.45 g, 37.59 mmol) was added to a solution of 3 (1.8 g, 4.42 mmol) in acetic acid (20 ml) at 0° C. and the reaction mixture was stirred at 25° C. for 3 h. The reaction mixture was concentrated under reduced pressure, the residue was taken up in ethyl acetate and the mixture was washed 4× with sat. $NaHCO_3$ solution. The ethyl acetate phase was washed with sat. NaCl solution, dried over $Na_2SO_4$, filtered and concentrated in vacuo and the residue was employed in the next stage without further purification. Yield: 97%

(III) A solution of 4 (0.75 g, 1.98 mmol) in toluene (20 ml) was heated under reflux for 18 h. Toluene was distilled off in vacuo and the crude product (Boc-AMN-03) was purified by column chromatography (100-200 mesh silica gel, 5% methanol in methylene chloride). Yield: 38%

Synthesis of the amine unit AMN-04: 8-Pyridin-4-yl-3,8-diazaspiro[4.4]nonane dihydrochloride (AMN-04)

The synthesis was carried out analogously to the synthesis of amine AMN-01. For this, in stage (i) tert-butyl 2,7-diazaspiro[4.4]nonane-2-carboxylate was reacted with 4-chloropyridinium chloride (yield: 50%). The Boc protective group was then split off in stage (ii). When the reaction had ended and the methanol had been removed in vacuo, the residue was taken up in ethanol, the mixture was cooled and acetone was added. The resulting suspension was stirred in an ice bath for 30 min and the precipitate was filtered off with suction, washed with acetone and dried in vacuo. Yield (AMN-04): 73%

Synthesis of the amine unit AMN-05: 8-Pyridin-4-Yl-3,8-diazaspiro[4.5]decane dihydrochloride (AMN-05)

The synthesis was carried out analogously to the synthesis of amine AMN-01. For this, in stage (i) tert-butyl 2,8-diazaspiro[4.5]decane-2-carboxylate was reacted with 4-chloropyridinium chloride (yield: 22%). The Boc protective group was then split off in stage (ii). When the reaction had ended and the methanol had been removed in vacuo, the residue . . . taken up in ethanol, the mixture . . . cooled and acetone . . . added. The resulting suspension was stirred in an ice bath for 30 min and the precipitate was filtered off with suction, washed with acetone and dried in vacuo. Yield (AMN-05): 92%.

Synthesis of the amine unit AMN-06: 9-(3,3-Difluoro-azetidin-1-yl)-3-azaspiro[5.5]undecane dihydrochloride (AMN-06)

Stage (i): tert-Butyl 9-(3,3-difluoroazetidin-1-yl)-3-azaspiro[5.5]undecane-3-carboxylate tert-Butyl 9-oxo-3-azaspiro[5.5]undecane-3-carboxylate (stage (iv) AMN-08) (1 g, 3.74 mmol) was added to 3,3-difluoroazetidine hydrochloride (0.484 g, 3.74 mmol) and triethylamine (0.52 ml, 3.74 mmol) in 1,2-dichloroethane (15 ml). The mixture was stirred for 5 min and sodium triacetoxyborohydride (1.1 g, 5.23 mmol) was then added and the mixture was stirred at room temperature for 3 d. Saturated sodium bicarbonate solution was added and closely separation of the phases the aqueous phase was extracted with methylene chloride (2×). The combined organic phases were washed with saturated sodium chloride solution (1×), dried over magnesium sulfate and concentrated in vacuo. Yield: 1.26 g (98%)

Stage (ii): 9-(3,3-Difluoro-azetidin-1-yl)-3-azaspiro[5.5]undecane dihydrochloride tert-Butyl 9-(3,3-difluoroazetidin-1-yl)-3-azaspiro[5.5]undecane-3-carboxylate (1.26 g, 3.66 mmol) was dissolved in hydrogen chloride in methanol (1.25 mol/l, 29 ml) and the solution was refluxed for 45 min. The solvent was removed in vacuo and the residue was dissolved in a small amount of ethanol. A solid was then precipitated out by addition of acetone. The mixture was stirred at room temperature for 10 min, diethyl ether was then added and the mixture was stirred at room temperature for a further 30 min. The precipitate formed was filtered off with suction, washed with diethyl ether and dried in vacuo. Yield: 1.1 g (95%)

Synthesis of the amine unit AMN-07: 9-(Azetidin-1-Yl)-3-azaspiro[5.5]undecane dihydrochloride (AMN-07)

Stage (i): tert-Butyl 9-(azetidin-1-yl)-3-azaspiro[5.5]undecane-3-carboxylate tert-Butyl 9-oxo-3-azaspiro[5.5]undecane-3-carboxylate (stage (iv) AMN-08) (1 g, 3.74 mmol) and azetidine (0.25 ml, 3.74 mmol) were initially introduced into 1,2-dichloroethane (15 ml), and sodium triacetoxyborohydride (1.1 g, 5.23 mmol) was added. The reaction mixture was stirred at room temperature for 3 d and saturated sodium bicarbonate solution was then added. After separation of the phases, the aqueous phase was extracted with methylene chloride (2×). The combined organic phases were washed with saturated sodium chloride solution (1×), dried over magnesium sulfate and concentrated in vacuo. The crude product was purified by column chromatography (silica gel, ethyl acetate/methanol/ammonia (25% aq.) 100:10:1). Yield: 1 g (89%)

Stage (ii): 9-(Azetidin-1-Yl)-3-azaspiro[5.5]undecane dihydrochloride

Hydrogen chloride in methanol (1.25 mol/l, 15.5 ml) was added to tert-butyl 9-(azetidin-1-yl)-3-azaspiro[5.5]undecane-3-carboxylate (1 g, 3.24 mmol) and the mixture was refluxed for 45 min. The solvent was removed in vacuo and the residue was dissolved in a small amount of ethanol. A solid was then precipitated out by addition of acetone, and finally diethyl ether was added and the precipitate formed was filtered off with suction. Yield: 0.87 g (95%)

Synthesis of the amine unit AMN-08: 9-Pyridin-4-yloxy)-3-azaspiro[5.5]undecane dihydrochloride (AMN-08)

Stage (i): 1-(Benzyloxycarbonyl)piperidine-4-carboxylic acid

Water (75 ml) was added to piperidine-4-carboxylic acid (25 g) in THF (75 ml), followed by sodium bicarbonate (30.8 g). The mixture was cooled to 0° C. and Cbz chloride (38.9 ml) was added dropwise. The reaction mixture was then stirred at room temperature for 5 h (TLC control). When the reaction was complete, the organic solvent was distilled off and the residue was taken up in water (200 ml), and the mixture was washed with ethyl acetate (2×150 ml). The aqueous phase was acidified with dilute aqueous HCl solution and extracted with ethyl acetate. The organic phase was dried ($Na_2SO_4$) and concentrated in vacuo. Yield: 48.5 g (96%)

Stage (ii): 1-Benzyl 4-methyl piperidine-1,4-dicarboxylate 1-(Benzyloxycarbonyl)piperidine-4-carboxylic acid (48.5 g) in methanol (485 ml) was cooled to 0° C. and thionyl chloride (13.34 ml) was added dropwise. The mixture was then refluxed for 20 min (TLC control). When the reaction was complete, the methanol was distilled off, the residue was taken up in water (15 ml) and extracted with ethyl acetate (2×150 ml). The combined organic phases were extracted with water and sat. sodium chloride solution and the extract was dried ($Na_2SO_4$) and concentrated in vacuo. Yield: 38 g (67%)

Stage (iii): Benzyl 4-formylpiperidine-1-carboxylate

A solution of 1-benzyl 4-methyl piperidine-1,4-dicarboxylate (10 g) in toluene (100 ml) under nitrogen was cooled to −78° C. DIBAL-H (60.9 ml) was then added dropwise at −78° C. and the mixture was stirred at this temperature for 1 h (TLC control). Because the reaction was incomplete, a further 0.2 eq. of DIBAL-H was added and the mixture was stirred for a further 30 min (TLC control: some educt and the corresponding alcohol were to be detected). Methanol (40 ml), followed by sat. sodium chloride solution (40 ml) were added slowly to the reaction mixture at −78° C. The mixture was filtered over Celite and the solvent was removed in vacuo. The residue was extracted with ethyl acetate (3×75 ml) and the extract was dried ($Na_2SO_4$) and concentrated in vacuo. The crude product obtained in this way was purified by column chromatography (silica gel, 20% ethyl acetate/hexane). Yield: 4.3 g (49%)

Stage (iv): Benzyl 9-oxo-3-azaspiro[5.5]undec-7-ene-3-carboxylate

Methyl vinyl ketone (1.64 ml), ethanol (5 ml) and water (5 ml) were added to benzyl 4-formylpiperidine-1-carboxylate (5 g). The mixture was then added to a boiling solution of potassium hydroxide (0.22 g) in ethanol (10 ml) and the resulting reaction mixture was refluxed for 1 h (TLC control). When the reaction was complete, the mixture was added to water (25 ml) and extracted with ethyl acetate (2×50 ml). The combined organic phases were dried ($Na_2SO_4$) and concentrated in vacuo. The crude product obtained in this way was purified by column chromatography (silica gel, 25% ethyl acetate/hexane). Yield: 2.8 g (46%)

Stage (v): tert-Butyl 9-oxo-3-azaspiro[5.5]undecane-3-carboxylate

Boc anhydride (9.4 ml) and potassium carbonate (7.56 g) were added to benzyl 9-oxo-3-azaspiro[5.5]undec-7-ene-3-carboxylate (8.2 g) in EtOH/water (9:1) (200 ml). Pd/C (1 g) was then added and hydrogenolysis was carried out under 80 psi for 4 h (TLC control). When the reaction was complete, the mixture was filtered over Celite and the residue was rinsed with ethanol and ethyl acetate. The filtrate was dried ($Na_2SO_4$) and concentrated in vacuo. The residue was taken up in ethyl acetate and water and the aqueous phase was extracted with ethyl acetate. The combined organic phases were dried ($Na_2SO_4$) and concentrated in vacuo. The crude product obtained in this way was purified by column chromatography (silica gel, 20% ethyl acetate/hexane). Yield: 2.92 g, 40%

Stage (vi): tert-Butyl 9-hydroxy-3-azaspiro[5.5]undecane-3-carboxylate tert-Butyl 9-oxo-3-azaspiro[5.5]undecane-3-carboxylate (1.5 g) was dissolved in THF (7.5 ml) and the solution was cooled to −5° C. $NaBH_4$ (0.212 g) was then added and the mixture was stirred at room temperature for 1 h (TLC control). When the reaction was complete, acetic acid was added to the mixture and the methanol was then distilled off. The residue was taken up in water (50 ml) and the mixture was extracted with ethyl acetate (2×50 ml). The combined organic phases were dried ($Na_2SO_4$) and concentrated in vacuo. The crude product obtained in this way was purified by column chromatography (silica gel, 30% ethyl acetate/hexane). Yield: 1.2 g (80%)

Stage (vii): tert-Butyl 9-(pyridin-4-yloxy)-3-azaspiro[5.5]undecane-3-carboxylate 4-Chloropyridine hydrochloride (1.3 g) was added to sodium hydride (0.89 g) in DMSO (20 ml) and the mixture was stirred for 10 min. tert-Butyl 9-hydroxy-3-azaspiro[5.5]undecane-3-carboxylate (2.0 g) in DMSO (20 ml) was then added slowly and the mixture was stirred overnight (TLC control: conversion approx. 30-35%). A catalytic amount of sodium iodide was added and the reaction mixture was stirred at 80° C. for 8 h (TLC control). Methanol and $NaHCO_3$ solution was added to the reaction mixture and the mixture was stirred for 20 min. It was then extracted with ethyl acetate and the extract was washed again with $NaHCO_3$ solution and cold water. The organic phase was dried ($Na_2SO_4$) and concentrated in vacuo. The crude product obtained in this way was purified by column chromatography (silica gel, 70% ethyl acetate/hexane). Yield: 1.0 g (40%)

Stage (viii): 9-Pyridin-4-Yloxy-3-azaspiro[5.5]undecane dihydrochloride tert-Butyl 9-(pyridin-4-yloxy)-3-azaspiro[5.5]undecane-3-carboxylate (1 g, 2.886 mmol) was dissolved in methanol (2 ml), hydrogen chloride in methanol (1.25 mol/l, 11.5 ml) was added and the mixture was refluxed for 30 min. The solvent was removed in vacuo and the residue was dissolved in a small amount of ethanol. Acetone (approx. 25 ml) was then added, the mixture was stirred at 0° C. for 30 min and the solid formed was finally filtered off with suction. Yield: 0.96 g (>99%)

Synthesis of the amine unit AMN-09: 3-Pyridin-4-yl-1-oxa-2,8-diazaspiro[4.5]dec-2-ene bis-trifluoroacetate (AMN-09)

Stage (i): tert-Butyl 4-methylenepiperidine-1-carboxylate

Methyltriphenylphosphonium bromide (53.82 g, 150 mmol) was suspended in diethyl ether (300 ml) in a thoroughly heated apparatus flooded with an inert gas and the suspension was cooled to 0° C. Potassium tert-butylate (15.78 g, 140 mmol) was added in portions and the suspension was stirred for 30 min. Boc-4-piperidone (20 g, 100 mmol), dissolved in diethyl ether (200 ml), was slowly added dropwise and the mixture was then warmed to room temperature and stirred for 15 h. The reaction mixture was cooled, ammonium chloride solution (300 ml, 10%) was added, and after separation of the phases the aqueous phase was extracted with ether (3×200 ml) and the combined organic phases were dried ($MgSO_4$) and concentrated in vacuo. The crude product was purified by column chromatography (silica gel) with ether/hexane (1:1). Yield: 18.57 g (93%)

Stage (ii): tert-Butyl 3-(pyridin-4-yl)-1-oxa-2,8-diazaspiro[4.5]dec-2-ene-8-carboxylate (a): (Z)-N-Hydroxyisonicotinimidoyl chloride: pyridine-4-carbaldoxime (1 g, 8.19 mmol) was dissolved in DMF (10 ml), a solution of N-chlorosuccinimide (1.31 g, 9.83 mmol) in DMF (5 ml) was slowly added dropwise and the reaction mixture was stirred at room temperature. When the reaction was complete (thin layer chromatography control, here 6 h), diethyl ether (50 ml) and water (20 ml) were added, phase separation, extraction of the aqueous phase with diethyl ether (5×30 ml). The combined organic phases were washed with water (50 ml) and saturated sodium chloride solution (50 ml), dried ($MgSO_4$) and concentrated in vacuo. The crude substance was reacted without further purification and analysis. Yield: 0.74 g (100%)

(b): tert-Butyl 4-methylenepiperidine-1-carboxylate (0.7 g, 3.55 mmol) was dissolved in methylene chloride (10 ml) and the solution was dissolved at 0° C. under an inert gas. (Z)-N-Hydroxyisonicotinimidoyl chloride (1.67 g, 10.64 mmol), dissolved in methylene chloride (15 ml), was added, followed by triethylamine (1.2 ml, 8.5 mmol) in methylene chloride (10 ml). The reaction mixture was warmed slowly to room temperature and stirred for 15 h. The mixture was diluted with methylene chloride (50 ml) and washed with water, 10% strength citric acid and saturated sodium chloride solution (30 ml of each), dried ($MgSO_4$) and concentrated in vacuo. The crude product was purified by column chromatography (silica gel) with ethyl acetate/hexane 10/1. Yield: 0.48 g (42%)

Stage (iii): 3-Pyridin-4-yl-1-oxa-2,8-diazaspiro[4.5]dec-2-ene bis(2,2,2-trifluoroacetate)

tert-Butyl 3-(pyridin-4-yl)-1-oxa-2,8-diazaspiro[4.5]dec-2-ene-8-carboxylate (0.48 g, 1.5 mmol) was dissolved in methylene chloride (10 ml), the solution was cooled and trifluoroacetic acid (1.2 ml, 15 mmol) was slowly added. After refluxing for 2 h, the solvent was removed in vacuo and the residue was co-evaporated with 30 ml each of toluene and methanol. Yield: 0.74 g (100%)

C.) Individual Substances

1) Synthesis of the Benzimidazole Derivatives I

General Method for Synthesis of the Benzimidazole Derivatives I

Figure 7: Synthesis of the benzimidazoles derivatives (I)

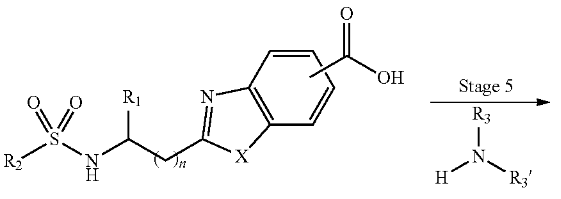

G

AMN

-continued

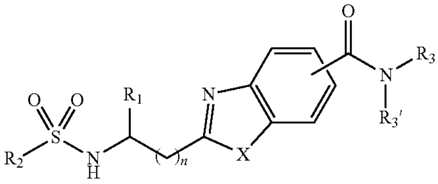

I

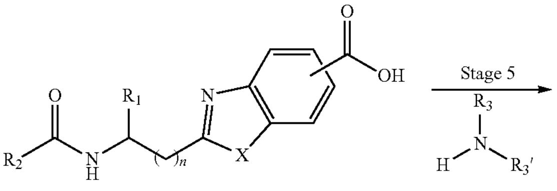

G

AMN

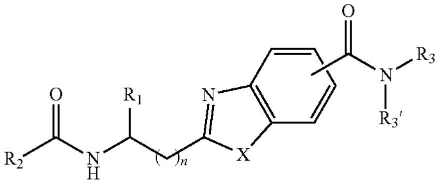

I

General working instructions 11 (GWI-11): 1-Hydroxybenzotriazole hydrate (0.3 eq.) and N-ethyl-diisopropylamine (3.5 eq.) were added to a solution of (ACI) (1.25 eq.) in methylene chloride. The reaction mixture was cooled to 0° C. and 1-(3-dimethylaminopropyl)-3-ethylcarbodiimide hydrochloride (1.5 eq.) was then added. The mixture was stirred at this temperature for 15 min, before the amine (1 eq.) was finally added. The reaction mixture was then stirred at room temperature overnight. For working up, the reaction mixture was washed 3× with sat. $NaHCO_3$ solution and the organic phase was dried over $MgSO_4$, filtered and concentrated. The crude product was purified 2× by column chromatography (1st purification over silica; methylene chloride/methanol, 2nd purification over neutral aluminium oxide; methylene chloride/methanol) to obtain the product (I) in a pure form.

General working instructions 12 (GWI-12): O-(1H-Benzotriazol-1-yl)-N,N,N',N'-tetramethyluronium tetrafluoroborate (1 eq.) and 1-hydroxybenzotriazole hydrate (1 eq.) were added to a solution of (ACI) (1 eq.) in tetrahydrofuran and the reaction mixture was stirred at room temperature for 0.5 h. The amine (1 eq.) and N-ethyl-diisopropylamine (3.5 eq.) were then added and the mixture was stirred at room temperature overnight. For working up, the reaction mixture was concentrated, ethyl acetate and sat. $NaHCO_3$ solution were added to the residue and the aqueous phase was extracted with ethyl acetate a further 3×. The combined organic phases were washed with sat. NaCl solution a further 1×, dried over $Na_2SO_4$, filtered and concentrated. The crude product was purified by column chromatography (silica; ethyl acetate/hexane/methanol 10:1:1+$NH_3$) to obtain the product (I) in a pure form.

General working instructions 13 (GWI-13): 1-Hydroxybenzotriazole hydrate (0.3 eq.) and N-ethyl-diisopropylamine (4 eq.) were added to a solution of (ACI) (1 eq.) in methylene chloride. The reaction mixture was cooled to 0° C. and 1-(3-dimethylaminopropyl)-3-ethylcarbodiimide hydrochloride (1.5 eq.) was then added. The mixture was stirred at this temperature for 15 min, before the amine (1 eq.) was finally added. The reaction mixture was then stirred at room temperature overnight. For working up, the reaction mixture was washed 3× with 0.5 M KOH solution and the organic phase was dried over $MgSO_4$, filtered and concentrated. The crude product was purified by column chromatography (silica; methylene chloride/methanol) to obtain the product (I) in a pure form.

General working instructions 14 (GWI-14): To a solution of (ACI) (1.0 eq.) in THF was added diisopropyl ethylamine (4.0 eq.) at 0° C. followed by HATU (1.5 eq.). The resultant reaction mixture was allowed to stir at room temperature for 15 min. It was again cooled to 0° C. and a solution of the amine (1.3 eq.) in THF-DMF (3:1) was added. The reaction mixture was allowed to stir at room temperature for 16 h. The mixture was then diluted with methylene chloride, washed with saturated ammonium chloride solution, saturated sodium bicarbonate solution and finally with brine. The organic layer was dried over sodium sulfate and evaporated to dryness under reduced pressure to give the crude product which was purified by neutral alumina column chromatography to obtain desired product.

TABLE 6

Synthesis of the benzimidazoles (I)

| Example no. | Structure | Name | Benzimidazole (ACI) | Amine (AMN) | Synthesis according to | Yield | Comments |
|---|---|---|---|---|---|---|---|
| I-01 | 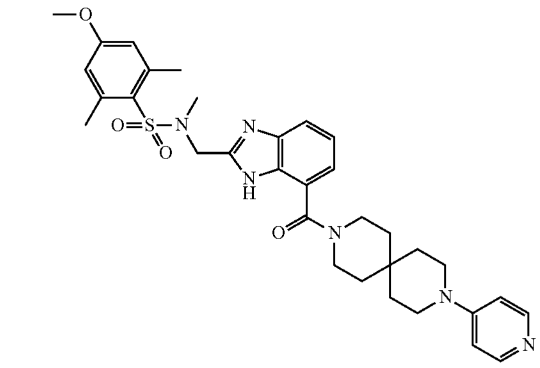 | 4-methoxy-N,2,6-trimethyl-N-[[7-(9-pyridin-4-yl-3,9-diazaspiro[5.5]undecane-3-carbonyl)-1H-benzoimidazol-2-yl]-methyl]-benzenesulfonic acid (ACI-05) | 2-[[[(4-methoxy-2,6-dimethyl-phenyl)sulfonyl]-methyl-amino]-methyl]-3H-benzoimidazole-4-carboxylic acid amide (1-01) | 9-pyridin-4-Yl-3,9-diazaspiro[5.5]undecane dihydrochloride (AMN-01) | GWI-11 | 39% (0.15 mmol) | - 1st CC over silica: methylene chloride/ methanol 99:1→95:5 - 2nd CC over alox: methylene chloride/ methanol 99:1 |
| I-02 | 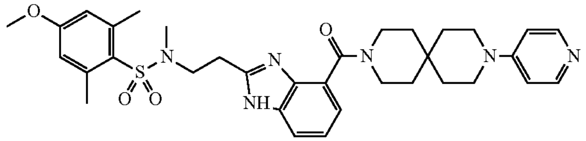 | 4-methoxy-N,2,6-trimethyl-N-[2-[4-(9-pyridin-4-yl-3,9-diazaspiro[5.5]undecane-3-carbonyl)-1H-benzoimidazol-2-yl]-ethyl]-benzenesulfonic acid amide (1-02) | 2-[2-[[(4-methoxy-2,6-dimethyl-phenyl)sulfonyl]-methyl-amino]-ethyl]-3H-benzoimidazole-4-carboxylic acid (ACI-04) | 9-pyridin-4-Yl-3,9-diazaspiro[5.5]undecane dihydrochloride (AMN-01) | GWI-11 | 38% (0.15 mmol) | - CC over alox: methylene chloride/ methanol 995:5→ 980:20 |
| I-03 | 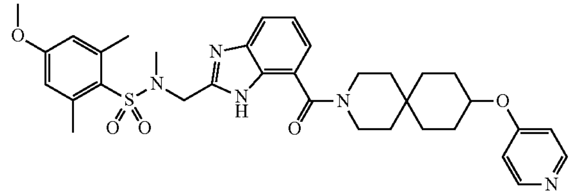 | 4-methoxy-N,2,6-trimethyl-N-[[7-(9-pyridin-4-yloxy-3-azaspiro[5.5]undecane-3-carbonyl)-1H-benzoimidazol-2-yl]-methyl]-benzenesulfonic acid amide (1-03) | 2-[[[(4-methoxy-2,6-dimethyl-phenyl)sulfonyl]-methyl-amino]-methyl]-3H-benzoimidazole-4-carboxylic acid (ACI-05) | 9-pyridin-4-yloxy)-3-azaspiro[5.5]undecane dihydrochloride (AMN-08) | GWI-12 | 85% (0.32 mmol) | - CC: ethyl acetate/ hexane/ methanol 10:1:1 + $NH_3$ |
| I-04 | 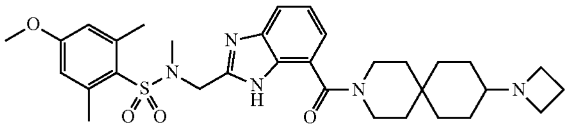 | N-[[7-[9-(azetidin-1-yl)-3-azaspiro[5.5]undecane-3-carbonyl]-1H-benzoimidazol-2-yl]-methyl]-4-methoxy-N,2,6-trimethyl-benzenesulfonic acid amide (1-04) | 2-[[[(4-methoxy-2,6-dimethyl-phenyl)sulfonyl]-methyl-amino]-methyl]-3H-benzoimidazole-4-carboxylic acid (ACI 05) | 9-(azetidin-1-Yl)-3-azaspiro[5.5]undecane dihydrochloride (AMN-07) | GWI-12 | 68% (0.25 mmol) | No purification via CC necessary! |

TABLE 6-continued

Synthesis of the benzimidazoles (I)

| Example no. | Structure | Name | Benzimidazole (ACI) | Amine (AMN) | Synthesis according to | Yield | Comments |
|---|---|---|---|---|---|---|---|
| I-05 | 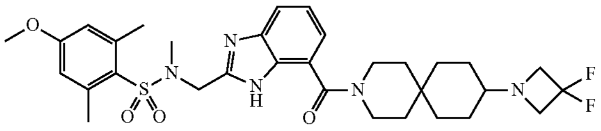 | N-[[7-[9-(3,3-difluoro-azetidin-1-yl)-3-azaspiro[5.5]undecane-3-carbonyl]-1H-benzoimidazol-2-yl]-methyl]-4-methoxy-N,2,6-trimethyl-benzenesulfonic acid amide (I-05) | 2-[[[(4-methoxy-2,6-dimethyl-phenyl)sulfonyl]-methyl-amino]-methyl]-3H-benzoimidazole-4-carboxylic acid (ACI-05) | 9-(3,3-difluoro-azetidin-1-yl)-3-azaspiro[5.5]undecane dihydrochloride (AMN-06) | GWI-12 | 81% (0.30 mmol) | - CC: ethyl acetate/hexane 10:1 + $NH_3$ |
| I-06 | 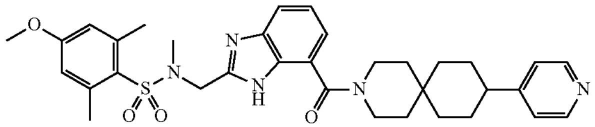 | 4-methoxy-N,2,6-trimethyl-N-[1-[7-(9-pyridin-4-yl-3,9-diazaspiro[5.5]undecane-3-carbonyl)-1H-benzoimidazol-2-yl]-ethyl]-benzenesulfonic acid amide (1-06) | 2-[1-[[(4-methoxy-2,6-dimethyl-phenyl)sulfonyl]-methyl-amino]-ethyl]-3H-benzoimidazole-4-carboxylic acid (ACI-02) | 9-pyridin-4-Yl-3,9-diazaspiro[5.5]undecane dihydrochloride (AMN-01) | GWI-13 | 42% (0.15 mmol) | - CC: methylene chloride/methanol 95:5→92:8 |
| I-07 | 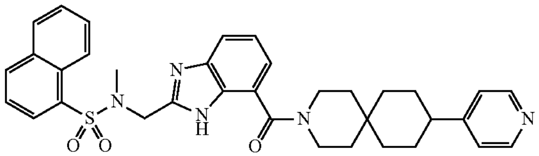 | N-methyl-N-[[7-(9-pyridin-4-yl-3,9-diazaspiro[5.5]undecane-3-carbonyl)-1H-benzoimidazol-2-yl-methyl]-naphthalene-1-sulfonic acid amide (I-07) | 2-[[methyl-(naphthalen-1-ylsulfonyl)-amino]-methyl]-3H-benzoimidazole-4-carboxylic acid (ACI-03) | 9-pyridin-4-Yl-3,9-diazaspiro[5.5]undecane dihydrochloride (AMN-01) | GWI-13 | 41% (0.15 mmol) | - CC: methylene chloride/methanol 95:5→92:8 |
| I-08 | 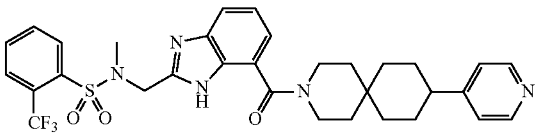 | N-methyl-N-[[7-(9-pyridin-4-yl-3,9-diazaspiro[5.5]undecane-3-carbonyl)-1H-benzoimidazol-2-yl]-methyl]-2-(trifluoromethyl)-benzenesulfonic acid amide (I-08) | 2-[[methyl-[[2-(trifluoromethyl)-phenyl]sulfonyl]-amino]-methyl]-3H-benzoimidazole-4-carboxylic acid (ACI-01) | 9-pyridin-4-Yl-3,9-diazaspiro[5.5]undecane dihydrochloride (AMN-01) | GWI-13 | 33% (0.12 mmol) | - CC: methylene chloride/methanol 95:5→92:8 |
| I-09 | 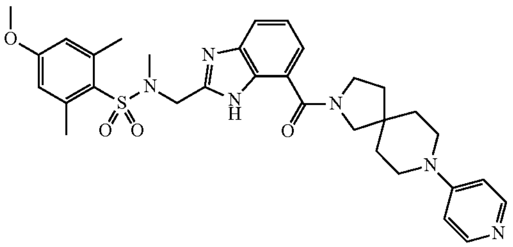 | 4-methoxy-N,2,6-trimethyl-N-[[7-(8-pyridin-4-yl-3,8-diazaspiro[4.5]decane-3-carbonyl)-1H-benzoimidazol-2-yl]-methyl]-benzenesulfonic acid amide (I-09) | 2-[[[(4-methoxy-2,6-dimethyl-phenyl)sulfonyl]-methyl-amino]-methyl]-3H-benzoimidazole-4-carboxylic acid (ACI-05) | 8-pyridin-4-Yl-3,8 diazaspiro[4.5]decane dihydrochloride (AMN-05) | GWI-12 | 82% (0.26 mmol) | - CC: ethyl acetate/methanol 1.5:1 + $NH_3$ |

TABLE 6-continued

Synthesis of the benzimidazoles (I)

| Example no. | Structure | Name | Benzimidazole (ACI) | Amine (AMN) | Synthesis according to | Yield | Comments |
|---|---|---|---|---|---|---|---|
| I-10 | 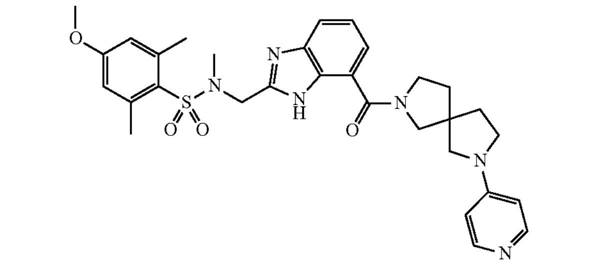 | 4-methoxy-N,2,6-trimethyl-N-[[7-(8-pyridin-4-yl-3,8-diazaspiro[4.4]nonane-3-carbonyl)-1H-benzoimidazol-2-yl]methyl]-benzenesulfonic acid amide (1-10) | 2-[[[(4-methoxy-2,6-dimethyl-phenyl)sulfonyl]-methyl-amino]-methyl]-3H-benzoimidazole-4-carboxylic acid (ACI-05) | 8-pyridin-4-Yl-3,8-diazaspiro[4.4]nonane dihydrochloride (AMN-04) | GWI-12 | 87% (0.32 mmol) | - CC: ethyl acetate/ methanol 1.5:1 + $NH_3$ |
| I-11 | 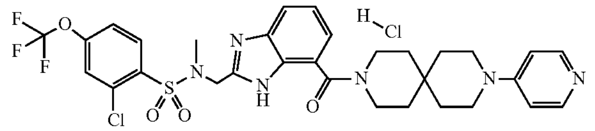 | 2-chloro-N-methyl-N-[[7-(9-pyridin-4-yl-3,9-diazaspiro[5.5]undecane-3-carbonyl)-1H-benzoimidazol-2-yl-methyl]-4-(trifluoromethyloxy)-benzenesulfonic acid amide hydrochloride (I-11) | 2-[[[[2-chloro-4-(trifluoromethyloxy)-phenyl]sulfonyl]-methyl-amino]-methyl]-3H-benzoimidazole-4-carboxylic acid (ACI-06) | 9-pyridin-4-Yl-3,9-diazaspiro[5.5]undecane dihydrochloride (AMN-01) | GWI-12 | 40% (0.14 mmol) | -extraction with methylene chloride - CC: ethyl acetate/ methanol 10:1 + $NH_3$ - HCI salt formation |
| I-12 | 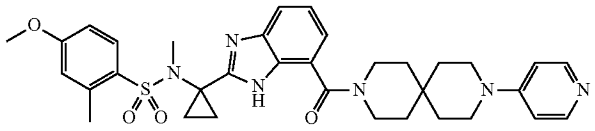 | 4-methoxy-N,2,6-trimethyl-N-[1-[7-(9-pyridin-4-yl-3,9-diazaspiro[5.5]undecane-3-carbonyl)-1H-benzoimidazol-2-yl]-cyclopropyl]-benzenesulfonic acid amide (I-12) | 2-[1-[[(4-methoxy-2,6-dimethyl-phenyl)sulfonyl]-methyl-amino]-cyclopropyl]-3H-benzoimidazole-4-carboxylic acid (ACI-07) | 9-pyridin-4-Yl-3,9-diazaspiro[5.5]undecane dihydrochloride (AMN-01) | GWI-12 | 78% (0.11 mmol) | -extraction with methylene chloride - CC: ethyl acetate/ methanol 5:1 + $NH_3$ |
| I-13 | 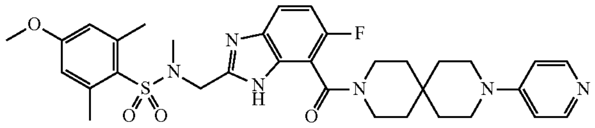 | N-[[6-fluoro-7-(9-pyridin-4-yl-3,9-diazaspiro[5.5]undecane-3-carbonyl)-1H-benzoimidazol-2-yl]-methyl]-4-methoxy-N,2,6-trimethyl-benzenesulfonic acid amide (I-13) | 5-fluoro-2-[[[(4-methoxy-2,6-dimethyl-phenyl)sulfonyl]-methyl-amino]-methyl]-3H-benzoimidazole-4-carboxylic acid (ACI-20) | 9-pyridin-4-Yl-3,9-diazaspiro[5.5]undecane dihydrochloride (AMN-01) | | | see below |

TABLE 6-continued

| Synthesis of the benzimidazoles (I) | | | | | | | |
|---|---|---|---|---|---|---|---|
| Example no. | Structure | Name | Benzimidazole (ACI) | Amine (AMN) | Synthesis according to | Yield | Comments |
| I-14 | 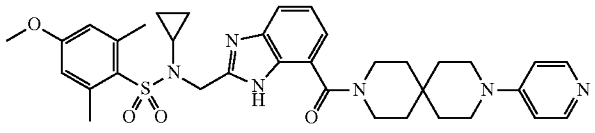 | N-cyclopropyl-4-methoxy-2,6-dimethyl-N17-(9-pyridin-4-yl-3,9-diazaspiro[5.5]undecane-3-carbonyl)-1H-benzoimidazol-2-yl]-methyl]-benzenesulfonic acid amide (I-14) | 2-[[cyclopropyl-[(4-methoxy-2,6-dimethyl-phenyl)sulfonyl]-amino]-methyl]-3H-benzoimidazole-4-carboxylic acid (ACI-08) | 9-pyridin-4-Yl-3,9-diazaspiro[5.5]undecane dihydrochloride (AMN-01) | | | see below |
| I-15 | 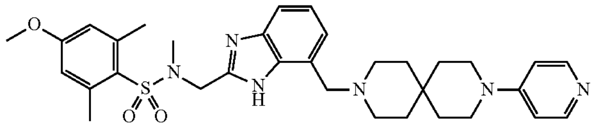 | 4-methoxy-N,2,6-trimethyl-N-[[7-[(9-pyridin-4-yl-3,9-diazaspiro[5.5]undecan-3-yl)-methyl]-1H-benzoimidazol-2-yl]-methyl]-benzenesulfonic acid amide (1-15) | | 9-pyridin-4-YL-3,9-diazaspiro[5.5]undecane dihydrochloride (AMN-01) | | | see below |
| I-16 | 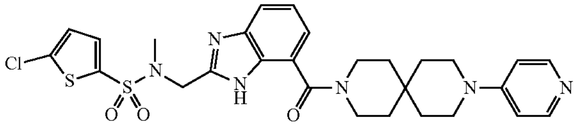 | 5-chloro-N-methyl-N-[[7-(9-pyridin-4-yl-3,9-diazaspiro[5.5]undecane-3-carbonyl)-1H-benzoimidazol-2-yl]-methyl]-thiophene-2-carboxylic acid amide (I-16) | 2-[[(5-chloro-thiophene-2-carbonyl)-methyl-amino]-methyl]-3H-benzoimidazole-4-carboxylic acid (ACI-27) | 9-pyridin-4-Yl-3,9-diazaspiro[5.5]undecane dihydrochloride (AMN-01) | | | see below |
| I-17 | 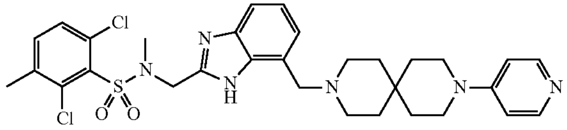 | 2,6-dichloro-N,3-dimethyl-N-[[7-(9-pyridin-4-yl-3,9-diazaspiro[5.5]undecane-3-carbonyl)-1H-benzoimidazol-2-yl]-methyl]-benzenesulfonic acid amide (I-17) | 2-[[[(2,6-dichloro-3-methyl-phenyl)sulfonyl]-methyl-amino]-methyl]-3H-benzoimidazole-4-carboxylic acid (ACI-17) | 9-pyridin-4-Yl-3,9-diazaspiro[5.5]undecane dihydrochloride (AMN-01) | GWI-12 | 80% (0.28 mmol) | -1.2 eq. amine 400 eq. THF -extraction with methylene chloride - CC: ethyl acetate/ methanol/ methylene chloride 10:1:1 + $NH_3$ |

TABLE 6-continued

| Example no. | Structure | Name | Benzimidazole (ACI) | Amine (AMN) | Synthesis according to | Yield | Comments |
|---|---|---|---|---|---|---|---|
| Synthesis of the benzimidazoles (I) | | | | | | | |
| I-18 | 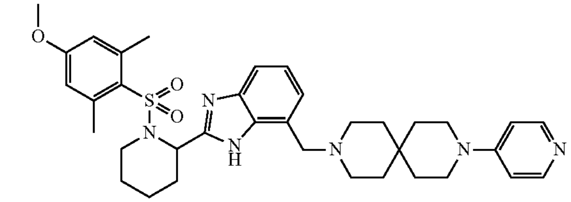 | [2-[1-[(4-methoxy-2,6-dimethyl-phenyl)sulfonyl]-piperidin-2-yl]-3H-benzoimidazol-4-yl]-(9-pyridin-4-yl-3,9-diazaspiro[5.5]undecan-3-yl)-methanone (1-18) | 2-[1-[(4-methoxy-2,6-dimethyl-phenyl)sulfonyl]-piperidin-2-yl]-3H-benzoimidazole-4-carboxylic acid (ACI-18) | 9-pyridin-4-Yl-3,9-diazaspiro[5.5]undecane dihydrochloride (AMN-01) | GWI-12 | 101% (0.23 mmol) | -1.2 eq. amine -400 eq. THF -extraction with methylene chloride - CC: ethyl acetate/ methanol/ methylene chloride/ $NH_3$ 10:1:1:0.5 |
| I-19 | 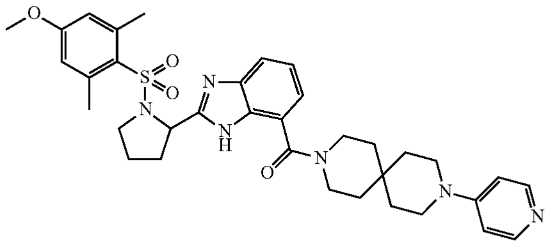 | [2-[1-[(4-methoxy-2,6-dimethyl-phenyl)sulfonyl]-pyrrolidin-2-yl]-3H-benzoimidazol-4-yl]-(9-pyridin-4-yl-3,9-diazaspiro[5.5]undecan-3-yl)-methanone (1-19) | 2-[1-[(4-methoxy-2,6-dimethyl-phenyl)sulfonyl]-pyrrolidin-2-yl]-3H-benzoimidazole-4-carboxylic acid (ACI-19) | 9-pyridin-4-Yl-3,9-diazaspiro[5.5]undecane dihydrochloride (AMN-01) | GWI-12 | 65% (0.45 mmol) | -1.2 eq. amine -extraction with methylene chloride - CC: ethyl acetate/ methanol 4:1 + $NH_3$ |
| I-20 | 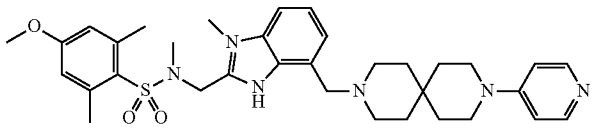 | 4-methoxy-N,2,6-trimethyl-N-[[1-methyl-4-(9-pyridin-4-yl-3,9-diazaspiro[5.5]undecane-3-carbonyl)-1H-benzoimidazol-2-yl]-methyl]-benzenesulfonic acid amide (I-20) | 2-[[[(4-methoxy-2,6-dimethyl-phenyl)sulfonyl]-methyl-amino]-methyl]-1-methyl-1H-benzoimidazole-4-carboxylic acid (ACI-26) | 9-pyridin-y-Yl-3,9-diazaspiro[5.5]undecane dihydrochloride (AMN-01) | GWI-14 | 10% | |

TABLE 6-continued

| Synthesis of the benzimidazoles (I) | | | | | | | |
|---|---|---|---|---|---|---|---|
| Example no. | Structure | Name | Benzimidazole (ACI) | Amine (AMN) | Synthesis according to | Yield | Comments |
| 1-21 | 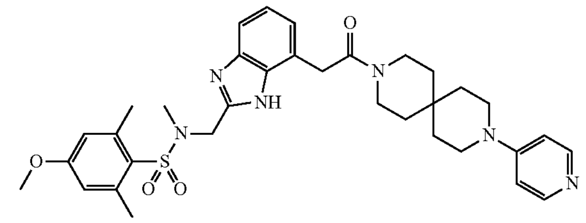 | 4-methoxy-N,2,6-trimethyl-N-[[7-[2-oxo-2-(9-pyridin-4-yl-3,9-diazaspiro[5.5]undecan-3-yl)-ethyl]-1H-benzoimidazol-2-yl]-methyl]-benzenesulfonic acid amide (I-21) | 2-[2-[[[(4-methoxy-2,6-dimethyl-phenyl)sulfonyl]-methyl-amino]-methyl]-3H-benzoimidazol-4-yl]-acetic acid (ACI-21) | 9-pyridin-4-YL-3,9-diazaspiro[5.5]undecane dihydrochloride (AMN-01) | GWI-14 | 25% | |
| I-22 | 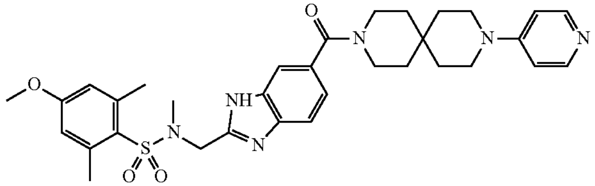 | 4-methoxy-N,2,6-trimethyl-N-[[6-(9-pyridin-4-yl-3,9-diazaspiro[5.5]undecane-3-carbonyl)-1H-benzoimidazol-2-yl]-methyl]-benzenesulfonic acid amide (1-22) | 2-[[[(4-methoxy-2,6-dimethyl-phenyl)sulfonyl]-methyl-amino]methyl]-3H-benzoimidazole-5-carboxylic acid (ACI-29) | 9-pyridin-4-Yl-3,9-diazaspiro[5.5]undecane dihydrochloride (AMN-01) | GWI-13 | 42% (0.21 mmol) | -1.5 eq. acid CC: methylene chloride/ methanol 98:2→96:4 - 2nd CC over alox: methylene chloride/ methanol 998:2→ 990:10 |
| I-23 | 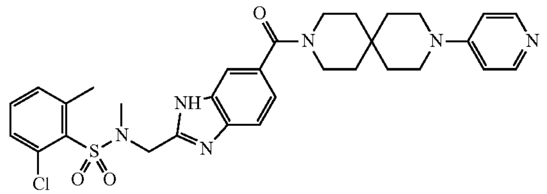 | 2-chloro-N,6-dimethyl-N-[[6-(9-pyridin-4-yl-3,9-diazaspiro[5.5]undecane-3-carbonyl)-1H-benzoimidazol-2-yl]-methyl]-benzenesulfonic acid amide (I-23) | 2-[[[(2-chloro-6-methyl-phenyl)sulfonyl]-methyl-amino]-methyl]-3H-benzoimidazole-5-carboxylic acid (ACI-30) | 9-pyridin-4-Yl-3,9-diazaspiro[5.5]undecane dihydrochloride (AMN-01) | GWI-13 | 51% (0.19 mmol) | - CC: methylene chloride/ methanol 95:5→92:8 |
| I-24 | 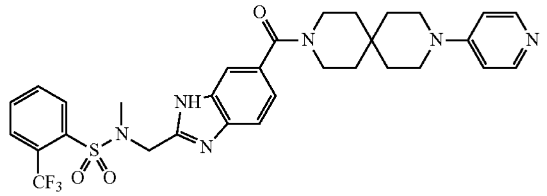 | N-methyl-N4[6-(9-pyridin-4-yl-3,9-diazaspiro[5.5]undecane-3-carbonyl)-1H-benzoimidazol-2-yl]-methyl]-2-(trifluoromethyl)-benzenesulfonic acid amide (I-24) | 2-[[methyl-[[2-(trifluoromethyl)-phenyl]sulfonyl]-amino]-methyl]-3H-benzoimidazole-5-carboxylic acid (ACI-31) | 9-pyridin-4-Yl-3,9-diazaspiro[5.5]undecane dihydrochloride (AMN-01) | GWI-13 | 39% (0.14 mmol) | - CC: methylene chloride/ methanol 95:5→92:8 |

TABLE 6-continued

| Synthesis of the benzimidazoles (I) | | | | | | | |
|---|---|---|---|---|---|---|---|
| Example no. | Structure | Name | Benzimidazole (ACI) | Amine (AMN) | Synthesis according to | Yield | Comments |
| I-25 | 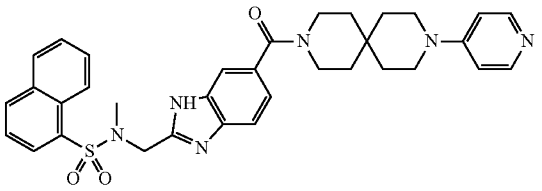 | N-methyl-N-[[6-(9-pyridin-4-yl-3,9-diazaspiro[5.5]undecane-3-carbonyl)-1H-benzoimidazol-2-yl]-methyl]-naphthalene-1-sulfonic acid amide (1-25) | 2-[[methyl-(naphthalen-1-ylsulfonyl)-amino]-methyl]-3H-benzoimidazole-5-carboxylic acid (ACI-32) | 9-pyridin-4-Yl-3,9-diazaspiro[5.5]undecane dihydrochloride (AMN-01) | GWI-13 | 20% (0.08 mmol) | - CC: methylene chloride/ methanol 95:5→ 92:8 |
| I-26 | 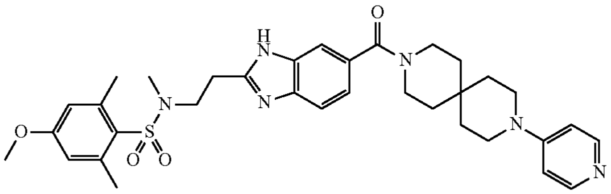 | 4-methoxy-N,2,6-trimethyl-N-[2-[6-(9-(9-4-yl-3,9-diazaspiro[5.5]undecane-3-carbonyl)-1H-benzoimidazol-2-yl]-ethyl]-benzenesulfonic acid amide (I-26) | 2-[2-[[(4-methoxy-2,6-dimethyl-phenyl)sulfonyl]-methyl-amino]-ethyl]-3H-benzoimidazole-5-carboxylic acid (ACI-33) | 9-pyridin-4-yl-3,9-diazaspiro[5.5]undecane dihydrochloride (AMN-01) | GWI-13 | 6 % (0.31 mmol) | -1.5 eq. Acid - CC: methylene chloride/ methanol 96:4→92:8 - 2nd CC over alox: methylene chloride/ methanol 99:1→97:3 |
| I-27 | 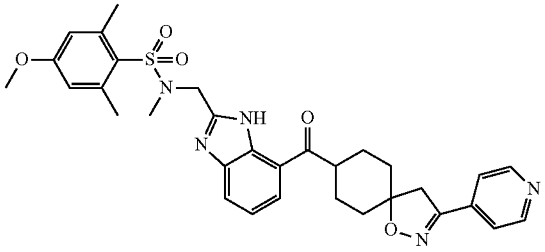 | 4-methoxy-N,2,6-trimethyl-N-[[7-(3-pyridin-4-yl-1-oxa-2,8-diazaspiro[4.5]dec-2-ene-8-carbonyl)-1H-benzoimidazol-2-yl]-methyll-benzenesulfonic acid amide (1-27) | 2-[[[(4-methoxy-2,6-dimethyl-phenyl)sulfonyl]-methyl-amino]-methyl]-3H-benzoimidazole-4-carboxylic acid (ACI-05) | 3-pyridin-4-yl-1-oxa-2,8-diazaspiro[4.5]dec-2-ene bistrifluoroacetate (AMN-09) | GWI-12 | 49% | reaction time: 2.5 d |

Synthesis of benzimidazole (I-13): N-[[6-Fluoro-7-(9-pyridin-4-yl-3,9-diazaspiro[5.5]undecane-3-carbonyl)-1H-benzoimidazol-2-yl]-methyl]-4-methoxy-N,2,6-trimethyl-benzenesulfonic acid amide (I-13)

Ethyl 6-fluoro-2-((4-methoxy-N,2,6-trimethylphenylsulfonamido)methyl)-1H-benzo[d]imidazole-7-carboxylate (F-20) (2.4 mmol, 1 eq.) was hydrolysed with LiOH in THF/$H_2O$ (1:1). After the hydrolysis, the solvent was removed completely from the reaction mixture in vacuo and the residue was taken up in water and washed with ethyl acetate. The aqueous phase was adjusted to pH=4 and then extracted with ethyl acetate. The free acid 6-fluoro-2-((4-methoxy-N,2,6-trimethylphenyl-sulfonamido)methyl)-1H-benzo[d]imidazole-7-carboxylic acid (ACI-20) obtained in this way was coupled with 9-pyridin-4-Yl-3,9-diazaspiro[5.5]undecane dihydrochloride (AMN-01) under standard peptide coupling conditions. Yield: 20%

Synthesis of benzimidazole (I-14): N-Cyclopropyl-4-methoxy-2,6-dimethyl-N-[[7-(9-pyridin-4-yl-3,9-diazaspiro[5.5]undecane-3-carbonyl)-1H-benzoimidazol-2-yl]-methyl]-benzenesulfonic acid amide (I-14)

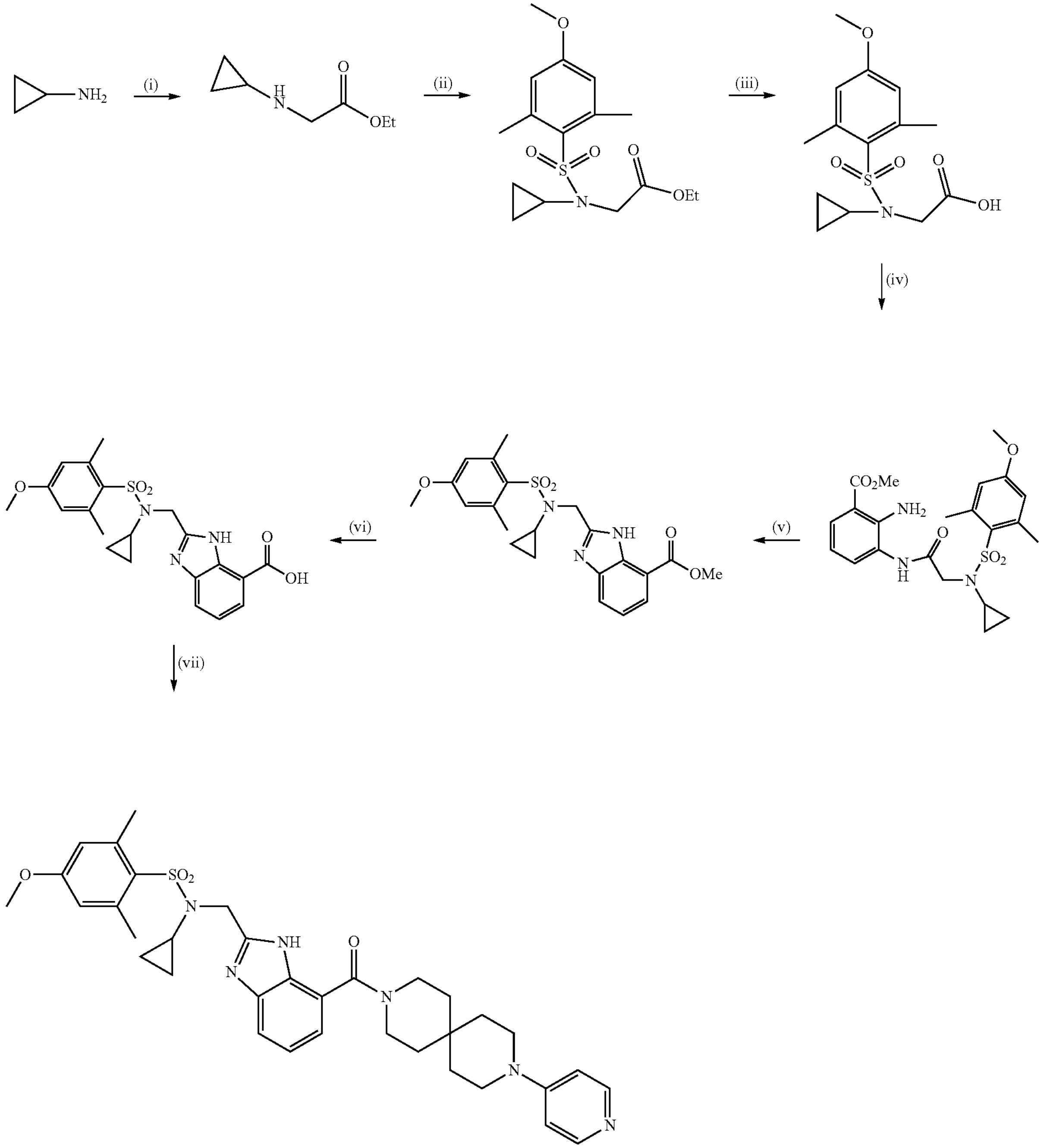

Stage (i): Ethyl 2-(cyclopropylamino)acetate

Ethyl bromoacetate (1 eq.) was added slowly to an ice-cold solution of cyclopropylamine (17.5 mmol, 3 eq.) and $K_2CO_3$ (2 eq.) in DMF (25 ml) and the reaction mixture was then stirred at room temperature for 16 h. For working up, the mixture was diluted with an excess of water and extracted with 20% ethyl acetate/hexane solution. The organic phase was washed with water and sat. NaCl solution and dried over $Na_2SO_4$. After the solvent had been removed completely, the crude product was employed in the next stage without further purification. Yield: 52%

Stage (ii): Ethyl 2-(N-cyclopropyl-4-methoxy-2,6-dimethylphenylsulfonamido)acetate 4-Methoxy-2,6-dimethylbenzenesulfonyl chloride (1.2 eq. in methylene chloride) was added slowly to a solution of ethyl 2-(cyclopropylamine)acetate (8.9 mmol, 1 eq.) and triethylamine (6 eq.) in methylene chloride and the mixture was stirred at room temperature for 16 h. For working up, the reaction mixture was diluted with methylene chloride, washed with water and sat. NaCl and dried over $Na_2SO_4$. After the solvent had been removed completely, the crude product was purified by column chromatography over silica gel. Yield: 30%

Stage (iii): 2-(N-Cyclopropyl-4-methoxy-2,6-dimethylphenylsulfonamido)acetic acid (C-08)

A solution of ethyl 2-(N-cyclopropyl-4-methoxy-2,6-dimethylphenyl-sulfonamido)acetate (2.7 mmol, 1 eq.) and LiOH (5 eq.) in THF/$H_2O$ (1:1) was stirred at room temperature for 12 h. The solvent was removed completely, in vacuo. The crude product was taken up in water and the mixture was washed with ethyl acetate. The aqueous phase was acidified to pH=4 with 1 M HCl and was then extracted with ethyl acetate. The organic phase was dried over $Na_2SO_4$. After the solvent had been distilled off completely, the crude product was obtained, and was employed in the next stage without further purification. Yield: 83%

Stage (iv): Methyl 2-amino-3-(2-(N-cyclopropyl-4-methoxy-2,6-dimethylphenyl-sulfonamido)acetamido)benzoate (E-08)

2-(N-Cyclopropyl-4-methoxy-2,6-dimethylphenylsulfonamido)acetic acid was reacted with methyl 2,3-diaminobenzoate (1.3 eq.) in the presence of EDCl (1 eq.), HOBT (1 eq.) and DIPEA (10 eq.) and the desired product thereby formed was employed directly in the next stage without further working up. Yield: 75%

Stage (v): Methyl 2-(N-cyclopropyl-4-methoxy-2,6-dimethylphenylsulfonamido)-methyl)-1H-benzo[d]imidazole-7-carboxylate (F-08)

A solution of methyl 2-amino-3-(2-(N-cyclopropyl-4-methoxy-2,6-dimethylphenylsulfonamido)acetamido)benzoate (1.6 mmol, 1 eq.) and AcOH (5 ml) in xylene (12 ml) was refluxed for 1 h. The reaction mixture was cooled to room temperature and concentrated and the residue was dissolved in methylene chloride. The organic phase was washed with $NaHCO_3$ solution, dried over $Na_2SO_4$ and concentrated to dryness in vacuo, The crude product was employed in the next stage without further purification. Yield: 92%

Stage (vi): 2-(N-Cyclopropyl-4-methoxy-2,6-dimethylphenylsulfonamido)methyl)-1H-benzo[d]imidazole-7-carboxylic acid (ACI-08)

Methyl 2-((N-cyclopropyl-4-methoxy-2,6-dimethylphenylsulfonamido)methyl)-1H-benzo[d]imidazole-7-carboxylate was converted into the desired product analogously to the process described in stage (iii).

Stage (vii): N-Cyclopropyl-4-methoxy-2,6-dimethyl-N-[[7-(9-pyridin-4-yl-3,9-diazaspiro[5.5]undecane-3-carbonyl)-1H-benzoimidazol-2-yl]-methyl]-benzenesulfonic acid amide (I-14)

2-((N-Cyclopropyl-4-methoxy-2,6-dimethylphenylsulfonamido)methyl)-1H-benzo[d]imidazole-7-carboxylic acid was converted into the desired product analogously to the process described in stage (iv) by reaction with 9-pyridin-4-Yl-3,9-diazaspiro[5.5]undecane dihydrochloride (AMN-01). Yield: 20%

Synthesis of benzimidazole (I-15): 4-Methoxy-N,2,6-trimethyl-N-[[7-[(9-pyridin-4-yl-3,9-diazaspiro[5.5]undecan-3-yl)-methyl]-1H-benzoimidazol-2-yl]-methyl]-benzenesulfonic acid amide (I-15)

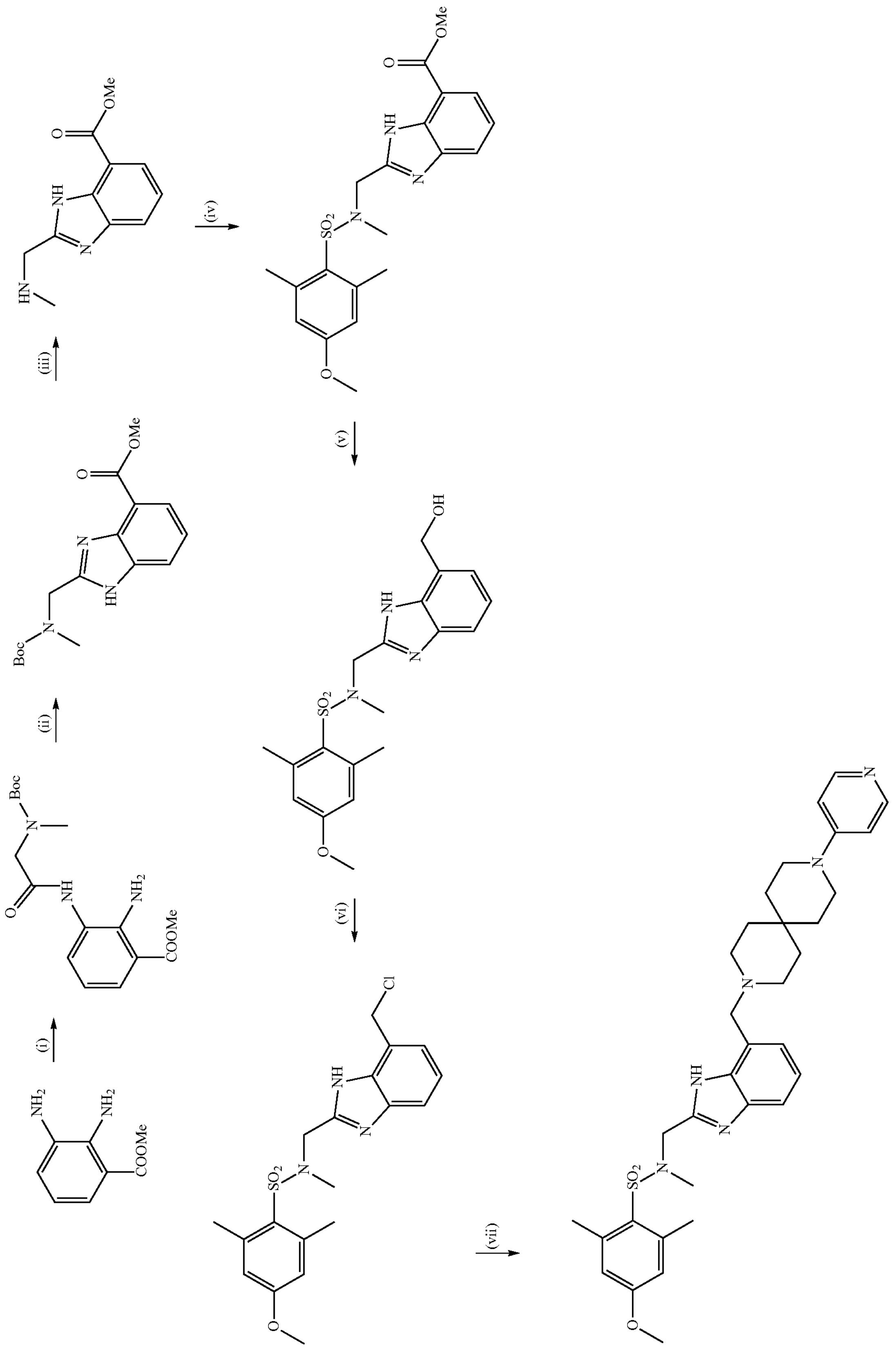
(i)
(ii)
(iii)
(iv)
(v)
(vi)
(vii)

Stage (i): Methyl 2-amino-3-(2-(tert-butoxycarbonyl (methyl)amino)acetamido)-benzoate First N-methyl-morpholine (4 eq.) and then HATU (2.0 eq.) was added to a solution of N-Boc-sarcosine (30.12 mmol, 1.0 eq.) in DMF (3 ml/mmol) at 0° C. The reaction mixture was stirred at room temperature for 15 min and then cooled again to 0° C. in order to add a solution of methyl 2,3-diaminobenzoate (30.12 mmol, 1.0 eq.) in DMF (1 ml/mmol). The reaction mixture was then stirred at room temperature for 16 h. For working up, the reaction mixture was diluted with water and extracted with ethyl acetate and the organic phase was washed with sat. $NH_4Cl$ solution, sat. $NaHCO_3$ solution and sat. NaCl solution. The organic phase was dried over $Na_2SO_4$ and concentrated in vacuo in order to obtain the crude product. This was purified by a column chromatography (silica gel) to obtain the desired product. Yield: 60%

Stage (ii): Methyl 2-((tert-butoxycarbonyl(methyl) amino)methyl)-1H-benzo[d]imidazole-4-carboxylate Acetic acid (45 ml) was added to a solution of methyl 2-amino-3-(2-(tert-butoxycarbonyl(methyl)amino)acetamido)benzoate (19.28 mmol, 1.0 eq.) in xylene (130 ml) and the reaction mixture was heated under reflux for 1 h. When the reaction was complete (checking by TLC), the solvent was evaporated to dryness, the residue was dissolved in ethyl acetate and the solution was washed with water and NaCl solution. The organic phase was concentrated to dryness in vacuo in order to obtain the desired product, which was employed in the next stage without further purification. Yield: 90%

Stage (iii): Methyl 2-((methylamino)methyl)-1H-benzo[d]imidazole-7-carboxylate

TFA (15 ml) was added to a cooled solution (0° C.) of methyl 2-((tert-butoxy-carbonyl(methyl)amino)methyl)-1H-benzo[d]imidazole-4-carboxylate (12.54 mmol) in methylene chloride (60 ml) and the reaction mixture was stirred at room temperature for 2 h. The solvent was evaporated off completely, in vacuo, and the residue was co-distilled 2× with methylene chloride and employed in the next stage.

Stage (iv): Methyl 2-((4-methoxy-N,2,6-trimethylphenylsulfonamido)methyl)-1H-benzo[d]imidazole-7-carboxylate A solution of 2,6-dimethyl-4-methoxybenzenesulfonyl chloride (12.54 mmol, 1.0 eq.) in methylene chloride (12 ml) was added to a cooled solution (0° C.) of methyl 2-((methylamino)methyl)-1H-benzo[d]imidazole-7-carboxylate (12.54 mmol, 1.0 eq.) and TEA (2.5 eq.) in abs. methylene chloride (60 ml). The reaction mixture was stirred at room temperature for 16 h. The reaction mixture was then diluted with methylene chloride and washed successively with water and sat. NaCl solution. The organic phase was dried over $Na_2SO_4$ and the solvent was evaporated off in vacuo to obtain the crude product, which led to the desired product by purification by column chromatography (silica gel). Yield: 46%

Stage (v): N-((7-(Hydroxymethyl)-1H-benzo[d]imidazol-2-yl)methyl)-4-methoxy-N,2,6-trimethylbenzenesulfonamide A solution of methyl 2-((4-methoxy-N,2,6-trimethylphenylsulfonamido)methyl)-1H-benzo[d]imidazole-7-carboxylate (2.40 mmol, 1.0 eq.) was added dropwise to a suspension of LAH (5.28 mmol, 2.2 eq.) in abs. THF (5 ml) under $N_2$ at 0° C. When the addition had ended, the reaction mixture was warmed to room temperature and stirred for 2 h. The reaction mixture was then quenched with THF/water (9:1; 3 ml), while cooling, and filtered over Celite. The filtrate was concentrated to dryness and the crude product was purified by column chromatography over silica gel to obtain the desired product. Yield: 75%

Stage (vi): N-((7-(Chloromethyl)-1H-benzo[d]imidazol-2-yl)methyl)-4-methoxy-N,2,6-trimethylbenzenesulfonamide Thionyl chloride (3.22 mmol, 2.5 eq.) was added to a cooled (0° C.) solution of N-((7-(hydroxymethyl)-1H-benzo[d]imidazol-2-yl)methyl)-4-methoxy-N,2,6-trimethylbenzenesulfonamide (1.29 mmol, 1.0 eq.) in abs. THF (10 ml). The reaction mixture was stirred at room temperature for 24 h. The mixture was then diluted with ethyl acetate and washed successively with $NaHCO_3$ solution and NaCl solution. The organic phase was dried over $Na_2SO_4$ and the solvent was distilled off in vacuo to obtain the crude product, which led to the desired product by purification by column chromatography over silica gel. Yield: 76%

Stage (vii): 4-methoxy-N,2,6-trimethyl-N-[[7-[(9-pyridin-4-yl-3,9-diazaspiro[5.5]undecan-3-yl)-methyl]-1H-benzoimidazol-2-yl]-methyl]-benzene-sulfonic acid amide (I-15)

A mixture of N-((7-(chloromethyl)-1H-benzo[d]imidazol-2-yl)methyl)-4-methoxy-N,2,6-trimethylbenzenesulfonamide (0.74 mmol, 1.0 eq.), $K_2CO_3$ (2.5 eq.) and 9-pyridin-4-Yl-3,9-diazaspiro[5.5]undecane dihydrochloride (AMN-01) (0.88 mmol, 1.2 eq.) in abs. acetone (20 ml) was heated under reflux for 16 h. The reaction mixture was filtered off and the filtrate was concentrated in order to obtain the crude product, which was purified by column chromatography over neutral aluminium oxide. Yield: 25%

Synthesis of benzimidazole (I-16): 5-Chloro-N-methyl-N-[[7-(9-pyridin-4-yl-3,9-diazaspiro[5.5]undecane-3-carbonyl)-1H-benzoimidazol-2-yl]-methyl]-thiophene-2-carboxylic acid amide (I-16)

Diisopropylamine (4.0 eq.) and then HATU (1.5 eq.) was added to a solution of 2-((5-chloro-N-methylthiophene-2-carboxamido)methyl)-1H-benzo[d]imidazole-7-carboxylic acid (ACI-27) (0.43 mmol, 1.0 eq.) in THF (6 ml) at 0° C.). The solution was stirred at room temperature for 15 min and then cooled again to 0° C., and a solution of 3-(pyridin-4-yl)-3,9-diazaspiro[5.5]undecane 9-pyridin-4-Yl-3,9-diazaspiro [5.5]undecane dihydrochloride (AMN-01) (0.43 mmol, 1.0 eq.) in THF-DMF (3:1, 2 ml) was added. The reaction mixture was then stirred at room temperature for 16 h. For working up, the reaction mixture was diluted with ethyl acetate and washed with sat. $NH_4Cl$ solution, sat. $NaHCO_3$ solution and sat. NaCl solution. The organic phase was dried over $Na_2SO_4$ and concentrated to dryness in vacuo. After purification by column chromatography over silica gel, the desired product was obtained. Yield: 26%

Analytical Data:

Materials and methods for HPLC-MS analytics: HPLC: Waters Alliance 2795 with PDA Waters 2998; MS: Micromass Quattro Micro™ API; Column: Waters Atlantis® T3, 3 μm, 100 Å, 2.1×30 mm; Col. temp.: 40° C., Eluent A: purified water+0.1% formic acid; Eluent B: acetonitrile (gradient grade)+0.1% formic acid; Gradient: 0% B to 100% B in 8.8 min, 100% B for 0.4 min, 100% B to 0% B in 0.01 min, 0% B for 0.8 min; Flow: 1.0 mL/min; Ionisation: ES+, 25 V; make up: 100 μL/min 70% methanol+0.2% formic acid; UV: 200-400 nm.

| Example no. | [M+] found | R.t. [min] |
|---|---|---|
| I-01 | 617.1 | 2.9 min |
| I-02 | 631.1 | 2.4 min |
| I-03 | 632.4 | 3.1 min |
| I-04 | 594.4 | 2.8 min |
| I-05 | 630.4 | 3.0 min |
| I-06 | 631.4 | 3.2 min |
| I-07 | 609.4 | 3.0 min |
| I-08 | 627.3 | 2.9 min |
| I-09 | 634.2 | 2.8 min |
| I-10 | 589.4 | 28 min |
| I-11 | 677.3 | 3.3 min |
| I-12 | 643.4 | 3.1 min |
| I-13 | 635.5 | 3.1 min |
| I-14 | 322.4 | 3.1 min |
| I-15 | 302.2 (M + 2H)/2 | 2.4 min |
| I-16 | 563.2 | 2.6 min |
| I-17 | 641.1 | 3.2 min |
| I-18 | 657.3 | 3.6 min |
| I-19 | 643.3 | 3.3 min |
| I-20 | 631.1 | 3.4 min |
| I-21 | 631.2 | 2.9 min |
| I-22 | 617.4 | 2.7 min |
| I-23 | 607.4 | 2.7 min |
| I-24 | 627.4 | 2.8 min |
| I-25 | 305.4 | 2.8 min |
| I-26 | 531.4 | 2.3 min |
| I-27 | 603.3 | 3.4 min |

Parallel Synthesis of Benzimidazoles I_CC

Library No. 1

General:

Figure 8: Synthesis of the benzimidazoles (I_CC)

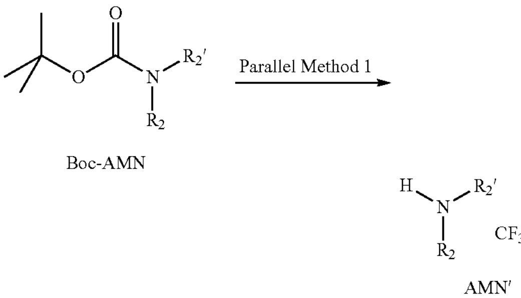

Boc-AMN

AMN'

-continued

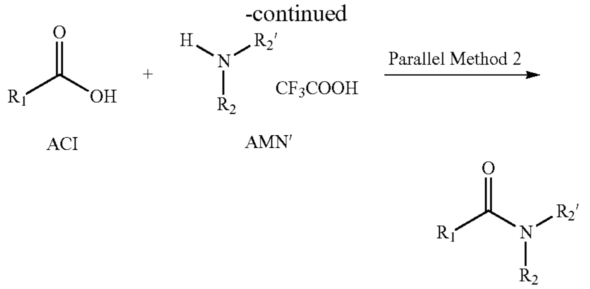

ACI

AMN'

I_CC

The amine units AMN' were prepared from the Boc-protected amines Boc-AMN by Parallel Method 1 in accordance with the above equation. The amine trifluoroacetic acid salts AMN' obtained in this way were reacted in parallel synthesis by Parallel Method 2 with the acids ACI to give the amidic benzimidazoles I_CC. The correlation of products (I_CC) to the units used (ACI and AMN) and can be seen from the synthesis matrix. The crude products of the parallel synthesis were purified by column chromatography. It was possible to demonstrate the identity of the products by analytical HPLC-MS measurements (cf. HPLC-MS data).

Parallel Synthesis of Benzimidazoles (I_CC):

Parallel Method 1: Amine Liberation

20% trifluoroacetic acid in methylene chloride (10 ml/mol) was added to the corresponding Boc-protected amine (1 eq., AMN) at 0° C. The reaction mixture obtained was stirred at 25° C. for 4 hours. The course of the reaction was monitored by means of thin layer chromatography. The solvent was then removed under reduced pressure and the residue was dried thoroughly in order to remove traces of trifluoroacetic acid. The crude product obtained in this way was used for synthesis of the libraries without further purification.

Parallel Method 2: Amide Formation

EDCl (1.5 eq.), HOBT (1 eq.) and DIPEA (2.5 eq.) were added in succession to a solution of the corresponding acid unit (unit ACI; 1 eq.) in methylene chloride (3 ml/mmol). The reaction mixture obtained was stirred at 25° C. for 15 minutes. A solution of the corresponding Boc-deprotected amine unit (AMN; 1.5 eq.) in methylene chloride (1 ml/mmol) was cooled in an ice bath in a further flask, and DIPEA (4 eq.) was added. The solutions from the two flasks were combined. The reaction mixture obtained in this way was stirred at 25° C. for 16 hours and then diluted with methylene chloride. The organic phase was washed successively with aqueous ammonium chloride solution, sodium carbonate and saturated sodium chloride solution. The organic phase was dried over sodium sulfate. After the solvent had been removed under reduced pressure, the crude product obtained was purified by column chromatography.

Synthesis Matrix and Biological Data of the Parallel Synthesis Examples:

TABLE 7

Synthesis of the benzimidazoles (I_CC)

| Example | Name | Acid (ACI) | Amine (AMN) | [M+] found | R.t. [min] |
|---|---|---|---|---|---|
| I_CC-01 | 4-chloro-N,2,5-trimethyl-N-[[7-(3-pyridin-4-yl-3,9-diazaspiro[5.5]undecane-9-carbonyl)-1H-benzoimidazol-2-yl]-methyl]-benzenesulfonic acid amide (I-CC-01) | 2-[[[(4-chloro-2,5-dimethyl-phenyl)sulfonyl]-methyl-amino]-methyl]-3H-benzoimidazole-4-carboxylic acid (ACI-11) | 9-pyridin-4-Yl-3,9-diazaspiro[5.5]undecane dihydrochloride (AMN-01) | 621.4 | 2.8 |
| I_CC-02 | 2-chloro-N-methyl-N-[[7-(4-oxo-1-pyridin-4-yl-3,8-diazaspiro[4.5]decane-8-carbonyl)-1H-benzoimidazol-2-yl]-methyl]-benzamide (I_CC-02) | 2-[[[(4-methoxy-2,6-dimethyl-phenyl)sulfonyl]-methyl-amino]-methyl]-1-methyl-1H-benzoimidazole-4-carboxylic acid (ACI-25) | 4-oxo-1-pyridin-4-yl-3,8-diazaspiro[4.5]decane-8-carboxylic acid tert-butyl ester (AMN-03) | 557.4 | 4.2 |

TABLE 7-continued

| Synthesis of the benzimidazoles (I_CC) | | | | | |
|---|---|---|---|---|---|
| Example | Name | Acid (ACI) | Amine (AMN) | [M+] found | R.t. [min] |
| I_CC-03 | 4-methoxy-N,2,6-trimethyl-N-[[7-(3-pyridin-4-yl-3,9-diazaspiro[5.5]undecane-9-carbonyl)-1H-benzoimidazol-2-yl]-methyl]-benzenesulfonic acid amide (I_CC-03) | 2-[[[(4-methoxy-2,6-dimethyl-phenyl)sulfonyl]-methyl-amino]-methyl]-3H-benzoimidazole-4-carboxylic acid (ACI-05) | 9-pyridin-4-Yl-3,9-diazaspiro[5.5]undecane dihydrochloride (AMN-01) | 617.5 | 2.69 |
| I_CC-04 | 2-chloro-N-methyl-N-[[7-(3-pyridin-4-yl-3,9-diazaspiro[5.5]undecane-9-carbonyl)-1H-benzoimidazol-2-yl]-methyl]-benzamide (I_CC-04) | 2-[[[(4-methoxy-2,6-dimethyl-phenyl)sulfonyl]-methyl-amino]-methyl]-1-methyl-1H-benzoimidazole-4-carboxylic acid (ACI-25) | 9-pyridin-4-Yl-3,9-diazaspiro[5.5]undecane dihydrochloride (AMN-01) | 557.5 | 2.34 |
| I_CC-05 | 3-chloro-N-methyl-N-[[7-(3-pyridin-4-yl-3,9-diazaspiro[5.5]undecane-9-carbonyl)-1H-benzoimidazol-2-yl]-methyl]-thiophene-2-carboxylic acid amide (I_CC-05) | 2-[[(3-chloro-thiophene-2-carbonyl)-methyl-amino]-methyl]-3H-benzoimidazole-4-carboxylic acid (ACI-27) | 9-pyridin-4-Yl-3,9-diazaspiro[5.5]undecane dihydrochloride (AMN-01) | 563.4 | 2.29 |
| I_CC-06 | 4-methoxy-N,2,6-trimethyl-N-[[7-(3-pyridin-4-yl-3,8-diazaspiro[4.5]decane-8-carbonyl)-1H-benzoimidazol-2-yl]-methyl]-benzenesulfonic acid amide (I_CC-06) | 2-[[[(4-methoxy-2,6-dimethyl-phenyl)sulfonyl]-methyl-amino]-methyl]-3H-benzoimidazole-4-carboxylic acid (ACI-05) | 3-pyridin-4-yl-3,8-diazaspiro[4.5]decane-8-carboxylic acid tert-butyl ester (AMN-02) | 603.3 | 2.64 |
| I_CC-07 | 2-chloro-N,6-dimethyl-N-[[7-(3-pyridin-4-yl-3,8-diazaspiro[4.5]decane-8-carbonyl)-1H-benzoimidazol-2-yl]-methyl]-benzenesulfonic acid amide (I_CC-07) | 2-[[[(2-chloro-6-methyl-phenyl)sulfonyl]-methyl-amino]-methyl]-3H-benzoimidazole-4-carboxylic acid (ACI-10) | 3-pyridin-4-yl-3,8-diazaspiro[4.5]decane-8-carboxylic acid tert-butyl ester (AMN-02) | 593.5 | 2.62 |
| I_CC-08 | 2-chloro-N-methyl-N-[[7-(3-pyridin-4-yl-3,8-diazaspiro[4.5]decane-8-carbonyl)-1H-benzoimidazol-2-yl]-methyl]-benzamide (I_CC-08) | 2-[[[(4-methoxy-2,6-dimethyl-phenyl)sulfonyl]-methyl-amino]-methyl]-1-methyl-1H-benzoimidazole-4-carboxylic acid (ACI-25) | 3-pyridin-4-yl-3,8-diazaspiro[4.5]decane-8-carboxylic acid tert-butyl ester (AMN-02) | 543.3 | 2.26 |
| I_CC-09 | 3-chloro-N-methyl-N-[[7-(3-pyridin-4-yl-3,8-diazaspiro[4.5]decane-8-carbonyl)-1H-benzoimidazol-2-yl]-methyl]-thiophene-2-carboxylic acid amide (I_CC-09) | 2-[[(3-chloro-thiophene-2-carbonyl)-methyl-amino]-methyl]-3H-benzoimidazole-4-carboxylic acid (ACI-27) | 3-pyridin-4-yl-3,8-diazaspiro[4.5]decane-8-carboxylic acid tert-butyl ester (AMN-02) | 549.3 | 2.21 |
| I_CC-10 | 4-chloro-N,2,5-trimethyl-N-[[7-(3-pyridin-4-yl-3,8-diazaspiro[4.5]decane-8-carbonyl)-1H-benzoimidazol-2-yl]-methyl]-benzenesulfonic acid amide (I_CC-10) | 2-[[[(4-chloro-2,5-dimethyl-phenyl)sulfonyl]-methyl-amino]-methyl]-3H-benzoimidazole-4-carboxylic acid (ACI-11) | 3-pyridin-4-yl-3,8-diazaspiro[4.5]decane-8-carboxylic acid tert-butyl ester (AMN-02) | 607.5 | 2.79 |
| I_CC-11 | 2-chloro-N,6-dimethyl-N-[[7-(3-pyridin-4-yl-3,9-diazaspiro[5.5]undecane-9-carbonyl)-1H-benzoimidazol-2-yl]-methyl]-benzenesulfonic acid amide (I_CC-11) | 2-[[[(2-cvhloro-6-methyl-phenyl)sulfonyl]-methyl-amino]-methyl]-3H-benzoimidazole-4-carboxylic acid (ACI-10) | 9-pyridin-4-Yl-3,9-diazaspiro[5.5]undecane dihydrochloride (AMN-01) | 607.4 | 2.67 |
| I_CC-12 | 7-chloro-2-[[7-(3-pyridin-4-yl-3,9-diazaspiro[5.5]undecane-9-carbonyl)-1H-benzoimidazol-2-yl]-methyl]-2,3-dihydro-isoindol-1-one (I_CC-12) | 2-[(4-chloro-3-oxo-1,2-dihydro-isoindol-2-yl)-methyl]-3H-benzoimidazole-4-carboxylic acid (ACI-23) | 9-pyridin-4-Yl-3,9-diazaspiro[5.5]undecane dihydrochloride (AMN-01) | 555.3 | 2.32 |
| I_CC-13 | 7-chloro-2-[[7-(3-pyridin-4-yl-3,8-diazaspiro[4.5]decane-8-carbonyl)-1H-benzoimidazol-2-yl]-methyl]-2,3-dihydro-isoindol-1-one (I_CC-13) | 2-[(4-chloro-3-oxo-1,2-dihydro-isoindol-2-yl)-methyl]-3H-benzoimidazole-4-carboxylic acid (ACI-23) | 3-pyridin-4-yl-3,8-diazaspiro[4.5]decane-8-carboxylic acid tert-butyl ester (AMN-02) | 541.3 | 2.28 |
| I_CC-14 | 4-methoxy-N,2,6-trimethyl-N-[1-methyl-7-(3-pyridin-4-yl-3,9-diazaspiro[5.5]undecane-9-carbonyl)-1H-benzoimidazol-2-yl]-benzenesulfonic acid amide (I_CC-14) | 2-[[(4-methoxy-2,6-dimethyl-phenyl)sulfonyl]-methyl-amino]-3-methyl-3H-benzoimidazole-4-carboxylic acid (ACI-13) | 9-pyridin-4-Yl-3,9-diazaspiro[5.5]undecane dihydrochloride (AMN-01) | 617.6 | 2.88 |
| I_CC-15 | 4-methoxy-N,2,6-trimethyl-N-[1-methyl-7-(3-pyridin-4-yl-3,8-diazaspiro[4.5]decane-8-carbonyl)-1H-benzoimidazol-2-yl]-benzenesulfonic acid amide (I_CC-15) | 2-[[(4-methoxy-2,6-dimethyl-phenyl)sulfonyl]-methyl-amino]-3-methyl-3H-benzoimidazole-4-carboxylic acid (ACI-13) | 3-pyridin-4-yl-3,8-diazaspiro[4.5]decane-8-carboxylic acid tert-butyl ester (AMN-02) | 603.4 | 2.87 |
| I_CC-16 | 4-methoxy-N,2,6-trimethyl-N-[1-methyl-7-(4-oxo-1-pyridin-4-yl-3,8-diazaspiro[4.5]decane-8-carbonyl)-1H-benzoimidazol-2-yl]-benzenesulfonic acid amide (I_CC-16) | 2-[[(4-methoxy-2,6-dimethyl-phenyl)sulfonyl]-methyl-amino]-3-methyl-3H-benzoimidazole-4-carboxylic acid (ACI-13) | 4-oxo-1-pyridin-4-yl-3,8-diazaspiro[4.5]decane-8-carboxylic acid tert-butyl ester (AMN-03) | 617.4 | 6.11 |
| I_CC-17 | 4-methoxy-N,2,6-trimethyl-N-[1-methyl-6-(3-pyridin-4-yl-3,9-diazaspiro[5.5]undecane-9-carbonyl)-1H-benzoimidazol-2-yl]-benzenesulfonic acid amide (I_CC-17) | 2-[[(4-methoxy-2,6-dimethyl-phenyl)sulfonyl]-methyl-amino]-3-methyl-3H-benzoimidazole-5-carboxylic acid (ACI-14) | 9-pyridin-4-Yl-3,9-diazaspiro[5.5]undecane dihydrochloride (AMN-01) | 617.4 | 2.81 |
| I_CC-18 | 4-methoxy-N,2,6-trimethyl-N-[1-methyl-6-(3-pyridin-4-yl-3,8-diazaspiro[4.5]decane-8-carbonyl)-1H-benzoimidazol-2-yl]-benzenesulfonic acid amide (I_CC-18) | 2-[[(4-methoxy-2,6-dimethyl-phenyl)sulfonyl]-methyl-amino]-3-methyl-3H-benzoimidazole-5-carboxylic acid (ACI-14) | 3-pyridin-4-yl-3,8-diazaspiro[4.5]decane-8-carboxylic acid tert-butyl ester (AMN-02) | 603.4 | 2.81 |
| I_CC-19 | 4-methoxy-N,2,6-trimethyl-N-[4-(3-pyridin-4-yl-3,9-diazaspiro[5.5]undecane-9-carbonyl)-benzothiazol-2-yl]-benzenesulfonic acid amide (I_CC-19) | 2-[[(4-methoxy-2,6-dimethyl-phenyl)sulfonyl]-methyl-amino]-benzothiazole-4-carboxylic acid (ACI-16) | 9-pyridin-4-Yl-3,9-diazaspiro[5.5]undecane dihydrochloride (AMN-01) | 620.2 | 2.99 |
| I_CC-20 | 4-methoxy-N,2,6-trimethyl-N-[[4-(3-pyridin-4-yl-3,8-diazaspiro[4.5]decane-8- | 2-[[[(4-methoxy-2,6-dimethyl-phenyl)sulfonyl]-methyl-amino]- | 3-pyridin-4-yl-3,8-diazaspiro[4.5]decane-8- | 620.2 | 2.93 |

TABLE 7-continued

| Synthesis of the benzimidazoles (I_CC) | | | | | |
|---|---|---|---|---|---|
| Example | Name | Acid (ACI) | Amine (AMN) | [M+] found | R.t. [min] |
| | carbonyl)-benzothiazol-2-yl]-methyl]-benzenesulfonic acid amide (I_CC-20) | methyl]-benzothiazole-4-carboxylic acid (ACI-22) | carboxylic acid tert-butyl ester (AMN-02) | | |
| I_CC-21 | 4-methoxy-N,2,6-trimethyl-N-[4-(3-pyridin-4-yl-3,8-diazaspiro[4.5]decane-8-carbonyl)-benzothiazol-2-yl]-benzenesulfonic acid amide (I_CC-21) | 2-[[(4-methoxy-2,6-dimethyl-phenyl)sulfonyl]-methyl-amino]-benzothiazole-4-carboxylic acid (ACI-16) | 3-pyridin-4-yl-3,8-diazaspiro[4.5]decane-8-carboxylic acid tert-butyl ester (AMN-02) | 606.4 | 2.97 |
| I_CC-22 | 4-methoxy-N,2,6-trimethyl-N-[[4-(3-pyridin-4-yl-3,9-diazaspiro[5.5]undecane-9-carbonyl)-benzothiazol-2-yl]-methyl]-benzenesulfonic acid amide (I_CC-22) | 2-[[[(4-methoxy-2,6-dimethyl-phenyl)sulfonyl]-methyl-amino]-methyl]-benzothiazole-4-carboxylic acid (ACI-22) | 9-pyridin-4-Yl-3,9-diazaspiro[5.5]undecane dihydrochloride (AMN-01) | 634.6 | 2.95 |
| I_CC-23 | 4-methoxy-N,2,6-trimethyl-N-[[7-(3-pyridin-4-yl-3,9-diazaspiro[5.5]undecane-9-carbonyl)-1H-benzoimidazol-2-yl]-methyl]-benzamide (I_CC-23) | 2-[[(4-methoxy-2,6-dimethyl-benzoyl)-methyl-amino]-methyl]-3H-benzoimidazole-4-carboxylic acid (ACI-24) | 9-pyridin-4-Yl-3,9-diazaspiro[5.5]undecane dihydrochloride (AMN-01) | 581.6 | 2.37 |
| I_CC-24 | 4-methoxy-N,2,6-trimethyl-N-[[7-(3-pyridin-4-yl-3,8-diazaspiro[4.5]decane-8-carbonyl)-1H-benzoimidazol-2-yl]-methyl]-benzamide (I_CC-24) | 2-[[(4-methoxy-2,6-dimethyl-benzoyl)-methyl-amino]-methyl]-3H-benzoimidazole-4-carboxylic acid (ACI-24) | 3-pyridin-4-yl-3,8-diazaspiro[4.5]decane-8-carboxylic acid tert-butyl ester (AMN-02) | 567.4 | 2.33 |

Library No. 2
Synthesis of the Amine Units (ASN_CC):
Overview:

| ASN_CC unit no. | Structure | ASN-CC name |
|---|---|---|
| ASN_CC-01 | 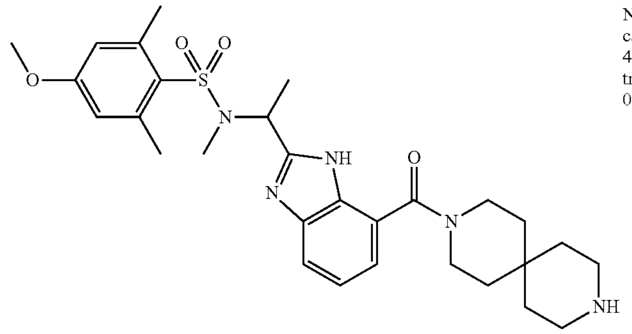 | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) |

Synthesis of: N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01)

Step 1: 2-[1-[[(4-methoxy-2,6-dimethyl-phenyl)sulfonyl]-methyl-amino]-ethyl]-3H-benzoimidazole-4-carboxylic acid (ACI-02; 6.228 mol; 2.6 g) was dissolved in dichlormethane (136 mL), 1-hydroxybenzotriazolhydrat (1.557 mol, 0.204 g) and N-ethyl-diisopropylamine (10.38 mol, 1.759 mL) were added at room temperature. The reaction mixture was cooled to 0° C. and 1-(3-dimethylaminopropyl)-3-ethylcarbodiimide hydrochloride (7.785 mol, 1.489 g) was added stirring was continued at 0° C. for 15 min. Finally 3,9-Diaza-spiro-[5.5]-undecane-3-carboxylic acid tert-butylester (5.19 mol, 1.32 g) was added and the reaction mixture was stirred at room temperature overnight. The reaction mixture was washed with aqueous 0.5 M KOH solution for three times, the organic layer was dried over magnesium sulfate and concentrated under reduced pressure.

The crude product was purified by flash chromatography over silica with ethylacetate/n-hexane (30:70→100:0) as mobile phase. Yield: 80.15% (2.72 g)

Step 2: The boc-protected amine prepared in step 1 (4.16 mol, 2.72 g) was dissolved in 20 ml ethanol and acetyl chloride (20.8 mol, 1.462 mL) was added at 0° C. The reaction mixture was stirred at room temperature overnight. Afterwards the solvent was concentrated under reduced pressure. The free base was prepared by treating the corresponding hydrochloride with 1M NaOH solution and extracting with dichloromethane The crude product was used without further purification. Yield: 98.59% (2.27 g)

Synthesis of the Acid Chloride, Sulfonyl Chloride and Aldehyde Units (ACL_CC, SCL_CC & ALD_CC)

Overview:

| CC unit no. | Structure | ASN-CC name |
|---|---|---|
| ACL_CC-01 | 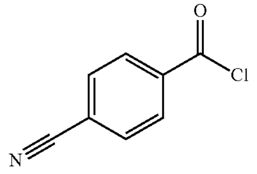 | 4-Cyano-benzoyl chloride |

-continued

| CC unit no. | Structure | ASN-CC name |
|---|---|---|
| ACL_CC-02 | 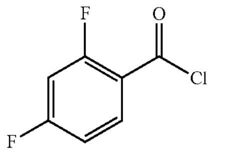 | 2,4-Difluoro-benzoyl chloride |
| ACL_CC-03 | 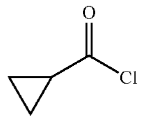 | Cyclopropanecarbonyl chloride |
| ACL_CC-04 | 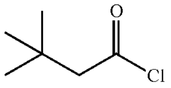 | 3,3-Dimethyl-butyryl chloride |
| ACL_CC-05 | 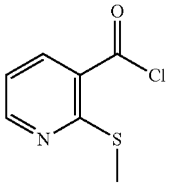 | 2-Methylsulfanyl-pyridine-3-carbonyl chloride |
| ACL_CC-06 | 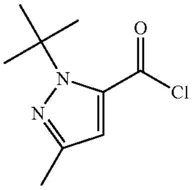 | 2-tert-Butyl-5-methyl-2H-pyrazole-3-carbonyl chloride |
| ACL_CC-07 | 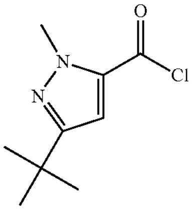 | 5-tert-Butyl-2-methyl-2H-pyrazole-3-carbonyl chloride |
| ACL_CC-08 | 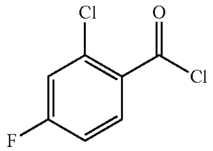 | 2-Chloro-4-fluoro-benzoyl chloride |
| ACL_CC-09 | 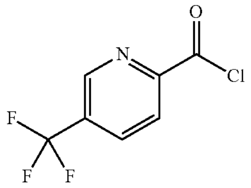 | 5-(Trifluoronnethyl)-pyridine-2-carbonyl chloride |
| ACL_CC-10 | 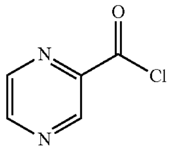 | Pyrazine-2-carbonyl chloride |

-continued

| CC unit no. | Structure | ASN-CC name |
|---|---|---|
| ALD_CC-01 | 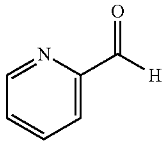 | Pyridine-2-carbaldehyde |
| ALD_CC-02 | 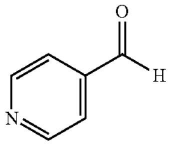 | Pyridine-4-carbaldehyde |
| ALD_CC-03 | 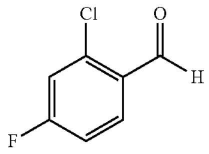 | 2-Chloro-4-fluoro-benzaldehyde |
| ALD_CC-04 | 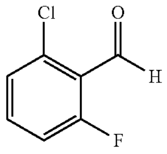 | 2-Chloro-6-fluoro-benzaldehyde |
| ALD_CC-05 | 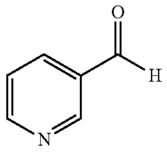 | Pyridine-3-carbaldehyde |
| ALD_CC-06 | 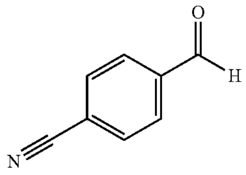 | 4-Formyl-benzonitrile |
| ALD_CC-07 | 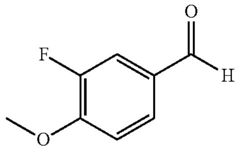 | 3-Fluoro-4-methoxy-benzaldehyde |
| ALD_CC-08 | 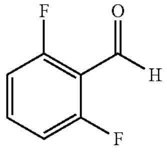 | 2,6-Difluoro-benzaldehyde |
| ALD_CC-09 | 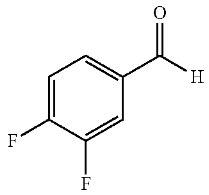 | 3,4-Difluoro-benzaldehyde |

-continued

| CC unit no. | Structure | ASN-CC name |
| --- | --- | --- |
| ALD_CC-10 | 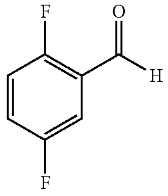 | 2,5-Difluoro-benzaldehyde |
| ALD_CC-11 | 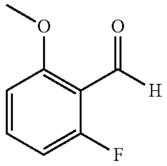 | 2-Fluoro-6-methoxy-benzaldehyde |
| ALD_CC-12 | 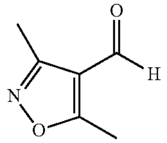 | 3,5-Dimethyl-isoxazole-4-carbaldehyde |
| ALD CC-13 | 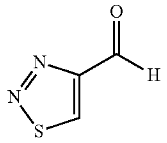 | [1,2,3]Thiadiazole-4-carbaldehyde |
| ALD_CC-14 | 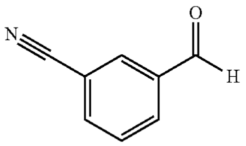 | 3-Formyl-benzonitrile |
| ALD_CC-15 | 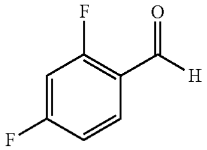 | 2,4-Difluoro-benzaldehyde |
| ALD_CC-16 | 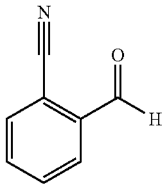 | 2-Formyl-benzonitrile |
| ALD_CC-17 | 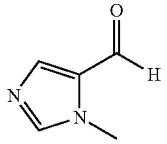 | 3-Methyl-3H-imidazole-4-carbaldehyde |
| ALD_CC-18 | 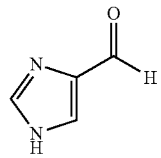 | 1H-Imidazole-4-carbaldehyde |

-continued

| CC unit no. | Structure | ASN-CC name |
| --- | --- | --- |
| ALD_CC-19 | 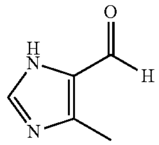 | 5-Methyl-3H-imidazole-4-carbaldehyde |
| ALD_CC-20 | 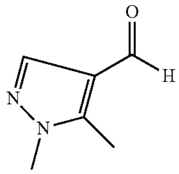 | 1,5-Dimethyl-1H-pyrazole-4-carbaldehyde |
| ALD_CC-21 | 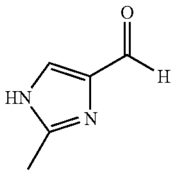 | 2-Methyl-1H-imidazole-4-carbaldehyde |
| SCL_CC-01 | 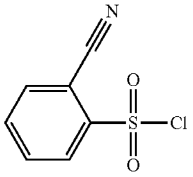 | 2-Cyano-benzenesulfonyl chloride |
| SCL_CC-02 | 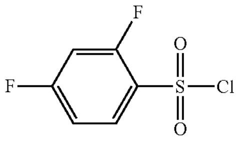 | 2,4-Difluoro-benzenesulfonyl chloride |
| SCL_CC-03 | 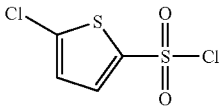 | 5-Chloro-thiophene-2-sulfonyl chloride |
| SCL_CC-04 | 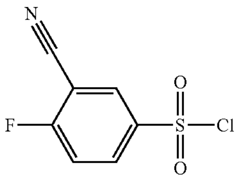 | 3-Cyano-4-fluoro-benzenesulfonyl chloride |
| SCL_CC-05 | 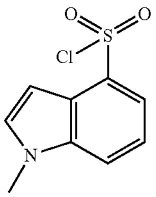 | 1-Methyl-1H-indole-4-sulfonyl chloride |

Parallel Synthesis:
General:

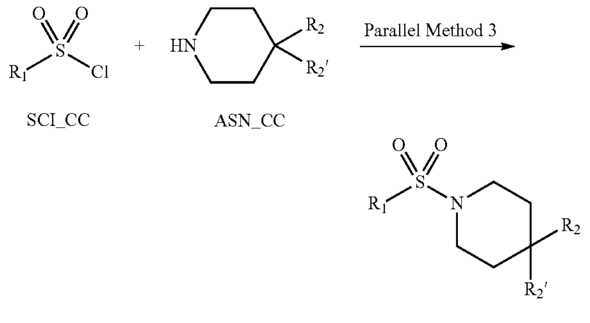

I_CC

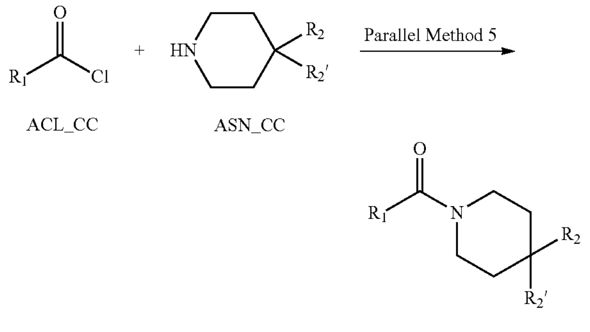

I_CC

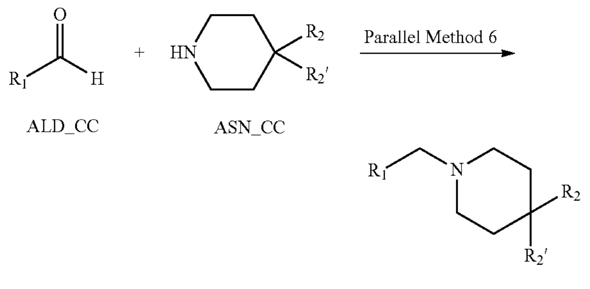

I_CC

The spiroamines amine ASN_CC were reacted in parallel fashion via Parallel Method 3 with sulfonyl chlorides SCI_CC to give the sulfonamidic products I_CC. ASN_CC were reacted in parallel fashion via Parallel Method 5 with acid chlorides ACL_CC to give the amidic products I_CC. ASN_CC were reacted in parallel fashion via Parallel Method 6 with aldehydes ALD_CC to give the reductively aminated products I_CC. The crude products of the parallel synthesis were purified by column chromatography. It was possible to demonstrate the identity of the products by analytical HPLC-MS measurements (cf. HPLC-MS data).

Parallel Method 3: Sulfonylation

To a solution of ASN_CC (100 μmol) in methylene chloride (1 ml) was added a mixture of the sulfonyl chloride (SCL_CC) (150 μmol) and diisopropylethylamine (300 μmol) in methylene chloride (1.5 ml). The reaction mixture was stirred at room temperature for 12 h. The reaction mixture was treated with aqueous NaOH solution (1.5 ml, 1 mol/l) and sat. NaCl solution (1.5 ml) and stirred at room temperature for 30 min. The organic phase was separated, the aqueous phase was extracted with methylene chloride for two times. The combined organic phases were concentrated under reduced pressure. The crude product was purified via a HPLCMS system.

Parallel Method 5: Amide Formation

To a solution of ASN_CC (100 μmol) in methylene chloride (1 ml) was added a mixture of the sulfonyl chloride (ACL_CC) (150 μmol) and diisopropylethylamine (300 μmol) in methylene chloride (1.5 ml). The reaction mixture was stirred at room temperature for 12 h. The reaction mixture was treated with aqueous NaOH solution (1.5 ml, 1 mol/l) and sat. NaCl solution (1.5 ml) and stirred at room temperature for 30 min. The organic phase was separated, the aqueous phase was extracted with methylene chloride for two times. The combined organic phases were concentrated under reduced pressure. The crude product was purified via a HPLCMS system.

Parallel Method 6: Reductive Amination

To a solution of ALD_CC (150 μmol) in methylene chloride (2.5 ml) were added the amine (ASN_CC) (100 μmol) in methylene chloride (1 ml) and acetic acid (12.5 μmol) in methylene chloride (0.5 ml). The reaction mixture was stirred at room temperature for 1 h. Sodium triacetoxyborohydride (250 μmol) was added and the reaction mixture was stirred at room temperature for 12 h. The reaction mixture was treated with halfsat. $NaHCO_3$ solution (2 ml) and sat. NaCl solution (1 ml) and stirred at room temperature for 15 min. The organic phase was separated, the aqueous phase was extracted with methylene chloride for two times. The combined organic phases were concentrated under reduced pressure. The crude product was purified via a HPLCMS system.

Synthesis Matrix:

| Example no. | Name | ACL_CC, SCL_CC or ALD_CC | Amine (ASN_CC) | Method no. |
|---|---|---|---|---|
| I_CC-25 | N-[1-[7-[9-(1H-Imidazol-4-yl-methyl)-3,9-diazaspiro[5.5]undecane-3-carbonyl]-1H-benzoimidazol-2-yl]-ethyl]-4-methoxy-N,2,6-trimethyl-benzenesulfonic acid amide (I_CC-25) | 1H-Imidazole-4-carbaldehyde (ALD_CC-18) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 6 |
| I_CC-26 | 4-Methoxy-N,2,6-trimethyl-N-[1-[7-[9-(pyridin-2-yl-methyl)-3,9-diazaspiro[5.5]undecane-3-carbonyl]-1H-benzoimidazol-2-yl]-ethyl]-benzenesulfonic acid amide (I_CC-26) | Pyridine-2-carbaldehyde (ALD_CC-01) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 6 |
| I_CC-27 | 4-Methoxy-N,2,6-trimethyl-N-[1-[7-[9-(pyridin-4-yl-methyl)-3,9-diazaspiro[5.5]undecane-3- | Pyridine-4-carbaldehyde (ALD_CC-02) | N-(1-(7-(3,9-diazaspiro[5.5]undecane-3-carbonyl)-1H- | No. 6 |

-continued

| Example no. | Name | ACL_CC, SCL_CC or ALD_CC | Amine (ASN_CC) | Method no. |
|---|---|---|---|---|
| | carbonyl]-1H-benzoimidazol-2-yl]-ethyl]-benzenesulfonic acid amide (I_CC-27) | | benzo[d]imidazol-2-yl)ethyl)-4-methoxy-N,2,6-trimethylbenzenesulfonamide (ASN_CC-01) | |
| I_CC-28 | 4-Methoxy-N,2,6-trimethyl-N-[1-[7-[9-(pyridin-3-yl-methyl)-3,9-diazaspiro[5.5]undecane-3-carbonyl]-1H-benzoimidazol-2-yl]-ethyl]-benzenesulfonic acid amide (I_CC-28) | Pyridine-3-carbaldehyde (ALD_CC-05) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 6 |
| I_CC-29 | N-[1-[7-[9-[(2,6-Difluoro-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-29) | 2,6-Difluoro-benzaldehyde (ALD_CC-08) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 6 |
| I_CC-30 | N-[1-[7-[9-[(3,4-Difluoro-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-30) | 3,4-Difluoro-benzaldehyde (ALD_CC-09) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 6 |
| I_CC-31 | N-[1-[7-[9-[(2,5-Difluoro-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-31) | 2,5-Difluoro-benzaldehyde (ALD_CC-10) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 6 |
| I_CC-32 | N-[1-[7-[9-[(2,4-Difluoro-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-32) | 2,4-Difluoro-benzaldehyde (ALD_CC-15) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 6 |
| I_CC-33 | N-[1-[7-[9-[(3-Fluoro-4-methoxy-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-33) | 3-Fluoro-4-methoxy-benzaldehyde (ALD_CC-07) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 6 |
| I_CC-34 | N-[1-[7-[9-[(2-Fluoro-6-methoxy-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-34) | 2-Fluoro-6-methoxy-benzaldehyde (ALD_CC-11) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 6 |
| I_CC-35 | 4-Methoxy-N,2,6-trimethyl-N-[1-[7-[9-[(5-methyl-3H-imidazol-4-yl)-methyl]-3,9-diazaspiro[5.5]undecane-3-carbonyl]-1H-benzoimidazol-2-yl]-ethyl]-benzenesulfonic acid amide (I_CC-35) | 5-Methyl-3H-imidazole-4-carbaldehyde (ALD_CC-19) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 6 |
| I_CC-36 | 4-Methoxy-N,2,6-trimethyl-N-[1-[7-[9-[(3-methyl-3H-imidazol-4-yl)-methyl]-3,9-diazaspiro[5.5]undecane-3-carbonyl]-1H-benzoimidazol-2-yl]-ethyl]-benzenesulfonic acid amide (I_CC-36) | 3-Methyl-3H-imidazole-4-carbaldehyde (ALD_CC-17) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 6 |
| I_CC-37 | 4-Methoxy-N,2,6-trimethyl-N-[1-[7-[9-[(2-methyl-1H-imidazol-4-yl)-methyl]-3,9-diazaspiro[5.5]undecane-3-carbonyl]-1H-benzoimidazol-2-yl]-ethyl]-benzenesulfonic acid amide (I_CC-37) | 2-Methyl-1H-imidazole-4-carbaldehyde (ALD_CC-21) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 6 |
| I_CC-38 | 4-Methoxy-N,2,6-trimethyl-N-[1-[7-[9-([1,2,3]thiadiazol-4-yl-methyl)-3,9- | [1,2,3]Thiadiazole-4-carbaldehyde (ALD_CC-13) | N-(1-(7-(3,9-diazaspiro[5.5]undecane-3-carbonyl)-1H- | No. 6 |

-continued

| Example no. | Name | ACL_CC, SCL_CC or ALD_CC | Amine (ASN_CC) | Method no. |
|---|---|---|---|---|
| | diazaspiro[5.5]undecane-3-carbonyl]-1H-benzoimidazol-2-yl]-ethyl]-benzenesulfonic acid amide (I_CC-38) | | benzo[d]imidazol-2-yl)ethyl)-4-methoxy-N,2,6-trimethylbenzenesulfonamide (ASN_CC-01) | |
| I_CC-39 | N-[1-[7-[9-[(2-Chloro-4-fluoro-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-39) | 2-Chloro-4-fluoro-benzaldehyde (ALD_CC-03) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 6 |
| I_CC-40 | N-[1-[7-[9-[(2-Chloro-6-fluoro-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-40) | 2-Chloro-6-fluoro-benzaldehyde (ALD_CC-04) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 6 |
| I_CC-41 | N-[1-[7-[9-[(1,5-Dimethyl-1H-pyrazol-4-yl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-41) | 1,5-Dimethyl-1H-pyrazole-4-carbaldehyde (ALD_CC-20) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 6 |
| I_CC-42 | N-[1-[7-[9-[(3,5-Dimethyl-isoxazol-4-yl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-42) | 3,5-Dimethyl-isoxazole-4-carbaldehyde (ALD_CC-12) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 6 |
| I_CC-43 | N-[1-[7-[9-[(4-Cyano-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-43) | 4-Formyl-benzonitrile (ALD_CC-06) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 6 |
| I_CC-44 | N-[1-[7-[9-[(3-Cyano-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-44) | 3-Formyl-benzonitrile (ALD_CC-14) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 6 |
| I_CC-45 | N-[1-[7-[9-[(2-Cyano-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-45) | 2-Formyl-benzonitrile (ALD_CC-16) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 6 |
| I_CC-46 | 4-Methoxy-N,2,6-trimethyl-N-[1-[7-[9-[5-(trifluoromethyl)-pyridine-2-carbonyl]-3,9-diazaspiro[5.5]undecane-3-carbonyl]-1H-benzoimidazol-2-yl]-ethyl]-benzenesulfonic acid amide (I_CC-46) | 5-(Trifluoromethyl)-pyridine-2-carbonyl chloride (ACL_CC-09) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 5 |
| I_CC-47 | 4-Methoxy-N,2,6-trimethyl-N-[1-[7-[9-(pyrazine-2-carbonyl)-3,9-diazaspiro[5.5]undecane-3-carbonyl]-1H-benzoimidazol-2-yl]-ethyl]-benzenesulfonic acid amide (I_CC-47) | Pyrazine-2-carbonyl chloride (ACL_CC-10) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 5 |
| I_CC-48 | 4-Methoxy-N,2,6-trimethyl-N-[1-[7-[9-(2-methylsulfanyl-pyridine-3-carbonyl)-3,9-diazaspiro[5.5]undecane-3-carbonyl]-1H-benzoimidazol-2-yl]-ethyl]-benzenesulfonic acid amide (I_CC-48) | 2-Methylsulfanyl-pyridine-3-carbonyl chloride (ACL_CC-05) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 5 |
| I_CC-49 | N-[1-[7-[9-(4-Cyano-benzoyl)-3,9-diazaspiro[5.5]undecane-3-carbonyl]-1H-benzoimidazol-2-yl]- | 4-Cyano-benzoyl chloride (ACL_CC-01) | N-(1-(7-(3,9-diazaspiro[5.5]undecane-3-carbonyl)-1H- | No. 5 |

-continued

| Example no. | Name | ACL_CC, SCL_CC or ALD_CC | Amine (ASN_CC) | Method no. |
|---|---|---|---|---|
| | ethyl]-4-methoxy-N,2,6-trimethyl-benzenesulfonic acid amide (I_CC-49) | | benzo[d]imidazol-2-yl)ethyl)-4-methoxy-N,2,6-trimethylbenzenesulfonamide (ASN_CC-01) | |
| I_CC-50 | N-[1-[7-[9-(Cyclopropanecarbonyl)-3,9-diazaspiro[5.5]undecane-3-carbonyl]-1H-benzoimidazol-2-yl]-ethyl]-4-methoxy-N,2,6-trimethyl-benzenesulfonic acid amide (I_CC-50) | Cyclopropanecarbonyl chloride (ACL_CC-03) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 5 |
| I_CC-51 | N-[1-[7-[9-(3,3-Dimethyl-butanoyl)-3,9-diazaspiro[5.5]undecane-3-carbonyl]-1H-benzoimidazol-2-yl]-ethyl]-4-methoxy-N,2,6-trimethyl-benzenesulfonic acid amide (I_CC-51) | 3,3-Dimethyl-butyryl chloride (ACL_CC-04) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 5 |
| I_CC-52 | N-[1-[7-[9-(2-Chloro-4-fluoro-benzoyl)-3,9-diazaspiro[5.5]undecane-3-carbonyl]-1H-benzoimidazol-2-yl]-ethyl]-4-methoxy-N,2,6-trimethyl-benzenesulfonic acid amide (I_CC-52) | 2-Chloro-4-fluoro-benzoyl chloride (ACL_CC-08) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 5 |
| I_CC-53 | N-[1-[7-[9-(2,4-Difluoro-benzoyl)-3,9-diazaspiro[5.5]undecane-3-carbonyl]-1H-benzoimidazol-2-yl]-ethyl]-4-methoxy-N,2,6-trimethyl-benzenesulfonic acid amide (I_CC-53) | 2,4-Difluoro-benzoyl chloride (ACL_CC-02) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 5 |
| I_CC-54 | N-[1-[7-[9-(5-tert-Butyl-2-methyl-2H-pyrazole-3-carbonyl)-3,9-diazaspiro[5.5]undecane-3-carbonyl]-1H-benzoimidazol-2-yl]-ethyl]-4-methoxy-N,2,6-trimethyl-benzenesulfonic acid amide (I_CC-54) | 5-tert-Butyl-2-methyl-2H-pyrazole-3-carbonyl chloride (ACL_CC-07) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 5 |
| I_CC-55 | N-[1-[7-[9-(2-tert-Butyl-5-methyl-2H-pyrazole-3-carbonyl)-3,9-diazaspiro[5.5]undecane-3-carbonyl]-1H-benzoimidazol-2-yl]-ethyl]-4-methoxy-N,2,6-trimethyl-benzenesulfonic acid amide (I_CC-55) | 2-tert-Butyl-5-methyl-2H-pyrazole-3-carbonyl chloride (ACL_CC-06) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 5 |
| I_CC-56 | N-[1-[7-[9-[(5-Chloro-thiophen-2-yl)sulfonyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-56) | 5-Chloro-thiophene-2-sulfonyl chloride (SCL_CC-03) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 3 |
| I_CC-57 | N-[1-[7-[9-[(2,4-Difluoro-phenyl)sulfonyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-57) | 2,4-Difluoro-benzenesulfonyl chloride (SCL_CC-02) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 3 |
| I_CC-58 | N-[1-[7-[9-[(3-Cyano-4-fluoro-phenyl)sulfonyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-58) | 3-Cyano-4-fluoro-benzenesulfonyl chloride (SCL_CC-04) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 3 |
| I_CC-59 | N-[1-[7-[9-[(2-Cyano-phenyl)sulfonyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-59) | 2-Cyano-benzenesulfonyl chloride (SCL_CC-01) | N-(1-(7-(3,9-diazaspiro[5.5]undecane-3-carbonyl)-1H-benzo[d]imidazol-2-yl)ethyl)-4-methoxy-N,2,6-trimethylbenzenesulfonamide (ASN_CC-01) | No. 3 |
| I_CC-60 | 4-Methoxy-N,2,6-trimethyl-N-[1-[7-[9-[(1-methyl-1H-indol-4-yl)sulfonyl]-3,9- | 1-Methyl-1H-indole-4-sulfonyl chloride (SCL_CC-05) | N-(1-(7-(3,9-diazaspiro[5.5]undecane-3-carbonyl)-1H- | No. 3 |

-continued

| Example no. | Name | ACL_CC, SCL_CC or ALD_CC | Amine (ASN_CC) | Method no. |
|---|---|---|---|---|
| | diazaspiro[5.5]undecane-3-carbonyl]-1H-benzoimidazol-2-yl]-ethyl]-benzenesulfonic acid amide (I_CC-60) | | benzo[d]imidazol-2-yl)ethyl)-4-methoxy-N,2,6-trimethylbenzenesulfonamide (ASN_CC-01) | |

Analytical Data:

| Example no. | [M+] found | R.t. [min] |
|---|---|---|
| I_CC-25 | 643.5 | 0.46 |
| I_CC-26 | 645.5 | 0.53 |
| I_CC-27 | 645.4 | 0.49 |
| I_CC-28 | 645.4 | 0.49 |
| I_CC-29 | 680.5 | 0.55 |
| I_CC-30 | 680.5 | 0.57 |
| I_CC-31 | 680.5 | 0.56 |
| I_CC-32 | 680.5 | 0.56 |
| I_CC-33 | 692.5 | 0.57 |
| I_CC-34 | 692.5 | 0.57 |
| I_CC-35 | 648.5 | 0.44 |
| I_CC-36 | 648.5 | 0.42 |
| I_CC-37 | 648.4 | 0.43 |
| I_CC-38 | 652.4 | 0.52 |
| I_CC-39 | 696.4 | 0.59 |
| I_CC-40 | 696.5 | 0.57 |
| I_CC-41 | 662.5 | 0.51 |
| I_CC-42 | 663.5 | 0.53 |

-continued

| Example no. | [M+] found | R.t. [min] |
|---|---|---|
| I_CC-43 | 669.5 | 0.55 |
| I_CC-44 | 669.4 | 0.55 |
| I_CC-45 | 669.5 | 0.55 |
| I_CC-46 | 727.4 | 0.75 |
| I_CC-47 | 660.5 | 0.66 |
| I_CC-48 | 705.4 | 0.73 |
| I_CC-49 | 683.4 | 0.72 |
| I_CC-50 | 622.4 | 0.70 |
| I_CC-51 | 652.5 | 0.76 |
| I_CC-52 | 710.4 | 0.76 |
| I_CC-53 | 694.4 | 0.75 |
| I_CC-54 | 718.5 | 0.77 |
| I_CC-55 | 718.5 | 0.77 |
| I_CC-56 | 734.3 | 0.83 |
| I_CC-57 | 730.4 | 0.79 |
| I_CC-58 | 737.4 | 0.78 |
| I_CC-59 | 719.4 | 0.76 |
| I_CC-60 | 747.4 | 0.79 |

Pharmacological Data

| Example | Name | % Inhibition (rat B1R) at 10 µM | % Inhibition (human B1R) at 10 µM |
|---|---|---|---|
| I_01 | 4-methoxy-N,2,6-trimethyl-N-[[7-(9-pyridin-4-yl-3,9-diazaspiro[5.5]undecane-3-carbonyl)-1H-benzoimidazol-2-yl]-methyl]-benzenesulfonic acid amide (I_01) | 96 | 98 |
| I_02 | 4-methoxy-N,2,6-trimethyl-N-[2-[4-(9-pyridin-4-yl-3,9-diazaspiro[5.5]undecane-3-carbonyl)-1H-benzoimidazol-2-yl]-ethyl]-benzenesulfonic acid amide (I_02) | 100 | 97 |
| I_03 | 4-methoxy-N,2,6-trimethyl-N-[[7-(9-pyridin-4-yloxy-3-azaspiro[5.5]undecane-3-carbonyl)-1H-benzoimidazol-2-yl]-methyl]-benzenesulfonic acid amide (I_03) | 86 | 99 |
| I_04 | N-[[7-[9-(azetidin-1-yl)-3-azaspiro[5.5]undecane-3-carbonyl]-1H-benzoimidazol-2-yl]-methyl]-4-methoxy-N,2,6-trimethyl-benzenesulfonic acid amide (I_04) | 97 | 99 |
| I_05 | N-[[7-[9-(3,3-difluoro-azetidin-1-yl)-3-azaspiro[5.5]undecane-3-carbonyl]-1H-benzoimidazol-2-yl]-methyl]-4-methoxy-N,2,6-trimethyl-benzenesulfonic acid amide (I_05) | 72 | 55 |
| I_06 | 4-methoxy-N,2,6-trimethyl-N-[1-[7-(9-pyridin-4-yl-3,9-diazaspiro[5.5]undecane-3-carbonyl)-1H-benzoimidazol-2-yl]-ethyl]-benzenesulfonic acid amide (I_06) | 90 | 94 |
| I_07 | N-methyl-N-[[7-(9-pyridin-4-yl-3,9-diazaspiro[5.5]undecane-3-carbonyl)-1H-benzoimidazol-2-yl]-methyl]-naphthalene-1-sulfonic acid amide (I_07) | 96 | 98 |
| I_08 | N-methyl-N-[[7-(9-pyridin-4-yl-3,9-diazaspiro[5.5]undecane-3-carbonyl)- | 99 | 100 |

-continued

| Example | Name | % Inhibition (rat B1R) at 10 μM | % Inhibition (human B1R) at 10 μM |
|---|---|---|---|
| | 1H-benzoimidazol-2-yl]-methyl]-2-(trifluoromethyl)-benzenesulfonic acid amide (I_08) | | |
| I_09 | 4-methoxy-N,2,6-trimethyl-N-[[7-(8-pyridin-4-yl-3,8-diazaspiro[4.5]decane-3-carbonyl)-1H-benzoimidazol-2-yl]-methyl]-benzenesulfonic acid amide (I_09) | 104 | 99 |
| I_10 | 4-methoxy-N,2,6-trimethyl-N-[[7-(8-pyridin-4-yl-3,8-diazaspiro[4.4]nonane-3-carbonyl)-1H-benzoimidazol-2-yl]-methyl]-benzenesulfonic acid amide (I_10) | 104 | 100 |
| I_11 | 2-chloro-N-methyl-N-[[7-(9-pyridin-4-yl-3,9-diazaspiro[5.5]undecane-3-carbonyl)-1H-benzoimidazol-2-yl]-methyl]-4-(trifluoromethyloxy)-benzenesulfonic acid amide hydrochloride (I_11) | 99 | 99 |
| I_12 | 4-methoxy-N,2,6-trimethyl-N-[1-[7-(9-pyridin-4-yl-3,9-diazaspiro[5.5]undecane-3-carbonyl)-1H-benzoimidazol-2-yl]-cyclopropyl]-benzenesulfonic acid amide (I_12) | 92 | 98 |
| I_13 | N-[[6-fluoro-7-(9-pyridin-4-yl-3,9-diazaspiro[5.5]undecane-3-carbonyl)-1H-benzoimidazol-2-yl]-methyl]-4-methoxy-N,2,6-trimethyl-benzenesulfonic acid amide (I_13) | 93 | 98 |
| I_14 | N-cyclopropyl-4-methoxy-2,6-dimethyl-N-[[7-(9-pyridin-4-yl-3,9-diazaspiro[5.5]undecane-3-carbonyl)-1H-benzoimidazol-2-yl]-methyl]-benzenesulfonic acid amide (I_14) | 95 | 99 |
| I_15 | 4-methoxy-N,2,6-trimethyl-N-[[7-[(9-pyridin-4-yl-3,9-diazaspiro[5.5]undecan-3-yl)-methyl]-1H-benzoimidazol-2-yl]-methyl]-benzenesulfonic acid amide (I_15) | 103 | 100 |
| I_16 | 5-chloro-N-methyl-N-[[7-(9-pyridin-4-yl-3,9-diazaspiro[5.5]undecane-3-carbonyl)-1H-benzoimidazol-2-yl]-methyl]-thiophene-2-carboxylic acid amide (I_16) | 105 | 91 |
| I_17 | 2,6-dichloro-N,3-dimethyl-N-[[7-(9-pyridin-4-yl-3,9-diazaspiro[5.5]undecane-3-carbonyl)-1H-benzoimidazol-2-yl]-methyl]-benzenesulfonic acid amide (I_17) | 24 | 95 |
| I_18 | [2-[1-[(4-methoxy-2,6-dimethyl-phenyl)sulfonyl]-piperidin-2-yl]-3H-benzoimidazol-4-yl]-(9-pyridin-4-yl-3,9-diazaspiro[5.5]undecan-3-yl)-methanone (I_18) | 49 | 97 |
| I_19 | [2-[1-[(4-methoxy-2,6-dimethyl-phenyl)sulfonyl]-pyrrolidin-2-yl]-3H-benzoimidazol-4-yl]-(9-pyridin-4-yl-3,9-diazaspiro[5.5]undecan-3-yl)-methanone (I_19) | 76 | 100 |
| I_20 | 4-methoxy-N,2,6-trimethyl-N-[[1-methyl-4-(9-pyridin-4-yl-3,9-diazaspiro[5.5]undecane-3-carbonyl)-1H-benzoimidazol-2-yl]-methyl]-benzenesulfonic acid amide (I_20) | 30 | 98 |
| I_21 | 4-methoxy-N,2,6-trimethyl-N-[[7-[2-oxo-2-(9-pyridin-4-yl-3,9-diazaspiro[5.5]undecan-3-yl)-ethyl]-1H-benzoimidazol-2-yl]-methyl]-benzenesulfonic acid amide (I_21) | 55 | 99 |
| I_22 | 4-methoxy-N,2,6-trimethyl-N-[[6-(9-pyridin-4-yl-3,9-diazaspiro[5.5]undecane-3-carbonyl)-1H-benzoimidazol-2-yl]-methyl]-benzenesulfonic acid amide (I_22) | 103 | 100 |
| I_23 | 2-chloro-N,6-dimethyl-N-[[6-(9-pyridin-4-yl-3,9- | 101 | 100 |

-continued

| Example | Name | % Inhibition (rat B1R) at 10 μM | % Inhibition (human B1R) at 10 μM |
|---|---|---|---|
| | diazaspiro[5.5]undecane-3-carbonyl)-1H-benzoimidazol-2-yl]-methyl]-benzenesulfonic acid amide (I_23) | | |
| I_24 | N-methyl-N-[[6-(9-pyridin-4-yl-3,9-diazaspiro[5.5]undecane-3-carbonyl)-1H-benzoimidazol-2-yl]-methyl]-2-(trifluoromethyl)-benzenesulfonic acid amide (I_24) | 102 | 100 |
| I_25 | N-methyl-N-[[6-(9-pyridin-4-yl-3,9-diazaspiro[5.5]undecane-3-carbonyl)-1H-benzoimidazol-2-yl]-methyl]-naphthalene-1-sulfonic acid amide (I_25) | 96 | 95 |
| I_26 | 4-methoxy-N,2,6-trimethyl-N-[2-[6-(9-pyridin-4-yl-3,9-diazaspiro[5.5]undecane-3-carbonyl)-1H-benzoimidazol-2-yl]-ethyl]-benzenesulfonic acid amide (I_26) | 103 | 98 |
| I_27 | 4-methoxy-N,2,6-trimethyl-N-[[7-(3-pyridin-4-yl-1-oxa-2,8-diazaspiro[4.5]dec-2-ene-8-carbonyl)-1H-benzoimidazol-2-yl]-methyl]-benzenesulfonic acid amide (I_27) | 94 | 93 |
| I_CC-01 | 4-chloro-N,2,5-trimethyl-N-[[7-(3-pyridin-4-yl-3,9-diazaspiro[5.5]undecane-9-carbonyl)-1H-benzoimidazol-2-yl]-methyl]-benzenesulfonic acid amide (I_CC-01) | 92 | 96 |
| I_CC-02 | 2-chloro-N-methyl-N-[[7-(4-oxo-1-pyridin-4-yl-3,8-diazaspiro[4.5]decane-8-carbonyl)-1H-benzoimidazol-2-yl]-methyl]-benzamide (I_CC-02) | 46 | 10 |
| I_CC-03 | 4-methoxy-N,2,6-trimethyl-N-[[7-(3-pyridin-4-yl-3,9-diazaspiro[5.5]undecane-9-carbonyl)-1H-benzoimidazol-2-yl]-methyl]-benzenesulfonic acid amide (I_CC-03) | 100 | 100 |
| I_CC-04 | 2-chloro-N-methyl-N-[[7-(3-pyridin-4-yl-3,9-diazaspiro[5.5]undecane-9-carbonyl)-1H-benzoimidazol-2-yl]-methyl]-benzamide (I_CC-04) | 102 | 65 |
| I_CC-05 | 3-chloro-N-methyl-N-[[7-(3-pyridin-4-yl-3,9-diazaspiro[5.5]undecane-9-carbonyl)-1H-benzoimidazol-2-yl]-methyl]-thiophene-2-carboxylic acid amide (I_CC-05) | 93 | 30 |
| I_CC-06 | 4-methoxy-N,2,6-trimethyl-N-[[7-(3-pyridin-4-yl-3,8-diazaspiro[4.5]decane-8-carbonyl)-1H-benzoimidazol-2-yl]-methyl]-benzenesulfonic acid amide (I_CC-06) | 102 | 100 |
| I_CC-07 | 2-chloro-N,6-dimethyl-N-[[7-(3-pyridin-4-yl-3,8-diazaspiro[4.5]decane-8-carbonyl)-1H-benzoimidazol-2-yl]-methyl]-benzenesulfonic acid amide (I_CC-07) | 97 | 100 |
| I_CC-08 | 2-chloro-N-methyl-N-[[7-(3-pyridin-4-yl-3,8-diazaspiro[4.5]decane-8-carbonyl)-1H-benzoimidazol-2-yl]-methyl]-benzamide (I_CC-08) | 64 | 26 |
| I_CC-09 | 3-chloro-N-methyl-N-[[7-(3-pyridin-4-yl-3,8-diazaspiro[4.5]decane-8-carbonyl)-1H-benzoimidazol- | 58 | 15 |

-continued

| Example | Name | % Inhibition (rat B1R) at 10 μM | % Inhibition (human B1R) at 10 μM |
|---|---|---|---|
| | 2-yl]-methyl]-thiophene-2-carboxylic acid amide (I_CC-09) | | |
| I_CC-10 | 4-chloro-N,2,5-trimethyl-N-[[7-(3-pyridin-4-yl-3,8-diazaspiro[4.5]decane-8-carbonyl)-1H-benzoimidazol-2-yl]-methyl]-benzenesulfonic acid amide (I_CC-10) | 88 | 94 |
| I_CC-11 | 2-chloro-N,6-dimethyl-N-[[7-(3-pyridin-4-yl-3,9-diazaspiro[5.5]undecane-9-carbonyl)-1H-benzoimidazol-2-yl]-methyl]-benzenesulfonic acid amide (I_CC-11) | 91 | 98 |
| I_CC-12 | 7-chloro-2-[[7-(3-pyridin-4-yl-3,9-diazaspiro[5.5]undecane-9-carbonyl)-1H-benzoimidazol-2-yl]-methyl]-2,3-dihydro-isoindol-1-one (I_CC-12) | 101 | 100 |
| I_CC-13 | 7-chloro-2-[[7-(3-pyridin-4-yl-3,8-diazaspiro[4.5]decane-8-carbonyl)-1H-benzoimidazol-2-yl]-methyl]-2,3-dihydro-isoindol-1-one (I_CC-13) | 49 | 71 |
| I_CC-14 | 4-methoxy-N,2,6-trimethyl-N-[1-methyl-7-(3-pyridin-4-yl-3,9-diazaspiro[5.5]undecane-9-carbonyl)-1H-benzoimidazol-2-yl]-benzenesulfonic acid amide (I_CC-14) | 90 | 96 |
| I_CC-15 | 4-methoxy-N,2,6-trimethyl-N-[1-methyl-7-(3-pyridin-4-yl-3,8-diazaspiro[4.5]decane-8-carbonyl)-1H-benzoimidazol-2-yl]-benzenesulfonic acid amide (I_CC-15) | 99 | 97 |
| I_CC-16 | 4-methoxy-N,2,6-trimethyl-N-[1-methyl-7-(4-oxo-1-pyridin-4-yl-3,8-diazaspiro[4.5]decane-8-carbonyl)-1H-benzoimidazol-2-yl]-benzenesulfonic acid amide (I_CC-16) | 82 | 72 |
| I_CC-17 | 4-methoxy-N,2,6-trimethyl-N-[1-methyl-6-(3-pyridin-4-yl-3,9-diazaspiro[5.5]undecane-9-carbonyl)-1H-benzoimidazol-2-yl]-benzenesulfonic acid amide (I_CC-17) | 56 | 71 |
| I_CC-18 | 4-methoxy-N,2,6-trimethyl-N-[1-methyl-6-(3-pyridin-4-yl-3,8-diazaspiro[4.5]decane-8-carbonyl)-1H-benzoimidazol-2-yl]-benzenesulfonic acid amide (I_CC-18) | 48 | 39 |
| I_CC-19 | 4-methoxy-N,2,6-trimethyl-N-[4-(3-pyridin-4-yl-3,9-diazaspiro[5.5]undecane-9-carbonyl)-benzothiazol-2-yl]-benzenesulfonic acid amide (I_CC-19) | 80 | 54 |
| I_CC-20 | 4-methoxy-N,2,6-trimethyl-N-[[4-(3-pyridin-4-yl-3,8-diazaspiro[4.5]decane-8-carbonyl)-benzothiazol-2-yl]-methyl]-benzenesulfonic acid amide (I_CC-20) | 100 | 93 |
| I_CC-21 | 4-methoxy-N,2,6-trimethyl-N-[4-(3-pyridin-4-yl-3,8-diazaspiro[4.5]decane-8-carbonyl)-benzothiazol-2-yl]-benzenesulfonic acid amide (I_CC-21) | 65 | 36 |

-continued

| Example | Name | % Inhibition (rat B1R) at 10 μM | % Inhibition (human B1R) at 10 μM |
|---|---|---|---|
| I_CC-22 | 4-methoxy-N,2,6-trimethyl-N-[[4-(3-pyridin-4-yl-3,9-diazaspiro[5.5]undecane-9-carbonyl)-benzothiazol-2-yl]-methyl]-benzenesulfonic acid amide (I_CC-22) | 93 | 95 |
| I_CC-23 | 4-methoxy-N,2,6-trimethyl-N-[[7-(3-pyridin-4-yl-3,9-diazaspiro[5.5]undecane-9-carbonyl)-1H-benzoimidazol-2-yl]-methyl]-benzamide (I_CC-23) | 105 | 100 |
| I_CC-24 | 4-methoxy-N,2,6-trimethyl-N-[[7-(3-pyridin-4-yl-3,8-diazaspiro[4.5]decane-8-carbonyl)-1H-benzoimidazol-2-yl]-methyl]-benzamide (I_CC-24) | 101 | 98 |
| I_CC-25 | N-[1-[7-[9-(1H-Imidazol-4-yl-methyl)-3,9-diazaspiro[5.5]undecane-3-carbonyl]-1H-benzoimidazol-2-yl]-ethyl]-4-methoxy-N,2,6-trimethyl-benzenesulfonic acid amide (I_CC-25) | 103 | 58 |
| I_CC-26 | 4-Methoxy-N,2,6-trimethyl-N-[1-[7-[9-(pyridin-2-yl-methyl)-3,9-diazaspiro[5.5]undecane-3-carbonyl]-1H-benzoimidazol-2-yl]-ethyl]-benzenesulfonic acid amide (I_CC-26) | 89 | 91 |
| I_CC-27 | 4-Methoxy-N,2,6-trimethyl-N-[1-[7-[9-(pyridin-4-yl-methyl)-3,9-diazaspiro[5.5]undecane-3-carbonyl]-1H-benzoimidazol-2-yl]-ethyl]-benzenesulfonic acid amide (I_CC-27) | 92 | 90 |
| I_CC-28 | 4-Methoxy-N,2,6-trimethyl-N-[1-[7-[9-(pyridin-3-yl-methyl)-3,9-diazaspiro[5.5]undecane-3-carbonyl]-1H-benzoimidazol-2-yl]-ethyl]-benzenesulfonic acid amide (I_CC-28) | 85 | 96 |
| I_CC-29 | N-[1-[7-[9-[(2,6-Difluoro-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-29) | 94 | 84 |
| I_CC-30 | N-[1-[7-[9-[(3,4-Difluoro-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-30) | 99 | 63 |
| I_CC-31 | N-[1-[7-[9-[(2,5-Difluoro-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-31) | 104 | 63 |
| I_CC-32 | N-[1-[7-[9-[(2,4-Difluoro-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-32) | 99 | 71 |
| I_CC-33 | N-[1-[7-[9-[(3-Fluoro-4-methoxy-phenyl)-methyl]-3,9- | 89 | 80 |

-continued

| Example | Name | % Inhibition (rat B1R) at 10 μM | % Inhibition (human B1R) at 10 μM |
|---|---|---|---|
| | diazaspiro[5.5]undecane-3-carbonyl]-1H-benzoimidazol-2-yl]-ethyl]-4-methoxy-N,2,6-trimethyl-benzenesulfonic acid amide (I_CC-33) | | |
| I_CC-34 | N-[1-[7-[9-[(2-Fluoro-6-methoxy-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-34) | 86 | 91 |
| I_CC-35 | 4-Methoxy-N,2,6-trimethyl-N-[1-[7-[9-[(5-methyl-3H-imidazol-4-yl)-methyl]-3,9-diazaspiro[5.5]undecane-3-carbonyl]-1H-benzoimidazol-2-yl]-ethyl]-benzenesulfonic acid amide (I_CC-35) | 104 | 68 |
| I_CC-36 | 4-Methoxy-N,2,6-trimethyl-N-[1-[7-[9-[(3-methyl-3H-imidazol-4-yl)-methyl]-3,9-diazaspiro[5.5]undecane-3-carbonyl]-1H-benzoimidazol-2-yl]-ethyl]-benzenesulfonic acid amide (I_CC-36) | 100 | 82 |
| I_CC-37 | 4-Methoxy-N,2,6-trimethyl-N-[1-[7-[9-[(2-methyl-1H-imidazol-4-yl)-methyl]-3,9-diazaspiro[5.5]undecane-3-carbonyl]-1H-benzoimidazol-2-yl]-ethyl]-benzenesulfonic acid amide (I_CC-37) | 101 | 80 |
| I_CC-38 | 4-Methoxy-N,2,6-trimethyl-N-[1-[7-[9-([1,2,3]thiadiazol-4-yl-methyl)-3,9-diazaspiro[5.5]undecane-3-carbonyl]-1H-benzoimidazol-2-yl]-ethyl]-benzenesulfonic acid amide (I_CC-38) | 97 | 85 |
| I_CC-39 | N-[1-[7-[9-[(2-Chloro-4-fluoro-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-39) | 95 | 49 |
| I_CC-40 | N-[1-[7-[9-[(2-Chloro-6-fluoro-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-40) | 99 | 49 |
| I_CC-41 | N-[1-[7-[9-[(1,5-Dimethyl-1H-pyrazol-4-yl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-41) | 98 | 83 |
| I_CC-42 | N-[1-[7-[9-[(3,5-Dimethyl-isoxazol-4-yl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-42) | 90 | 76 |
| I_CC-43 | N-[1-[7-[9-[(4-Cyano-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-43) | 98 | 85 |

-continued

| Example | Name | % Inhibition (rat B1R) at 10 μM | % Inhibition (human B1R) at 10 μM |
|---|---|---|---|
| I_CC-44 | N-[1-[7-[9-[(3-Cyano-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-44) | 101 | 84 |
| I_CC-45 | N-[1-[7-[9-[(2-Cyano-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-45) | 98 | 81 |
| I_CC-46 | 4-Methoxy-N,2,6-trimethyl-N-[1-[7-[9-[5-(trifluoromethyl)-pyridine-2-carbonyl]-3,9-diazaspiro[5.5]undecane-3-carbonyl]-1H-benzoimidazol-2-yl]-ethyl]-benzenesulfonic acid amide (I_CC-46) | 89 | 42 |
| I_CC-47 | 4-Methoxy-N,2,6-trimethyl-N-[1-[7-[9-(pyrazine-2-carbonyl)-3,9-diazaspiro[5.5]undecane-3-carbonyl]-1H-benzoimidazol-2-yl]-ethyl]-benzenesulfonic acid amide (I_CC-47) | 90 | 58 |
| I_CC-48 | 4-Methoxy-N,2,6-trimethyl-N-[1-[7-[9-(2-methylsulfanyl-pyridine-3-carbonyl)-3,9-diazaspiro[5.5]undecane-3-carbonyl]-1H-benzoimidazol-2-yl]-ethyl]-benzenesulfonic acid amide (I_CC-48) | 89 | 61 |
| I_CC-49 | N-[1-[7-[9-(4-Cyano-benzoyl)-3,9-diazaspiro[5.5]undecane-3-carbonyl]-1H-benzoimidazol-2-yl]-ethyl]-4-methoxy-N,2,6-trimethyl-benzenesulfonic acid amide (I_CC-49) | 87 | 72 |
| I_CC-50 | N-[1-[7-[9-(Cyclopropanecarbonyl)-3,9-diazaspiro[5.5]undecane-3-carbonyl]-1H-benzoimidazol-2-yl]-ethyl]-4-methoxy-N,2,6-trimethyl-benzenesulfonic acid amide (I_CC-50) | 88 | 62 |
| I_CC-51 | N-[1-[7-[9-(3,3-Dimethyl-butanoyl)-3,9-diazaspiro[5.5]undecane-3-carbonyl]-1H-benzoimidazol-2-yl]-ethyl]-4-methoxy-N,2,6-trimethyl-benzenesulfonic acid amide (I_CC-51) | 88 | 78 |
| I_CC-52 | N-[1-[7-[9-(2-Chloro-4-fluoro-benzoyl)-3,9-diazaspiro[5.5]undecane-3-carbonyl]-1H-benzoimidazol-2-yl]-ethyl]-4-methoxy-N,2,6-trimethyl-benzenesulfonic acid amide (I_CC-52) | 93 | 77 |
| I_CC-53 | N-[1-[7-[9-(2,4-Difluoro-benzoyl)-3,9-diazaspiro[5.5]undecane-3-carbonyl]-1H-benzoimidazol-2-yl]-ethyl]-4-methoxy-N,2,6-trimethyl-benzenesulfonic acid amide (I_CC-53) | 88 | 85 |
| I_CC-54 | N-[1-[7-[9-(5-tert-Butyl-2-methyl-2H-pyrazole-3-carbonyl)-3,9-diazaspiro[5.5]undecane-3-carbonyl]-1H-benzoimidazol-2-yl]-ethyl]-4-methoxy-N,2,6- | 92 | 63 |

-continued

| Example | Name | % Inhibition (rat B1R) at 10 µM | % Inhibition (human B1R) at 10 µM |
|---|---|---|---|
| | trimethyl-benzenesulfonic acid amide (I_CC-54) | | |
| I_CC-55 | N-[1-[7-[9-(2-tert-Butyl-5-methyl-2H-pyrazole-3-carbonyl)-3,9-diazaspiro[5.5]undecane-3-carbonyl]-1H-benzoimidazol-2-yl]-ethyl]-4-methoxy-N,2,6-trimethyl-benzenesulfonic acid amide (I_CC-55) | 89 | 71 |
| I_CC-56 | N-[1-[7-[9-[(5-Chloro-thiophen-2-yl)sulfonyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-56) | 101 | 15 |
| I_CC-57 | N-[1-[7-[9-[(2,4-Difluoro-phenyl)sulfonyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-57) | 103 | 22 |
| I_CC-58 | N-[1-[7-[9-[(3-Cyano-4-fluoro-phenyl)sulfonyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-58) | 101 | 18 |
| I_CC-59 | N-[1-[7-[9-[(2-Cyano-phenyl)sulfonyl]-3,9-diazaspiro[5.5]undecane-3-carbonyl]-1H-benzoimidazol-2-yl]-ethyl]-4-methoxy-N,2,6-trimethyl-benzenesulfonic acid amide (I_CC-59) | 103 | 20 |
| I_CC-60 | 4-Methoxy-N,2,6-trimethyl-N-[1-[7-[9-[(1-methyl-1H-indol-4-yl)sulfonyl]-3,9-diazaspiro[5.5]undecane-3-carbonyl]-1H-benzoimidazol-2-yl]-ethyl]-benzenesulfonic acid amide (I_CC-60) | 101 | |

The invention claimed is:

1. A compound corresponding to formula (I)

(I)

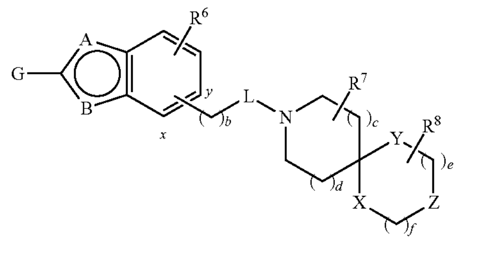

wherein

L represents C(=O) or $CH_2$;

A and B are each selected from the group consisting of N, $NR^{100}$, wherein $R^{100}$ represents H, $C_{1-6}$-alkyl, $C_{3-8}$-cycloalkyl, aryl, heteroaryl or a $C_{3-8}$-cycloalkyl, aryl or heteroaryl bonded via a $C_{1-6}$-alkylene group;

b represents 0, 1 or 2;

c, d, e and f each independently represent 0, 1 or 2;

G represents one of the following structures G1 or G2

G1

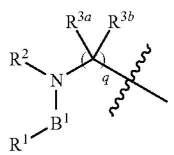

G2

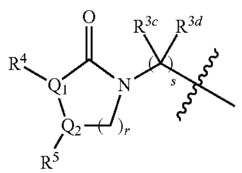

q represents 0, 1, 2 or 3;

s represents 0, 1, 2 or 3;

r represents 1, 2 or 3;

$B^1$ represents C(=O), $S(=O)_2$ or the group —C(=O)—N($R^9$), wherein the nitrogen atom thereof is bonded to $R^1$;

$Q_1$ and $Q_2$ each independently represent C, CH or N;

$R^1$ represents $C_{1-6}$-alkyl, aryl, heteroaryl, —CH(aryl)$_2$, $C_{3-8}$-cycloalkyl or an aryl, heteroaryl or $C_{3-8}$-cycloalkyl bonded via a $C_{1-6}$-alkylene group, $C_{2-6}$-alkenylene group or $C_{2-6}$-alkynylene group;

$R^2$ represents H, $C_{1-6}$-alkyl, $C_{3-8}$-cycloalkyl, aryl, heteroaryl or a $C_{3-8}$-cycloalkyl, aryl or heteroaryl bonded via a $C_{1-6}$-alkylene group;

$R^{3a}$ and $R^{3b}$ each independently denote H, F, $CF_3$, $C_{1-6}$-alkyl, $C_{3-8}$-cycloalkyl, aryl or heteroaryl, or represent a $C_{3-8}$-cycloalkyl, aryl or heteroaryl bonded via a $C_{1-6}$-alkylene group; or $R^{3a}$ and $R^{3b}$ together with the C atom joining them form a saturated 3-, 4-, 5- or 6-membered ring optionally containing one or more oxygen atoms, which ring is unsubstituted or substituted on one or more of its carbon ring members by one or more substituents independently selected from the group consisting of F, $CF_3$, $C_{1-6}$-alkyl, O—$C_{1-6}$-alkyl, OH, $OCF_3$, aryl and heteroaryl; or $R^2$ and one of $R^{3a}$ and $R^{3b}$ together with the N and C atoms joining them form a saturated 4-, 5-, 6- or 7-membered ring, which is unsubstituted or substituted on one or more of its carbon ring members by one or more substituents independently selected from the group consisting of F, $CF_3$, $C_{1-6}$-alkyl, O—$C_{1-6}$-alkyl, OH, $OCF_3$, aryl and heteroaryl; wherein the ring optionally may contain one or more hetero atoms or hetero atom groups independently selected from the group consisting of N, $NR^{100a}$, O, S, S(=O) and $S(=O)_2$; wherein $R^{100a}$ represents H, $C_{1-6}$-alkyl, $C_{3-8}$-cycloalkyl, aryl, heteroaryl or a $C_{3-8}$-cycloalkyl, aryl or heteroaryl bonded via a $C_{1-6}$-alkylene group;

$R^{3c}$ and $R^{3d}$ each independently denote H, F, $CF_3$, $C_{1-6}$-alkyl, $C_{3-8}$-cycloalkyl, aryl or heteroaryl, or represent a $C_{3-8}$-cycloalkyl, aryl or heteroaryl bonded via a $C_{1-6}$-alkylene group, or $R^{3c}$ and $R^{3d}$ together with the C atom joining them form a saturated 3-, 4-, 5- or 6-membered ring, which is unsubstituted or substituted on one or more of its carbon ring members by one or more substituents independently selected from the group consisting of F, $CF_3$, $C_{1-6}$-alkyl, O—$C_{1-6}$-alkyl, OH, $OCF_3$, aryl and heteroaryl, wherein the ring optionally may contain one or more oxygen atoms;

$R^4$ and $R^5$ together with the group -$Q_1$-$Q_2$- joining them form a 4-, 5-, 6- or 7-membered ring, which is unsubstituted or substituted on one or more of its carbon ring members by one or more substituents independently selected from the group consisting of F, Cl, Br, I, $CF_3$, $C_{1-6}$-alkyl, O—$C_{1-6}$-alkyl, OH, $OCF_3$, SH, $SCF_3$, aryl and heteroaryl and/or optionally may be fused with at least one aryl or heteroaryl, wherein the ring is saturated, mono- or poly-unsaturated or aromatic, and optionally may contain one or more hetero atoms or hetero atom groups independently selected from the group consisting of N, $NR^{50}$, O, S, S(=O) and $S(=O)_2$; wherein $R^{50}$ denotes H, $C_{1-6}$-alkyl, —C(=O)—$R^{51}$, $C_{3-8}$-cycloalkyl, aryl, heteroaryl or a $C_{3-8}$-cycloalkyl, aryl or heteroaryl bonded via a $C_{1-3}$-alkylene group, and $R^{51}$ denotes $C_{1-6}$-alkyl, $C_{3-8}$-cycloalkyl, aryl, heteroaryl or a $C_{3-8}$-cycloalkyl, aryl or heteroaryl bonded via a $C_{1-3}$-alkylene group;

$R^6$ represents 0, 1, 2 or 3 substituents each independently selected from the group consisting of F, Cl, $CF_3$, CN, $OCF_3$, OH, $C_{1-6}$-alkyl, $C_{3-8}$-cycloalkyl and O—$C_{1-6}$-alkyl;

$R^7$ and $R^8$ each independently represent 0, 1, 2, 3 or 4 substituents each independently selected from the group consisting of F, Cl, OH, =O, $C_{1-6}$-alkyl, O—$C_{1-6}$-alkyl, $C_{3-8}$-cycloalkyl, aryl, heteroaryl and $C_{3-8}$-cycloalkyl, aryl or heteroaryl bonded via a $C_{1-6}$-alkylene group and/or two adjacent substituents $R^7$ or $R^8$ form a fused-on aryl or heteroaryl;

$R^9$ represents H, $C_{1-6}$-alkyl, $C_{3-8}$-cycloalkyl, aryl, heteroaryl or a $C_{3-8}$-cycloalkyl, aryl or heteroaryl bonded via a $C_{1-3}$-alkylene group;

X represents $CR^{10a}R^{10b}$, $NR^{11}$ or O;

Y represents $CR^{12a}R^{12b}$, $NR^{13}$ or O;

with the proviso that X does not denote $NR^{11}$ if Y denotes $NR^{13}$; and with the proviso that X and Y do not simultaneously denote O;

wherein $R^{10a}$, $R^{10b}$, $R^{12a}$ and $R^{12b}$ each independently denote H, F, Cl, OH, $C_{1-6}$-alkyl, O—$C_{1-6}$-alkyl, $C_{3-8}$-cycloalkyl, aryl or heteroaryl, or represent a $C_{3-8}$-cycloalkyl, aryl or heteroaryl bonded via a $C_{1-6}$-alkylene group, and/or $R^{10a}$ and $R^{10b}$ together can represent =O and/or $R^{12a}$ and $R^{12b}$ together can represent =O;

$R^{11}$ and $R^{13}$ each independently represent H, $C_{1-6}$-alkyl, $C_{3-8}$-cycloalkyl, aryl or heteroaryl, or denote a $C_{3-8}$-cycloalkyl, aryl or heteroaryl bonded via a $C_{1-6}$-alkylene group;

Z represents $CR^{14a}R^{14b}$, $NR^{15}$ or O;

$R^{14a}$ represents H, $NR^{16}R^{17}$, $C_{1-6}$-alkylene-$NR^{16}R^{17}$, O—$C_{1-6}$-alkylene-$NR^{16}R^{17}$, C(=O)—$NR^{16}R^{17}$, $OR^{18}$, $C_{1-6}$-alkylene-$OR^{18}$, $C_{1-6}$-alkylene-O—$C_{1-6}$-alkylene-$OR^{18}$, $C_{1-6}$-alkyl, $C_{3-8}$-cycloalkyl, heterocyclyl, aryl or heteroaryl, or denotes a $C_{3-8}$-cycloalkyl, heterocyclyl, aryl or heteroaryl bonded via a $C_{1-6}$-alkylene group;

$R^{14b}$ represents H, $NR^{16}R^{17}$, $C_{1-6}$-alkylene-$NR^{16}R^{17}$, O—$C_{1-6}$-alkylene-$NR^{16}R^{17}$, C(=O)—$NR^{16}R^{17}$, $OR^{18}$, $C_{1-6}$-alkylene-$OR^{18}$, $C_{1-6}$-alkylene-O—$C_{1-6}$-alkylene-$OR^{18}$, $C_{1-6}$-alkyl, $C_{3-8}$-cycloalkyl, heterocyclyl, aryl or heteroaryl, or denotes a $C_{3-8}$-cycloalkyl, heterocyclyl, aryl or heteroaryl bonded via a $C_{1-6}$-alkylene group;

$R^{15}$ represents H, —C(=O)—$R^{19}$, —$S(=O)_2$—$R^{19}$, —C(=O)—N($R^{20}$)—$R^{19}$, $CHR^{25}R^{26}$, $C_{1-10}$-alkyl, $C_{3-8}$-cycloalkyl, heterocyclyl, aryl or heteroaryl or denotes a $CHR^{25}R^{26}$, $C_{3-8}$-cycloalkyl, heterocyclyl, aryl or heteroaryl bonded via a $C_{1-6}$-alkylene group;

$R^{16}$ and $R^{17}$ each independently represent H, $C_{1-6}$-alkyl or $C_{3-8}$-cycloalkyl, or $R^{16}$ and $R^{17}$ together with the nitrogen atom joining them form a 4-, 5-, 6- or 7-membered heterocycle, which is unsubstituted or substituted on one or more of its carbon ring members by one or more substituents independently selected from the group consisting of F, Cl, Br, I, $CF_3$, $C_{1-6}$-alkyl, O—$C_{1-6}$-alkyl, OH, $OCF_3$, SH, $SCF_3$, $NR^AR^B$, aryl and heteroaryl and/or optionally may be fused with at least one aryl or heteroaryl, wherein the heterocycle is saturated or mono- or poly-unsaturated and optionally may contain one or more hetero atoms or hetero atom groups independently selected from the group consisting of N, $NR^{50a}$, O, S, S(=O) and $S(=O)_2$; wherein $R^{50a}$ denotes H, $C_{1-6}$-alkyl, —C(=O)—$R^{51a}$, $C_{3-8}$-cycloalkyl, aryl, heteroaryl or a $C_{3-8}$-cycloalkyl, aryl or heteroaryl bonded via a $C_{1-3}$-alkylene group, and $R^{51a}$ denotes $C_{1-6}$-alkyl, $C_{3-8}$-cycloalkyl, aryl, heteroaryl or a $C_{3-8}$-cycloalkyl, aryl or heteroaryl bonded via a $C_{1-3}$-alkylene group;

$R^{18}$ represents H, $C_{1-6}$-alkyl, $C_{3-8}$-cycloalkyl, heterocyclyl, aryl, heteroaryl or $C_{2-6}$-alkylene-$NR^{16}R^{17}$ or denotes a heterocyclyl, $C_{3-8}$-cycloalkyl, aryl or heteroaryl bonded via a $C_{1-6}$-alkylene group;

$R^{19}$ represents $C_{1-6}$-alkyl, aryl, heteroaryl, —CH(aryl)$_2$, $C_{3-8}$-cycloalkyl, heterocyclyl or an aryl, heteroaryl, $C_{3-8}$-cycloalkyl or heterocyclyl bonded via a $C_{1-6}$-alkylene group, $C_{2-6}$-alkenylene group or $C_{2-6}$-alkynylene group;

$R^{20}$ represents H, $C_{1-6}$-alkyl, $C_{3-8}$-cycloalkyl, aryl, heteroaryl or a $C_{3-8}$-cycloalkyl, aryl or heteroaryl bonded via a $C_{1-3}$-alkylene group; or if X represents O and f represents 0, then Z denotes —(C($R^{21}$)—C($R^{22}$))—, wherein $R^{21}$ and $R^{22}$ together with the carbon atoms joining them form a fused-on aryl or heteroaryl; or if X represents O and f represents 0, then Z denotes ═(N(C$R^{23}$))—, wherein the N atom is bonded to the O atom via a single bond, and $R^{23}$ represents H, $C_{1-6}$-alkyl, $C_{3-8}$-cycloalkyl, aryl or heteroaryl or denotes a $C_{3-8}$-cycloalkyl, aryl or heteroaryl bonded via a $C_{1-6}$-alkylene group;

$R^{25}$ and $R^{26}$ each independently represent H, $C_{1-4}$-alkyl, $C_{3-8}$-cycloalkyl, aryl or heteroaryl, or $R^{25}$ and $R^{26}$ together with the CH grouping joining them form a 4-, 5-, 6- or 7-membered ring, which is unsubstituted or substituted on one or more of its carbon ring members by one or more substituents independently selected from the group consisting of F, Cl, Br, I, $CF_3$, $C_{1-6}$-alkyl, O—$C_{1-6}$-alkyl, OH, $OCF_3$, SH, $SCF_3$, $NR^AR^B$, aryl and heteroaryl, wherein the ring is saturated or mono- or poly-unsaturated but not aromatic, and optionally may contain one or more hetero atoms or hetero atom groups independently selected from the group consisting of N, $NR^{50b}$, O, S, S(═O) and S(═O)$_2$; wherein $R^{50b}$ denotes H, $C_{1-6}$-alkyl, —C(═O)—$R^{51b}$, $C_{3-8}$-cycloalkyl, aryl, heteroaryl or a $C_{3-8}$-cycloalkyl, aryl or heteroaryl bonded via a $C_{1-3}$-alkylene group, and $R^{51b}$ denotes $C_{1-6}$-alkyl, $C_{3-8}$-cycloalkyl, aryl, heteroaryl or a $C_{3-8}$-cycloalkyl, aryl or heteroaryl bonded via a $C_{1-3}$-alkylene group;

$R^A$ and $R^B$ each independently represent H, $C_{1-6}$-alkyl or $C_{3-8}$-cycloalkyl, or $R^A$ and $R^B$ together with the nitrogen atom joining them form a 4-, 5-, 6- or 7-membered heterocycle, which is unsubstituted or substituted on one or more of its carbon ring members by one or more substituents independently selected from the group consisting of F, Cl, Br, I, $CF_3$, $C_{1-6}$-alkyl, O—$C_{1-6}$-alkyl, OH, $OCF_3$, SH, $SCF_3$, aryl and heteroaryl, wherein the heterocycle is saturated or mono- or poly-unsaturated but not aromatic, and optionally may contain one or more hetero atoms or hetero atom groups independently selected from the group consisting of N, $NR^C$, O, S, S(═O) and S(═O)$_2$; wherein $R^C$ denotes H, $C_{1-6}$-alkyl, —C(═O)—$R^D$, $C_{3-8}$-cycloalkyl, aryl, heteroaryl or a $C_{3-8}$-cycloalkyl, aryl or heteroaryl bonded via a $C_{1-3}$-alkylene group, and $R^D$ denotes $C_{1-6}$-alkyl, $C_{3-8}$-cycloalkyl, aryl, heteroaryl or a $C_{3-8}$-cycloalkyl, aryl or heteroaryl bonded via a $C_{1-3}$-alkylene group;

wherein the structural part

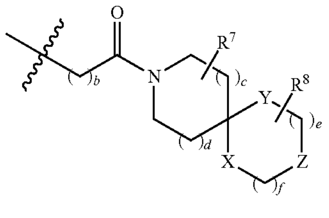

in the compounds of formula I is bonded to the base structure in position x or y, and wherein the abovementioned $C_{1-4}$-alkyl, $C_{1-6}$-alkyl, $C_{1-10}$-alkyl, $C_{1-3}$-alkylene, $C_{1-6}$-alkylene, $C_{2-6}$-alkylene, $C_{2-6}$-alkenylene, $C_{2-6}$-alkynylene, $C_{3-8}$-cycloalkyl, $C_{4-8}$-cycloalkyl, heterocyclyl, aryl and heteroaryl groups may each be unsubstituted or substituted one or more times by identical or different substituents and the abovementioned radicals $C_{1-4}$-alkyl, $C_{1-6}$-alkyl, $C_{1-10}$-alkyl, $C_{1-3}$-alkylene, $C_{1-6}$-alkylene, $C_{2-6}$-alkylene, $C_{2-6}$-alkenylene and $C_{2-6}$-alkynylene can in each case be branched or unbranched;

or a physiologically acceptable salt thereof.

2. A compound as claimed in claim 1, wherein

L represents C(═O) to yield formula (I') as given below (I')

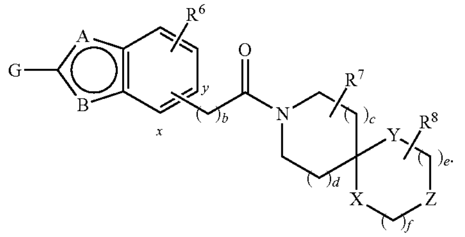

3. A compound as claimed in claim 1, wherein in formula (I) the structural part (Ac)

(Ac)

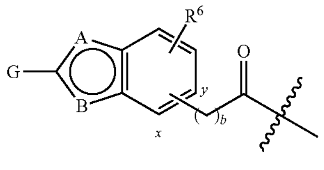

represents a structural part selected from the group consisting of:

(Ac 1)

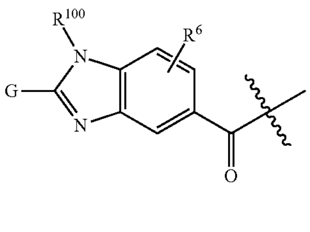

-continued
(Ac 2)
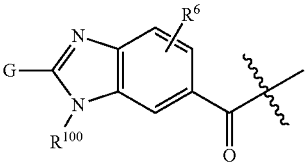
(Ac 3)
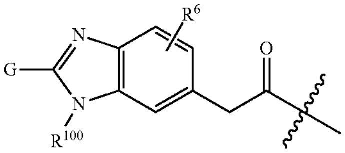
(Ac 4)
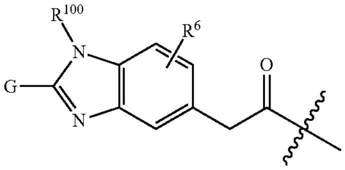
(Ac 13)
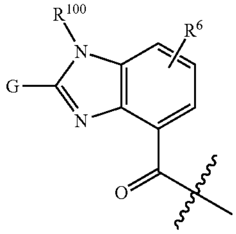
(Ac 14)
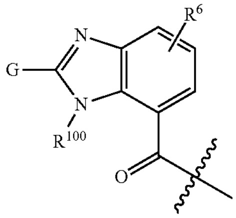
(Ac 15)
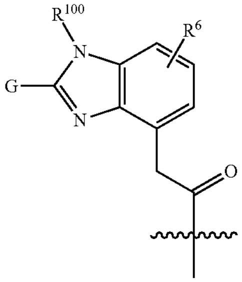
and
(Ac 16)
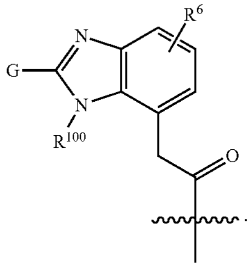
4. A compound as claimed in claim 1, wherein in formula (I) the structural part (Acc)
(Acc)
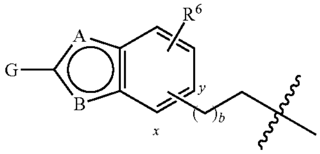
represents a structural part selected from the group consisting of:
(Acc 1)
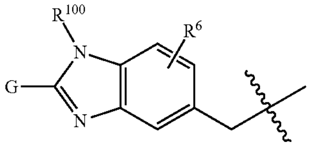
(Acc 2)
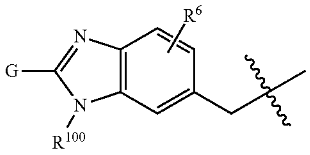
(Acc 3)
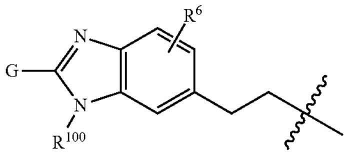
(Acc 4)
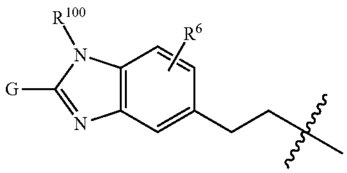
(Acc 13)
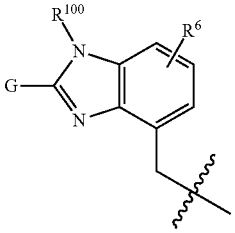
(Acc 14)
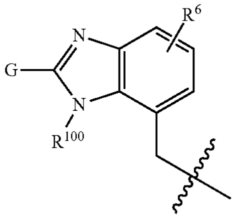

-continued
(Acc 15)
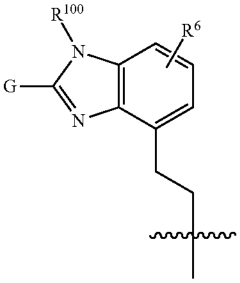
and
(Acc 16)
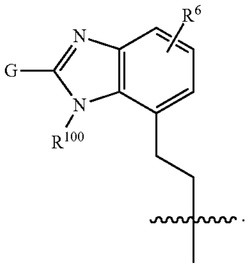
5. A compound as claimed in claim 1, wherein G1 is selected from the group consisting of:
G1-1
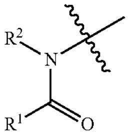
G1-2
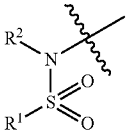
G1-3
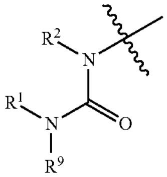
G1-4
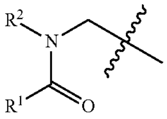
G1-5
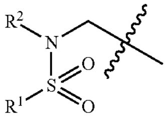
G1-6
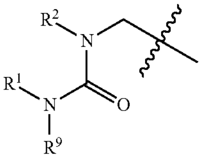
-continued
G1-7
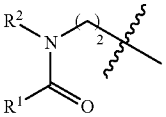
G1-8
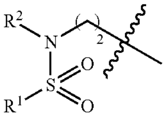
G1-9
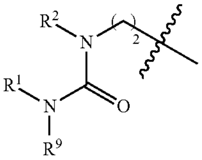
G1-10
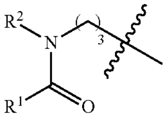
G1-11
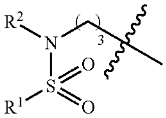
G1-12
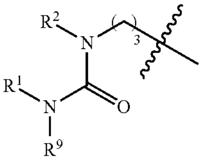
G1-13
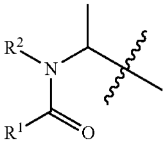
G1-14
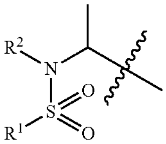
G1-15
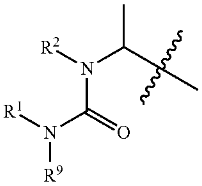
G1-16
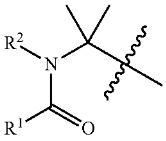

-continued
G1-17
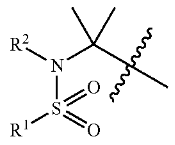
G1-18
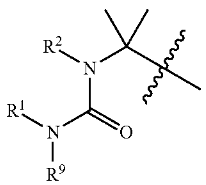
G1-19
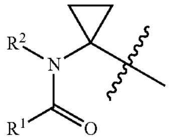
G1-20
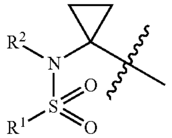
G1-21
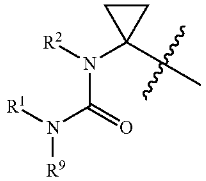
G1-22
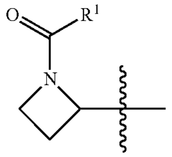
G1-23
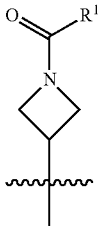
G1-24
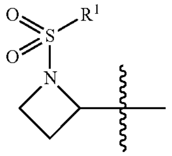
-continued
G1-25
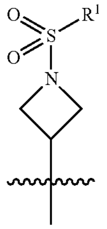
G1-26
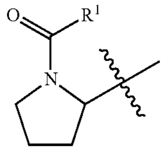
G1-27
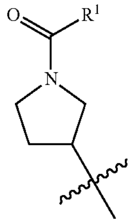
G1-28
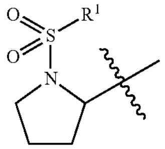
G1-29
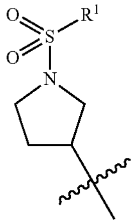
G1-30
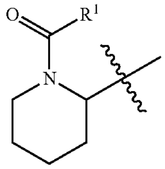
G1-31
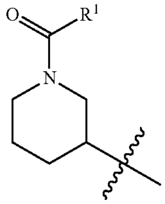

-continued

G1-32

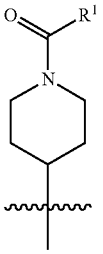

G1-33

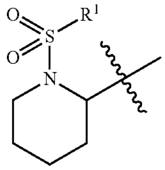

G1-34

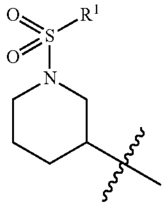

G1-35

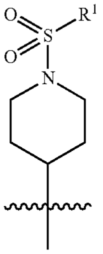

G1-36

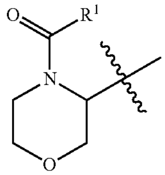

G1-37

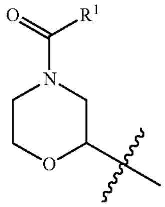

G1-38

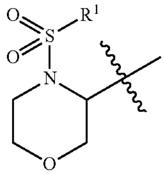

-continued

G1-39

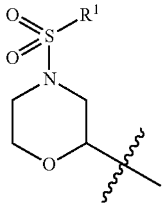

G1-40

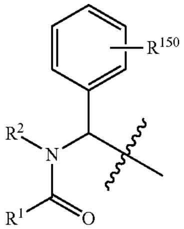

G1-41

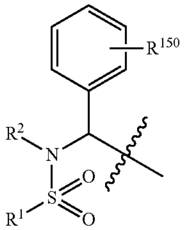

and

G1-42

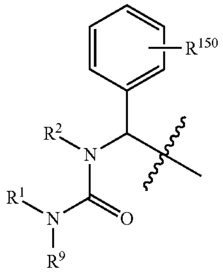

wherein $R^{150}$ represents 0, 1, 2, 3, 4 or 5 substituents each independently selected from the group consisting of F, Cl, Br, I, $CF_3$, O—$CF_3$, $C_{1-4}$-alkyl and O—$C_{1-4}$-alkyl.

6. A compound as claimed in claim 1, wherein $R^1$ represents $C_{1-6}$-alkyl, —CH(phenyl)$_2$, $C_{3-8}$-cycloalkyl, phenyl, naphthyl, chromanyl, indolyl, benzofuranyl, benzothiophenyl, benzooxazolyl, benzooxadiazolyl, pyrrolyl, furanyl, thienyl, pyridinyl, pyridazinyl, pyrimidinyl, pyrazinyl, imidazothiazolyl, carbazolyl, dibenzofuranyl, dibenzothiophenyl or a phenyl or naphthyl group bonded via a $C_{1-3}$-alkylene group, a $C_{2-3}$-alkenylene group or a $C_{2-3}$-alkynylene group, wherein the abovementioned aryl or heteroaryl groups are in each case unsubstituted or substituted one or more times by identical or different substituents independently selected from the group consisting of —O—$C_{1-3}$-alkyl, $C_{1-6}$-alkyl, F, Cl, Br, I, $CF_3$, $OCF_3$, OH, SH, phenyl, phenoxy, naphthyl, furyl, thienyl and pyridinyl, and wherein the abovementioned alkyl, alkylene, alkenylene and alkynylene groups are in each case unsubstituted or substituted one or more times by identical or different substituents independently selected from the group consisting of —O—$C_{1-3}$-alkyl, F, Cl, Br, I, $CF_3$, $OCF_3$, OH, SH, phenyl, phenoxy, naphthyl, furyl, thienyl and pyridinyl.

7. A compound as claimed in claim 6, wherein $R^1$ represents $C_{1-4}$-alkyl, —CH(phenyl)$_2$, $C_{3-6}$-cycloalkyl, phenyl, naphthyl, chromanyl, benzothiophenyl, benzooxadiazolyl, thienyl, pyridinyl, imidazothiazolyl, dibenzofuranyl or a phenyl group bonded via a $C_{1-3}$-alkylene group or a $C_{2-3}$-alkenylene group.

8. A compound as claimed in claim 1, wherein $R^2$ represents H, methyl, ethyl, n-propyl, iso-propyl, n-butyl, iso-butyl, sec-butyl, tert-butyl, cyclopropyl, cyclobutyl, cyclopentyl or cyclohexyl.

9. A compound as claimed in claim 1, wherein $R^9$ represents H, methyl, ethyl, n-propyl, iso-propyl, n-butyl, iso-butyl, sec-butyl, tert-butyl, cyclopropyl, cyclobutyl, cyclopentyl or cyclohexyl.

10. A compound as claimed in claim 1, wherein G2 represents a structure selected from the group consisting of:

G2-1

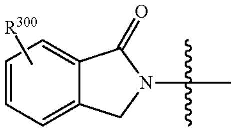

G2-2

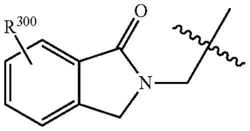

G2-3

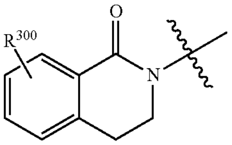

G2-4

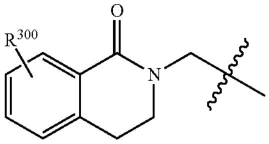

G2-5

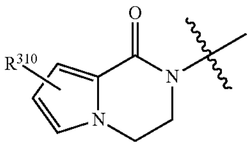

G2-6

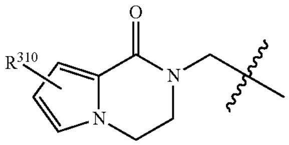

G2-7

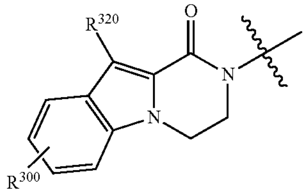

-continued

G2-8

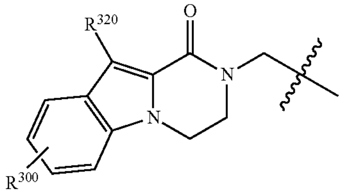

G2-9

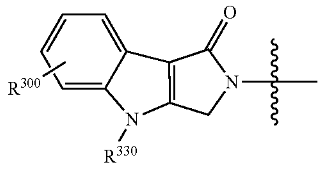

G2-10

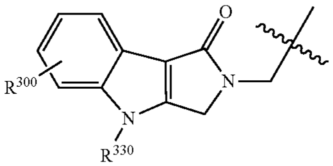

G2-11

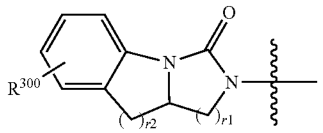

G2-12

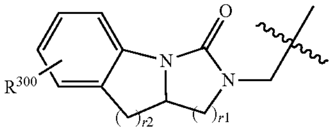

G2-13

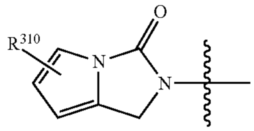

G2-14

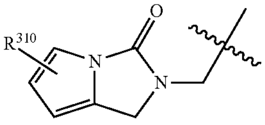

G2-15

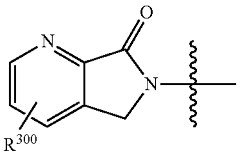

G2-16

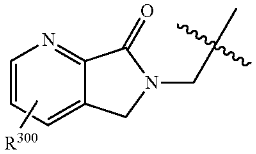

G2-17

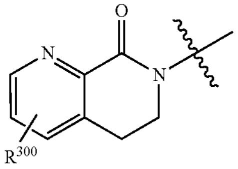

-continued

G2-18

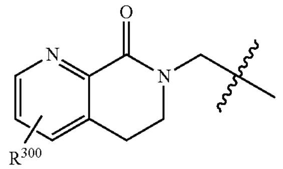

G2-19

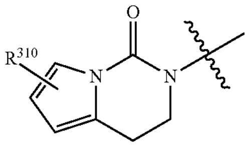

G2-20

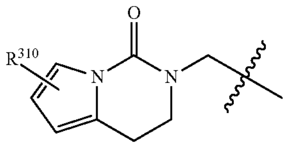

wherein $R^{300}$ represents 0, 1, 2, 3 or 4 substituents each independently selected from the group consisting of F, Cl, Br, I, $CF_3$, O—$CF_3$, $C_{1-4}$-alkyl and O—$C_{1-4}$-alkyl;

$R^{310}$ represents 0, 1, 2 or 3 substituents each independently selected from the group consisting of F, Cl, Br, I, $CF_3$, O—$CF_3$, $C_{1-4}$-alkyl and O—$C_{1-4}$-alkyl;

$R^{320}$ represents a substituent selected from the group consisting of H, F, Cl, Br, I, $CF_3$, O—$CF_3$ and $C_{1-4}$-alkyl;

$R^{330}$ represents a substituent selected from the group consisting of H, $C_{1-4}$-alkyl, aryl, $CH_2$-aryl and heteroaryl;

r1 represents 1 or 2, and r2 represents 1 or 2.

11. A compound as claimed in claim 1, wherein the following structural part (SP)

(SP)

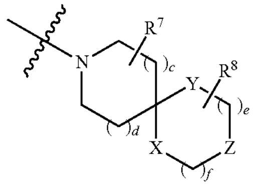

is selected from the group consisting of:

SP 1

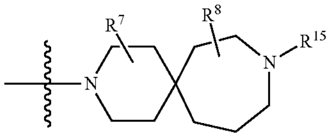

SP 2

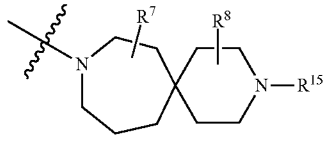

-continued

SP 3

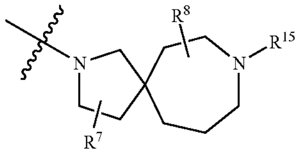

SP 4

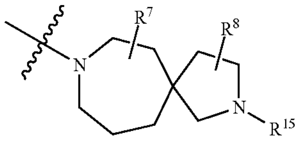

SP 5

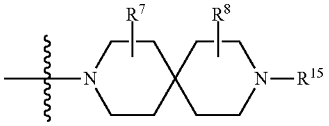

SP 6

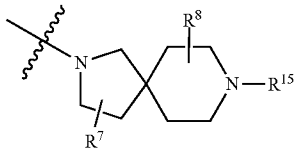

SP 7

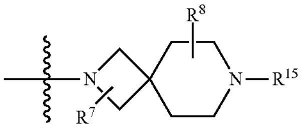

SP 8

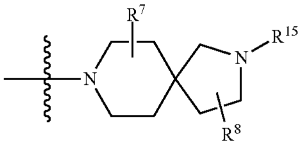

SP 9

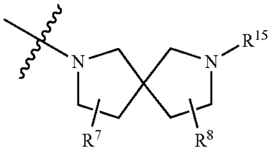

SP 10

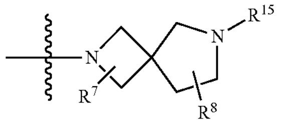

SP 11

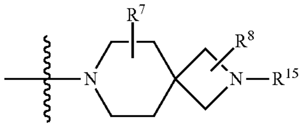

SP 12

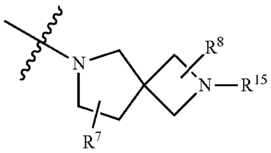

-continued
SP 13
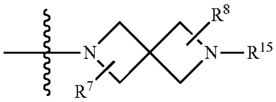
SP 14
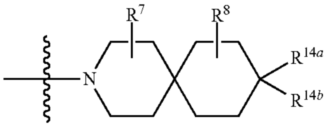
SP 15
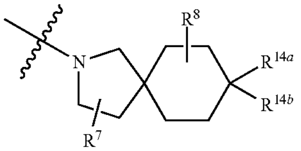
SP 16
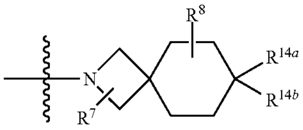
SP 17
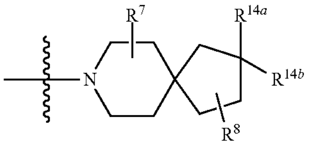
SP 18
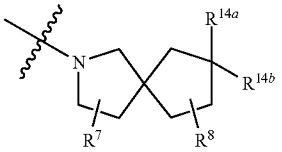
SP 19
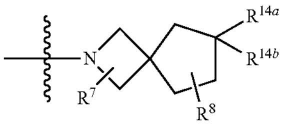
SP 20
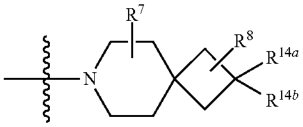
SP 21
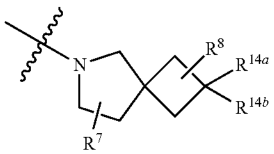
SP 22
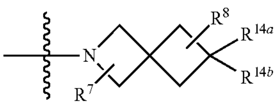
SP 23
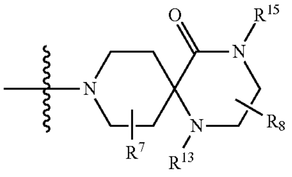
-continued
SP 24
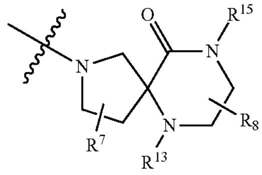
SP 25
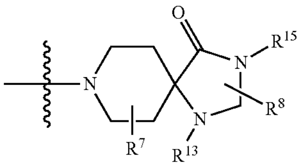
SP 26
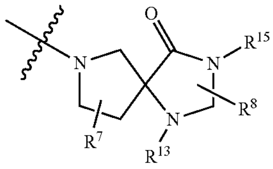
SP 27
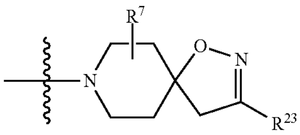
SP 28
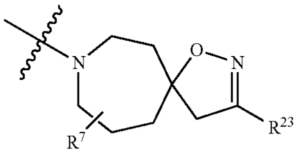
SP 29
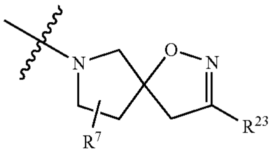
SP 30
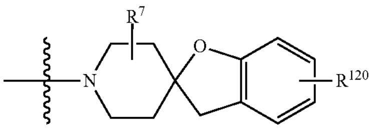
SP 31
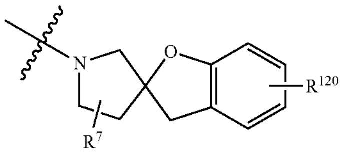
SP 32
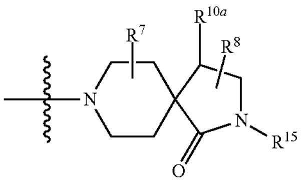

-continued

SP 33

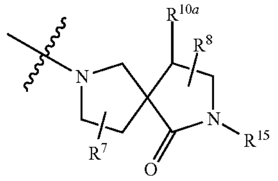

SP 34

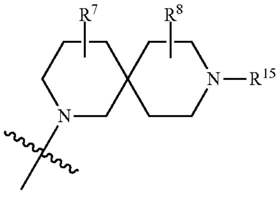

SP 35

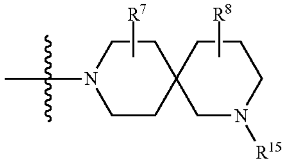

SP 36

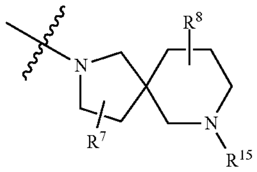

SP37

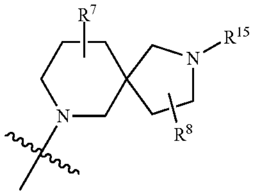

and

SP38

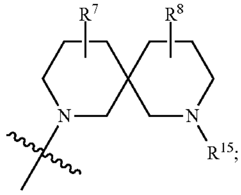

wherein $R^7$, $R^8$, $R^{10a}$, $R^{13}$, $R^{14a}$, $R^{14b}$, $R^{15}$ and $R^{23}$ have the meanings given in claim 1;

and $R^{120}$ represents 0, 1, 2, 3 or 4 substituents independently selected from the group consisting of F, Cl, $OCF_3$, $CF_3$, CN, methyl and methoxy.

12. A compound as claimed in claim 1, wherein $R^{14a}$ represents H, aryl, heteroaryl, $C_{1-3}$-alkylene-aryl or $C_{1-3}$-alkylene-heteroaryl;

$R^{14b}$ represents aryl, heteroaryl, $C_{1-3}$-alkylene-aryl, $C_{1-3}$-alkylene-heteroaryl, $NR^{16}R^{17}$, $C_{1-3}$-alkylene-$NR^{16}R^{17}$, C(=O)—$NR^{16}R^{17}$, $OR^{35}$ or $C_{1-3}$-alkylene-$OR^{35}$;

$R^{16}$ and $R^{17}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or $R^{16}$ and $R^{17}$ together with the nitrogen atom joining them form a structure selected from the group consisting of

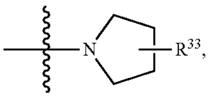

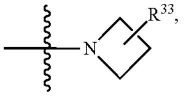

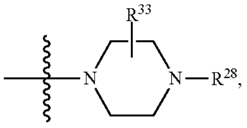

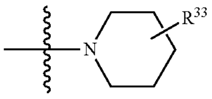

and

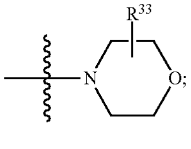

$R^{28}$ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl;

$R^{33}$ represents 0, 1 or 2 substituents each independently selected from the group consisting of F, Cl, $CF_3$, $OCF_3$, $C_{1-6}$-alkyl, O—$C_{1-3}$-alkyl and $NR^{34a}R^{34b}$;

$R^{34a}$ and $R^{34b}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or $R^{34a}$ and $R^{34b}$ together with the nitrogen atom joining them form a structure selected from the group consisting of:

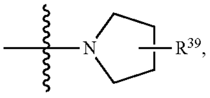

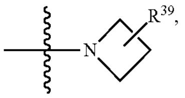

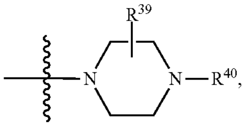

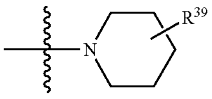

and

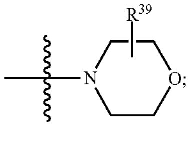

$R^{39}$ represents 0, 1 or 2 substituents each independently selected from the group consisting of F, Cl, $CF_3$, $OCF_3$, $C_{1-6}$-alkyl and O—$C_{1-3}$-alkyl;

$R^{40}$ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl;

$R^{35}$ represents H, $C_{1-6}$-alkyl, $C_{3-6}$-cycloalkyl, aryl, heteroaryl, $C_{1-3}$-alkylene-$C_{3-6}$-cycloalkyl, $C_{1-3}$-alkylene-aryl, $C_{1-3}$-alkylene-heteroaryl or the group

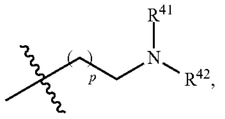

wherein p represents 1, 2 or 3, wherein $R^{41}$ and $R^{42}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or $R^{41}$ and $R^{42}$ together with the nitrogen atom joining them form a structure selected from the group consisting of

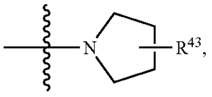

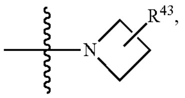

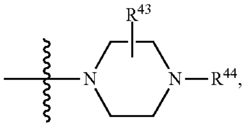

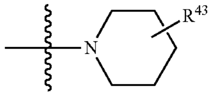

and

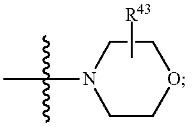

$R^{43}$ represents 0, 1 or 2 substituents each independently selected from the group consisting of F, Cl, $CF_3$, $OCF_3$, $C_{1-6}$-alkyl, O—$C_{1-3}$-alkyl and $NR^{45a}R^{45b}$;

$R^{44}$ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl;

$R^{45a}$ and $R^{45b}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or $R^{45a}$ and $R^{45b}$ together with the nitrogen atom joining them form a structure selected from the group consisting of:

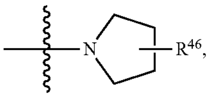

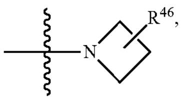

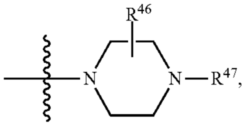

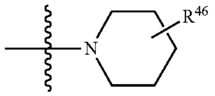

and

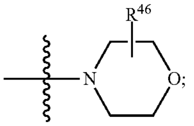

$R^{46}$ represents 0, 1 or 2 substituents each independently selected from the group consisting of F, Cl, $CF_3$, $OCF_3$, $C_{1-6}$-alkyl and O—$C_{1-3}$-alkyl; and $R^{47}$ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl.

13. A compound as claimed in claim 1, wherein $R^{15}$ represents H, $C_{1-6}$-alkyl, —$CHR^{25}R^{26}$, $C_{1-3}$-alkylene-$CHR^{25}R^{26}$, aryl, heteroaryl, $C_{1-3}$-alkylene-aryl, $C_{1-3}$-alkylene-heteroaryl, —C(═O)—$R^{19}$, —S(═O)$_2$—$R^{19}$ or the group —C(═O)—N($R^{20}$)—$R^{19}$;

$R^{25}$ and $R^{26}$ each independently represent H, $C_{1-4}$-alkyl, $C_{3-6}$-cycloalkyl, aryl or heteroaryl, or $R^{25}$ and $R^{26}$ together with the CH grouping joining them form a structure selected from the group consisting of

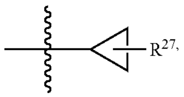

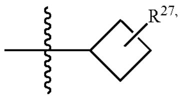

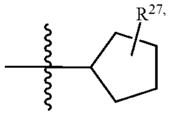

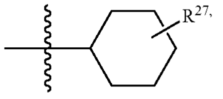

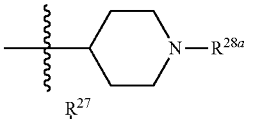

and

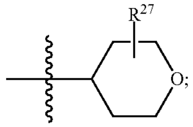

$R^{27}$ represents 0, 1 or 2 substituents each independently selected from the group consisting of F, Cl, $CF_3$, $OCF_3$, $C_{1-6}$-alkyl, O—$C_{1-3}$-alkyl and $NR^{48a}R^{48b}$;

$R^{28a}$ represents a substituent selected from the group consisting of H, methyl, ethyl, n-propyl, iso-propyl, n-butyl, iso-butyl, sec-butyl, tert-butyl, aryl and heteroaryl;

$R^{48a}$ and $R^{48b}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or $R^{48a}$ and $R^{48b}$ together with the nitrogen atom joining them form a structure selected from the group consisting of:

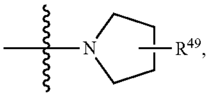

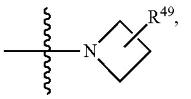

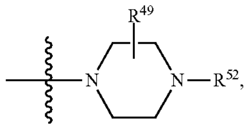

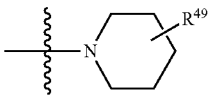

and

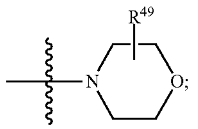

$R^{49}$ represents 0, 1 or 2 substituents each independently selected from the group consisting of F, Cl, $CF_3$, $OCF_3$, $C_{1-6}$-alkyl and O—$C_{1-3}$-alkyl;

$R^{52}$ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl;

$R^{19}$ represents $C_{1-6}$-alkyl, aryl, heteroaryl, —CH(aryl)$_2$, $C_{3-8}$-cycloalkyl, heterocyclyl or an aryl, heteroaryl, $C_{3-8}$-cycloalkyl or heterocyclyl bonded via a $C_{1-6}$-alkylene group, $C_{2-6}$-alkenylene group or $C_{2-6}$-alkynylene group; and $R^{20}$ represents H, methyl, ethyl, n-propyl, iso-propyl, n-butyl, iso-butyl, sec-butyl, tert-butyl, cyclopropyl, cyclobutyl, cyclopentyl or cyclohexyl.

14. A compound as claimed in claim 1, wherein the following structural part (SP)
(SP)
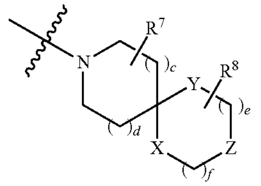
is selected from the group consisting of:
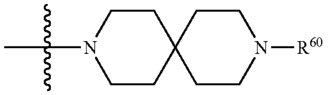
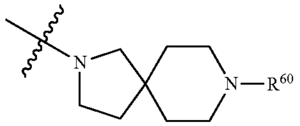
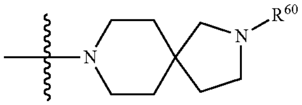
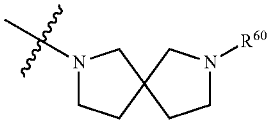
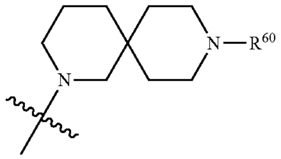
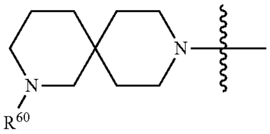
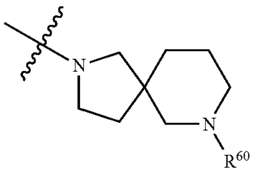
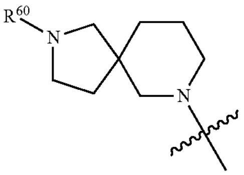
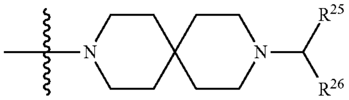
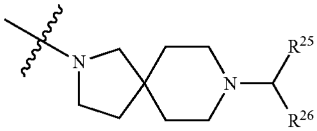
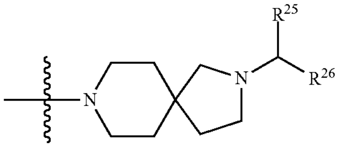
-continued
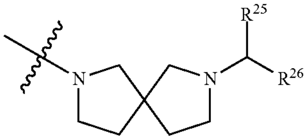
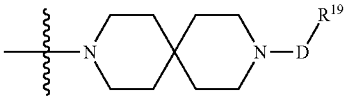
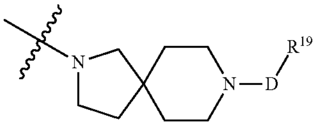
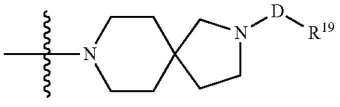
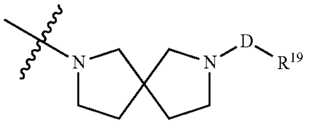
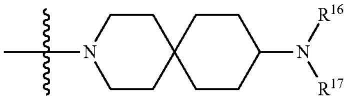
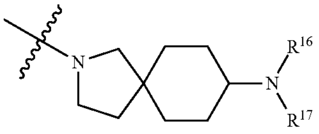
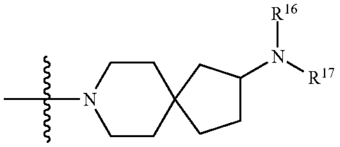
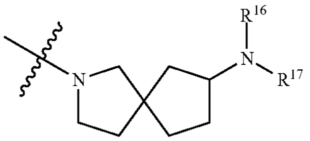
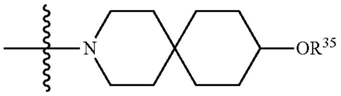
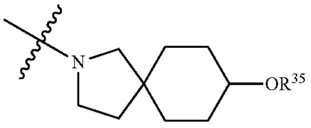
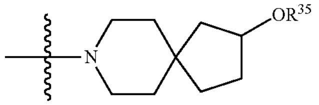
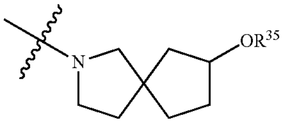
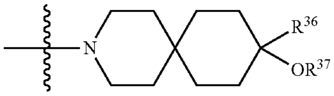

-continued
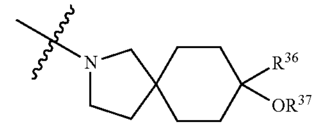
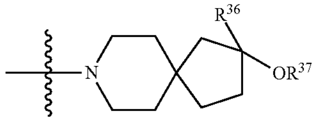
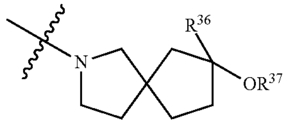
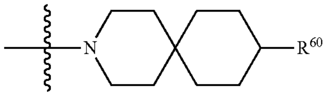
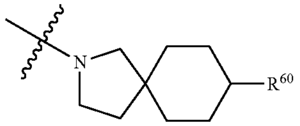
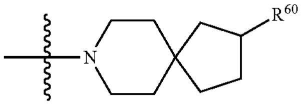
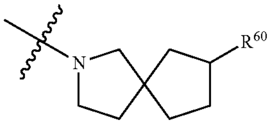
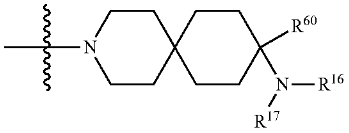
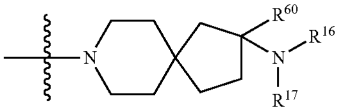
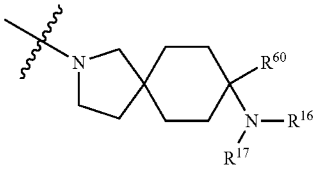
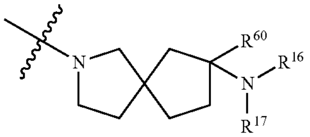
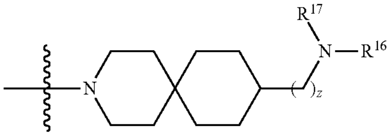
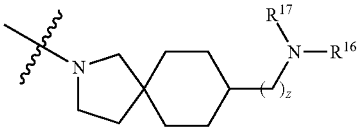
-continued
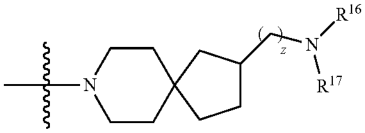
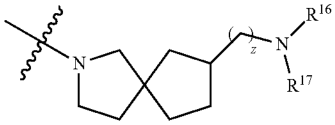
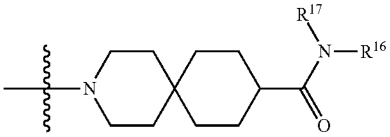
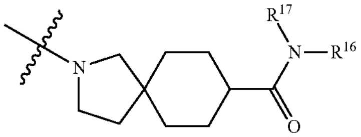
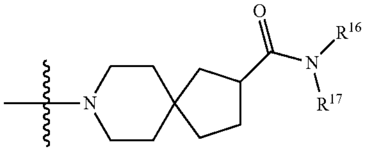
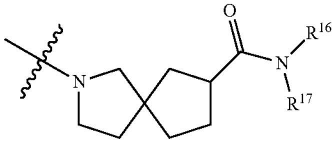
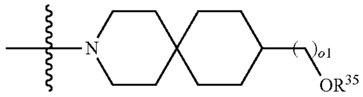
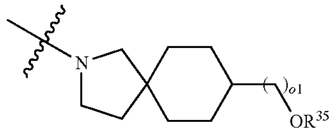
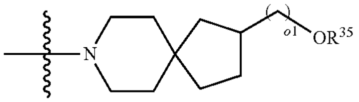
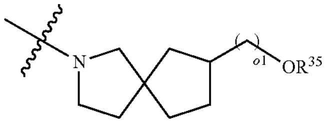
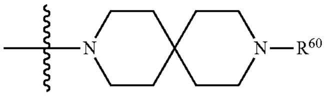
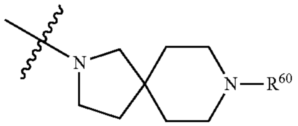
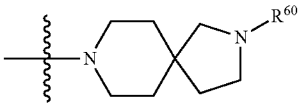

-continued
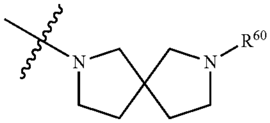
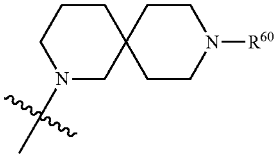
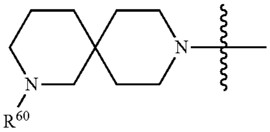
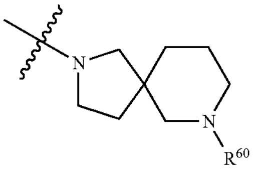
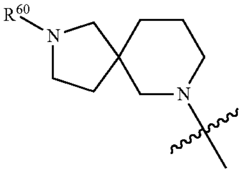
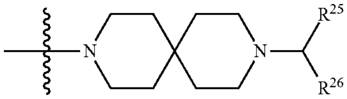
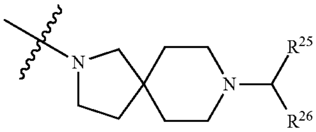
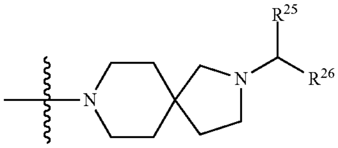
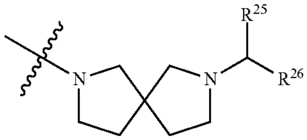
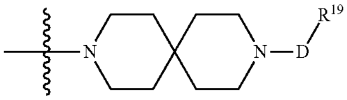
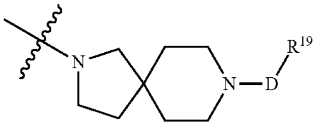
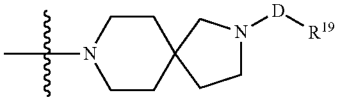
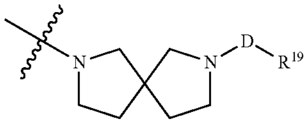
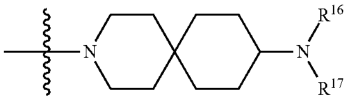
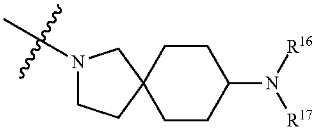
-continued
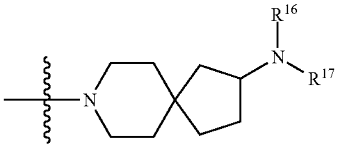
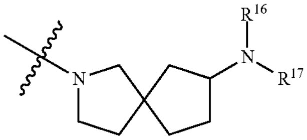
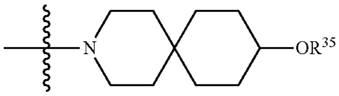
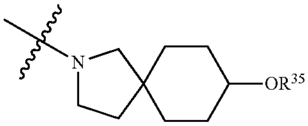
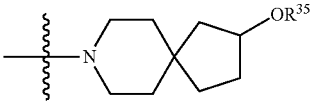
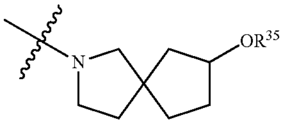
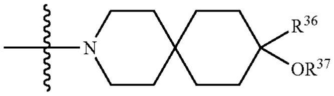
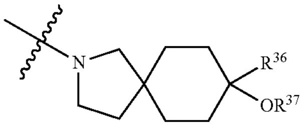
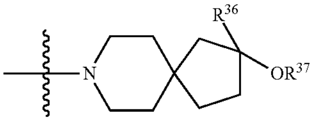
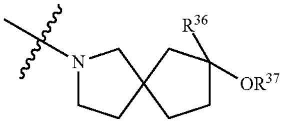
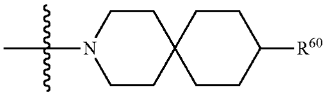
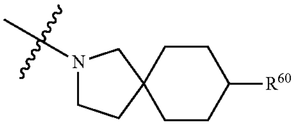
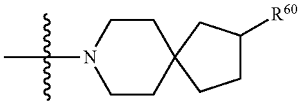
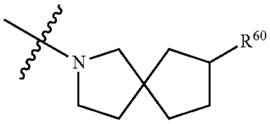

-continued

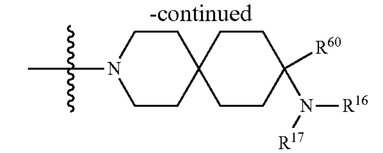

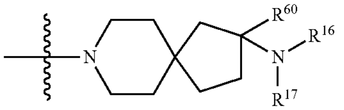

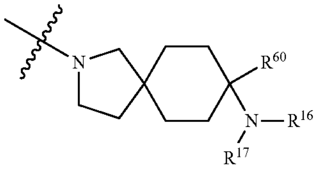

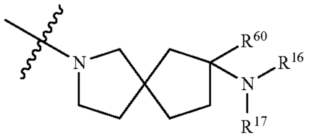

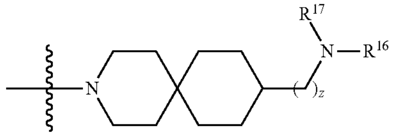

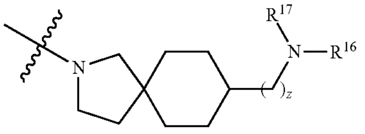

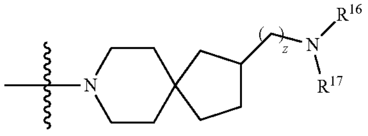

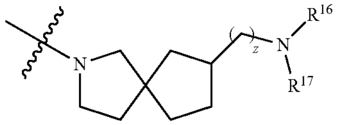

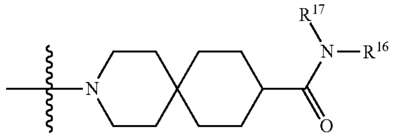

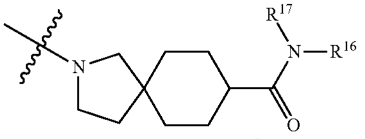

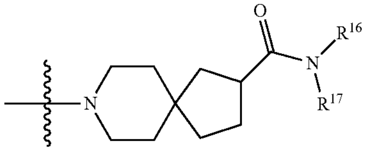

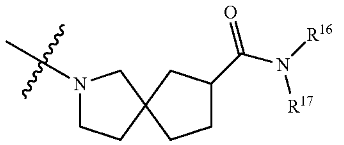

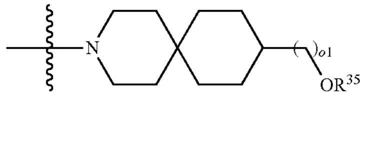

-continued

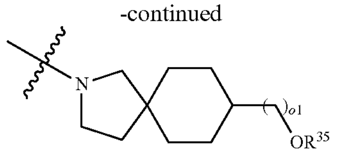

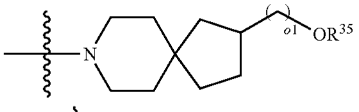

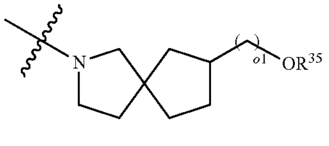

wherein z represents 1, 2 or 3;

o1 represents 1;

$R^{60}$ in each case represents (het)aryl or $C_{1-3}$-alkylene-(het)aryl;

$R^{25}$ and $R^{26}$ each independently represent H, $C_{1-6}$-alkyl, $C_{3-6}$-cycloalkyl or (het)aryl, or $R^{25}$ and $R^{26}$ together with the CH group joining them form a structure selected from the group consisting of

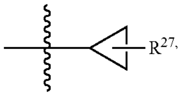

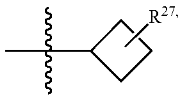

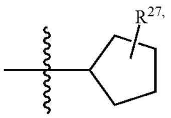

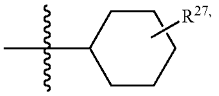

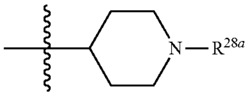

and

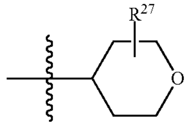

$R^{27}$ represents 0, 1 or 2 substituents each independently selected from the group consisting of F, Cl, $CF_3$, $OCF_3$, $C_{1-6}$-alkyl, O—$C_{1-3}$-alkyl and $NR^{48a}R^{48b}$;

$R^{28a}$ represents a substituent selected from the group consisting of H, methyl, ethyl, n-propyl, iso-propyl, n-butyl, iso-butyl, sec-butyl, tert-butyl and het(aryl);

$R^{48a}$ and $R^{48b}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or $R^{48a}$ and $R^{48b}$ together with the nitrogen atom joining them form a structure selected from the group consisting of:

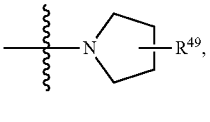

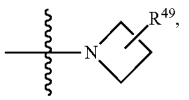

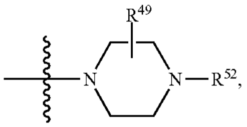

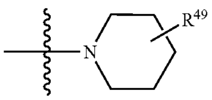

and

-continued

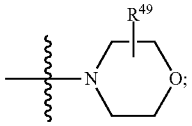

$R^{49}$ represents 0, 1 or 2 substituents each independently selected from the group consisting of F, Cl, $CF_3$, $OCF_3$, $C_{1-6}$-alkyl and O—$C_{1-3}$-alkyl;

$R^{52}$ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl and (het)aryl;

D represents C(═O), S(═O)$_2$ or the group —C(═O)—N($R^{20}$), wherein the nitrogen atom thereof is bonded to $R^{19}$, $R^{19}$ represents $C_{1-6}$-alkyl, (het)aryl, —CH(aryl)$_2$, $C_{3-8}$-cycloalkyl, heterocyclyl or a (het)aryl, $C_{3-8}$-cycloalkyl or heterocyclyl bonded via a $C_{1-6}$-alkylene group, $C_{2-6}$-alkenylene group or $C_{2-6}$-alkynylene group;

$R^{20}$ represents H, methyl, ethyl, n-propyl, iso-propyl, n-butyl, iso-butyl, sec-butyl, tert-butyl, cyclopropyl, cyclobutyl, cyclopentyl or cyclohexyl;

$R^{16}$ and $R^{17}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or $R^{16}$ and $R^{17}$ together with the nitrogen atom joining them form a structure selected from the group consisting of

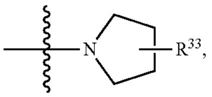 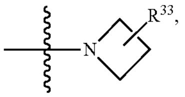

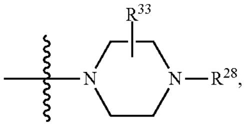 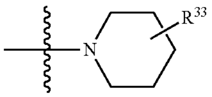 and

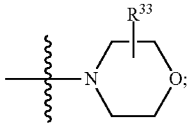

$R^{28}$ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl and (het)aryl;

$R^{33}$ represents 0, 1 or 2 substituents each independently selected from the group consisting of F, Cl, $CF_3$, $OCF_3$, $C_{1-6}$-alkyl, O—$C_{1-3}$-alkyl and $NR^{34a}R^{34b}$;

$R^{34a}$ and $R^{34b}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or $R^{34a}$ and $R^{34b}$ together with the nitrogen atom joining them form a structure selected from the group consisting of:

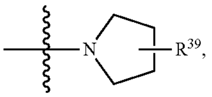 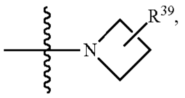

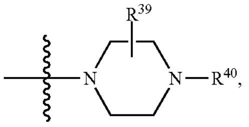 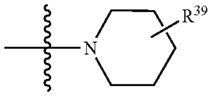 and

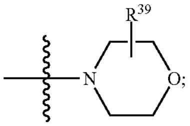

$R^{39}$ represents 0, 1 or 2 substituents each independently selected from the group consisting of F, Cl, $CF_3$, $OCF_3$, $C_{1-6}$-alkyl and O—$C_{1-3}$-alkyl;

$R^{40}$ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl;

$R^{35}$ represents H, $C_{1-6}$-alkyl, $C_{3-6}$-cycloalkyl, (het)aryl or a $C_{3-6}$-cycloalkyl or (het)aryl bonded via a $C_{1-3}$-alkylene group;

$R^{36}$ represents (het)aryl or $C_{1-3}$-alkylene-(het)aryl;

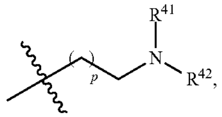

$R^{37}$ represents H, $C_{1-6}$-alkyl or for the group wherein p represents 1, 2 or 3, wherein $R^{41}$ and $R^{42}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or $R^{41}$ and $R^{42}$ together with the nitrogen atom joining them form a structure selected from the group consisting of

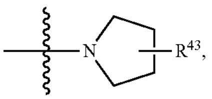 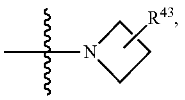

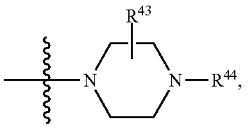 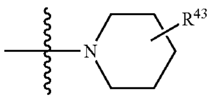 and

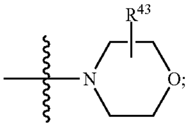

$R^{43}$ represents 0, 1 or 2 substituents each independently selected from the group consisting of F, Cl, $CF_3$, $OCF_3$, $C_{1-6}$-alkyl, O—$C_{1-3}$-alkyl and $NR^{45a}R^{45b}$;

$R^{44}$ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl;

$R^{45a}$ and $R^{45b}$ each independently represent H, methyl, ethyl, n-propyl, iso-propyl, n-butyl, iso-butyl, sec-butyl, tert-butyl, cyclopropyl, cyclobutyl, cyclopentyl or cyclohexyl, or $R^{45a}$ and $R^{45b}$ together with the nitrogen atom joining them form a structure selected from the group consisting of:

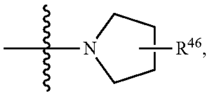

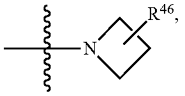

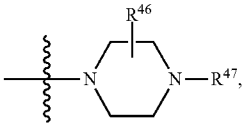

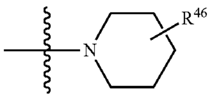

and

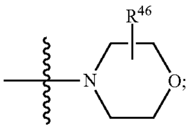

$R^{46}$ represents 0, 1 or 2 substituents each independently selected from the group consisting of F, Cl, $CF_3$, $OCF_3$, $C_{1-6}$-alkyl and O—$C_{1-3}$-alkyl;

$R^{47}$ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl, cyclohexyl, aryl and heteroaryl, and het(aryl) in each case represents a structure selected from the group consisting of (1)

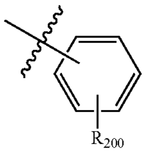

(2)

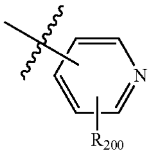

(3)

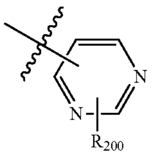

(4)

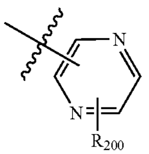

-continued (5)

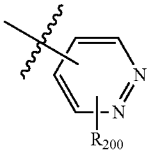

(6)

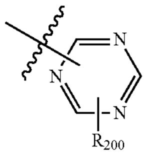

(7)

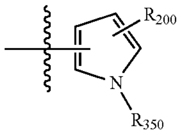

(8)

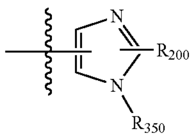

(9)

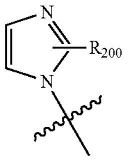

(10)

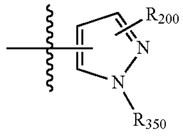

(11)

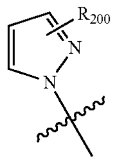

(12)

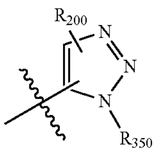

(13)

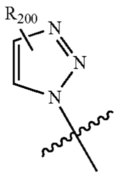

(14)

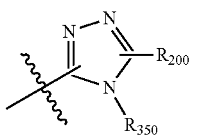

-continued
(15)
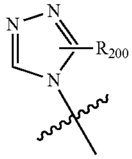
(16)
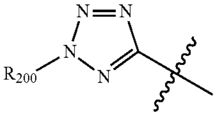
(17)
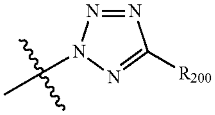
(18)
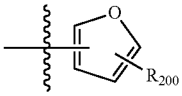
(19)
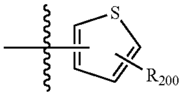
(20)
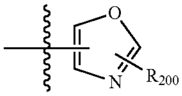
(21)
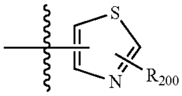
(22)
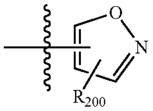
(23)
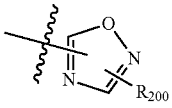
(24)
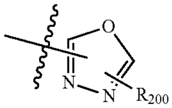
(25)
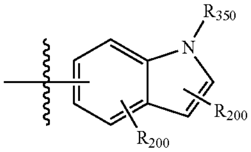
(26)
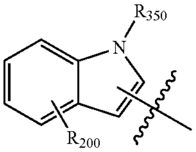
-continued
(27)
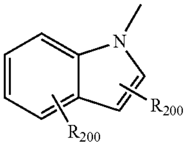
(28)
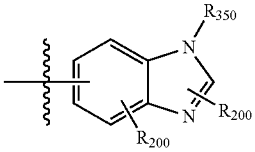
(29)
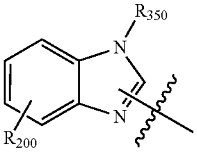
(30)
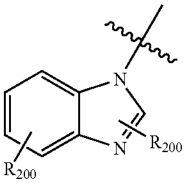
(31)
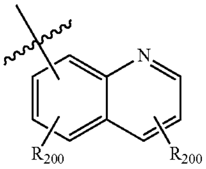
(32)
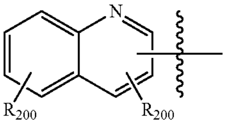
(33)
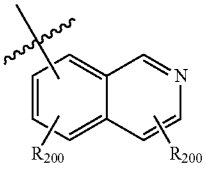
(34)
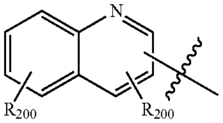
(35)
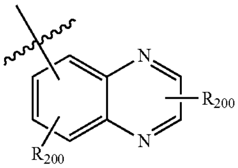

-continued (36)

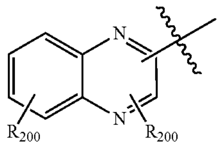

(37)

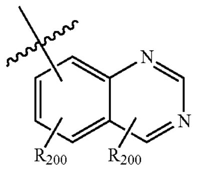

(38)

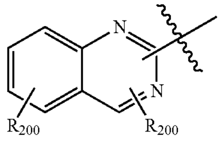

wherein $R^{200}$ represents 0, 1, 2 or 3 substituents each independently selected from the group consisting of F, Cl, $CF_3$, $OCF_3$, OH, O—$C_{1-6}$-alkyl, SH, S—$C_{1-6}$-alkyl, $C_{1-6}$-alkyl, $C_{3-6}$-cycloalkyl, O—$C_{3-6}$-cycloalkyl, $NR^{61}R^{62}$, C(═O)—$NR^{61}R^{62}$, phenyl, pyridyl, pyrimidyl or $OCF_3$, OH, SH, S—$C_{1-6}$-alkyl, $C_{3-6}$-cycloalkyl, O—$C_{3-6}$-cycloalkyl, $NR^{61}R^{62}$, C(═O)—$NR^{61}R^{62}$, phenyl, pyridyl or pyrimidyl bonded via a $C_{1-6}$-alkylene group;

$R^{61}$ and $R^{62}$ each independently represent H, $C_{1-6}$-alkyl or $C_{3-6}$-cycloalkyl, or $R^{61}$ and $R^{62}$ together with the nitrogen atom joining them form a structure selected from the group consisting of:

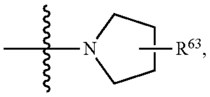

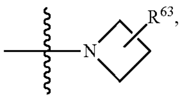

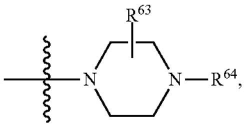

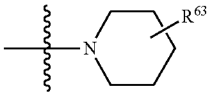

and

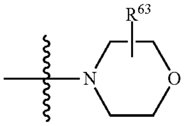

$R^{63}$ represents 0, 1 or 2 substituents each independently selected from the group consisting of F, Cl, $CF_3$, $OCF_3$, $C_{1-6}$-alkyl and O—$C_{1-3}$-alkyl;

$R^{64}$ represents a substituent selected from the group consisting of H, methyl, ethyl, n-propyl, iso-propyl, n-butyl, iso-butyl, sec-butyl, tert-butyl, cyclopropyl, cyclobutyl, cyclopentyl and cyclohexyl; and $R^{350}$ represents H, $CF_3$, phenyl, pyridyl, pyrimidyl or a phenyl, pyridyl or pyrimidyl bonded via a $C_{1-6}$-alkylene group.

15. A compound as claimed in claim 1, wherein the structural part corresponding to formula SP (SP)

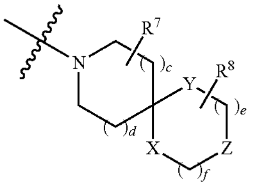

is selected from the group consisting of:

(1)

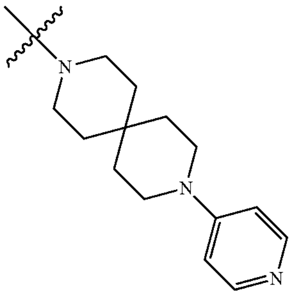

(2)

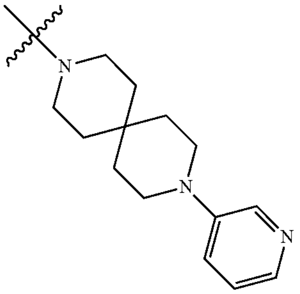

(3)

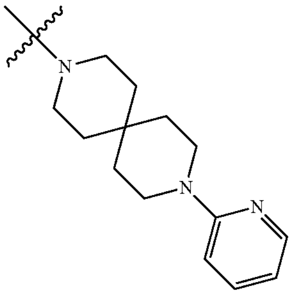

(4)

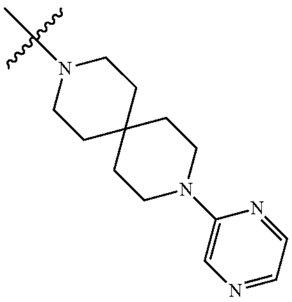

(5)
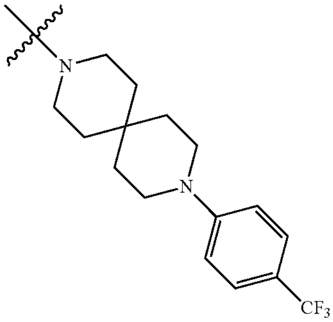
(6)
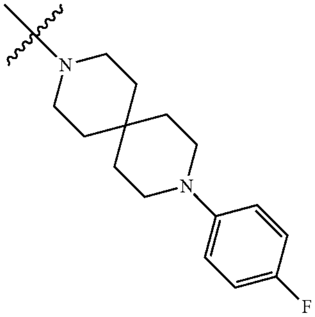
(7)
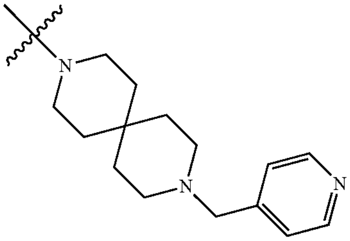
(8)
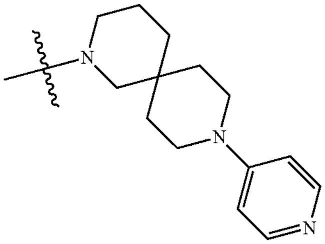
(9)
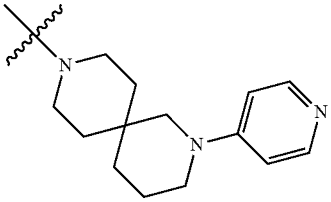
(10)
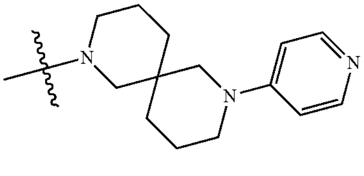
(11)
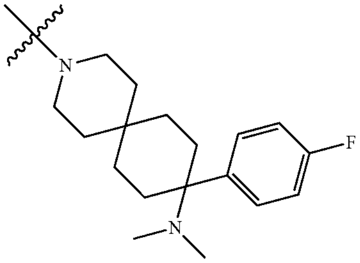
(12)
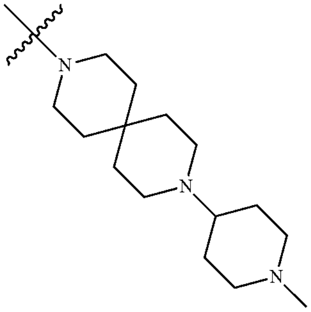
(13)
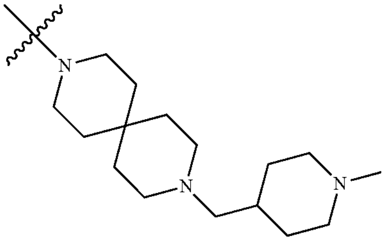
(14)
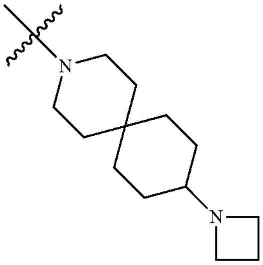
(15)
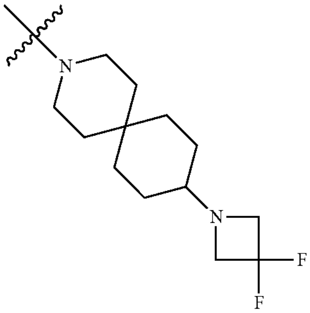

-continued
(16)
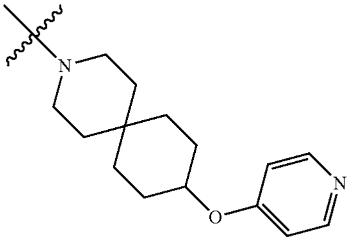
(17)
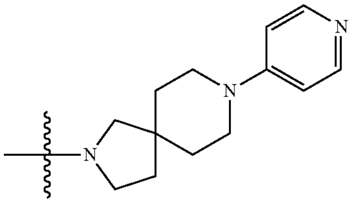
(18)
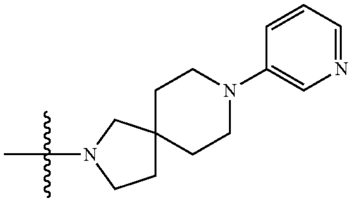
(19)
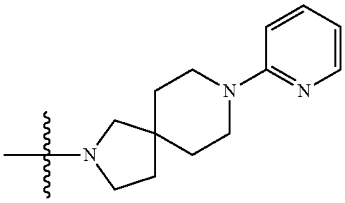
(20)
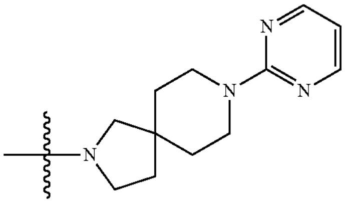
(21)
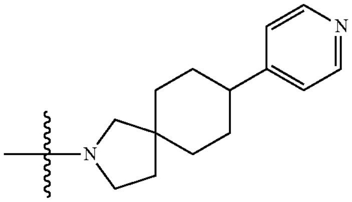
(22)
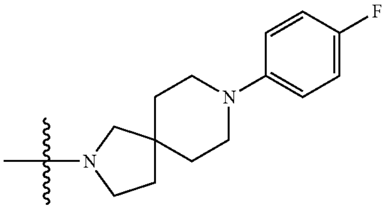
-continued
(23)
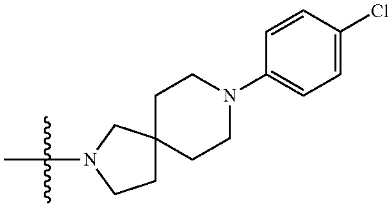
(24)
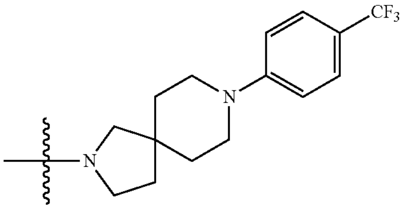
(25)
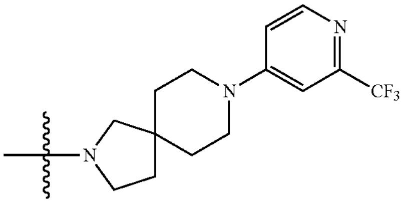
(26)
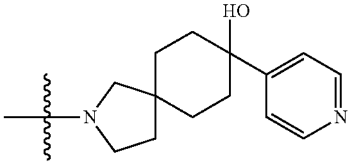
(27)
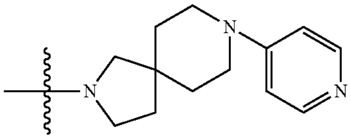
(28)
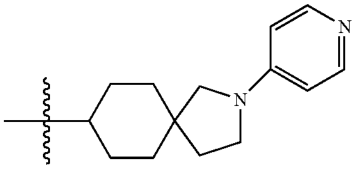
(29)
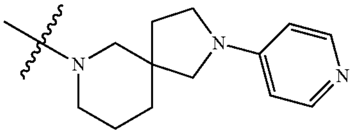
(30)
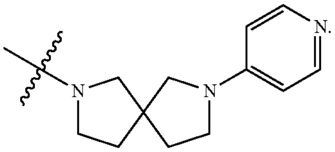
16. A compound as claimed in claim 1, selected from the group consisting of:
4-methoxy-N,2,6-trimethyl-N-[[7-(9-pyridin-4-yl-3,9-diazaspiro[5.5]undecane-3-carbonyl)-1H-benzoimidazol-2-yl]-methyl]-benzenesulfonic acid amide, 4-methoxy-N,2,6-trimethyl-N-[2-[4-(9-pyridin-4-yl-3,9-diazaspiro[5.5]undecane-3-carbonyl)-1H-benzoimidazol-2-yl]-ethyl]-benzenesulfonic acid amide, 4-methoxy-N,2,6-trimethyl-N-[[7-(9-pyridin-4-yloxy-3-azaspiro[5.5]undecane-3-carbonyl)-1H-benzoimidazol-2-yl]-methyl]-benzenesulfonic acid amide, N-[[7-[9-(azetidin-1-yl)-3-azaspiro[5.5]undecane-3-carbonyl]-1H-benzoimidazol-2-yl]-methyl]-4-methoxy-N,2,6-trimethyl-benzenesulfonic acid amide, N-[[7-[9-(3,3-difluoro-azetidin-1-yl)-3-azaspiro[5.5]undecane-3-carbonyl]-1H-benzoimidazol-2-yl]-methyl]-4-methoxy-N,2,6-trimethyl-benzenesulfonic acid amide, 4-methoxy-N,2,6-trimethyl-N-[1-[7-(9-pyridin-4-yl-3,9-diazaspiro[5.5]undecane-3-carbonyl)-1H-benzoimidazol-2-yl]-ethyl]-benzenesulfonic acid amide, N-methyl-N-[[7-(9-pyridin-4-yl-3,9-diazaspiro[5.5]undecane-3-carbonyl)-1H-benzoimidazol-2-yl]-methyl]-naphthalene-1-sulfonic acid amide, N-methyl-N-[[7-(9-pyridin-4-yl-3,9-diazaspiro[5.5]undecane-3-carbonyl)-1H-benzoimidazol-2-yl]-methyl]-2-(trifluoromethyl)-benzenesulfonic acid amide, 4-methoxy-N,2,6-trimethyl-N-[[7-(8-pyridin-4-yl-3,8-diazaspiro[4.5]decane-3-carbonyl)-1H-benzoimidazol-2-yl]-methyl]-benzenesulfonic acid amide, 4-methoxy-N,2,6-trimethyl-N-[[7-(8-pyridin-4-yl-3,8-diazaspiro[4.4]nonane-3-carbonyl)-1H-benzoimidazol-2-yl]-methyl]-benzenesulfonic acid amide, 2-chloro-N-methyl-N-[[7-(9-pyridin-4-yl-3,9-diazaspiro[5.5]undecane-3-carbonyl)-1H-benzoimidazol-2-yl]-methyl]-4-(trifluoromethyloxy)-benzenesulfonic acid amide, 4-methoxy-N,2,6-trimethyl-N-[1-[7-(9-pyridin-4-yl-3,9-diazaspiro[5.5]undecane-3-carbonyl)-1H-benzoimidazol-2-yl]-cyclopropyl]-benzenesulfonic acid amide, N-[[6-fluoro-7-(9-pyridin-4-yl-3,9-diazaspiro[5.5]undecane-3-carbonyl)-1H-benzoimidazol-2-yl]methyl]-4-methoxy-N,2,6-trimethyl-benzenesulfonic acid amide, N-cyclopropyl-4-methoxy-2,6-dimethyl-N-[[7-(9-pyridin-4-yl-3,9-diazaspiro[5.5]undecane-3-carbonyl)-1H-benzoimidazol-2-yl]-methyl]-benzenesulfonic acid amide, 4-methoxy-N,2,6-trimethyl-N-[[7-[(9-pyridin-4-yl-3,9-diazaspiro[5.5]undecan-3-yl)-methyl]-1H-benzoimidazol-2-yl]-methyl]-benzenesulfonic acid amide, 5-chloro-N-methyl-N-[[7-(9-pyridin-4-yl-3,9-diazaspiro[5,5]undecane-3-carbonyl)-1H-benzoimidazol-2-yl] methyl]thiophene-2-carboxylic acid amide, 2,6-dichloro-N,3-dimethyl-N-[[7-(9-pyridin-4-yl-3,9-diazaspiro[5.5]undecane-3-carbonyl)-1H-benzoimidazol-2-yl]-methyl]-benzenesulfonic acid amide,

[2-[1-[(4-methoxy-2,6-dimethyl-phenyl)sulfonyl]-piperidin-2-yl]-3H-benzoimidazol-4-yl]-(9-pyridin-4-yl-3,9-diazaspiro[5.5]undecan-3-yl)-methanone,

[2-[1-[(4-methoxy-2,6-dimethyl-phenyl)sulfonyl]-pyrrolidin-2-yl]-3H-benzoimidazol-4-yl]-(9-pyridin-4-yl-3,9-diazaspiro[5.5]undecan-3-yl)-methanone, 4-methoxy-N,2,6-trimethyl-N-[[1-methyl-4-(9-pyridin-4-yl-3,9-diazaspiro[5.5]undecane-3-carbonyl)-1H-benzoimidazol-2-yl]-methyl]-benzenesulfonic acid amide, 4-methoxy-N,2,6-trimethyl-N-[[7-[2-oxo-2-(9-pyridin-4-yl-3,9-diazaspiro[5.5]undecan-3-yl)-ethyl]-1H-benzoimidazol-2-yl]-methyl]-benzenesulfonic acid amide, 4-methoxy-N,2,6-trimethyl-N-[[6-(9-pyridin-4-yl-3,9-diazaspiro[5.5]undecane-3-carbonyl)-1H-benzoimidazol-2-yl]-methyl]-benzenesulfonic acid amide, 2-chloro-N,6-dimethyl-N-[[6-(9-pyridin-4-yl-3,9-diazaspiro[5.5]undecane-3-carbonyl)-1H-benzoimidazol-2-yl]-methyl]-benzenesulfonic acid amide, N-methyl-N-[[6-(9-pyridin-4-yl-3,9-diazaspiro[5.5]undecane-3-carbonyl)-1H-benzoimidazol-2-yl]-methyl]-2-(trifluoromethyl)-benzenesulfonic acid amide, N-methyl-N-[[6-(9-pyridin-4-yl-3,9-diazaspiro[5.5]undecane-3-carbonyl)-1H-benzoimidazol-2-yl]-methyl]-naphthalene-1-sulfonic acid amide, 4-methoxy-N,2,6-trimethyl-N-[2-[6-(9-pyridin-4-yl-3,9-diazaspiro[5.5]undecane-3-carbonyl)-1H-benzoimidazol-2-yl]-ethyl]-benzenesulfonic acid amide, 4-methoxy-N,2,6-trimethyl-N-[[7-(3-pyridin-4-yl-1-oxa-2,8-diazaspiro[4.5]dec-2-ene-8-carbonyl)-1H-benzoimidazol-2-yl]-methyl]-benzenesulfonic acid amide, 4-chloro-N,2,5-trimethyl-N-[[7-(3-pyridin-4-yl-3,9-diazaspiro[5.5]undecane-9-carbonyl)-1H-benzoimidazol-2-yl]-methyl]-benzenesulfonic acid amide, 2-chloro-N-methyl-N-[[7-(4-oxo-1-pyridin-4-yl-3,8-diazaspiro[4.5]decane-8-carbonyl)-1H-benzoimidazol-2-yl]-methyl]benzamide, 4-methoxy-N,2,6-trimethyl-N-[[7-(3-pyridin-4-yl-3,9-diazaspiro[5.5]undecane-9-carbonyl)-1H-benzoimidazol-2-yl]-methyl]-benzenesulfonic acid amide, 2-chloro-N-methyl-N-[[7-(3-pyridin-4-yl-3,9-diazaspiro[5.5]undecane-9-carbonyl)-1H-benzoimidazol-2-yl]-methyl]-benzamide, 3-chloro-N-methyl-N-[[7-(3-pyridin-4-yl-3,9-diazaspiro[5.5]undecane-9-carbonyl)-1H-benzoimidazol-2-yl]-methyl]-thiophene-2-carboxylic acid amide, 4-methoxy-N,2,6-trimethyl-N-[[7-(3-pyridin-4-yl-3,8-diazaspiro[4.5]decane-8-carbonyl)-1H-benzoimidazol-2-yl]-methyl]-benzenesulfonic acid amide, 2-chloro-N,6-dimethyl-N-[[7-(3-pyridin-4-yl-3,8-diazaspiro[4.5]decane-8-carbonyl)-1H-benzoimidazol-2-yl]-methyl]-benzenesulfonic acid amide, 2-chloro-N-methyl-N-[[7-(3-pyridin-4-O-3,8-diazaspiro[4.5]decane-8-carbonyl)-1H-benzoimidazol-2-yl]-methyl]-benzamide, 3-chloro-N-methyl-N-[[7-(3-pyridin-4-yl-3,8-diazaspiro[4.5]decane-8-carbonyl)-1H-benzoimidazol-2-yl]-methyl]-thiophene-2-carboxylic acid amide, 4-chloro-N,2,5-trimethyl-N-[[7-(3-pyridin-4-yl-3,8-diazaspiro[4.5]decane-8-carbonyl)-1H-benzoimidazol-2-yl]methyl]-benzenesulfonic acid amide, 2-chloro-N,6-dimethyl-N-[[7-(3-pyridin-4-yl-3,9-diazaspiro[5.5]undecane-9-carbonyl)-1H-benzoimidazol-2-yl]-methyl]-benzenesulfonic acid amide, 7-chloro-2-[[7-(3-pyridin-4-yl-3,9-diazaspiro[5.5]undecane-9-carbonyl)-1H-benzoimidazol-2-yl]-methyl]-2,3-dihydro-isoindol-1-one, 7-chloro-2-[[7-(3-pyridin-4-yl-3,8-diazaspiro[4.5]decane-8-carbonyl)-1H-benzoimidazol-2-yl]-methyl]-2,3-dihydro-isoindol-1-one, 4-methoxy-N,2,6-trimethyl-N-[1-methyl-7-(3-pyridin-4-yl-3,9-diazaspiro[5.5]undecane-9-carbonyl)-1H-benzoimidazol-2-yl]benzenesulfonic acid amide, 4-methoxy-N,2,6-trimethyl-N-[1-methyl-7-(3-pyridin-4-yl-3,8-diazaspiro[4.5]decane-8-carbonyl)-1H-benzoimidazol-2-yl]-benzenesulfonic acid amide, 4-methoxy-N,2,6-trimethyl-N-[1-methyl-7-(4-oxo-1-pyridin-4-yl-3,8-diazaspiro[4.5]decane-8-carbonyl)-1H-benzoimidazol-2-yl]-benzenesulfonic acid amide, 4-methoxy-N,2,6-trimethyl-N-[1-methyl-6-(3-pyridin-4-yl-3,9-diazaspiro[5.5]undecane-9-carbonyl)-1H-benzoimidazol-2-yl]-benzenesulfonic acid amide, 4-methoxy-N,2,6-trimethyl-N-[1-methyl-6-(3-pyridin-4-yl-3,8-diazaspiro[4.5]decane-8-carbonyl)-1H-benzoimidazol-2-yl]-benzenesulfonic acid amide, 4-methoxy-N,2,6-trimethyl-N-[[7-(3-pyridin-4-yl-3,9-diazaspiro[5.5]undecane-9-carbonyl)-1H-benzoimidazol-2-yl]-methyl]-benzamide, 4-methoxy-N,2,6-trimethyl-N-[[7-(3-pyridin-4-yl-3,8-diazaspiro[4.5]decane-8-carbonyl)-1H-benzoimidazol-2-yl]-methyl]-benzamide, N-[1-[7-[9-(1H-Imidazol-4-yl-methyl)-3,9-diazaspiro[5.5]undecane-3-carbonyl]-1H-benzoimidazol-2-yl]ethyl]-4-methoxy-N,2,6-trimethyl-benzenesulfonic acid amide, 4-Methoxy-N,2,6-trimethyl-N-[1-[7-[9-(pyridin-2-yl-methyl)-3,9-diazaspiro[5.5]undecane-3-carbonyl]-1H-benzoimidazol-2-yl]-ethyl]-benzenesulfonic acid amide, 4-Methoxy-N,2,6-trimethyl-N-[1-[7-[9-(pyridin-4-yl-methyl)-3,9-diazaspiro[5.5]undecane-3-carbonyl]-1H-benzoimidazol-2-yl]ethyl]-benzenesulfonic acid amide, 4-Methoxy-N,2,6-trimethyl-N-[1-[7-[9-(pyridin-3-yl-methyl)-3,9-diazaspiro[5.5]undecane-3-carbonyl]-1H-benzoimidazol-2-yl]ethyl]-benzenesulfonic acid amide, N-[1-[7-[9-[(2,6-Difluoro-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide, N-[1-[7-[9-[(3,4-Difluoro-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide, N-[1-[7-[9-[(2,5-Difluoro-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide, N-[1-[7-[9-[(2,4-Difluoro-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide, N-[1-[7-[9-[(3-Fluoro-4-methoxy-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide, N-[1-[7-[9-[(2-Fluoro-6-methoxy-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide, 4-Methoxy-N,2,6-trimethyl-N-[1-[7-[9-[(5-methyl-3H-imidazol-4-yl)-methyl]-3,9-diazaspiro[5.5]undecane-3-carbonyl]-1H-benzoimidazol-2-yl]-ethyl]-benzenesulfonic acid amide, 4-Methoxy-N,2,6-trimethyl-N-[1-[7-[9-[(3-methyl-3H-imidazol-4-yl)-methyl]-3-diazaspiro[5.5]undecane-3-carbonyl]-1H-benzoimidazol-2-yl]-ethyl]-benzenesulfonic acid amide, 4-Methoxy-N,2,6-trimethyl-N-[1-[7-[9-[(2-methyl-1H-imidazol-4-yl)-methyl]-3,9-diazaspiro[5.5]undecane-3-carbonyl]-1H-benzoimidazol-2-yl]-ethyl]-benzenesulfonic acid amide, 4-Methoxy-N,2,6-trimethyl-N-[1-[7-[9-([1,2,3]thiadiazol-4-yl-methyl)-3,9-diazaspiro[5.5]undecane-3-carbonyl]-1H-benzoimidazol-2-yl]-ethyl]-benzenesulfonic acid amide, N-[1-[7-[9-[(2-Chloro-4-fluoro-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide, N-[1-[7-[9-[(2-Chloro-6-fluoro-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide, N-[1-[7-[9-[(1,5-Dimethyl-1H-pyrazol-4-yl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide, N-[1-[7-[9-[(3,5-Dimethyl-isoxazol-4-yl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide, N-[1-[7-[9-[(4-Cyano-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide, N-[1-[7-[9-[(3-Cyano-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide, N-[1-[7-[9-[(2-Cyano-phenyl)-methyl]-3,9-diazaspiro[5.5]undecane-3-carbonyl]-1H-benzoimidazol-2-yl]-ethyl]-4-methoxy-N,2,6-trimethyl-benzenesulfonic acid amide, 4-Methoxy-N,2,6-trimethyl-N-[1-[7-[9-[5-(trifluoromethyl)-pyridine-2-carbonyl]-3,9-diazaspiro[5.5]undecane-3-carbonyl]-1H-benzoimidazol-2-yl]-ethyl]-benzenesulfonic acid amide, 4-Methoxy-N,2,6-trimethyl-N-[1-[7-[9-(pyrazine-2-carbonyl)-3,9-diazaspiro[5.5]undecane-3-carbonyl]-1H-benzoimidazol-2-yl]-ethyl]-benzenesulfonic acid amide, 4-Methoxy-N,2,6-trimethyl-N-[1-[7-[9-(2-methylsulfanyl-pyridine-3-carbonyl)-3,9-diazaspiro[5.5]undecane-3-carbonyl]-1H-benzoimidazol-2-yl]-ethyl]-benzenesulfonic acid amide, N-[1-[7-[9-(4-Cyano-benzoyl)-3,9-diazaspiro[5.5]undecane-3-carbonyl]-1H-benzoimidazol-2-yl]-ethyl]-4-methoxy-N,2,6-trimethyl-benzenesulfonic acid amide, N-[1-[7-[9-(Cyclopropanecarbonyl)-3,9-diazaspiro[5.5]undecane-3-carbonyl]-1H-benzoimidazol-2-yl]-ethyl]-4-methoxy-N,2,6-trimethyl-benzenesulfonic acid amide, N-[1-[7-[9-(3,3-Dimethyl-butanoyl)-3,9-diazaspiro[5.5]undecane-3-carbonyl]-1H-benzoimidazol-2-yl]-ethyl]-4-methoxy-N,2,6-trimethyl-benzenesulfonic acid amide, N-[1-[7-[9-(2-Chloro-4-fluoro-benzoyl)-3,9-diazaspiro[5.5]undecane-3-carbonyl]-1H-benzoimidazol-2-yl]ethyl]-4-methoxy-N,2,6-trimethyl-benzenesulfonic acid amide, N-[1-[7-[9-(2,4-Difluoro-benzoyl)-3,9-diazaspiro[5.5]undecane-3-carbonyl]-1H-benzoimidazol-2-yl]-ethyl]-4-methoxy-N,2,6-trimethyl-benzenesulfonic acid amide, N-[1-[7-[9-(5-tert-Butyl-2-methyl-2H-pyrazole-3-carbonyl)-3,9-diazaspiro[5.5]undecane-3-carbonyl]-1H-benzoimidazol-2-yl]-ethyl]-4-methoxy-N,2,6-trimethyl-benzenesulfonic acid amide, N-[1-[7-[9-(2-tert-Butyl-5-methyl-2H-pyrazole-3-carbonyl)-3,9-diazaspiro[5.5]undecane-3-carbonyl]-1H-benzoimidazol-2-yl]-ethyl]-4-methoxy-N,2,6-trimethyl-benzenesulfonic acid amide, N-[1-[7-[9-[(5-Chloro-thiophen-2-yl)sulfonyl]-3,9-diazaspiro[5.5]undecane-3-carbonyl]-1H-benzoimidazol-2-yl]-ethyl]-4-methoxy-N,2,6-trimethyl-benzenesulfonic acid amide, N-[1-[7-[9-[(2,4-Difluoro-phenyl)sulfonyl]-3,9-diazaspiro[5.5]undecane-3-carbonyl]-1H-benzoimidazol-2-yl]-ethyl]-4-methoxy-N,2,6-trimethyl-benzenesulfonic acid amide, N-[1-[7-[9-[(3-Cyano-4-fluoro-phenyl)sulfonyl]-3,9-diazaspiro[5.5]undecane-3-carbonyl]-1H-benzoimidazol-2-yl]-ethyl]-4-methoxy-N,2,6-trimethyl-benzenesulfonic acid amide, N-[1-[7-[9-[(2-Cyano-phenyl)sulfonyl]-3,9-diazaspiro[5.5]undecane-3-carbonyl]-1H-benzoimidazol-2-yl]-ethyl]-4-methoxy-N,2,6-trimethyl-benzenesulfonic acid amide, and 4-Methoxy-N,2,6-trimethyl-N-[1-[7-[9-[(1-methyl-1H-indol-4-yl)sulfonyl]-3,9-diazaspiro[5.5]undecane-3-carbonyl]-1H-benzoimidazol-2-yl]-ethyl]-benzenesulfonic acid amide, or a physiologically acceptable salt thereof.

17. A compound as claimed in claim 1, wherein said compound is in the form of an isolated stereoisomer.

18. A compound as claimed in claim 1, wherein said compound is in the form of a mixture of stereoisomers in any mixing ratio.

19. A compound as claimed in claim 18, wherein said mixture is a racemic mixture.

20. A pharmaceutical composition comprising a compound as claimed in claim 1 and at least one pharmaceutically acceptable carrier or auxiliary substance.

21. A method of treating a disorder or disease state selected from the group consisting of pain, bronchial asthma, chronic obstructive pulmonary disease, allergies, cystic fibrosis, ulcerative colitis, Crohn's disease, atopic dermatitis, psoriasis, rheumatoid arthritis, and osteoarthritis, in a subject, said method comprising administering to said subject a pharmacologically effective amount of a compound as claimed in claim 1.

22. A method as claimed in claim 21, wherein said disorder or disease state is pain selected from the group consisting of acute pain, visceral pain, neuropathic pain, chronic pain and inflammation pain.

* * * * *